US009499537B2

(12) United States Patent
Son et al.

(10) Patent No.: US 9,499,537 B2
(45) Date of Patent: Nov. 22, 2016

(54) ANTIVIRAL PYRROLOPYRIDINE DERIVATIVES AND METHOD FOR PREPARING THE SAME

(71) Applicant: KOREA RESEARCH INSTITUTE OF CHEMICAL TECHNOLOGY, Daejeon (KR)

(72) Inventors: Jong Chan Son, Daejeon (KR); Bong Jin Kim, Daejeon (KR); Jae Hak Kim, Daejeon (KR); Ill Young Lee, Daejeon (KR); Chang Soo Yun, Daejeon (KR); Sang Ho Lee, Daejeon (KR); Chong Kgo Lee, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 14/278,955

(22) Filed: May 15, 2014

(65) Prior Publication Data
US 2014/0249162 A1 Sep. 4, 2014

Related U.S. Application Data

(63) Continuation-in-part of application No. PCT/KR2012/009689, filed on Nov. 15, 2012.

(30) Foreign Application Priority Data

Nov. 15, 2011 (KR) ........................ 10-2011-0119102

(51) Int. Cl.
*C07D 471/04* (2006.01)

(52) U.S. Cl.
CPC .................................. *C07D 471/04* (2013.01)

(58) Field of Classification Search
CPC combination set(s) only.
See application file for complete search history.

(56) References Cited

U.S. PATENT DOCUMENTS 8,609,653 B2 * 12/2013 De La Rosa ........ A61K 31/437
514/230.5
2006/0128661 A1 6/2006 Ebenbeck et al.
2010/0179139 A1 7/2010 Bamborough et al.

FOREIGN PATENT DOCUMENTS

| WO | 2005103003 A2 | 11/2005 |
|----|---------------|---------|
| WO | 2007/131350 A1 | 11/2007 |
| WO | 2009/062285 A1 | 5/2009 |
| WO | 2009/062288 A1 | 5/2009 |
| WO | 2009/062308 A1 | 5/2009 |
| WO | 2010/130034 A1 | 11/2010 |
| WO | 2010/130842 A1 | 11/2010 |
| WO | 2013-012649 A1 | 1/2013 |

OTHER PUBLICATIONS

De la Rosa, caplus an 2012:1117867.*
Prevent—Cold, 2016, http://www.medicinenet.com/script/main/art.asp?articlekey=53472.*
Prevent—hcv, 2016, http://answers.webmd.com/answers/1191677/how-can-hepatitis-c-be-prevented.*
Prevent—hpv, 2016, http://www.hpv.com.au/can-hpv-be-prevented.aspx.*
Alexandre L'Heureux, et al: "Synthesis of functionalized 7-azaindoles via directed ortho-metalations", Tetrahedron Letters, vol. 45, Issue 11, pp. 2317-2319, Mar. 8, 2004.
Carl Thibault, et al; "Concise and Efficient Synthesis of 4-Fluoro-1H-pyrrolo[2,3-b]pyridine", Organic Letters, vol. 5, No. 26, pp. 5023-5025; Published on Web Dec. 4, 2003.
Frauke Christ, et al; "Rational Design of small-molecule inhibitors of the LEDGF/p75-integrase Interaction and HIV replication", Nature Chemical Biology, vol. 6, Issue 6, 9 pages; Jun. 2010; Published online May 16, 2010.
First Japanese Office Action dated Mar. 31, 2015; Appln. No. 2014-542241.
Japanese Second Office Action dated Sep. 29, 2015; filed in JP 2014-522858 (counterpart to WO2013-012649).

* cited by examiner

*Primary Examiner* — Sun Jae Yoo
(74) *Attorney, Agent, or Firm* — Ladas & Parry LLP

(57) ABSTRACT

The present invention relates to a pyrrolopyridine derivative represented by the Chemical Formula I, and a racemate or a stereoisomer thereof, or a pharmaceutically acceptable salt thereof, and relates to an antiviral composition including the same as an active ingredient. The compound of the Chemical Formula I has excellent antiviral activity and selectivity for wild type and resistant HIV-1, and thereby is useful as a therapeutic agent for acquired immune deficiency syndrome (AIDS).

19 Claims, No Drawings

ANTIVIRAL PYRROLOPYRIDINE DERIVATIVES AND METHOD FOR PREPARING THE SAME

TECHNICAL FIELD

The present invention relates to a compound having high selectivity and antiviral activity for virus, particularly, human immunodeficiency virus (HIV), to a method for preparing the same, and to the use thereof.

BACKGROUND ART

Acquired immune deficiency syndrome (AIDS) is caused by human immunodeficiency virus (HIV) infection. There are two types of HIV, HIV-1 and HIV-2, and the type most prevalent globally is HIV-1. As major drugs approved for the treatment of AIDS, zidovudine, didanosine, zalcitabine, stavudine, lamivudine, abacavir, tenofovir and emtricitabine have been developed as nucleoside reverse transcriptase inhibitors (NRTI), and nevirapine, delavirdine, efavirenz, etravirine and rilpivirine have been developed as non-nucleoside reverse transcriptase inhibitors (NNRTI). Saquinavir, indinavir, ritonavir, nelfinavir, amprenavir, lopinavir, atazanavir, fosamprenavir, tipranavir and darunavir have been developed as protease inhibitors (PI), fuzeon has been developed as a fusion inhibitor, maraviroc was developed in 2007 as an entry inhibitor, and raltegravir was developed in 2008 as an integrase inhibitor.

These chemotherapeutic agents combine different target drugs and uses 2 to 4 types in one pill, are referred to as highly active antiretroviral therapy (HAART), and currently are very effective in extending the life of subjects having AIDS. However, they are not capable of fully curing AIDS, the drugs sometimes show toxicity, and mutants for current therapeutic agents are continuously appearing. Therefore, there has been a continuous demand for the development of new therapeutic agents that can solve these problems.

In view of the above, the inventors have conducted constant research on new AIDS therapeutic agents, and as a result have discovered that pyrrolopyridine derivatives, which have a novel skeleton, show powerful activities against HIV, thereby completing the present invention.

DISCLOSURE

Technical Problem

A first object of the present invention is to provide a novel pyrrolopyridine derivatives and a pharmaceutically acceptable salt thereof that inhibit the replication of HIV.

A second object of the present invention is to provide a method for preparing the compound.

A third object of the present invention is to provide an intermediate compound used for the preparation of the compound.

A fourth object of the present invention is to provide a pharmaceutical composition that includes the compound as an active ingredient.

Technical Solution

In order to solve the above problems, the present invention provides a compound represented by the following Chemical Formula I, a racemate or a stereoisomer thereof, or a pharmaceutically acceptable salt thereof:

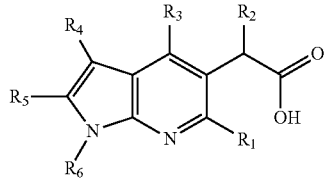

[Chemical Formula I]

In the formula, $R_1$ is $C_{1-6}$ alkyl, $C_{3-6}$ cycloalkyl, $C_{1-6}$ alkoxy, a halogen atom or CN; $R_2$ is $C_{1-6}$ alkoxy, $C_{3-6}$ cycloalkoxy unsubstituted or substituted with a $C_{1-6}$ alkyl group, or $C_{1-6}$ alkyl; $R_3$ is hydrogen, halogen, aryloxy, arylamino, thioaryl, phenyl, chromanyl, 3,4-dihydro-2H-benzo[b][1,4]oxazinyl or 2,3-dihydropyrano[4,3,2-de]quinolinyl, wherein the phenyl, chromanyl, 3,4-dihydro-2H-benzo[b][1,4]oxazinyl or 2,3-dihydropyrano[4,3,2-de]quinolinyl is either unsubstituted or substituted with 1 to 3 substituents each selected from the group consisting of amino, halogen, hydroxy, CN, $CF_3$, $C_{1-6}$ alkyl and $C_{1-6}$ alkoxy; $R_4$ and $R_5$ are each independently hydrogen, $C_{3-6}$ cycloalkyl or $C_{1-6}$ alkyl; $R_6$ is hydrogen, $C_{3-6}$ cycloalkyl, —COO—($C_{1-6}$ alkyl), —CO—($C_{1-6}$ alkyl) or —$(CH_2)_n$—$R_7$; $R_7$ is hydrogen; halogen; hydroxy; amino; azido; cyano; trifluoromethyl; $C_{2-6}$ alkenyl; $C_{2-6}$ alkynyl; $C_{1-6}$ alkoxy; —(S—$C_{1-6}$ alkyl); —$SO_2$—($C_{1-6}$ alkyl); carbamoyl; CONH ($C_{1-3}$ alkyl); CON($C_{1-3}$ alkyl)$_2$; COOH; piperazinyl unsubstituted or substituted with a $C_{1-3}$ alkyl group; morpholinyl; $C_{3-6}$ cycloalkyl unsubstituted or substituted with 1 or 2 substituents each selected from the group consisting of halogen, cyano, hydroxy, hydroxymethyl, carboxy and carbamoyl; phenyl unsubstituted or substituted with 1 to 3 substituents each selected from the group consisting of halogen, cyano, $C_{1-6}$ alkyl, $C_{1-6}$ alkoxy and amino; pyridinyl unsubstituted or substituted with 1 or 2 substituents each selected from the group consisting of halogen, cyano, $C_{1-6}$ alkyl, $C_{1-6}$ alkoxy and amino; pyrimidinyl unsubstituted or substituted with amino or halogen; pyrazinyl unsubstituted or substituted with amino or halogen; dioxoisoindolinyl; tetrahydrofuranyl; tetrahydropyranyl; oxazolyl; oxadiazolyl unsubstituted or substituted with $C_{1-6}$ alkyl; imidazolyl unsubstituted or substituted with $C_{1-6}$ alkyl; furanyl unsubstituted or substituted with $C_{1-6}$ alkyl or halogen; thiophenyl unsubstituted or substituted with $C_{1-6}$ alkyl or halogen; pyrrolidinyl unsubstituted or substituted with $C_{1-6}$ alkyl or halogen; 2-oxopyrrolidinyl; pyrazolyl unsubstituted or substituted with $C_{1-3}$ alkyl; or thiazolyl; and n is an integer of 1 to 5.

Preferably, $R_1$ is methyl; $R_2$ is $C_{1-6}$ alkoxy; $R_3$ is phenyl, chromanyl, 3,4-dihydro-2H-benzo[b][1,4]oxazinyl or 2,3-dihydropyrano[4,3,2-de]quinolinyl, wherein the phenyl, chromanyl, 3,4-dihydro-2H-benzo[b][1,4]oxazinyl or 2,3-dihydropyrano[4,3,2-de]quinolinyl is unsubstituted or substituted with 1 to 3 substituents each selected from the group consisting of amino, halogen, hydroxy, CN, $CF_3$, $C_{1-6}$ alkyl and $C_{1-6}$ alkoxy; $R_4$ and $R_5$ are each independently hydrogen or $C_{1-6}$ alkyl; $R_6$ is hydrogen, $C_{3-6}$ cycloalkyl, —COO—($C_{1-6}$ alkyl), —CO—($C_{1-6}$ alkyl) or —$(CH_2)_n$—$R_7$; $R_7$ is hydrogen; halogen; hydroxy; amino; azido; cyano; trifluoromethyl; $C_{2-6}$ alkenyl; $C_{2-6}$ alkynyl; $C_{1-6}$ alkoxy; —(S—$C_{1-6}$ alkyl); —$SO_2$—($C_{1-6}$ alkyl); carbamoyl; CONH($C_{1-3}$ alkyl); CON($C_{1-3}$ alkyl)$_2$; COOH; piperazinyl unsubstituted or substituted with a $C_{1-3}$ alkyl group; morpholinyl; $C_{3-6}$ cycloalkyl unsubstituted or substituted with 1 or 2 substituents each selected from the group consisting of halogen, cyano, hydroxy, hydroxymethyl, carboxy and carbamoyl; phenyl unsubstituted or substituted with 1 to 3 substituents each selected from the group consisting of halogen, cyano, $C_{1-6}$ alkyl, $C_{1-6}$ alkoxy and amino; pyridinyl unsubstituted or substituted with 1 or 2 substituents each selected from the group consisting of halogen, cyano, $C_{1-6}$ alkyl, $C_{1-6}$ alkoxy and amino; pyrimidinyl unsubstituted or substituted with amino or halogen; pyrazinyl unsubstituted or substituted with amino or halogen; dioxoisoindolinyl; tetrahydrofuranyl; tetrahydropyranyl; oxazolyl; oxadiazolyl unsubstituted or substituted with $C_{1-6}$ alkyl; imidazolyl unsubstituted or substituted with $C_{1-6}$ alkyl; furanyl unsubstituted or substituted with $C_{1-6}$ alkyl or halogen; thiophenyl unsubstituted or substituted with $C_{1-6}$ alkyl or halogen; pyrrolidinyl unsubstituted or substituted with $C_{1-6}$ alkyl or halogen; 2-oxopyrrolidinyl; pyrazolyl unsubstituted or substituted with $C_{1-3}$ alkyl; or thiazolyl; and n is an integer of 1 to 5.

Preferably, $R_1$ is methyl; $R_2$ is tert-butoxy; $R_3$ is phenyl or chromanyl, and the phenyl or chromanyl is unsubstituted or substituted with 1 to 3 substituents each selected from the group consisting of amino, halogen, hydroxy, CN, $CF_3$, $C_{1-6}$ alkyl and $C_{1-6}$ alkoxy; $R_4$ and $R_5$ are each independently hydrogen or methyl; $R_6$ is hydrogen or —$(CH_2)_n$—$R_7$; $R_7$ is hydrogen; halogen; hydroxy; amino; azido; cyano; trifluoromethyl; $C_{2-6}$ alkenyl; $C_{2-6}$ alkynyl; alkoxy; —(S—$C_{1-6}$ alkyl); —$SO_2$— ($C_{1-6}$ alkyl); carbamoyl; $CONH(C_{1-3}$ alkyl); $CON(C_{1-3}$ alkyl$)_2$; COOH; piperazinyl unsubstituted or substituted with a $C_{1-3}$ alkyl group; morpholinyl; $C_{3-6}$ cycloalkyl unsubstituted or substituted with 1 or 2 substituents each selected from the group consisting of halogen, cyano, hydroxy, hydroxymethyl, carboxy and carbamoyl; phenyl unsubstituted or substituted with 1 to 3 substituents each selected from the group consisting of halogen, cyano, $C_{1-6}$ alkyl, $C_{1-6}$ alkoxy or amino; pyridinyl unsubstituted or substituted with 1 or 2 substituents each selected from the group consisting of halogen, cyano, $C_{1-6}$ alkyl, $C_{1-6}$ alkoxy or amino; pyrimidinyl unsubstituted or substituted with amino or halogen; pyrazinyl unsubstituted or substituted with amino or halogen; dioxoisoindolinyl; tetrahydrofuranyl; tetrahydropyranyl; oxazolyl; oxadiazolyl unsubstituted or substituted with $C_{1-6}$ alkyl; imidazolyl unsubstituted or substituted with $C_{1-6}$ alkyl; furanyl unsubstituted or substituted with $C_{1-6}$ alkyl or halogen; thiophenyl unsubstituted or substituted with $C_{1-6}$ alkyl or halogen; pyrrolidinyl unsubstituted or substituted with $C_{1-6}$ alkyl or halogen; 2-oxopyrrolidinyl; pyrazolyl unsubstituted or substituted with $C_{1-3}$ alkyl; or thiazolyl; and n is an integer of 1 to 5.

Preferably, $R_1$ is methyl; $R_2$ is tert-butoxy; $R_3$ is phenyl or chromanyl, and the phenyl or chromanyl is unsubstituted or substituted with 1 to 3 substituents each selected from the group consisting of F, Cl, CN, hydroxy, methyl and methoxy; $R_4$ and $R_5$ are either all hydrogen or all methyl; $R_6$ is hydrogen, methyl, ethyl, propyl, isopropyl, butyl, isobutyl, isopentyl, propynyl, allyl or —$(CH_2)_n$—$R_7$; $R_7$ is F; hydroxy; cyano; trifluoromethyl; $C_{1-6}$ alkoxy; dimethylaminocarbonyl; dimethylamino; COOH; $C_{3-6}$ cycloalkyl unsubstituted or substituted with 1 or 2 substituents each selected from the group consisting of F, cyano and hydroxy; phenyl unsubstituted or substituted with substituents each selected from the group consisting of F, Cl, cyano and methoxy; pyridinyl unsubstituted or substituted with 1 or 2 substituents each selected from the group consisting of F, Cl, methyl and methoxy; pyrimidinyl; pyrazinyl; dioxoisoindolinyl; oxazolyl; furanyl; thiophenyl; pyrrolidinyl; 2-oxopyrrolidinyl; pyrazolyl unsubstituted or substituted with $C_{1-3}$ alkyl; or thiazolyl; and n is an integer of 1 to 3.

In particular, the present invention includes all racemates and stereoisomers of the compound represented by Chemical Formula I, and particularly, includes all racemates, (S)-stereoisomers and (R)-stereoisomers of the carbon position at which $R_2$ is substituted.

The present invention provides a method for preparing a compound represented by Chemical Formula I, which is shown in the following Reaction Formula 1.

[Reaction Formula 1]

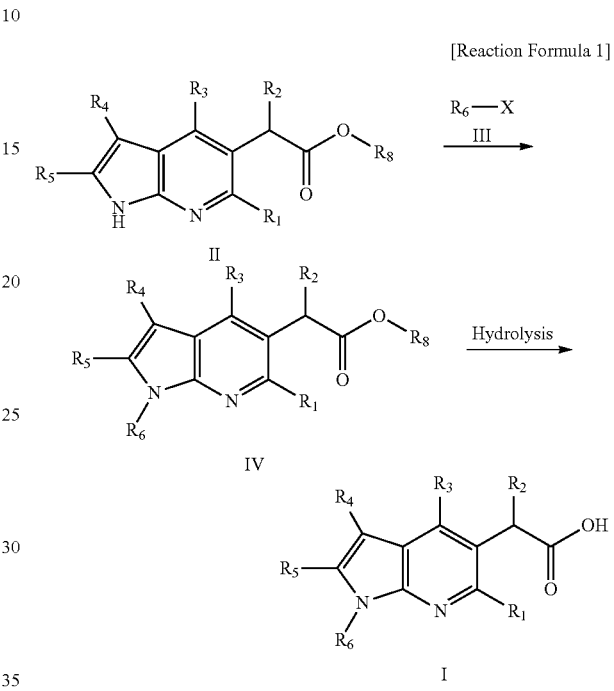

Specifically, the present invention provides a method for preparing a compound represented by the following Chemical Formula I, which, as described in Reaction Formula 1, includes the following steps:

1) the step of preparing a compound represented by the following Chemical Formula IV by reacting a compound represented by the following Chemical Formula II with a compound represented by the following Chemical Formula III (Step 1); and 2) the step of hydrolyzing the compound represented by Chemical Formula IV (Step 2).

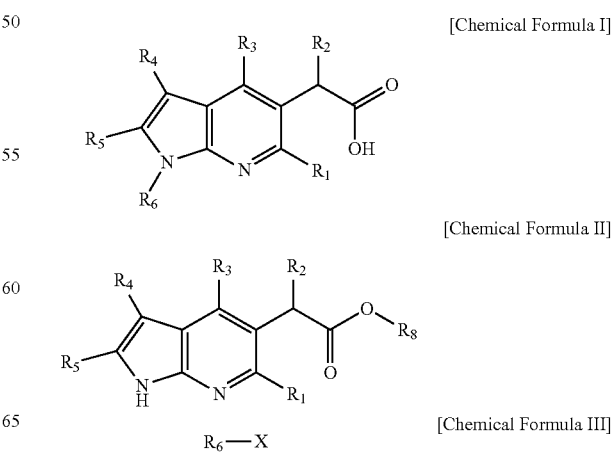

[Chemical Formula IV]

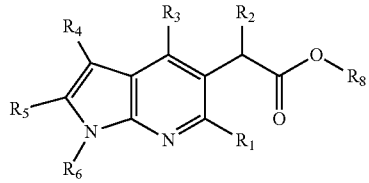

In the formula, $R_1$, $R_2$, $R_3$, $R_4$, $R_5$, $R_6$, $R_7$ and n are the same as those defined in the compound represented by Chemical Formula I, $R_8$ is $C_{1-6}$ alkyl, and X is halogen, methanesulfonyl, p-toluenesulfonyl or trifluoromethanesulfonyl.

However, when $R_6$ in the compound to be prepared, represented by Chemical Formula I, is H, Step 1) may be skipped.

Preferably, $R_8$ is methyl or ethyl.
Preferably, X is halogen.

In the present invention, the molar ratio of the compound represented by Chemical Formula II and the compound represented by Chemical Formula III in Step 1) is preferably 1:2 to 1:3. In the present invention, Step 1) may be carried out using dichloromethane, chloroform or a combination thereof as a solvent, however, the solvent is not limited thereto.

In the present invention, Step 1) may be carried out under the presence of potassium hydroxide and a catalytic amount of tetrabutylammonium bromide.

In the present invention, Step 1) is preferably carried out at room temperature, and more preferably at 20° C. to 40° C. In the present invention, Step 1) is preferably carried out for 2 to 18 hours.

In the present invention, Step 2) may be carried out using methanol, tetrahydrofuran or a combination thereof as a solvent, however, the solvent is not limited thereto.

In the present invention, the hydrolysis in Step 2) may be carried out using potassium hydroxide, lithium hydroxide or sodium hydroxide.

In one example of the present invention, the hydrolysis in Step 2) is carried out using 4N sodium hydroxide.

In the present invention, Step 2) is preferably carried out for 3 to 18 hours.

As one example, the compound represented by Chemical Formula II or (S)-II, which is used as a starting material in preparing the compound represented by Chemical Formula I, may be prepared as shown in the following Reaction Formula 2.

[Reaction Formula 2]

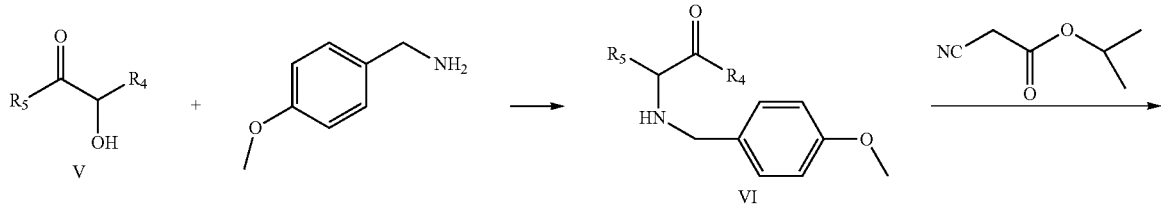

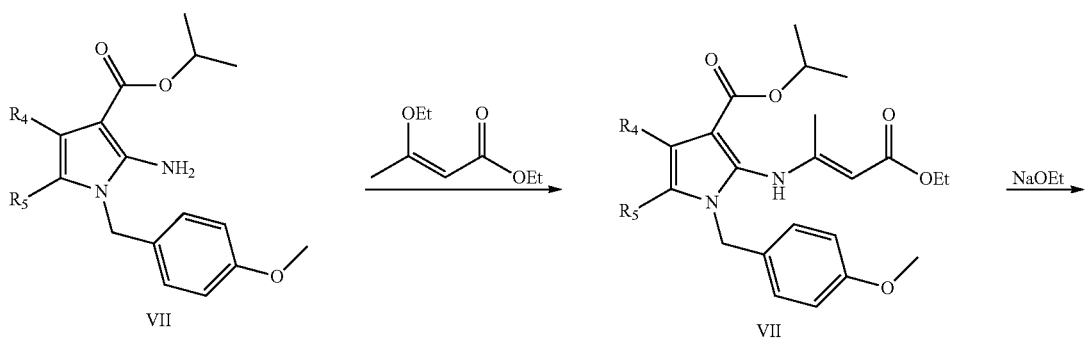

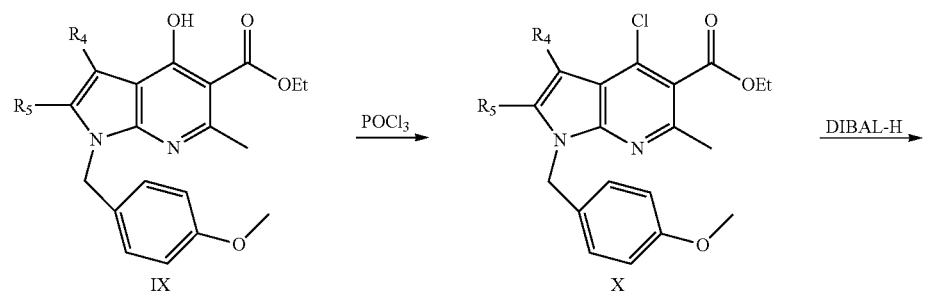

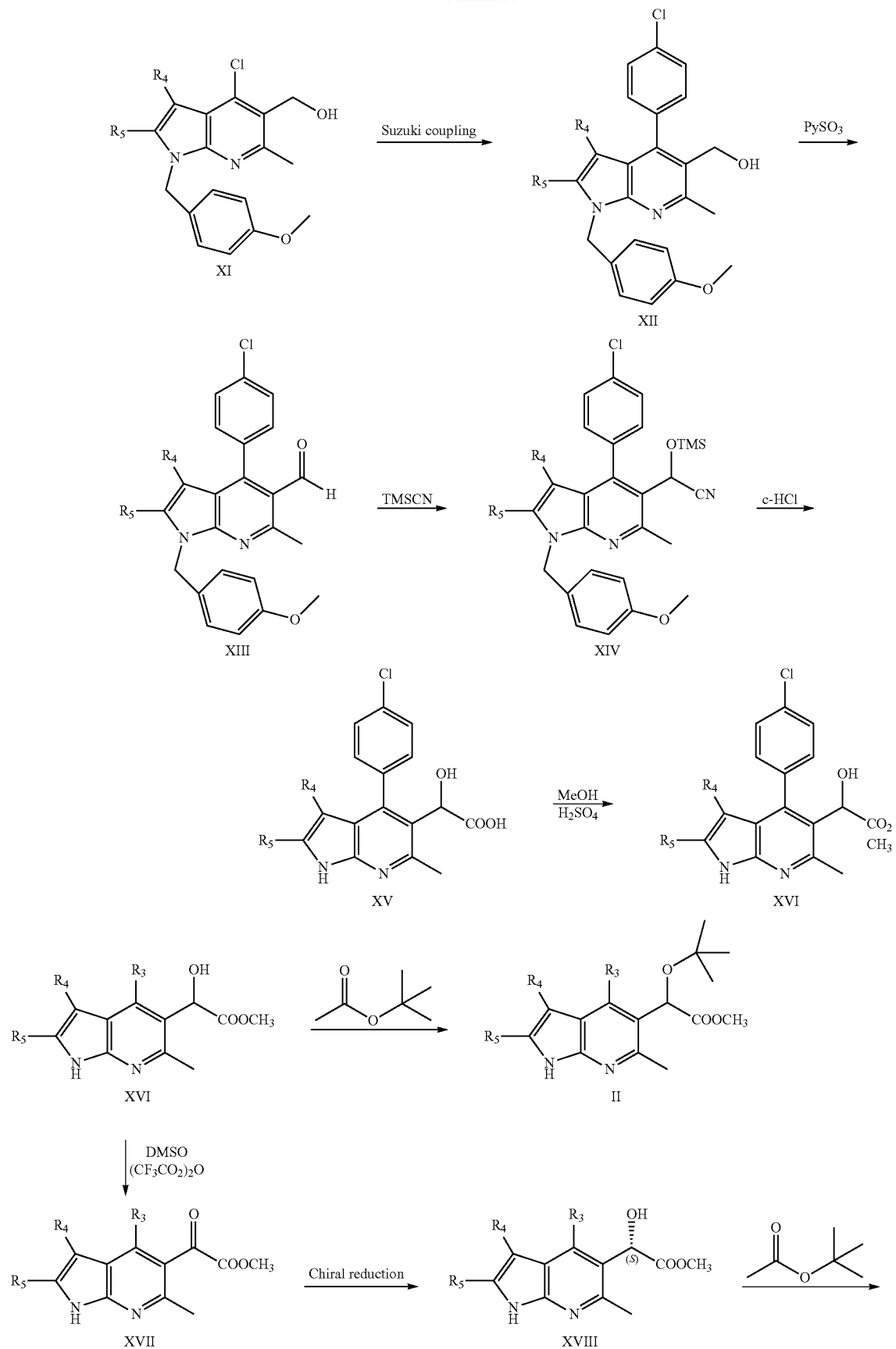

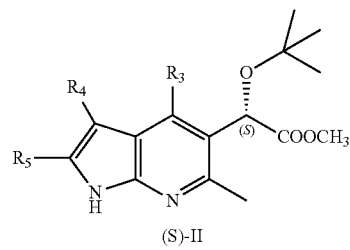

(S)-II

Specifically, an intermediate of Chemical Formula VI is first obtained by mixing a hydroxy ketone compound represented by Chemical Formula V with methoxybenzylamine in cyclohexane and heating the mixture for 2 hours while removing the produced water using a dean-stark trap, and a compound of Chemical Formula VII may be prepared by subsequently adding isopropyl cyanoacetate to the intermediate and heating the result for 2 hours. The isopropyl ester of Chemical Formula VII may be prepared with a methyl group or a tert-butyl group, however, choosing the above ester is preferable since the cyclization reaction most favorably occurs when a compound of Chemical Formula IX is prepared.

A compound of Chemical Formula VIII may obtained by refluxing the compound of Chemical Formula VII and 3-ethoxy-2-butanoic acid ethyl ester in an ortho-xylene solvent overnight with a catalytic amount of 4-toluenesulfonic acid as an example of an acid catalyst, and a compound of Chemical Formula IX may be prepared by heating the compound of Chemical Formula VIII overnight in 21% sodium ethoxide and anhydrous ethanol.

A compound of Chemical Formula X may be prepared by adding $POCl_3$ to the compound of Chemical Formula IX in a weight ratio of 4 to 5 times and heating the mixture for 4 to 8 hours at 50° C. to 60° C.

From the compound of Chemical Formula X, the reaction introducing an aryl group ($R_3$) may be progressed using a Suzuki reaction. A compound of Chemical Formula XI, which is a hydroxymethyl compound, may be prepared by reducing the ester using a general method of reacting the compound of Chemical Formula X with DABAL at −78° C. to 0° C.

The reaction introducing an aryl group ($R_3$) to the compound of Chemical Formula XI may be progressed using a Suzuki reaction, and for example, a compound of Chemical Formula XII may be prepared by adding 4-chlorophenylboronic acid pinacol ester and potassium carbonate to the compound of Chemical Formula XI in dimethylformamide, removing oxygen by strongly passing through nitrogen gas into the solution, adding $Pd(PPh_3)_4$ thereto, completely removing oxygen by continuously passing through nitrogen, and heating the result under nitrogen for 6 to 10 hours at 100° C. to 130° C.

A compound of Chemical Formula XIII, which is an aldehyde compound, may be prepared by reacting the compound of Chemical Formula XII, which is a hydroxymethyl derivative, in a dimethyl sulfoxide solvent for 2 to 5 hours with a pyridine sulfur trioxide complex using a generally known oxidation reaction.

A compound of Chemical Formula XIV, which is trimethylsilyloxy cyanide, may be prepared by reacting trimethylsilyl cyanide with the aldehyde compound of Chemical Formula XIII. The solvent in this reaction is preferably dichloromethane, the reaction may be progressed by adding zinc iodide in 1 to 1.5 equivalents, and the reaction may be completed by being progressed for 1 hour at a reaction temperature of 0° C., and for 3 to 5 hours at 25° C.

Next, a compound of Chemical Formula XV, which is a hydroxyacetic acid derivative, may be prepared at the same time when the compound of Chemical Formula XIV is heated in concentrated hydrochloric acid and the 4-methoxybenzyl group is removed. Herein, the concentrated hydrochloric acid may be used in 20 to 30 times in volume with respect to the compound of Chemical Formula XIV, and the reaction may be completed by reacting the result for 18 to 20 hours at 100° C.

A compound of Chemical Formula XVI may be prepared from the compound of Chemical Formula XV using a generally known esterification reaction, and a compound of Chemical Formula II (a racemate) may be prepared by dissolving the compound of Chemical Formula XVI in 50 to 60 times of dichloromethane, adding 10 to 20 times of tert-butyl acetate thereto, cooling the mixture to 10° C., adding 2 to 5 equivalents of 70% perchloric acid thereto over 30 minutes to 1 hour, then stirring the result for 5 to 8 hours at 20° C. to 25° C., and terminating the reaction.

In addition, in order to synthesize a chiral derivative of the compound of Chemical Formula II, the hydroxyester derivative of Chemical Formula XVI is dissolved in 50 to 60 times of anhydrous dichloromethane by adding 2 to 2.5 equivalents of trifluoroacetic anhydride thereto, and the result is cooled to −78° C. After 2 to 2.5 equivalents of dimethyl sulfoxide are diluted with twice the volume of dichloromethane, the result is slowly added to the mixed liquid described above, and the result is stirred for 30 minutes at the same temperature. A compound of Chemical Formula XVII may be prepared by dissolving the compound of compound XVI in 5 times the volume of dichloromethane, slowly adding the result to the above reaction solution, stirring the result for 1 hour at the same temperature, adding 5 equivalents of triethylamine thereto, stirring the result for 30 minutes, and then completing the reaction.

After a compound of Chemical Formula XVIII is prepared by stereoselectively reducing the compound of Chemical Formula XVII prepared above using a known method (International Publication No. WO2010/130034A1, Page 45, Example 2), a compound of Chemical Formula (S)-II may be prepared by reacting the compound of Chemical Formula XVIII with tert-butyl acetate and perchloric acid using the same method described above. The compound of Chemical Formula (S)-II may be used as an intermediate.

In addition, the intermediate represented by Chemical Formula XII in Reaction Formula 2 may be prepared using the method of Reaction Formula 3.

[Reaction Formula 3]

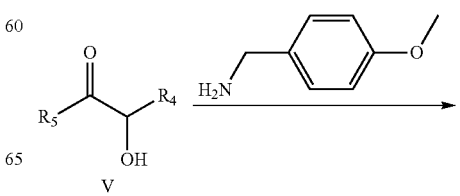

V

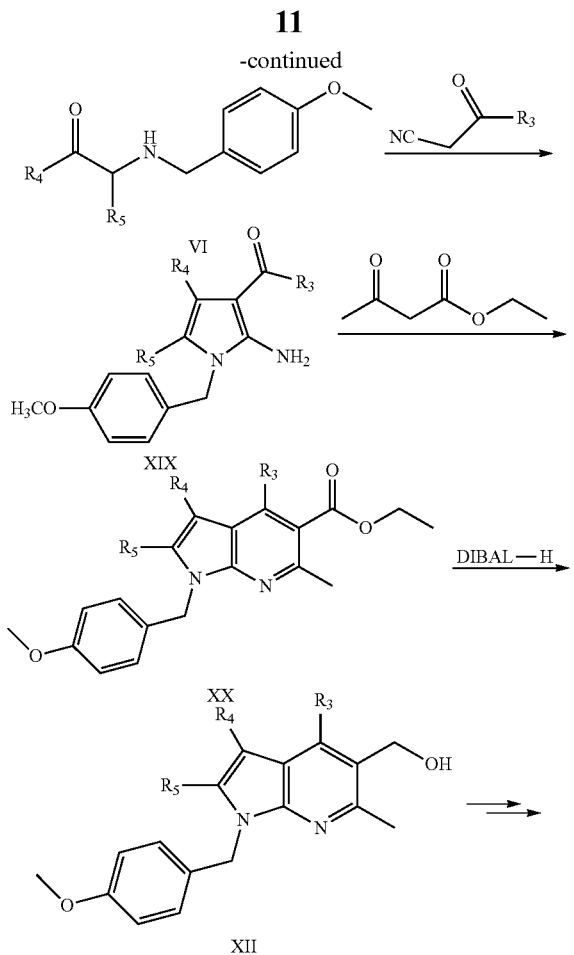

A compound of Chemical Formula VI is prepared by adding a compound of Chemical Formula V and param-ethoxybenzylamine to an organic solvent such as benzene, toluene and xylene, preferably toluene, setting up a dean-stark trap apparatus, heating the result under reflux for 2 to 5 hours, and then dehydrating, and a compound of Chemical Formula XIX may be prepared by adding 2-cyano-4-chloro-acetophenone thereto inside the apparatus, heating the result for the next 2 to 5 hours, and then dehydrating.

The compound of Chemical Formula XIX prepared above is dissolved in an organic solvent such as benzene, toluene and xylene, preferably toluene, and a compound of Chemical Formula XX may be prepared by adding ethyl acetoacetate and para-toluenesulfone (catalytic amount) thereto and then heating the result under reflux for 5 to 10 hours. The compound of Chemical Formula XX may be reacted in a similar manner as in Reaction Formula 1, and the compound of Chemical Formula II or Chemical Formula (S)-II may be prepared via the compound of Chemical Formula XII.

In addition, the compound of Chemical Formula I may be prepared using other preparation methods of Reaction Formula 4 and Reaction Formula 5.

An intermediate of Chemical Formula XXIX (racemate) and an intermediate of Chemical Formula XXVIII (S-isomer) in which the $R_3$ position is substituted with halogen (Cl), may be each prepared as in the following Reaction Formula 4, and the compound of Chemical Formula I and the compound of Chemical Formula (S)-I may be each prepared by reacting these intermediates as in Reaction Formula 5.

The preparation may be carried out in a similar manner as the reaction in the corresponding steps of Reaction Formula 1 and Reaction Formula 2, and detailed methods are shown in preparation examples and examples.

[Reaction Formula 4]

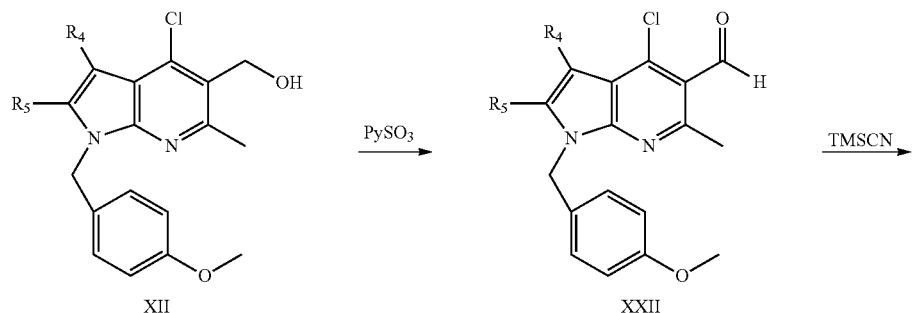

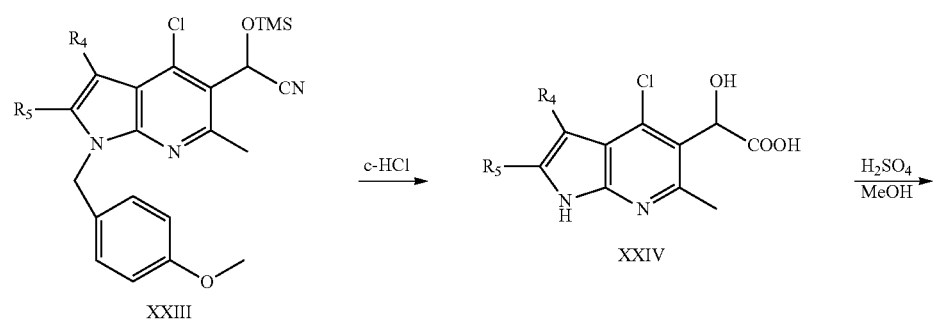

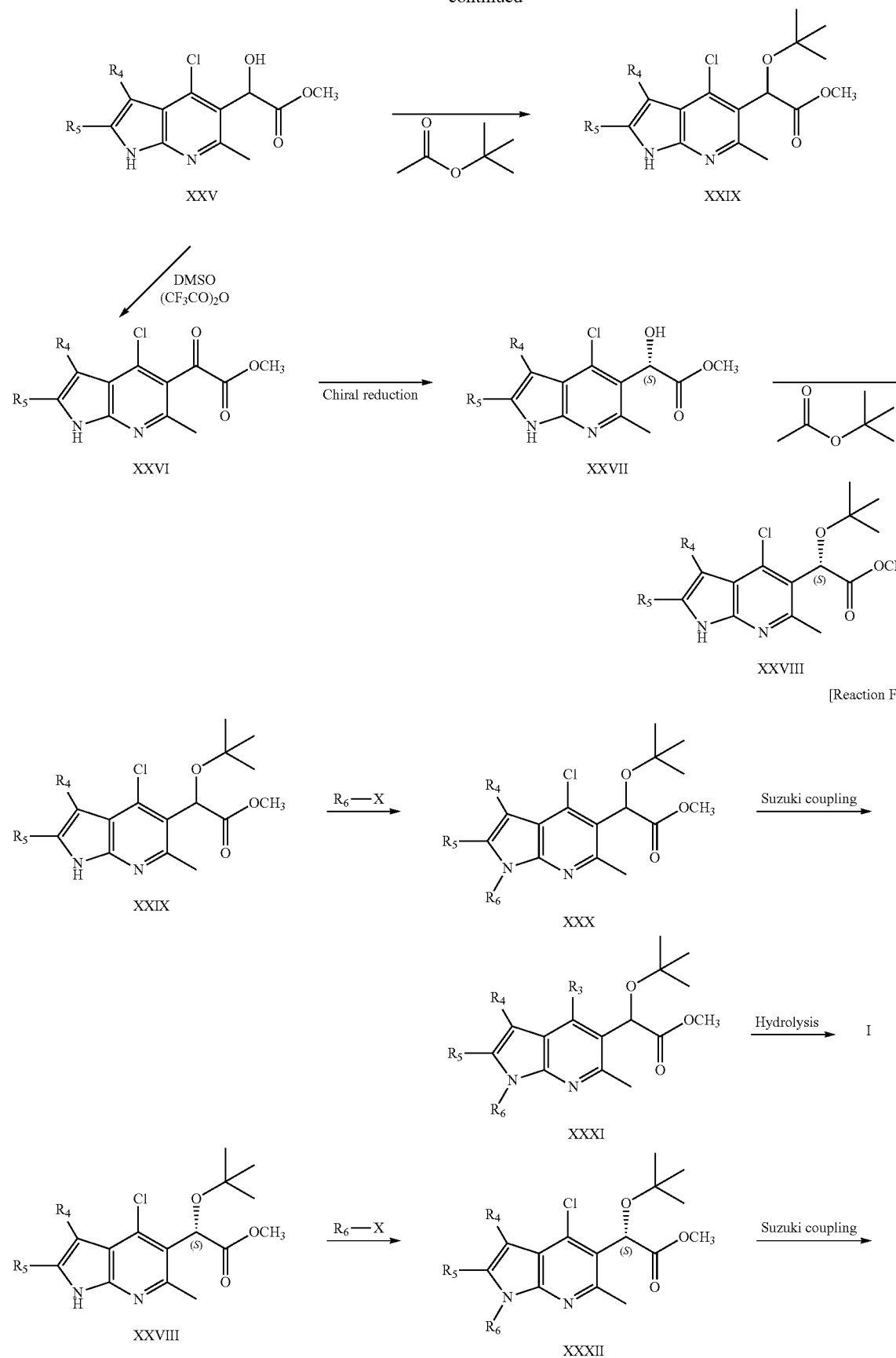

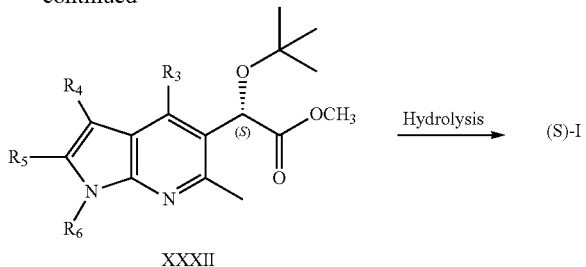

In addition, the compound represented by Chemical Formula I may be prepared from the compound of Chemical Formula II according to Reaction Formula 1, which is a racemic intermediate, and the compound of Chemical Formula I synthesized as above may be separated from a racemic mixture to each separate isomer as shown in the following Reaction Formula.

Chemical Formula I to a diastereoisomer using a chiral auxiliary, separating a stereoisomer, and then removing the auxiliary. The reaction may be carried out using a method known in page 55 of International Publication No. WO2009/062308A1. After the compound of Chemical Formula I is reacted with O-(benzotriazol-1-yl)-N,N,N',N'-tetramethyluronium tetrafluoroborate (TBTU) in a diisopropylethylam-

[Reaction Formula 6]

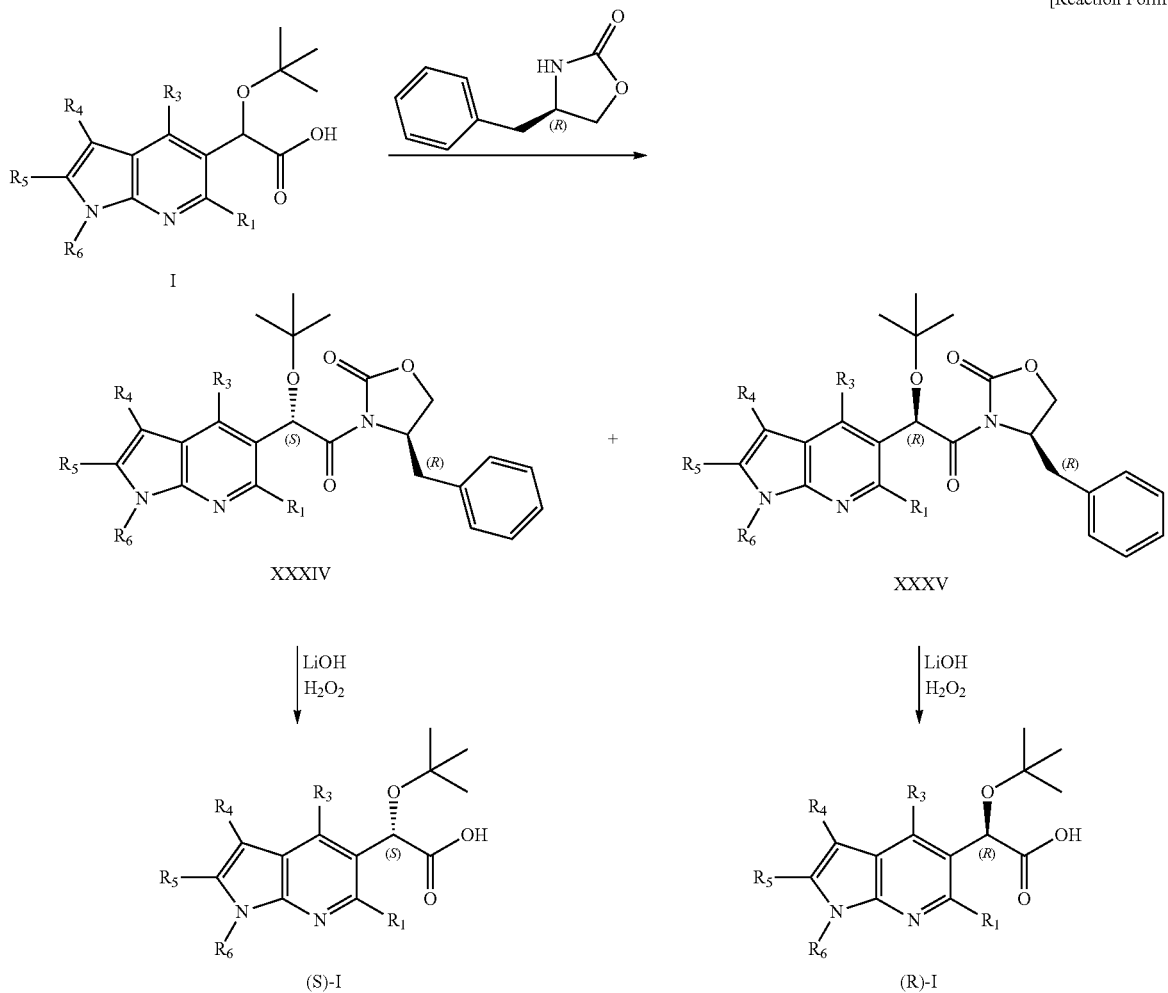

The compound of Chemical Formula I according to the present invention is a racemate, and, as shown in Reaction Formula 6, the compound of Chemical Formula (S)-I and (R)-I may be each obtained by converting the compound of ine base for 5 hours at 35° C. to activate carboxylic acid, (R)-(+)-4-benzyl-2-oxazolidinone is added to the solution in which sodium hydride is added to anhydrous tetrahydrofuran and the mixture is stirred for 30 minutes at room temperature. The reaction may be completed by stirring for 30 minutes, and using a chromatography method, a diastereoisomer of Chemical Formula XXXIV may be obtained in a 20% to 30% yield, and a diastereoisomer of Chemical Formula XXXV may be obtained in a 30% to 40% yield.

The separated compound of Chemical Formula XXXIV and the compound of Chemical Formula XXXV are each reacted according to known methods using 30% hydrogen peroxide and a lithium hydroxide hydrate in tetrahydrofuran and water, which is a solvent, and the compound of Chemical Formula (S)-I and the compound of Chemical Formula (R)-I may be each obtained in a 60% to 75% yield. The reaction solvents and the amounts thereof may be used in accordance with known similar reactions to obtain target compounds.

Examples of the compound of General Formula (I) of the present invention, which may be prepared using the methods described above, are shown as the following structural formulae, however, the compound of General Formula (I) is not limited thereto.

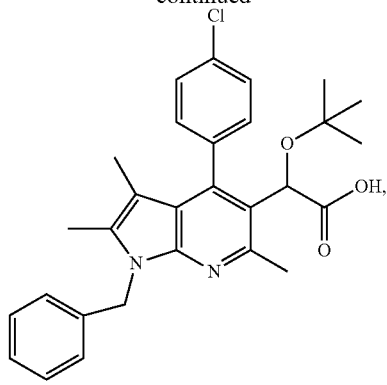

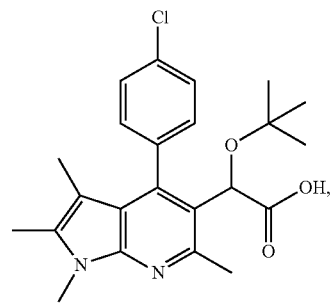

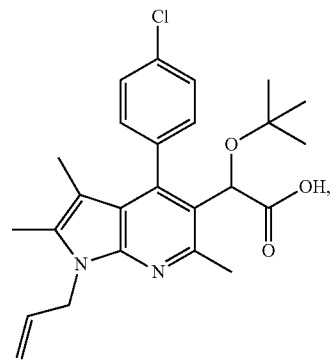

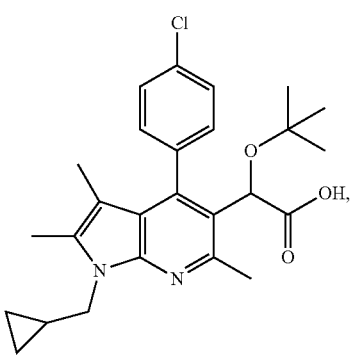

-continued

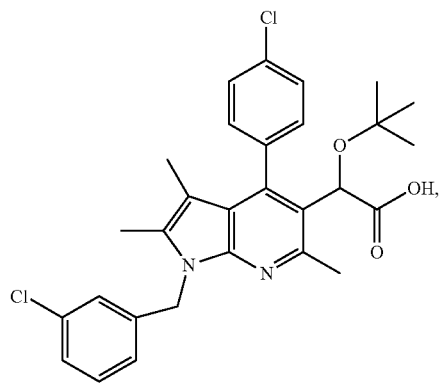

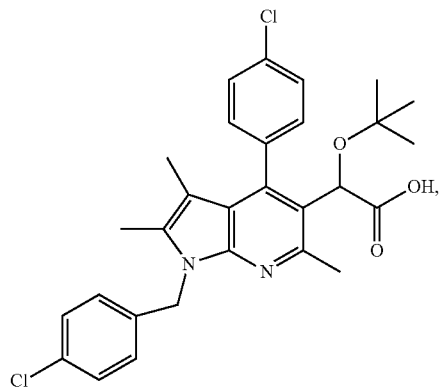

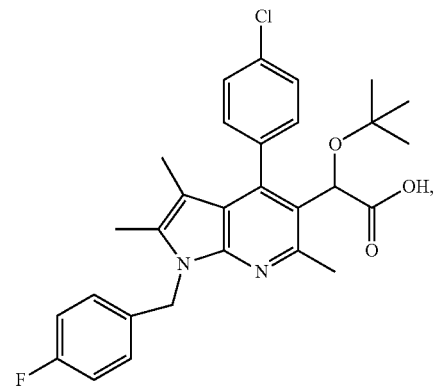

-continued

-continued
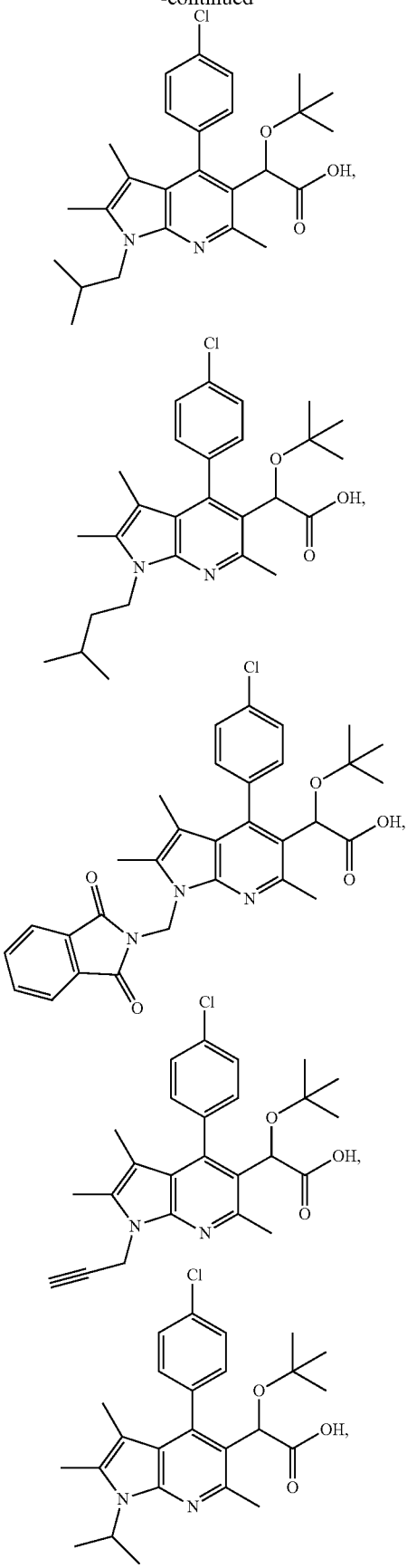
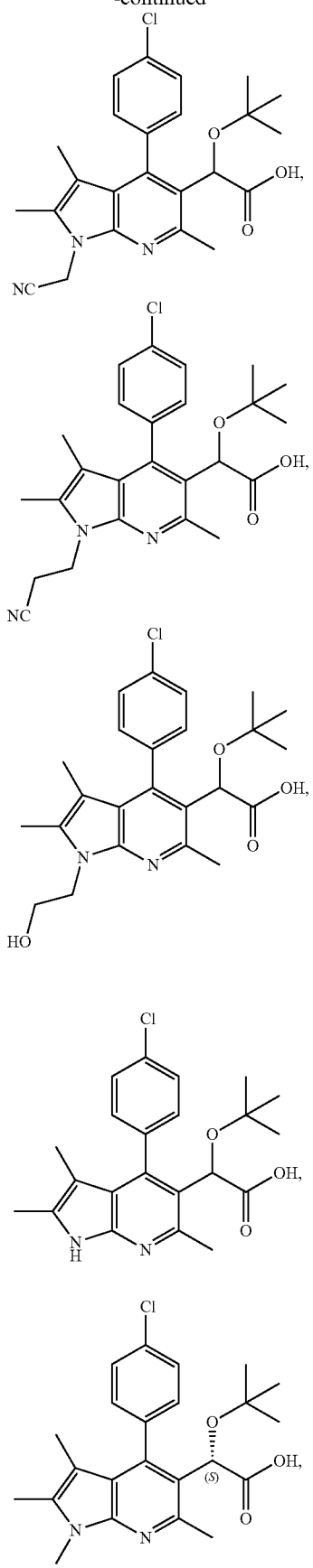

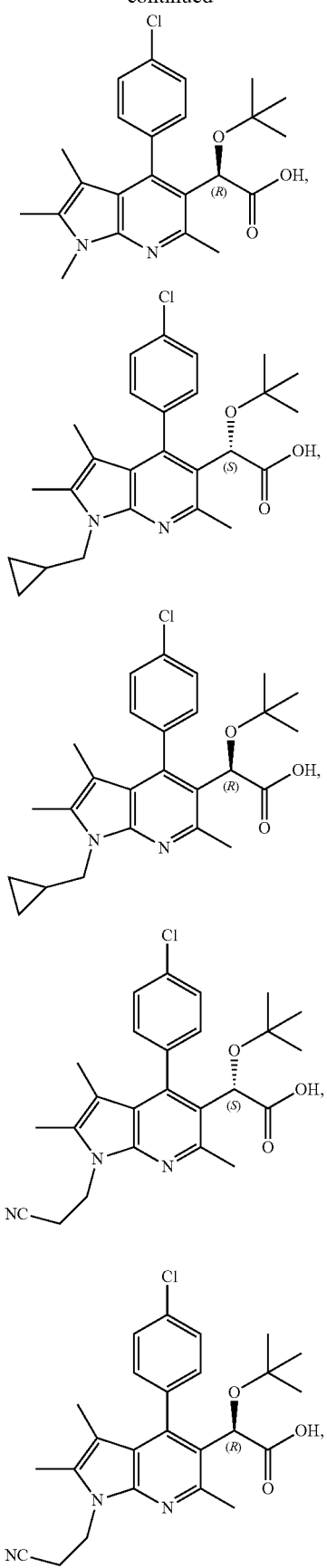
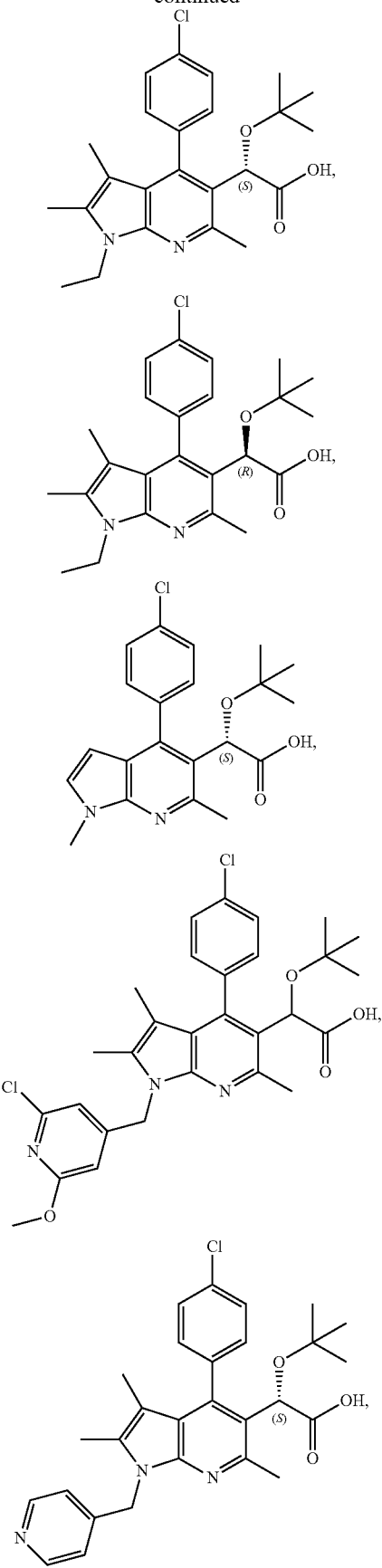

-continued
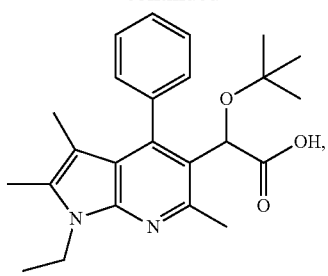
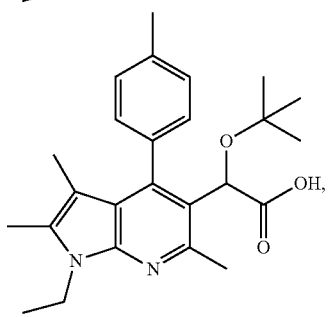
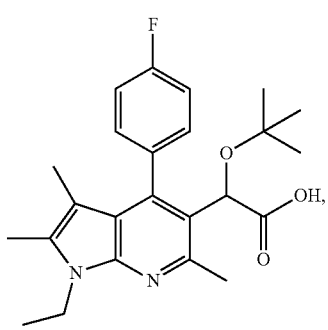
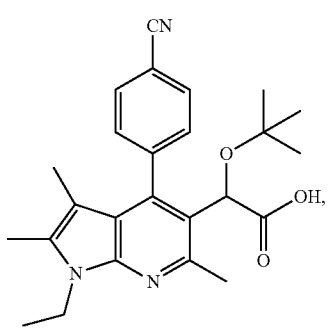
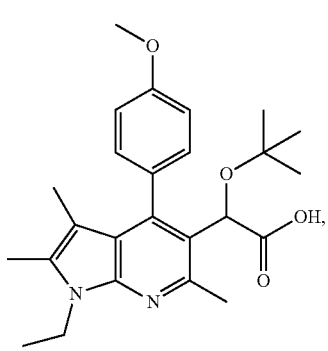
-continued
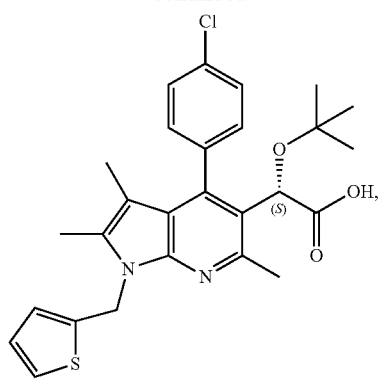
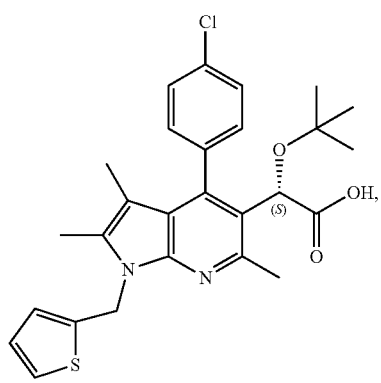
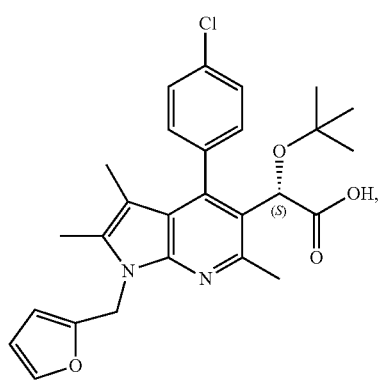
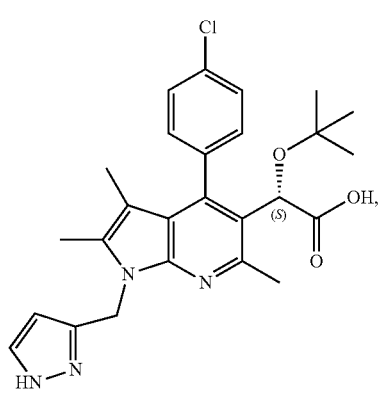

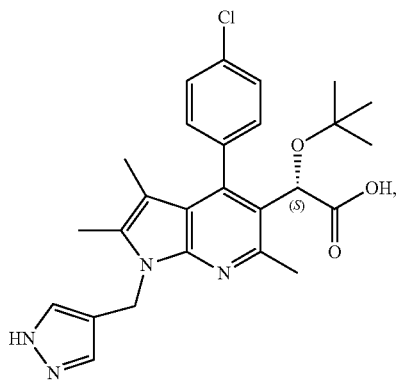
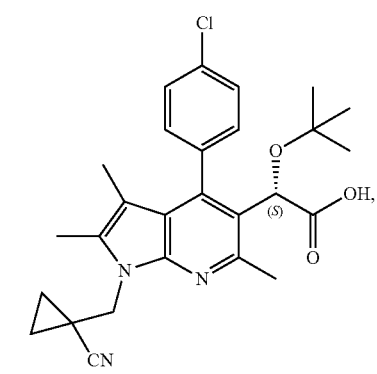
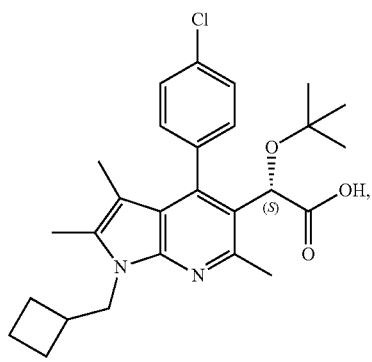
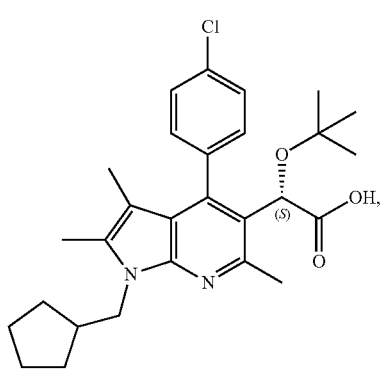
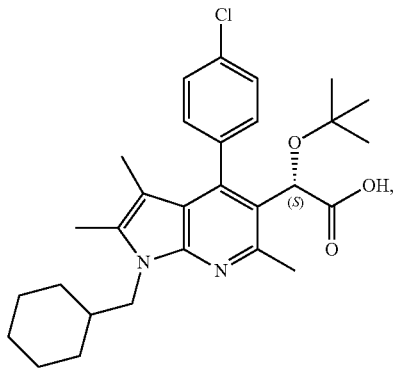
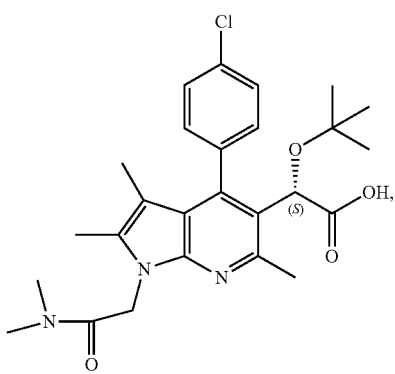
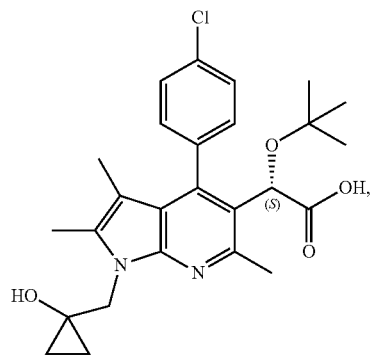
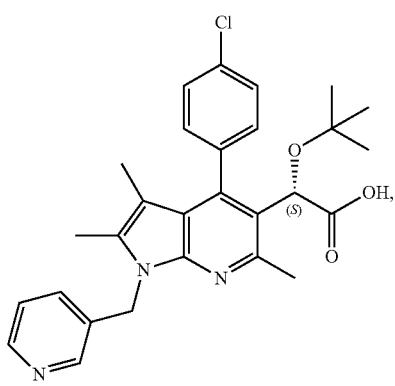

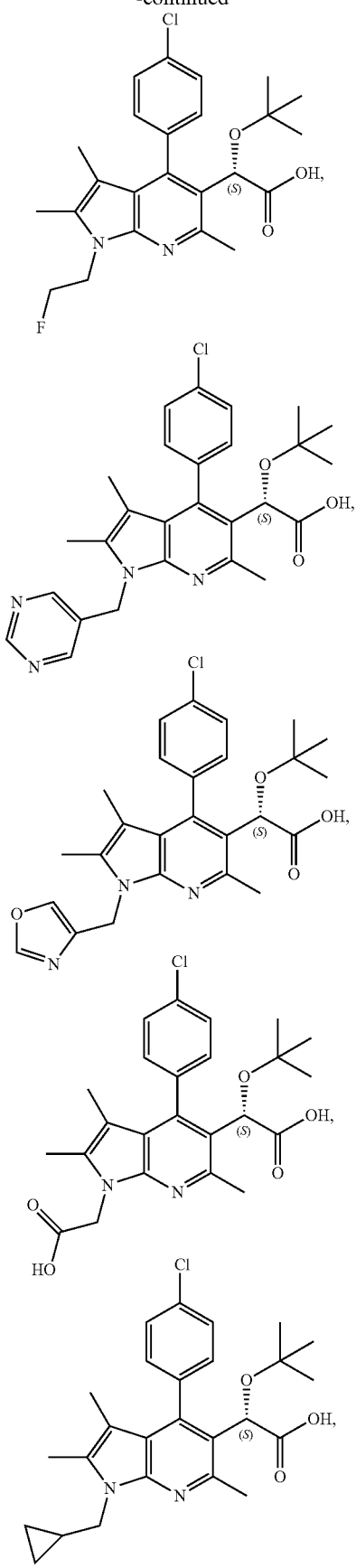
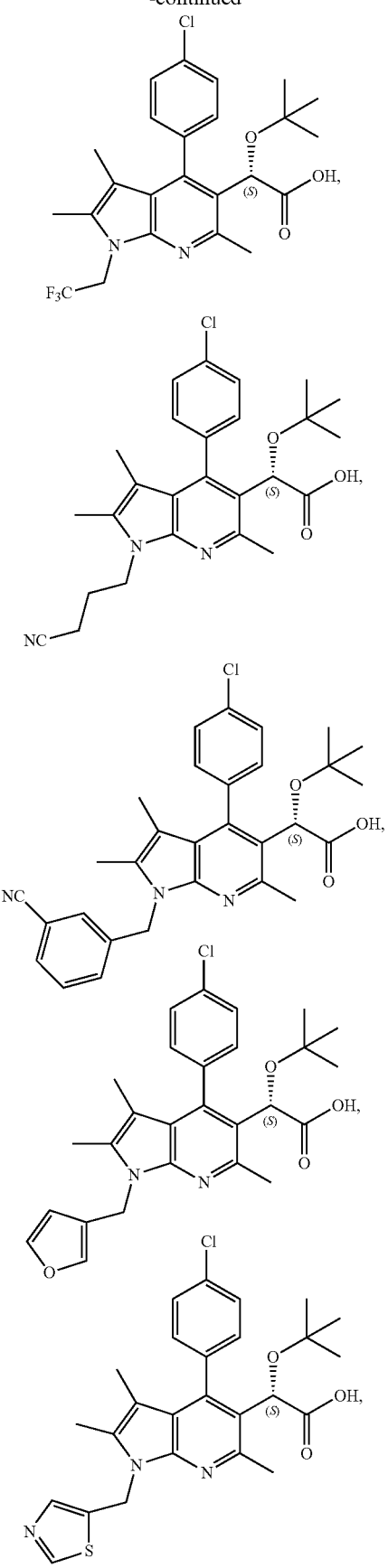

31
-continued
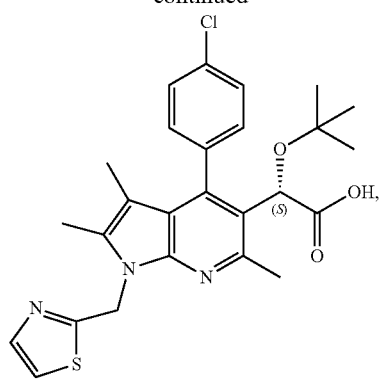
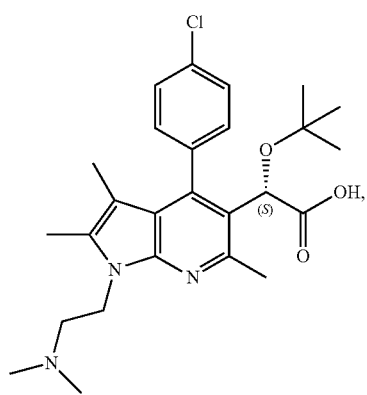
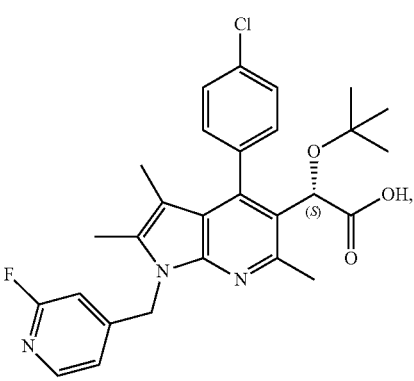
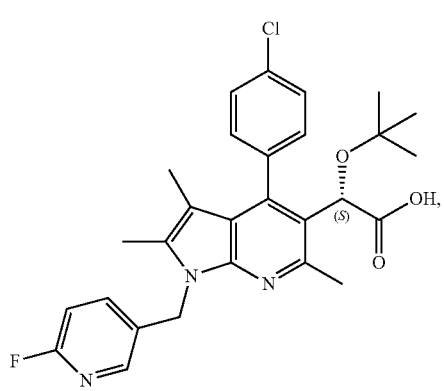
32
-continued
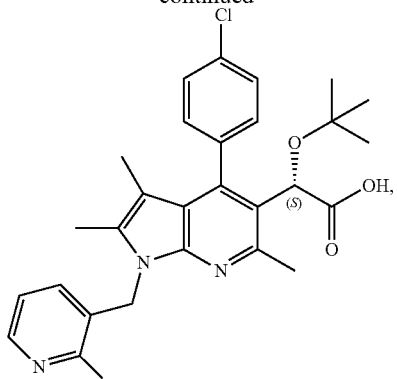
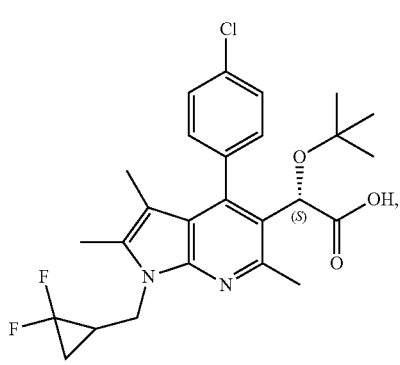
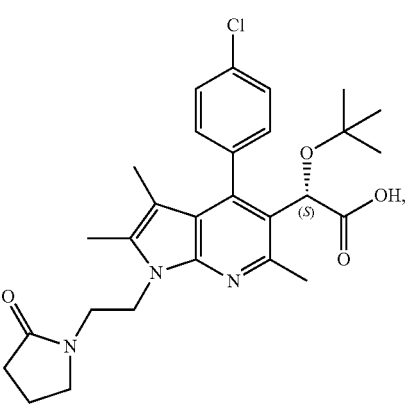
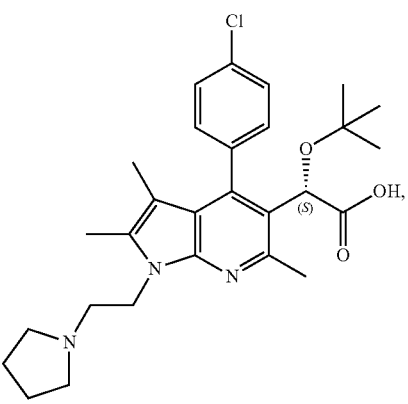

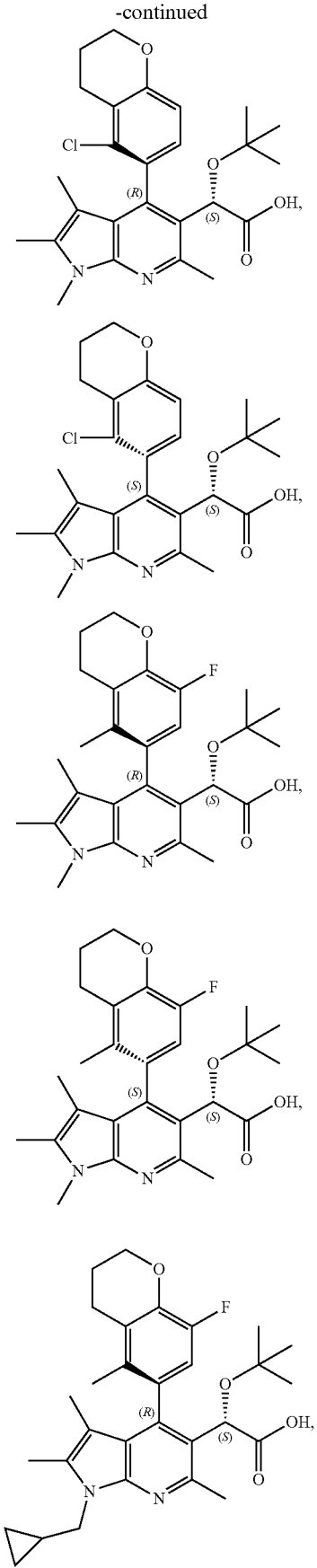

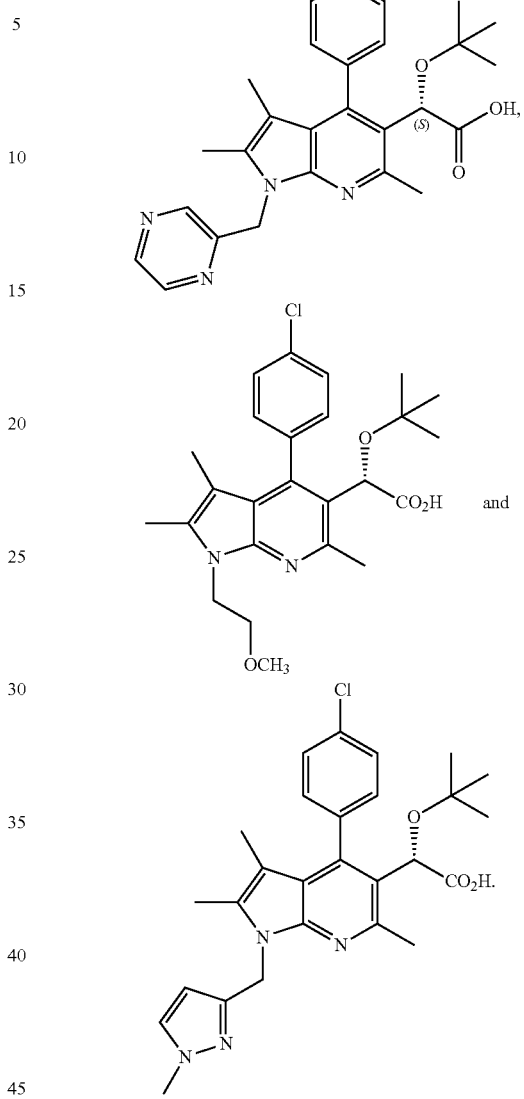

The compound of Chemical Formula I of the present invention prepared as above may form a salt, particularly, a pharmaceutically acceptable salt. The suitable pharmaceutically acceptable salt is a salt commonly used in the related arts, such as an acid addition salt, and is not particularly limited (refer to the literature [J. Pharm. Sci., 1977, 66, 1]). Examples of the pharmaceutically acceptable acid addition salt include an inorganic acid such as hydrochloric acid, hydrobromic acid, phosphoric acid, ortho-phosphoric acid or sulfuric acid; or an organic acid such as methanesulfonic acid, benzenesulfonic acid, toluenesulfonic acid, acetic acid, propionic acid, lactic acid, citric acid, fumaric acid, malic acid, succinic acid, salicylic acid, maleic acid, glycerophosphoric acid or acetylsalicylic acid.

In addition, a pharmaceutically acceptable metal salt may be obtained according to common methods using a base. For example, a pharmaceutically acceptable metal salt may be obtained by dissolving the compound of Chemical Formula I in an excess alkali metal hydroxide or alkaline-earth metal hydroxide solution, filtering the non-dissolved compound salt, then evaporating the filtrate, and drying the result. At this time, preparing a sodium salt, potassium salt or calcium salt as a metal salt is particularly preferable, and these metal salts may be reacted with proper salts (for example, nitric acid).

A pharmaceutically unacceptable salt or solvate of the compound of Chemical Formula I may be used as an intermediate when preparing the compound of Chemical Formula I, or the pharmaceutically acceptable salt or the solvate thereof.

The compound of the Chemical Formula I of the present invention includes not only pharmaceutically acceptable salts thereof, but all solvates and hydrates that can be prepared therefrom, and includes all possible stereoisomers as well. The solvate, the hydrate and the stereoisomer of the compound of Chemical Formula I may be prepared and used from the compound of Chemical Formula I using common methods.

In addition, the compound of Chemical Formula I according to the present invention may be prepared either in a crystalline form or in a non-crystalline form, and when the compound of Chemical Formula I is prepared in a crystalline form, it may be randomly hydrated or solvated. In the present invention, the compound of Chemical Formula I may not only include a stoichiometric hydrate, but include a compound containing various amounts of water. The solvate of the compound of Chemical Formula I according to the present invention includes both stoichiometric solvates and non-stoichiometric solvates.

Furthermore, the present invention provides the compound represented by Chemical Formula II, which is an intermediate compound useful in preparing the compound represented by Chemical Formula I.

Moreover, the present invention provides an antiviral composition in which the compound of Chemical Formula I, or the pharmaceutically acceptable salt, the hydrate, the solvate or the isomer thereof is included as an active ingredient. Herein, the antiviral composition is particularly a composition for anti-human immunodeficiency virus (HIV).

In experimental examples of the present invention, it was verified that the compound of Chemical Formula I has excellent suppression effect for HIV-1 while having low cytotoxicity, and thereby has high selectivity and antiviral activity for HIV-1.

The pharmaceutical composition of the present invention may be formulated in an oral administration form or an injection form. Examples of the oral administration formulation include tablets, capsules and the like, and these formulations contain a diluent (for example: lactose, dextrose, sucrose, mannitol, sorbitol, cellulose and/or glycine) and a glidant (for example: silica, talc, stearic acid and a magnesium or calcium salt thereof and/or polyethylene glycol), in addition to an active substance. The tablet may also contain a binder such as magnesium aluminum silicate, starch paste, gelatin, tragacanth, methyl cellulose, sodium carboxymethyl cellulose and/or polyvinyl picolidine, and depending on the case, may include a disintegrating agent such as starch, agar, alginic acid or a sodium salt thereof, or a boiling mixture and/or an absorbent, a colorant, a flavoring agent, and a sweeting agent. The injection formulation is preferably an isotonic aqueous solution or suspension.

The composition may be sterilized and/or contain an adjuvant such as a preservative, a stabilizer, a wettable powder or an emulsion accelerator, a salt for osmotic pressure regulation and/or a buffer agent, and other therapeutically useful substances.

The formulation may be prepared using typical mixing, granulation or coating methods, and may contain an active ingredient in the range of approximately 0.1 to 75% by weight, and preferably in the range of approximately 1 to 50% by weight. The unit formulation for a mammal of approximately 50 to 70 kg contains approximately 10 to 200 mg of an active ingredient.

The preferable dosage of the compound of the present invention is different depending on the condition and the weight of patients, the progression of diseases, the form of drugs, the route and the time period of administration, but may be properly selected by those skilled in the related arts. However, for desirable efficacy, the compound of the present invention is preferably administered in 0.0001 to 100 mg/kg (weight), and preferably administered in 0.001 to 100 mg/kg (weight) per 1 day. Administration may be orally or non-orally given once or partitively per one day.

The pharmaceutical composition of the present invention may be administered to mammals including rats, mice, domestic animals, human beings and the like, through various routes. All types of administered can be used, and for example, administration can be given orally, or by a rectal or intravenous, intramuscular, hyperdermic, intrauterine dural or intracerbroventricular injection.

Advantageous Effects

As described above, a compound of Chemical Formula I of the present invention, or a pharmaceutically acceptable salt, a hydrate, a solvate or an isomer thereof is effective in treating virus infection, particularly human immunodeficiency virus (HIV) infection, since they have high selectivity and antiviral activity against HIV-1 of human immunodeficiency virus (HIV) while having low toxicity.

MODE FOR DISCLOSURE

Herein, the present invention will be described in more detail with reference to the following preparation examples and examples. However, the following preparation examples and the examples are for illustrative purposes only, and the scope of the present invention is not limited thereto.

Preparation Example 1

Preparation of methyl 2-tert-butoxy-2-(4-(4-chlorophenyl)-2,3,6-trimethyl-1H-pyrrolo[2,3-b]pyridin-5-yl)acetate (1n and 1o)

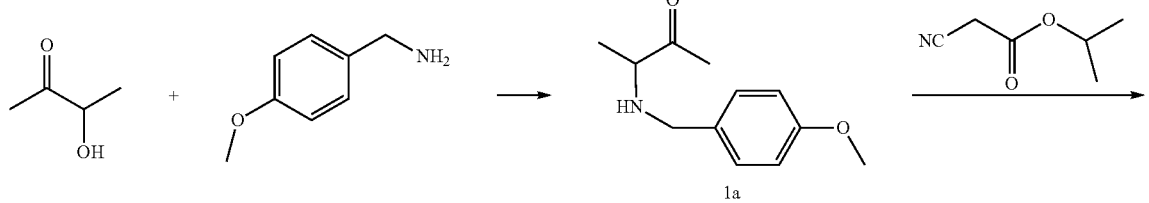

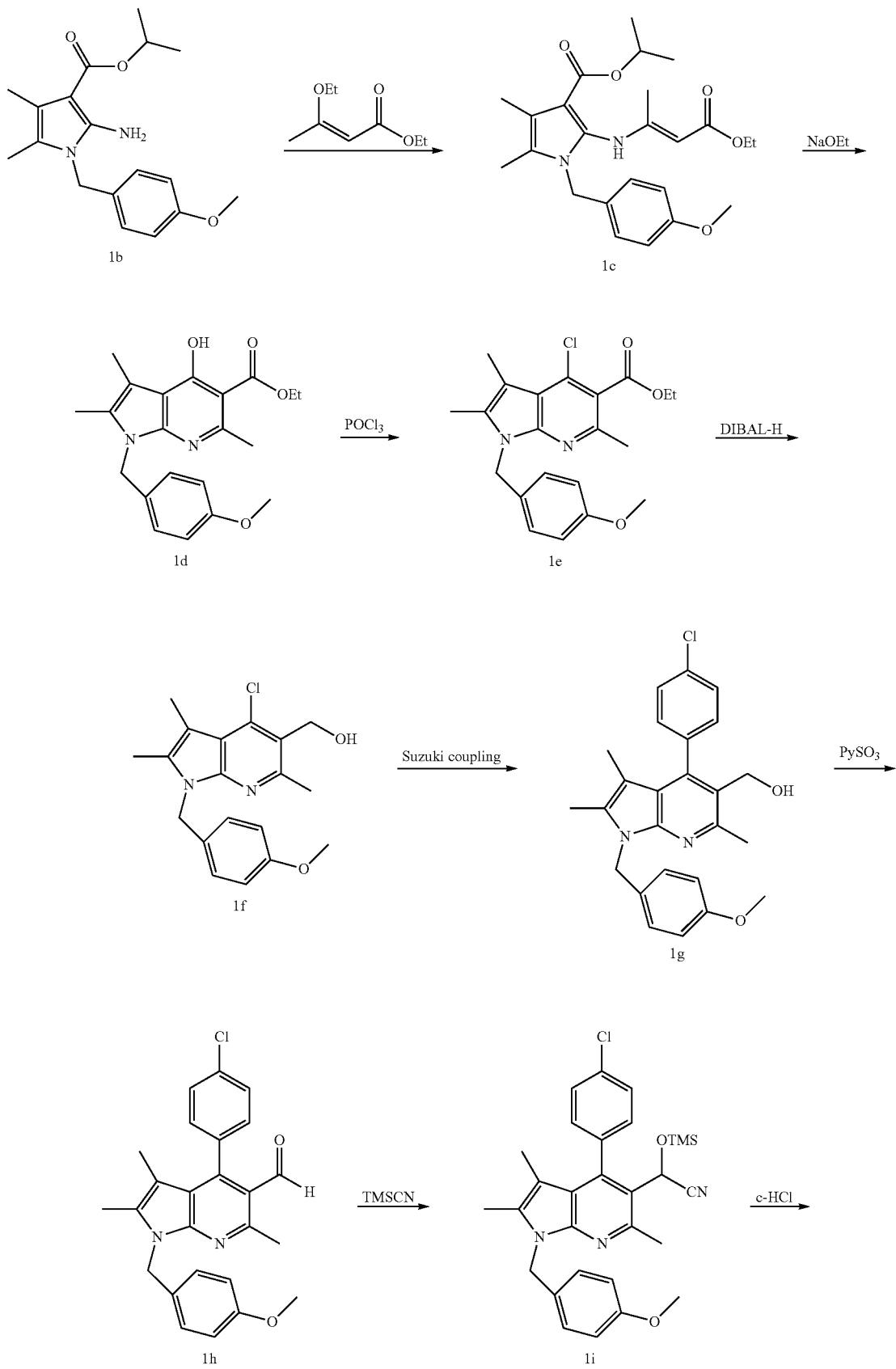

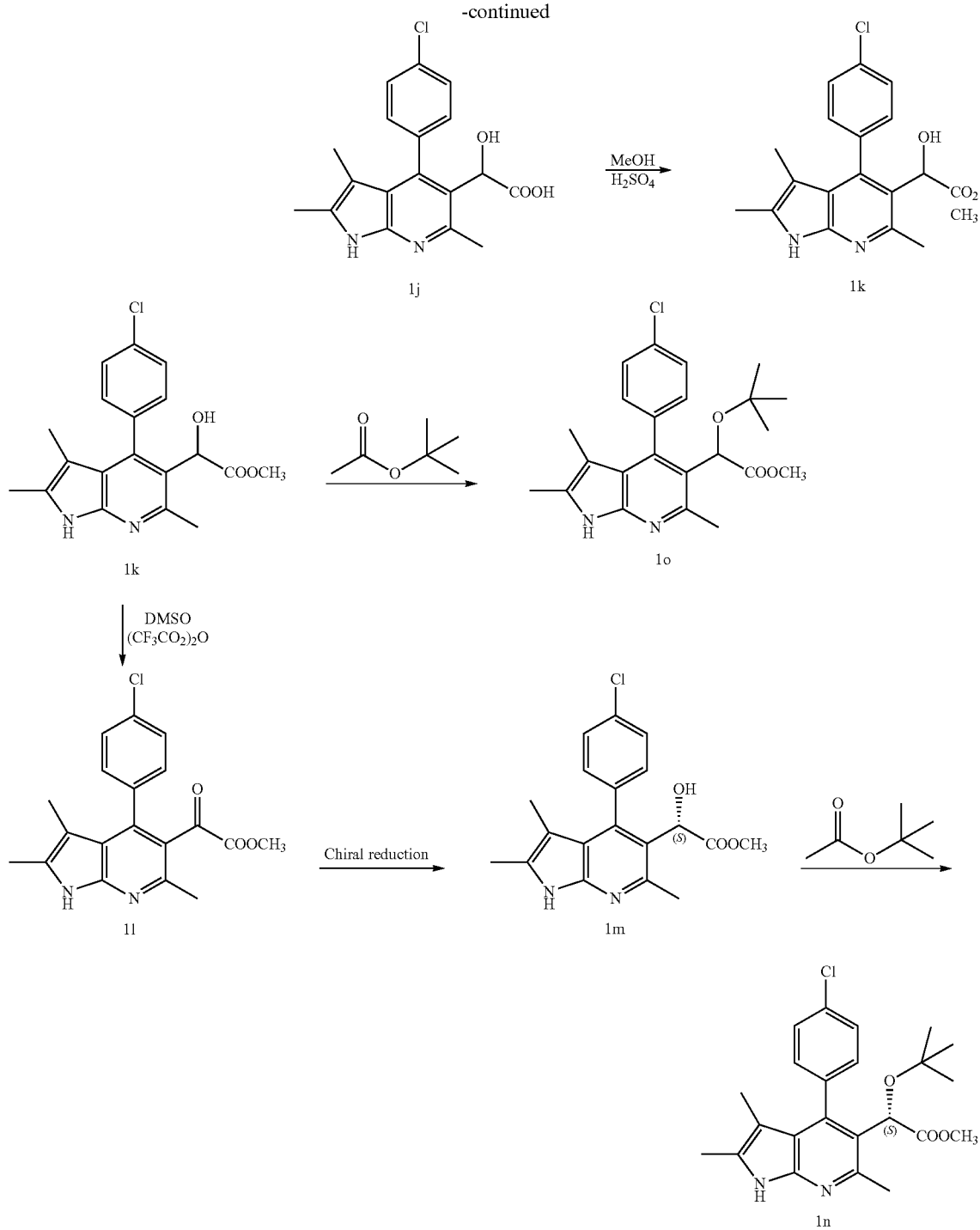

Step 1: Preparation of isopropyl 2-amino-1-(4-methoxybenzyl)-4,5-dimethyl-1H-pyrrolo-3-carboxylate (1b)

Acetoin (88 g, 1.0 mol) and 4-methoxybenzylamine (132 mL, 1.0 mol) were dissolved in cyclohexane (500 mL), and the mixture was refluxed for 2 hours after setting up a dean-stark trap apparatus. Next, the reaction material was cooled to 0° C., isopropylcyanoacetate (126 mL, 1.0 mol) was slowly added thereto, and then the result was refluxed for 2 hours in the same manner as above. The reaction material was cooled to room temperature, and the solvent was concentrated under reduced pressure. The residue was purified using silica gel column chromatography (normal-hexane/ethyl acetate=5/1), and 112 g (35%) of a target compound 1b was obtained in a brown solid form.

$^1$H-NMR (300 MHz, CDCl$_3$) δ 1.31 (d, J=6.2 Hz, 6H), 2.03 (s, 3H), 2.15 (s, 3H), 3.78 (s, 3H), 4.78 (s, 2H), 4.82 (s, 2H), 5.15 (m, 1H), 6.85 (d, J=8.7 Hz, 2H), 6.98 (d, J=8.7 Hz, 2H); MS (EI, m/e)=316 (M$^+$).

Step 2: Preparation of isopropyl 2-(4-ethoxy-4-oxobut-2-en-2-ylamino)-1-(4-methoxybenzyl)-4,5-dimethyl-1H-pyrrolo-3-carboxylate (1c)

After the compound 1b (40 g, 126.4 mmol) and 3-methoxy-but-2-enoic acid ethyl ester (24 g, 151.7 mmol) prepared using the following method were dissolved in ortho-xylene (300 mL), 4-toluenesulfonic acid (730 mg, 3.7 mmol) was added thereto, and the mixture was heated under reflux for 18 hours. The reaction solution was cooled to room temperature and the solvent was concentrated under reduced pressure. The residue was purified using silica gel column chromatography (normal-hexane/ethyl acetate=9/1), and a target compound 1c (46.5 g, 86%) was obtained in a yellow liquid state.

$^1$H-NMR (300 MHz, CDCl$_3$) δ 1.27 (m, 9H), 1.57 (s, 3H), 2.07 (s, 3H), 2.24 (s, 3H), 3.79 (s, 3H), 4.14 (q, J=7.1 Hz, 2H), 4.75 (s, 1H), 4.95 (d, 2H), 5.14 (m, 1H), 6.83 (d, J=8.7 Hz, 2H), 6.93 (d, J=8.7 Hz, 2H), 9.63 (s, 1H); MS (EI, m/e)=428 (M$^+$).

Preparation of 3-methoxy-but-2-enoic acid ethyl ester

After ethyl acetoacetate (300 mL, 2.35 mol) and trimethyl orthoformate (390 mL, 2.35 mol) were mixed, concentrated sulfuric acid (4.3 mL, 0.08 mol) was slowly added thereto, and the mixture was stirred for 18 hours at room temperature. After the completion of the reaction was assured, potassium carbonate (34 g, 0.25 mol) was added thereto, and the result was fiercely stirred for 30 minutes. The produced solids were removed by filtration, and the filtrate was concentrated under reduced pressure. A small amount of normal-hexane was added to the residue, the result was cooled to −40° C. to produce solids, and the solids were filtered, washed with normal-hexane that was cooled to −40° C., and dried under reduced pressure to give a target compound (142 g, 38%).

$^1$H-NMR (300 MHz, CDCl$_3$) δ 1.27 (t, J=7.1 Hz, 3H), 1.34 (t, J=7.0 Hz, 3H), 2.29 (s, 3H), 3.81 (q, J=7.0 Hz, 2H), 4.14 (q, J=7.1 Hz, 2H), 4.99 (s, 1H).

Step 3: Preparation of ethyl 4-hydroxy-1-(4-methoxybenzyl)-2,3,6-trimethyl-1H-pyrrolo[2,3-b]pyridine-5-carboxylate (1d)

After the compound 1c (55 g, 128.3 mmol) was dissolved in anhydrous ethanol (600 mL), 21% sodium ethoxide (80 mL, 205.3 mmol) was added thereto, and the mixture was heated under reflux for 18 hours. After the reaction solution was cooled to room temperature, the result was concentrated under reduced pressure so that the volume became 1/2. This solution was cooled to 0° C., and neutralized to pH 7 or so using acetic acid. Water (300 mL) and normal-hexane (300 mL) were added to this solution, and the result was stirred for 1 hour at the same temperature. The produced precipitates were filtered, sufficiently washed with normal-hexane, and then dried to give a target compound 1d (34 g, 70%).

$^1$H-NMR (300 MHz, CDCl$_3$) δ 1.47 (t, J=7.1 Hz, 3H), 2.17 (s, 3H), 2.40 (s, 3H), 2.81 (s, 3H), 3.78 (s, 3H), 4.47 (q, J=7.1 Hz, 2H), 5.38 (s, 2H), 6.82 (d, J=8.6 Hz, 2H), 7.04 (d, J=8.6 Hz, 2H), 12.67 (s, 1H); MS (EI, m/e)=368 (M$^+$).

Step 4: Preparation of ethyl 4-chloro-1-(4-methoxybenzyl)-2,3,6-trimethyl-1H-pyrrolo[2,3-h]pyridine-5-carboxylate (1e)

Phosphorous(V) oxychloride (170 mL, 1.09 mol) was added to the compound 1d (40.3 g, 0.11 mol), and the mixture was stirred for 4 hours at 60° C. After the reaction was completed, excess phosphorous(V) oxychloride was removed by concentration under reduced pressure, the result was cooled to 0° C., and then dichloromethane (400 mL) was added thereto. Ice water was slowly added thereto, the result was stirred for 30 minutes to decompose residual phosphorous(V) oxychloride, and then the organic layer was separated. After the aqueous layer was extracted with dichloromethane (300 mL×3), the organic layers were combined, dried with anhydrous magnesium sulfate, and the solvent was concentrated under reduced pressure. The residue was purified using silica gel column chromatography (normal-hexane/ethyl acetate=15/1) to give a target compound 1e (36 g, 85%) in a solid state.

$^1$H-NMR (300 MHz, CDCl$_3$) δ 1.43 (t, J=7.1 Hz, 3H), 2.21 (s, 3H), 2.40 (s, 3H), 2.57 (s, 3H), 3.75 (s, 3H), 4.47 (q, J=7.1 Hz, 2H), 5.39 (s, 2H), 6.79 (d, J=8.6 Hz, 2H); MS (EI, m/e)=386 (M$^+$).

Step 5: Preparation of (4-chloro-1-(4-methoxybenzyl)-2,3,6-trimethyl-1H-pyrrolo[2,3-b]pyridin-5-yl)methanol (1f)

The compound 1e (30 g, 77.5 mmol) was dissolved in anhydrous dichloromethane (350 mL) under nitrogen atmosphere, and the mixture was cooled to −78° C. After a 1.5 M DIBAL/toluene solution (60 mL, 90 mmol) was added thereto over 5 minutes, the result was stirred for 2 hours at the same temperature. After the reaction was completed, a 2N aqueous HCl solution was slowly added thereto, and the result was diluted with dichloromethane (400 mL), and then stirred for 30 minutes while slowly raising the temperature to room temperature. The organic layer was separated, and the aqueous layer was extracted with dichloromethane (300 mL×2). The organic layers were combined, washed with water and then dried with anhydrous magnesium sulfate, and the solvent was concentrated under reduced pressure. A moderate amount of normal-hexane was added to the produced solids, and the result was stirred. The solids were filtered, washed with normal-hexane, and dried to give a target compound 1f (22.5 g, 84%).

$^1$H-NMR (300 MHz, CDCl$_3$) δ 1.68 (t, J=6.0 Hz, 1H, —OH), 2.22 (s, 3H), 2.42 (s, 3H), 2.72 (s, 3H), 3.75 (s, 3H), 4.97 (d, J=6.0 Hz, 2H), 5.39 (s, 2H), 6.80 (d, J=8.6 Hz, 2H), 7.00 (d, J=8.6 Hz, 2H); MS (EI, m/e)=344 (M$^+$).

Step 6: Preparation of (4-(4-chlorophenyl)-1-(4-methoxybenzyl)-2,3,6-trimethyl-1H-pyrrolo[2,3-b]pyridin-5-yl)methanol (1g)

After the compound 1f (7.72 g, 22.3 mmol) was dissolved in dimethylformamide (110 mL), 4-chlorophenylboronic acid pinacol ester (5.96 g, 25.73 mmol) and potassium carbonate (9.3 g, 111.9 mmol) were added thereto, and oxygen was removed by passing through nitrogen gas into the solution. After that, tetrakis-triphenylphosphine palladium (Pd(PPh$_3$)$_4$) (5.16 g, 4.5 mmol) was added thereto, and then oxygen was completely removed by continuously passing through nitrogen, and the result was heated under nitrogen for 6 hours at 100° C. to 110° C. The reaction solution was cooled to room temperature, and at the time, the insoluble substances were removed by filtration through a celite layer. The filtrate was concentrated under reduced pressure, and then the residue was purified using silica gel column chromatography (normal-hexane/ethyl acetate=8/1 and 4/1) to give a target compound 1g (4.33 g, 46%). The unreacted starting material (3.2 g) was collected.

¹H-NMR (300 MHz, CDCl₃) δ 1.52 (s, 3H), 2.17 (s, 3H), 2.77 (s, 3H), 3.75 (s, 3H), 4.52 (s, 2H), 5.45 (s, 2H), 6.80 (d, J=8.6 Hz, 2H), 7.05 (d, J=8.6 Hz, 2H), 7.26 (d, J=8.3 Hz, 2H), 7.42 (d, J=8.3 Hz, 2H); MS (EI, m/e)=420 (M⁺).

Step 7: Preparation of 4-(4-chlorophenyl)-1-(4-methoxybenzyl)-2,3,6-trimethyl-1H-pyrrolo[2,3-b]pyridine-5-carboaldehyde (1h)

After the compound 1g (3.6 g, 8.55 mmol) was dissolved in dimethyl sulfoxide (18 mL), triethylamine (4.17 mL, 29.9 mmol) was added thereto, and the mixture was cooled to 10° C. A sulfur trioxide pyridine complex (4.08 g, 25.7 mmol) dissolved in dimethyl sulfoxide (8 mL) was added to the above solution over 5 minutes. After that, the result was stirred for 3 hours at 25° C. to complete the reaction, and the reaction solution was poured into water (100 mL). The produced solids were filtered and sufficiently washed with water. The obtained solids were dissolved in ethyl acetate (100 mL), dried with anhydrous magnesium sulfate, and then the solvent was concentrated under reduced pressure. The residue was purified using column chromatography (normal-hexane/ethyl acetate=6/1) to give a pure target compound 1h (2.32 g, 64%) in a solid state.

¹H-NMR (300 MHz, CDCl₃) δ 1.54 (s, 3H), 2.19 (s, 3H), 2.92 (s, 3H), 3.77 (s, 3H), 5.47 (s, 2H), 6.82 (d, J=8.6 Hz, 2H), 7.08 (d, J=8.6 Hz, 2H), 7.29 (d, J=8.3 Hz, 2H), 7.45 (d, J=8.3 Hz, 2H), 9.94 (s, 1H); MS (EI, m/e)=418 (M⁺).

Step 8: Preparation of 2-(4-(4-chlorophenyl)-1-(4-methoxybenzyl)-2,3,6-trimethyl-1H-pyrrolo[2,3-b]pyridin-5-yl)-2-(trimethylsilyloxy)acetonitrile (1i)

After the compound 1h (2.32 g, 5.5 mmol) was dissolved in dichloromethane (48 mL) and the mixture was cooled to 0° C., zinc iodide (ZnI₂) (1.93 g, 6.0 mmol) was quickly added thereto under nitrogen, and trimethylsilyl cyanide (1.22 mL, 22.1 mmol) was subsequently added thereto over 5 minutes using a syringe. The result was stirred for 1 hour at 0° C. and 3 hours at 25° C. to complete the reaction. The reaction solution was diluted with dichloromethane (70 mL), washed with water (60 mL), dried with anhydrous magnesium sulfate, and the solvent was concentrated under reduced pressure to give a target compound 1i. The compound 1i was used for the reaction of the next step without purification.

Step 9: Preparation of 2-(4-(4-chlorophenyl)-2,3,6-trimethyl-1H-pyrrolo[2,3-b]pyridin-5-yl)-2-hydroxyacetic acid (1j)

Concentrated hydrochloric acid (51 mL) was added to the compound 1i (theoretical amount 5.5 mmol), and the mixture was stirred for 18 hours at 100° C. Subsequently, the reaction material was cooled to room temperature and concentrated under reduced pressure. Methanol was added to the residue, and the result was concentrated once again under reduced pressure and dried under a high vacuum to give a target compound 1j (theoretical amount 5.5 mmol). The compound 1j was used for the next reaction without purification.

Step 10: Preparation of methyl 2-(4-(4-chlorophenyl)-2,3,6-trimethyl-1H-pyrrolo[2,3-b]pyridin-5-yl)-2-hydroxyacetate (1k)

After the compound 1j (theoretical amount 5.5 mmol) was dissolved in methanol (65 mL), concentrated sulfuric acid (3.8 mL) was added thereto, and the mixture was refluxed for 18 hours. The reaction material was cooled to 5° C., and then adjusted to pH 7.5 using a 2N aqueous NaOH solution. The methanol of the reaction material was removed by concentration under reduced pressure, water (20 mL) was added to the result, and a product was extracted with dichloromethane (100 mL×2), dried with anhydrous magnesium sulfate, and then concentrated under reduced pressure. The residue was purified using silica gel column chromatography (normal-hexane/ethyl acetate=4/1 and 1/1) to give a pure target compound 1k (2.32 g, 64%) in a solid state.

¹H-NMR (300 MHz, CDCl₃) δ 1.49 (s, 3H), 2.32 (s, 3H), 2.60 (s, 3H), 3.48 (s, 1H, —OH), 3.70 (s, 3H), 5.22 (s, 1H), 7.27 (d, J=8.6 Hz, 2H), 7.42 (d, J=8.6 Hz, 2H), 9.69 (s, 1H, —NH); MS (EI, m/e)=359 (M⁺).

Step 11: Preparation of methyl 2-(4-(4-chlorophenyl)-2,3,6-trimethyl-1H-pyrrolo[2,3-b]pyridin-5-yl)-2-oxoacetate (1l)

After trifluoroacetic anhydride (2.4 mL, 15.88 mmol) was added to dichloromethane (50 mL) and the mixture was cooled to −78° C., dimethyl sulfoxide (1.2 mL) dissolved in dichloromethane (5 mL) was slowly added thereto, and the result was stirred for 30 minutes. The compound 1k (2.85 g, 7.9 mmol) dissolved in dichloromethane (15 mL) was slowly added to the above solution, the result was stirred for 1 hour at the same temperature, then triethylamine (5 mL, 35.7 mmol) was slowly added thereto, and the result was stirred for 30 minutes. A saturated aqueous ammonium chloride solution (30 mL) was added to the reaction material to complete the reaction, the temperature was slowly raised to 0° C., and the result was stirred for 30 minutes at 0° C. After the result was extracted with dichloromethane (30 mL×3), the organic layers were combined, washed with water, dried with anhydrous magnesium sulfate, and concentrated under reduced pressure. After dichloromethane (5 mL) and ethyl acetate (5 ml) were added to the residue and the result was stirred for 10 minutes, the produced solids were filtered, combined, and washed with a mixed liquid of dichloromethane/ethyl acetate=1/1 (10 mL) to give a first target compound. The filtrate was concentrated under reduced pressure, and the residue was separated using silica gel column chromatography (effluent, hexane:ethyl acetate=3:1) to give a second target compound. The obtained first and second compounds were combined to give 2.48 g (87%) of a target compound 1l.

¹H-NMR (300 MHz, DMSO-D₆) δ1.56 (s, 3H), 2.28 (s, 3H), 3.38 (s, 3H), 4.04 (s, 3H), 7.27 (s, 2H), 7.53 (s, 2H), 11.71 (s, 1H); MS (EI, m/e)=357 (M⁺).

Step 12: Preparation of (S)-methyl 2-(4-(4-chlorophenyl)-2,3,6-trimethyl-1H-pyrrolo[2,3-b]pyridin-5-yl)-2-hydroxyacetate (1m)

After the compound 1l (2.48 g, 6.95 mmol) was dissolved in toluene (30 mL) and dichloromethane (30 mL) and the mixture was cooled to −35° C., a R-(+)-2-methyl-CBS-oxazaborolidine 1M-toluene solution (2.76 mL, 2.76 mmol) was added thereto, and then catecholborane (1.25 g, 0.22 mmol) dissolved in dichloromethane (30 mL) was slowly added to the result over 1 hour. The temperature was slowly raised to near −15° C. to 0° C., and when the reaction solution became transparent, the result was stirred for 5 hours at the same temperature. After an aqueous potassium carbonate solution (300 mL×3) was added thereto and the result was stirred for 1 hour at room temperature, the organic layer was separated, the aqueous layer was extracted with ethyl acetate (100 mL×3), and the organic layers were combined, washed with water, dried with anhydrous magnesium sulfate, and then concentrated under reduced pressure. After dichloromethane (10 mL) was added to the residue and the result was stirred for 10 minutes, the produced solids were filtered, combined, and washed with dichloromethane (twice using 10 mL each) to give a first target compound. The filtrate was concentrated under reduced pressure, and the residue was purified using silica gel column chromatography (hexane:ethyl acetate=1:1) to give a second target compound, and a total of 1.93 g (77%) of a target compound 1m was obtained.

$^1$H-NMR (300 MHz, CDCl$_3$) δ 1.49 (s, 3H), 2.32 (s, 3H), 2.60 (s, 3H), 3.48 (s, 1H, —OH), 3.70 (s, 3H), 5.22 (s, 1H), 7.27 (d, J=8.6 Hz, 2H), 7.42 (d, J=8.6 Hz, 2H), 9.69 (s, 1H, —NH); MS (EI, m/e)=359 (M$^+$).

Step 13: Preparation of (S)-methyl 2-tert-butoxy-2-(4-(4-chlorophenyl)-2,3,6-trimethyl-1H-pyrrolo[2,3-b]pyridin-5-yl)acetate (1n)

After the compound 1m (1.49 g, 3.6 mmol) was dissolved in dichloromethane (90 mL) and tert-butyl acetate (50 mL) was added thereto, the result was cooled to 10° C., and then 70% perchloric acid (1.24 mL) was added thereto over 30 minutes. After that, the result was stirred for 5 hours at 20° C., cooled with ice water, adjusted to pH 8.0 using a 20% aqueous Na$_2$CO$_3$ solution, and the result was stirred for 20 minutes. The organic layer was separated, the aqueous layer was extracted with dichloromethane (100 mL×2), and then the organic layers were combined, dried with anhydrous magnesium sulfate, and the solvent was concentrated under reduced pressure. The residue was purified using silica gel column chromatography (normal-hexane/ethyl acetate=4/1) to give a pure target compound 1n (1.13 g, 76%).

$^1$H-NMR (300 MHz, CDCl$_3$) δ 0.98 (s, 9H), 1.46 (s, 3H), 2.30 (s, 3H), 2.69 (s, 3H), 3.67 (s, 3H), 5.08 (s, 1H), 7.24 (m, 1H), 7.43 (m, 3H), 8.59 (s, 1H, —NH); MS (EI, m/e)=414 (M$^+$).

Step 14: Preparation of methyl 2-tert-butoxy-2-(4-(4-chlorophenyl)-2,3,6-trimethyl-1H-pyrrolo[2,3-b]pyridin-5-yl)acetate (1o)

After the compound 1k (5.61 g, 15.63 mmol) was dissolved in dichloromethane (300 mL), the mixture was cooled to 0° C., and 70% perchloric acid (9.3 mL, 108.23 mmol) was added thereto. Tert-butyl acetate (300 mL) was very slowly added to the above reaction solution, and the result was stirred for 4 hours at room temperature. The result was neutralized using an aqueous potassium carbonate solution at 0° C., ethyl acetate (300 mL) was added thereto, and the result was stirred for 10 minutes. After the organic layer was separated and the aqueous layer was extracted with ethyl acetate (300 mL×2) once again, the combined organic layer was dried with anhydrous magnesium sulfate and concentrated under reduced pressure. The obtained residue was purified using silica gel column chromatography (hexane/ethyl acetate=3/1) to give a target compound 1o (4.48 g, 65%).

$^1$H-NMR (300 MHz, CDCl$_3$) δ 0.98 (s, 9H), 1.46 (s, 3H), 2.30 (s, 3H), 2.69 (s, 3H), 3.67 (s, 3H), 5.08 (s, 1H), 7.24 (m, 1H), 7.43 (m, 3H), 8.59 (s, 1H, —NH); MS (EI, m/e)=414 (M$^+$).

Preparation Example 2

Another Method for Preparing 4-(4-chlorophenyl)-1-(4-methoxybenzyl)-2,3,6-trimethyl-1H-pyrrolo[2,3-b]pyridin-5-yl)methanol (1g) of Preparation Example 1

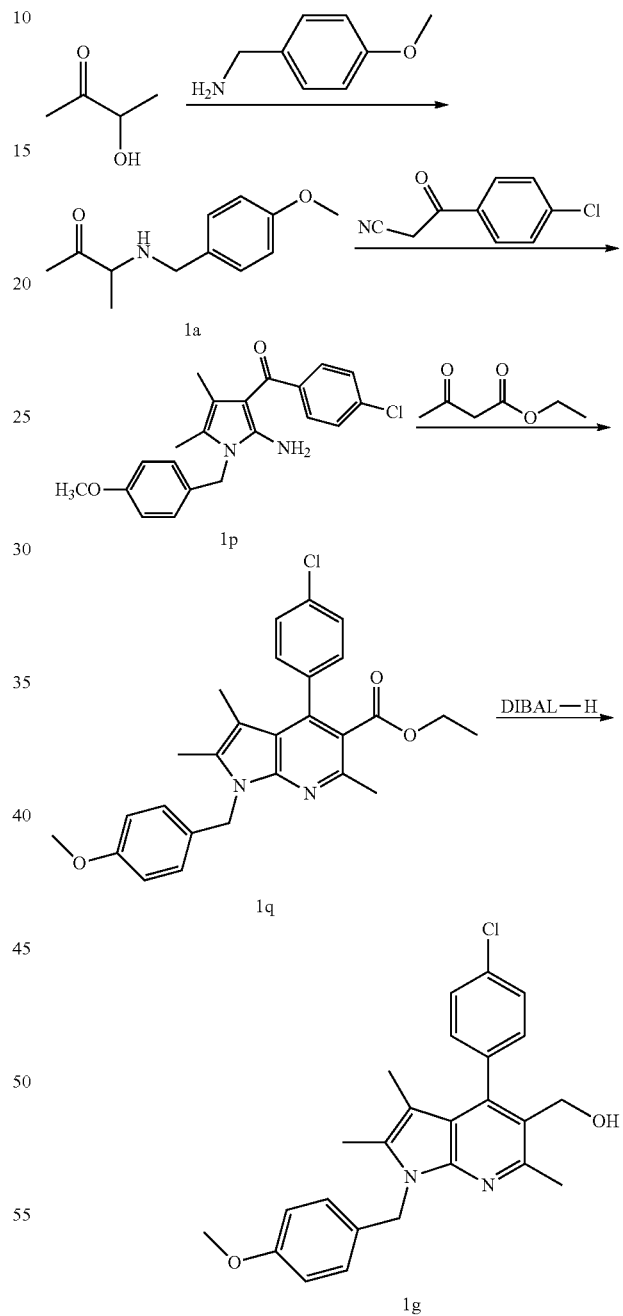

Step 1: Preparation of (2-amino-1-(4-methoxybenzyl)-4,5-dimethyl-1H-pyrrol-3-yl)(4-chlorophenyl)methanone (1p)

Acetoin (17.3 g, 196.3 mmol) and paramethoxybenzylamine (25.5 mL, 196.3 mmol) were dissolved in toluene (400 mL), and the mixture was heated under reflux for 2 hours after setting up a dean-stark trap apparatus. It was assured that the water produced in the reaction was received quantitatively in the trap, and the reaction solution was cooled to 0° C. 2-cyano-4-chloro-acetophenone (35.2 g, 196.3 mmol) was added to the reaction solution, and the result was stirred for 30 minutes at the same temperature, and then refluxed for 2 hours. After the reaction solution was cooled to room temperature and concentrated under reduced pressure, dichloromethane (100 mL) was added thereto, and the result was stirred for 10 minutes and then filtered to give a first target compound. The filtrate was concentrated under reduced pressure, and the residue was purified using silica gel column chromatography (normal-hexane/ethyl acetate=4/1) to give a second target compound. The first and second target compounds were combined to give a compound 1p (21.4 g, yield 30%).

$^1$H-NMR (300 MHz, CDCl$_3$) δ 1.54 (s, 3H), 2.00 (s, 3H), 3.77 (s, 3H), 4.83 (s, 2H), 5.84 (s, 2H), 6.86 (d, J=9 Hz, 2H), 7.01 (d, J=9 Hz, 2H), 7.37 (d, J=9 Hz, 2H), 7.43 (d, J=9 Hz, 2H); MS (EI, m/e)=367 (M$^+$).

Step 2: Preparation of ethyl 4-(4-chlorophenyl)-1-(4-methoxybenzyl)-2,3,6-trimethyl-1H-pyrrolo[2,3-b]pyridine-5-carboxylate (1q)

The compound 1p (21.4 g, 57.9 mmol) was dissolved in benzene (300 mL), ethyl acetoacetate (11 mL, 86.8 mmol) and para-toluenesulfonic acid (1.1 g, 5.8 mmol) were added thereto, and the mixture was refluxed for 5 hours. After the reaction solution was cooled to room temperature, the solvent was concentrated under reduced pressure, and the residue was purified using silica gel column chromatography (normal-hexane/ethyl acetate=9/1) to give a target compound 1q (21.2 g, yield 79%).

$^1$H-NMR (300 MHz, CDCl$_3$) δ 0.99 (t, J=7 Hz, 3H), 1.60 (s, 3H), 2.18 (s, 3H), 2.65 (s, 3H), 3.76 (s, 3H), 4.02 (q, J=6.75 Hz, 2H), 5.44 (s, 2H), 5.84 (s, 2H), 6.79 (d, J=9, 2H), 7.03 (d, J=9, 2H), 7.27 (m, 2H), 7.38 (d, J=9, 2H); MS (EI, m/e)=461 (M$^+$).

Step 3: Preparation of 4-(4-chlorophenyl)-1-(4-methoxybenzyl)-2,3,6-trimethyl-1H-pyrrolo[2,3-b]pyridin-5-yl)methanol (1g)

The compound 1q (35.88 g, 77.5 mmol) was dissolved in anhydrous dichloromethane (350 mL) under nitrogen atmosphere, and the mixture was cooled to −78° C. After a 1.5 M DIBAL/toluene solution (60 mL, 90 mmol) was added thereto over 5 minutes, the result was stirred for 2 hours at the same temperature. After the reaction was completed, a 2N aqueous HCl solution was slowly added thereto, the result was diluted with dichloromethane (400 mL), and then the result was stirred for 30 minutes while slowly raising the temperature to room temperature. The organic layer was separated, and the aqueous layer was extracted with dichloromethane (300 mL×2). The organic layers were combined, washed with water, dried with anhydrous magnesium sulfate, and then the solvent was concentrated under reduced pressure. After a moderate amount of normal-hexane was added to the produced solids, the result was stirred, and the solids were filtered, washed with normal-hexane, and then dried to give a target compound 1g (26.4 g, 81%).

$^1$H-NMR (300 MHz, CDCl$_3$) δ 1.52 (s, 3H), 2.17 (s, 3H), 2.77 (s, 3H), 3.75 (s, 3H), 4.52 (s, 2H), 5.45 (s, 2H), 6.80 (d, J=8.6 Hz, 2H), 7.05 (d, J=8.6 Hz, 2H), 7.26 (d, J=8.3 Hz, 2H), 7.42 (d, J=8.3 Hz, 2H); MS (EI, m/e)=420 (M$^+$).

Preparation Example 3

Preparation of methyl 2-tert-butoxy-2-(4-(4-chlorophenyl)-2,3,6-trimethyl-1H-pyrrolo[2,3-b]pyridin-5-yl)acetate (1y) and (S)-methyl 2-tert-butoxy-2-(4-chloro-2,3,6-trimethyl-1H-pyrrolo[2,3-b]pyridin-5-yl)acetate (1x)

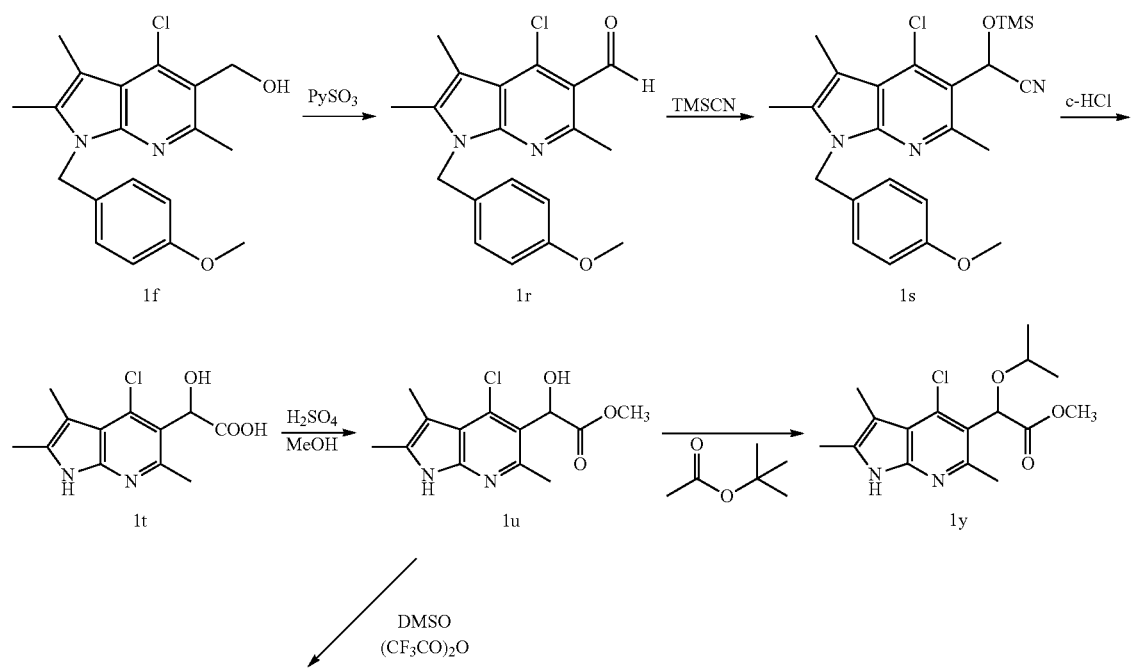

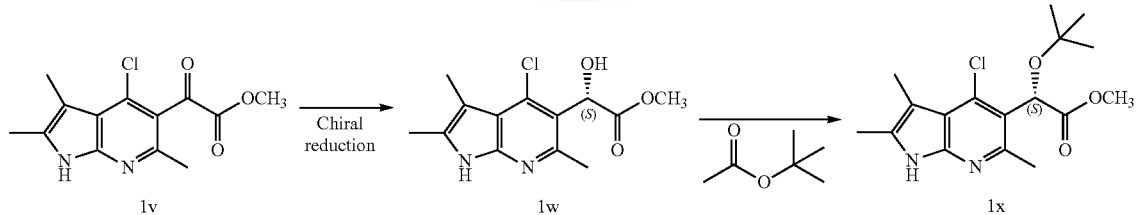

Step 1: Preparation of 4-chloro-1-(4-methoxybenzyl)-2,3,6-trimethyl-1H-pyrrolo[2,3-b]pyridine-5-carboaldehyde (1r)

After the compound 1f (34.9 g, 114.25 mmol) was dissolved in dimethyl sulfoxide (230 mL), triethylamine (65 mL, 466.3 mmol) was added thereto, and the mixture was cooled to 10° C. A sulfur trioxide pyridine complex (55 g, 345.5 mmol) dissolved in dimethyl sulfoxide (120 mL) was added to the above solution over 1 hour. After that, the result was stirred for 3 hours at 25° C. to complete the reaction, and the reaction solution was poured into ice water (1,500 mL). The produced solids were filtered and sufficiently washed with water. The obtained solids were dissolved in ethyl acetate, dried with anhydrous magnesium sulfate, and then the solvent was concentrated under reduced pressure. The residue was purified using column chromatography (normal-hexane/ethyl acetate=6/1) to give a pure target compound 1r (38.9 g, 99%) in a solid state.

$^1$H-NMR (300 MHz, CDCl$_3$) δ 2.23 (s, 3H), 2.45 (s, 3H), 2.84 (s, 3H), 3.75 (s, 3H), 5.41 (s, 2H), 6.81 (d, J=8.6 Hz, 2H), 6.99 (d, J=7.5 Hz, 2H), 10.75 (s, 1H): MS (EI, m/e)=342 (M+).

Step 2: Preparation of 2-(4-chloro-1-(4-methoxybenzyl)-2,3,6-trimethyl-1H-pyrrolo[2,3-b]pyridin-5-yl)-2-(trimethylsilyloxy)acetonitrile (1s)

After the compound 1r (38.9 g, 113.6 mmol) was dissolved in dichloromethane (1,200 mL) and the mixture was cooled to 0° C., zinc iodide (ZnI$_2$) (36.6 g, 114.7 mmol) was quickly added under nitrogen, and trimethylsilyl cyanide (29.0 mL, 227.2 mmol) was subsequently added over 5 minutes. The result was stirred for 1 hour at 0° C. and 3 hours at 25° C. to complete the reaction. The reaction solution was cooled to 0° C., ice water (500 mL) was added thereto, and the result was stirred for 10 minutes. After the organic layer was separated and the aqueous layer was extracted with dichloromethane (1,000 mL), the organic layers were combined, dried with anhydrous magnesium sulfate, and the solvent was concentrated under reduced pressure to give a target compound 1s. The compound 1s was used for the reaction of the next step without purification.

Step 3: Preparation of 2-(4-chloro-2,3,6-trimethyl-1H-pyrrolo[2,3-b]pyridin-5-yl)-2-hydroxyacetic acid (1t)

Concentrated hydrochloric acid (500 mL) was added to the compound 1s (theoretical amount 113.58 mmol), and the mixture was stirred for 18 hours at 100° C. Subsequently, the reaction material was cooled to room temperature and concentrated under reduced pressure. Methanol was added to the residue, and the result was once again concentrated under reduced pressure and dried under high-degree vacuum to give a target compound 1t (theoretical amount 113.58 mmol). The compound 1t was used for the next reaction without purification.

Step 4: Preparation of methyl 2-(4-chloro-2,3,6-trimethyl-1H-pyrrolo[2,3-b]pyridin-5-yl)-2-hydroxyacetate (1u)

After the compound 1t (theoretical amount 113.58 mmol) was dissolved in methanol (1,000 mL), concentrated sulfuric acid (18 mL) was added thereto, and the mixture was refluxed for 18 hours. The reaction material was cooled to 0° C., and then adjusted to pH 7.5 using a 2N aqueous NaOH solution. The methanol of the reaction material was removed by concentration under reduced pressure, water (20 mL) was added to the result, and a product was extracted with dichloromethane (1,500 mL×2), dried with anhydrous magnesium sulfate, and then concentrated under reduced pressure. The residue was purified using silica gel column chromatography (normal-hexane/ethyl acetate=4/1 and 1/1) to give a pure target compound 1u (16 g, 50%) in a solid state.

$^1$H-NMR (300 MHz, CDCl$_3$) δ 2.20 (s, 3H), 2.40 (s, 3H), 2.62 (s, 3H), 3.47 (s, 1H, —OH), 3.76 (s, 3H), 5.38 (s, 1H), 9.69 (s, 1H, —NH); MS (EI, m/e)=282 (M+).

Step 5: Preparation of methyl 2-(4-chloro-2,3,6-trimethyl-1H-pyrrolo[2,3-b]pyridin-5-yl)-2-oxoacetate (1v)

After trifluoroacetic anhydride (15.7 mL, 112.95 mmol) was added to dichloromethane (300 mL) and the mixture was cooled to −78° C., dimethyl sulfoxide (8 mL, 112.6 mmol) dissolved in dichloromethane (30 mL) was slowly added thereto, and the result was stirred for 30 minutes. The compound 1u (14.67 g, 51.9 mmol) dissolved in dichloromethane (100 mL) was slowly added to the above solution, the result was stirred for 1 hour at the same temperature, then triethylamine (33 mL, 236.7 mmol) was slowly added thereto, and the result was stirred for 30 minutes. A saturated aqueous ammonium chloride solution (300 mL) was added to the reaction material to complete the reaction, the temperature was slowly raised to 0° C., and the result was stirred for 30 minutes at 0° C. After the result was extracted with dichloromethane (300 mL×3), the organic layers were combined, washed with water, dried with anhydrous magnesium sulfate, and concentrated under reduced pressure. After dichloromethane (50 mL) and ethyl acetate (50 mL) were added to the residue and the result was, stirred for 10 minutes, the produced solids were filtered, combined, and washed with a mixed liquid of dichloromethane/ethyl acetate=1/1 (10 mL) to give a first target compound. The filtrate was concentrated under reduced pressure, and the residue was separated using silica gel column chromatography (hexane:ethyl acetate=3:1) to give a second target compound. The obtained first and second compounds were combined to give 9.35 g (64%) of a target compound 1v.

$^1$H-NMR (300 MHz, CDCl$_3$) δ 2.38 (s, 6H), 2.59 (s, 3H), 3.94 (s, 3H), 9.42 (s, 1H, NH); MS (EI, m/e)=280 (M$^+$).

Step 6: Preparation of (S)-methyl 2-(4-chloro-2,3,6-trimethyl-1H-pyrrolo[2,3-b]pyridin-5-yl)-2-hydroxy-acetate (1w)

After the compound 1v (9.35 g, 33.3 mmol) was dissolved in toluene (280 mL) and dichloromethane (140 mL) and the mixture was cooled to −35° C., a R-(+)-2-methyl-CBS-oxazaborolidine 1M-toluene solution (13.3 mL, 13.3 mmol) was added thereto, and then catecholborane (6 g, 50 mmol) dissolved in dichloromethane (150 mL) was slowly added to the result over 2 hours. The temperature was slowly raised to near −15° C. to 0° C., and when the reaction solution became transparent, the result was stirred for 5 hours at the same temperature. After an aqueous potassium carbonate solution (300 mL×3) was added thereto and the result was stirred for 1 hour at room temperature, the organic layer was separated, the aqueous layer was extracted with ethyl acetate (300 mL×3), and the organic layers were combined, washed with water, dried with anhydrous magnesium sulfate, and then concentrated under reduced pressure. After dichloromethane (40 mL) was added to the residue and the result was stirred for 10 minutes, the produced solids were filtered, combined, and washed with dichloromethane (twice using 30 mL each) to give a first target compound. The filtrate was concentrated under reduced pressure, and the residue was purified using silica gel column chromatography (hexane:ethyl acetate=1:1) to give a second target compound, and a total of 9.03 g (96%) of a target compound 1w was obtained.

$^1$H-NMR (300 MHz, CDCl$_3$) δ 2.20 (s, 3H), 2.40 (s, 3H), 2.62 (s, 3H), 3.47 (s, 1H, —OH), 3.76 (s, 3H), 5.38 (s, 1H), 9.69 (s, 1H, —NH); MS (EI, m/e)=282 (M$^+$).

Step 7: Preparation of (S)-methyl 2-tert-butoxy-2-(4-chloro-2,3,6-trimethyl-1H-pyrrolo[2,3-b]pyridin-5-yl)acetate (1x)

After the compound 1w (6.93 g, 24.51 mmol) was dissolved in dichloromethane (400 mL), perchloric acid (1.24 mL) was added thereto, and tert-butyl acetate (300 mL) was added over 8 hours at 10° C. After that, the result was stirred for 12 hours at 20° C., cooled with ice water, adjusted to pH 8.0 using a 20% aqueous Na$_2$CO$_3$ solution, and the result was stirred for 20 minutes. The organic layer was separated, the aqueous layer was extracted with ethyl acetate (300 mL×2), and then the organic layers were combined, dried with anhydrous magnesium sulfate, and the solvent was concentrated under reduced pressure. The residue was purified using silica gel column chromatography (normal-hexane/ethyl acetate=4/1) to give a pure target compound 1x (6.77 g, 81%).

$^1$H-NMR (300 MHz, CDCl$_3$) δ 1.23 (s, 9H), 2.36 (s, 6H), 2.42 (s, 3H), 2.67 (s, 3H), 3.68 (s, 3H), 5.94 (s, 1H), 9.89 (s, 1H, —NH); MS (EI, m/e)=338 (M$^+$).

Step 8: Preparation of methyl 2-tert-butoxy-2-(4-(4-chlorophenyl)-2,3,6-trimethyl-1H-pyrrolo[2,3-b]pyridin-5-yl)acetate (1y)

After the compound 1u (5.61 g, 19.9 mmol) was dissolved in dichloromethane (300 mL), the mixture was cooled to 0° C., and 70% perchloric acid (9.3 mL, 108.23 mmol) was added thereto. Tert-butyl acetate (300 mL) was very slowly added to the above reaction solution, and the result was stirred for 4 hours at room temperature. The result was neutralized using an aqueous potassium carbonate solution at 0° C., ethyl acetate (300 mL) was added thereto, and the result was stirred for 10 minutes. After the organic layer was separated and the aqueous layer was extracted with ethyl acetate (300 mL×2) once again, the combined organic layer was dried with anhydrous magnesium sulfate and concentrated under reduced pressure. The obtained residue was purified using silica gel column chromatography (hexane/ethyl acetate=3/1) to give a target compound 1y (4.38 g, 65%).

$^1$H-NMR (300 MHz, CDCl$_3$) δ 1.23 (s, 9H), 2.36 (s, 6H), 2.42 (s, 3H), 2.67 (s, 3H), 3.68 (s, 3H), 5.94 (s, 1H), 9.89 (s, 1H, —NH); MS (EI, m/e)=338 (M$^+$).

Example 1

2-Tert-butoxy-2-(4-(4-chlorophenyl)-1,2,3,6-tetramethyl-1H-pyrrolo[2,3-b]pyridin-5-yl)acetic acid (1)

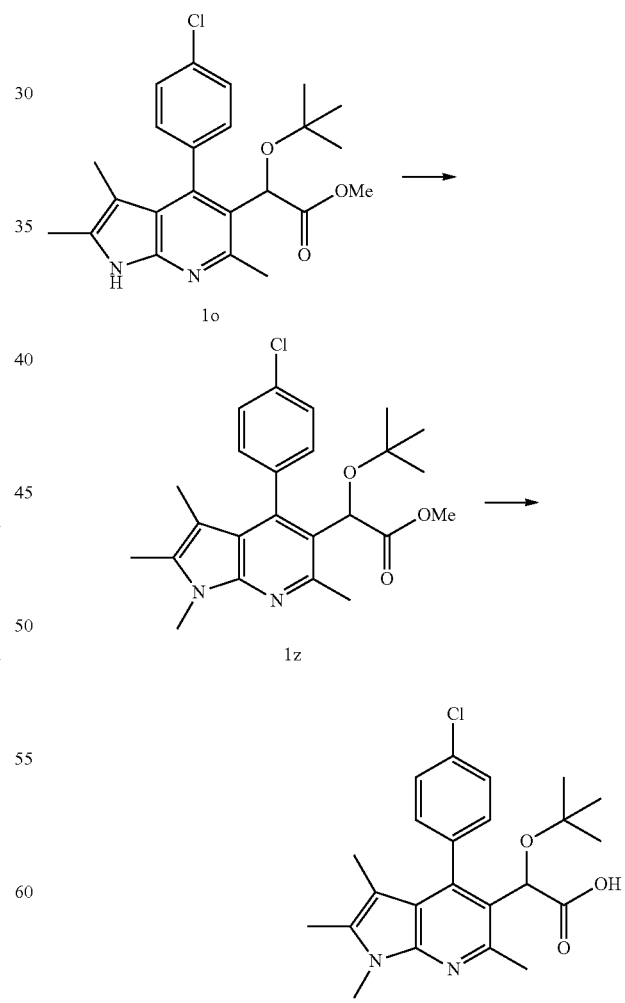

Step 1: Preparation of methyl 2-tert-butoxy-2-(4-(4-chlorophenyl)-1,2,3,6-tetramethyl-1H-pyrrolo[2,3-b]pyridin-5-yl)acetate (1z)

After the compound 1o (700 mg, 1.68 mmol) was dissolved in dichloromethane (15 mL), potassium hydroxide (278 mg, 4.22 mmol) and tetrabutylammonium bromide (60 mg) were added thereto, and iodomethyl (0.525 mL, 8.435 mmol) was slowly added thereto at room temperature. This solution was stirred for 10 hours at 25° C. Cooling water was added to the reaction material, and the result was adjusted to pH 5 to 6 using a 2N aqueous hydrochloric acid solution. After the organic layer was separated and taken, the aqueous layer was extracted once with dichloromethane, and the organic layers were combined, dried with anhydrous magnesium sulfate, and concentrated under reduced pressure. The residue was separated using silica gel column chromatography (normal-hexane/ethyl acetate=4/1) to give a pure target compound 1z (574 mg, 79%).

$^1$H-NMR (300 MHz, CDCl$_3$) δ 0.97 (s, 9H), 1.49 (s, 3H), 2.28 (s, 3H), 2.71 (s, 3H), 3.65 (s, 3H), 3.75 (s, 3H), 5.07 (s, 1H), 7.24 (m, 1H), 7.43 (m, 3H); MS (EI, m/e)=428 (M$^+$).

Step 2: Preparation of 2-tert-butoxy-2-(4-(4-chlorophenyl)-1,2,3,6-tetramethyl-1H-pyrrolo[2,3-b]pyridin-5-yl)acetic acid (1)

After the compound 1z (564 mg, 1.31 mmol) was dissolved in tetrahydrofuran (8.7 mL), a 4N sodium hydroxide/methanol solution (1 mL) was added thereto, and the mixture was stirred for 18 hours at 25° C. The same amount of a 4N aqueous hydrochloric acid solution was added thereto to neutralize the mixture, and the solvent was concentrated under reduced pressure and dried under a high vacuum. After a moderate amount of dichloromethane was added thereto, the insoluble substances were removed by filtration. The result was concentrated and the residue was separated using silica gel column chromatography (dichloromethane/methanol=50/1 or 20/1) to give a pure target compound 1 (494 mg, 91%) in white solids.

$^1$H-NMR (300 MHz, CD$_3$OD) δ 0.97 (s, 9H), 1.53 (s, 3H), 2.32 (s, 3H), 2.70 (s, 3H), 3.75 (s, 3H), 5.10 (s, 1H), 7.31 (m, 1H), 7.48 (m, 2H), 7.61 (m, 1H); MS (EI, m/e)=414 (M$^+$).

Example 2

2-Tert-butoxy-2-(4-(4-chlorophenyl)-1-ethyl-2,3,6-trimethyl-1H-pyrrolo[2,3-b]pyridin-5-yl)acetic acid (2)

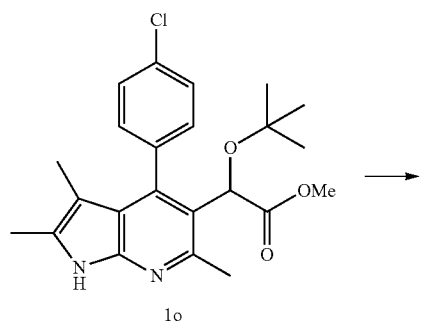

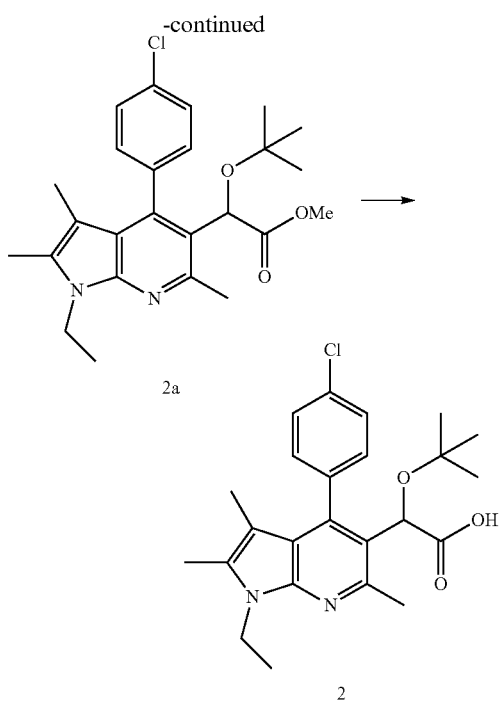

Step 1: Preparation of methyl 2-tert-butoxy-2-(4-(4-chlorophenyl)-1-ethyl-2,3,6-trimethyl-1H-pyrrolo[2,3-b]pyridin-5-yl)acetate (2a)

A target compound 2a (619 mg, 83%) was obtained by reacting the compound 1o (700 mg, 1.68 mmol) in the same manner as in Step 1 of Example 1, except that iodoethyl (2.5 equivalents) was used instead of iodomethyl.

$^1$H-NMR (300 MHz, CDCl$_3$) δ 0.97 (s, 9H), 1.34 (t, J=7.11 Hz, 3H), 1.48 (s, 3H), 2.29 (s, 3H), 2.70 (s, 3H), 3.66 (s, 3H), 4.28 (q, J=7.11 Hz, 2H), 5.07 (s, 1H), 7.23 (m, 1H), 7.43 (m, 3H); MS (EI, m/e)=442 (M$^+$).

Step 2: Preparation of 2-tert-butoxy-2-(4-(4-chlorophenyl)-1-ethyl-2,3,6-trimethyl-1H-pyrrolo[2,3-b]pyridin-5-yl)acetic acid (2)

A pure target compound 2 (370 mg, 87%) was obtained in white solids by reacting the compound 2a (440 mg, 1 mmol) in the same manner as in Step 2 of Example 1 using the same solvents and reagents in the same ratio.

$^1$H-NMR (300 MHz, CDCl$_3$) δ 1.01 (s, 9H), 1.31 (t, J=7.11 Hz, 3H), 1.36 (s, 3H), 2.30 (s, 3H), 2.67 (s, 3H), 4.28 (m, 2H), 5.19 (s, 1H), 7.26 (m, 1H), 7.43 (m, 2H), 7.60 (m, 1H); MS (EI, m/e)=428 (M$^+$)

Example 3

2-(1-Allyl-4-(4-chlorophenyl)-2,3,6-trimethyl-1H-pyrrolo[2,3-b]pyridin-5-yl)-2-tert-butoxyacetic acid (3)

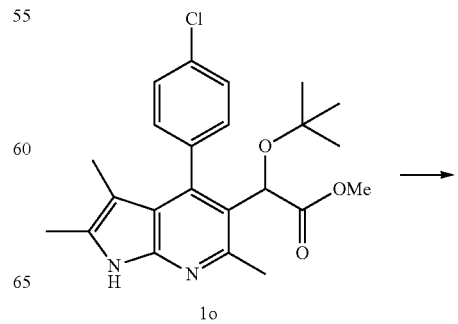

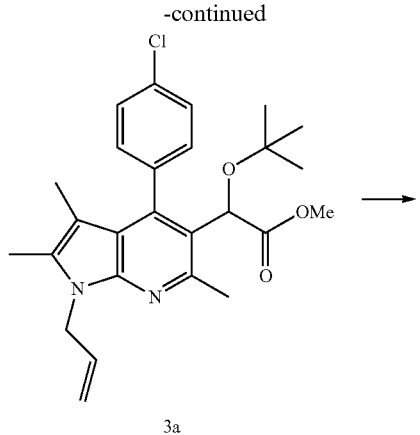

3a

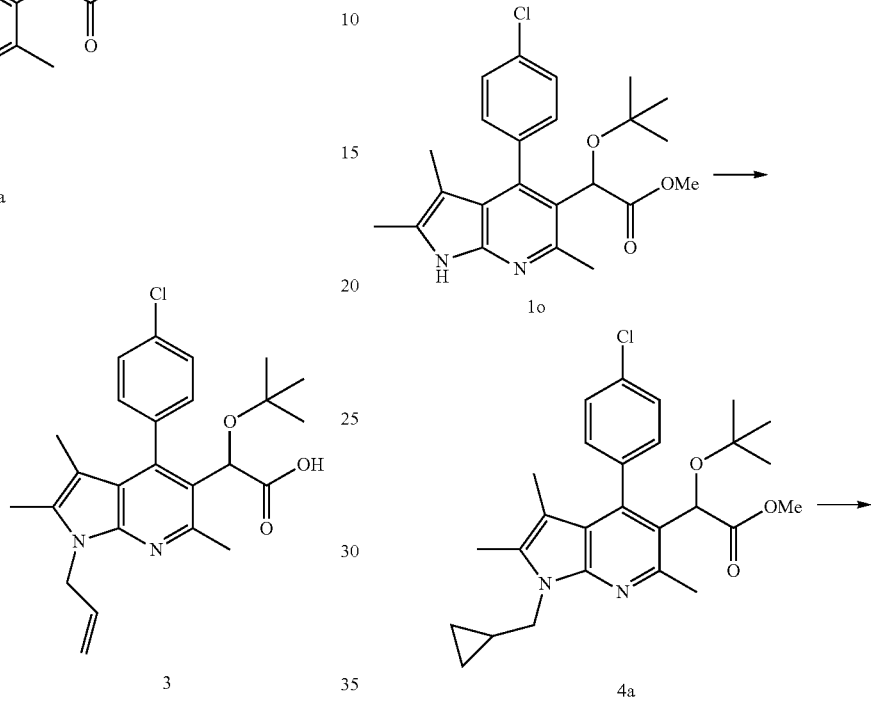

Example 4

2-Tert-butoxy-2-(4-(4-chlorophenyl)-1-(cyclopropyl-methyl)-2,3,6-trimethyl-1H-pyrrolo[2,3-b]pyridin-5-yl)acetic acid (4)

Step 1: Preparation of methyl 2-(1-allyl-4-(4-chlorophenyl)-2,3,6-trimethyl-1H-pyrrolo[2,3-b]pyridin-5-yl)-2-tert-butoxyacetate (3a)

A target compound 3a (200 mg, 44%) was obtained by reacting the compound 1o (415 mg, 1 mmol) in the same manner as in Step 1 of Example 1, except that allyl bromide (2.5 equivalents) was used instead of iodomethyl.

$^1$H-NMR (300 MHz, CDCl$_3$) δ 0.97 (s, 9H), 1.49 (s, 3H), 2.25 (s, 3H), 2.69 (s, 3H), 3.66 (s, 3H), 4.87-4.92 (m, 2H), 4.93 (d, 2H), 5.07 (s, 1H), 5.11 (d, 1H), 5.93 (m, 1H), 7.23 (m, 1H), 7.43 (m, 3H); MS (EI, m/e)=454 (M$^+$).

Step 2: Preparation of 2-(1-allyl-4-(4-chlorophenyl)-2,3,6-trimethyl-1H-pyrrolo[2,3-b]pyridin-5-yl)-2-tert-butoxyacetic acid (3)

A pure target compound 3 (300 mg, 78%) was obtained in white solids by reacting the compound 3a (400 mg, 0.879 mmol) in the same manner as in Step 2 of Example 1 using the same solvents and reagents in the same ratio.

$^1$H-NMR (300 MHz, CDCl$_3$) δ 1.00 (s, 9H), 1.52 (s, 3H), 2.16 (s, 3H), 2.63 (s, 3H), 4.80-4.92 (m, 2H), 4.92 (d, 1H) (s, 1H), 5.11 (d, 1H), 5.14 (s, 1H), 5.90 (m, 1H), 7.23 (m, 1H), 7.42 (m, 2H), 7.60-7.65 (m, 1H); MS (EI, m/e)=440 (M$^+$).

Step 1: Preparation of methyl 2-tert-butoxy-2-(4-(4-chlorophenyl)-1-(cyclopropylmethyl)-2,3,6-trimethyl-1H-pyrrolo[2,3-b]pyridin-5-yl)acetate (4a)

A target compound 4a (301 mg, 38%) was obtained by reacting the compound 1o (700 mg, 1.68 mmol) in the same manner as in Step 1 of Example 1, except that cyclopropylmethyl bromide (3 equivalents) was used instead of iodomethyl.

$^1$H-NMR (300 MHz, CDCl$_3$) δ 0.47-0.51 (m, 4H), 0.96 (s, 9H), 1.25 (m, 1H), 1.49 (s, 3H), 2.32 (s, 3H), 2.68 (s, 3H), 3.66 (s, 3H), 4.11 (d, J=6.75 Hz, 2H), 5.07 (s, 1H), 7.23 (m, 1H), 7.43 (m, 3H); MS (EI, m/e)=468 (M$^+$).

Step 2: Preparation of 2-tert-butoxy-2-(4-(4-chlorophenyl)-1-(cyclopropylmethyl)-2,3,6-trimethyl-1H-pyrrolo[2,3-b]pyridin-5-yl)acetic acid (4)

A pure target compound 4 (270 mg, 63%) was obtained in white solids by reacting the compound 4a (400 mg, 0.942 mmol) in the same manner as in Step 2 of Example 1 using the same solvents and reagents in the same ratio.

¹H-NMR (300 MHz, CDCl₃) δ 0.45-0.52 (m, 4H), 0.98 (s, 9H), 1.23 (m, 1H), 1.50 (s, 3H), 2.33 (s, 3H), 2.65 (s, 3H), 3.66 (s, 3H), 4.10 (d, J=6.75 Hz, 2H), 5.19 (s, 1H), 7.23 (m, 1H), 7.42 (m, 2H), 7.61 (m, 1H); MS (EI, m/e)=454 (M⁺).

Example 5

2-(1-Benzyl-4-(4-chlorophenyl)-2,3,6-trimethyl-1H-pyrrolo[2,3-b]pyridin-5-yl)-2-tert-butoxyacetic acid (5)

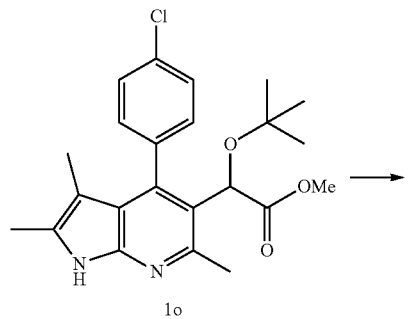

1o

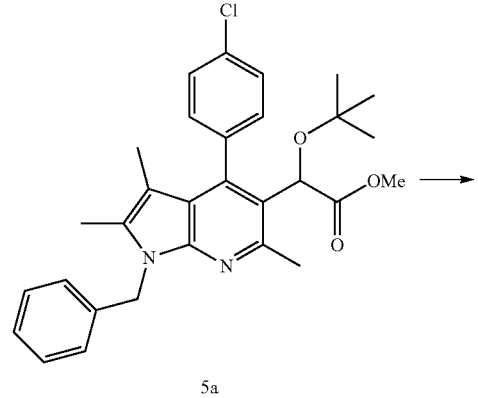

5a

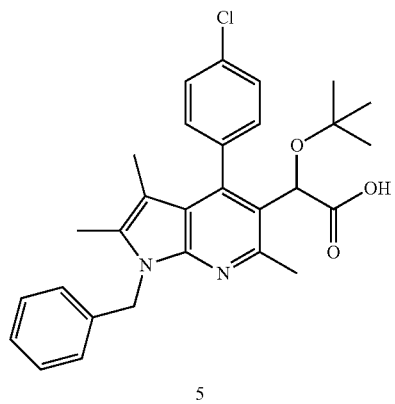

5

Step 1: Preparation of methyl 2-(1-benzyl-4-(4-chlorophenyl)-2,3,6-trimethyl-1H-pyrrolo[2,3-b]pyridin-5-yl)-2-tert-butoxyacetate (5a)

A target compound 5a (647 mg, 76%) was obtained by reacting the compound 1o 700 mg, 1.687 mmol) in the same manner as in Step 1 of Example 1, except that benzyl bromide (2.5 equivalents) was used instead of iodomethyl.

¹H-NMR (300 MHz, CDCl₃) δ 0.97 (s, 9H), 1.48 (s, 3H), 2.14 (s, 3H), 2.70 (s, 3H), 3.67 (s, 3H), 5.10 (s, 1H), 5.48 (AB-q, J=21.3 Hz, 2H), 7.23-7.18 (m, 2H), 7.21-7.30 (m, 4H), 7.39-7.50 (m, 3H); MS (EI, m/e)=504 (M⁺).

Step 2: Preparation of 2-(1-benzyl-4-(4-chlorophenyl)-2,3,6-trimethyl-1H-pyrrolo[2,3-b]pyridin-5-yl)-2-tert-butoxyacetic acid (5)

A pure target compound 5 (358 mg, 92%) was obtained in white solids by reacting the compound 5a (400 mg, 0.79 mmol) in the same manner as in Step 2 of Example 1 using the same solvents and reagents in the same ratio.

¹H-NMR (300 MHz, CDCl₃) δ 0.978s, 9H), 1.50 (s, 3H), 2.16 (s, 3H), 2.71 (s, 3H), 5.10 (s, 1H), 5.43 (AB-q, J=21.3 Hz, 2H), 7.23-7.18 (m, 2H), 7.21-7.30 (m, 4H), 7.39-7.50 (m, 2H); MS (EI, m/e)=490 (M⁺).

Example 6

2-Tert-butoxy-2-(1-(3-chlorobenzyl)-4-(4-chlorophenyl)-2,3,6-trimethyl-1H-pyrrolo[2,3-b]pyridin-5-yl) acetic acid (6)

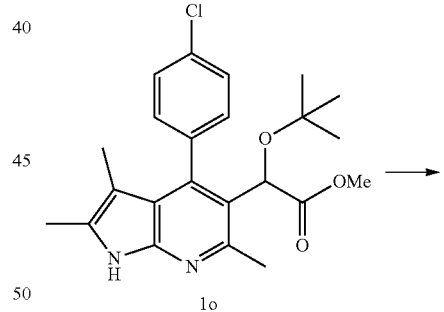

1o

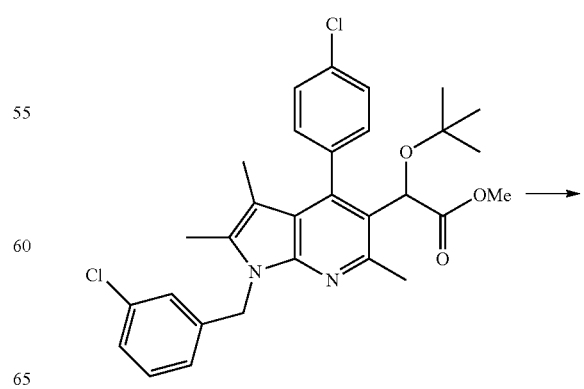

6a

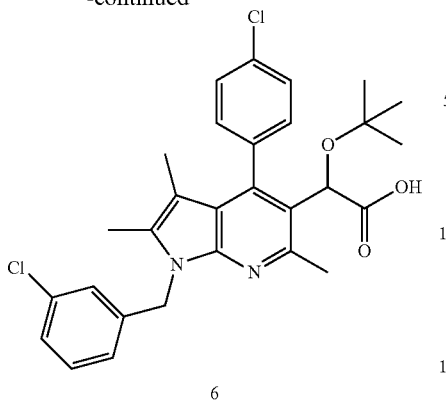

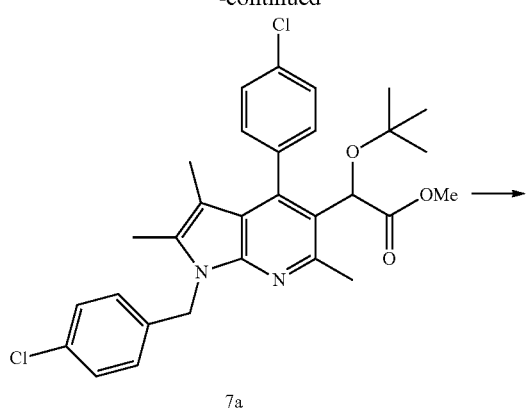

Step 1: Preparation of methyl 2-tert-butoxy-2-(1-(3-chlorobenzyl)-4-(4-chlorophenyl)-2,3,6-trimethyl-1H-pyrrolo[2,3-b]pyridin-5-yl)acetate (6a)

A target compound 6a (420 mg, 81%) was obtained by reacting the compound 1o (400 mg, 0.96 mmol) in the same manner as in Step 1 of Example 1, except that 3-chlorobenzyl bromide (2 equivalents) was used instead of iodomethyl.

$^1$H-NMR (300 MHz, CDCl$_3$) δ 0.99 (s, 9H), 1.48 (s, 3H), 2.14 (s, 3H), 2.69 (s, 3H), 3.68 (s, 3H), 5.10 (s, 1H), 5.44 (AB-q, J=21.4 Hz, 2H), 7.10-7.27 (m, 5H), 7.43-7.47 (m, 3H); MS (EI, m/e)=538 (M$^+$).

Step 2: Preparation of 2-tert-butoxy-2-(1-(3-chlorobenzyl)-4-(4-chlorophenyl)-2,3,6-trimethyl-1H-pyrrolo[2,3-b]pyridin-5-yl)acetic acid (6)

A pure target compound 6 (351 mg, 86%) was obtained in white solids by reacting the compound 6a (420 mg, 0.78 mmol) in the same manner as in Step 2 of Example 1 using the same solvents and reagents in the same ratio.

$^1$H-NMR (300 MHz, CD$_3$OD) δ 0.86 (s, 9H), 1.44 (s, 3H), 2.07 (s, 3H), 2.57 (s, 3H), 5.03 (s, 1H), 5.39 (s, 2H), 6.82 (d, J=0.7 Hz, 1H), 6.95 (s, 1H), 7.25 (m, 2H), 7.28 (d, 1H), 7.39-7.44 (m, 2H), 7.53 (d, 2H); MS (EI, m/e)=525 (M$^+$).

Example 7

2-Tert-butoxy-2-(1-(4-chlorobenzyl)-4-(4-chlorophenyl)-2,3,6-trimethyl-1H-pyrrolo[2,3-b]pyridin-5-yl)acetic acid (7)

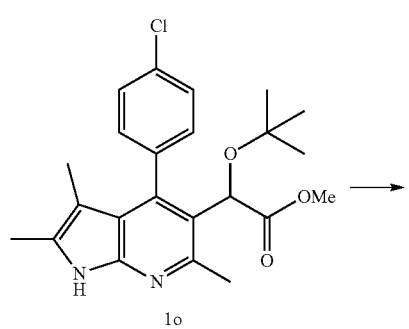

Step 1: Preparation of methyl 2-tert-butoxy-2-(1-(4-chlorobenzyl)-4-(4-chlorophenyl)-2,3,6-trimethyl-1H-pyrrolo[2,3-b]pyridin-5-yl)acetate (7a)

A target compound 7a (127 mg, 62%) was obtained by reacting the compound 1o (158 mg, 0.38 mmol) in the same manner as in Step 1 of Example 1, except that 4-chlorobenzyl bromide (2 equivalents) was used instead of iodomethyl.

$^1$H-NMR (300 MHz, CDCl$_3$) δ 0.99 (s, 9H), 1.48 (s, 3H), 2.14 (s, 3H), 2.69 (s, 3H), 3.67 (s, 3H), 5.10 (s, 1H), 5.44 (AB-q, J=21.4 Hz, 2H), 7.08 (d, J=8.4 Hz, 2H), 7.23-7.26 (m, 3H), 7.43-7.47 (m, 3H); MS (EI, m/e)=538 (M$^+$).

Step 2: Preparation of 2-tert-butoxy-2-(1-(4-chlorobenzyl)-4-(4-chlorophenyl)-2,3,6-trimethyl-1H-pyrrolo[2,3-b]pyridin-5-yl)acetic acid (7)

A pure target compound 7 (113 mg, 98%) was obtained in white solids by reacting the compound 7a (120 mg, 0.22 mmol) in the same manner as in Step 2 of Example 1 using the same solvents and reagents in the same ratio.

$^1$H-NMR (300 MHz, CDCl$_3$) δ 1.04 (s, 9H), 1.53 (s, 3H), 2.16 (s, 3H), 2.68 (s, 3H), 5.24 (s, 1H), 5.42 (AB-q, J=21.4 Hz, 2H), 7.06 (d, J=8.4 Hz, 2H), 7.23-7.26 (m, 3H), 7.44-7.49 (m, 2H), 7.65 (m, 1H); MS (EI, m/e)=525 (M$^+$).

Example 8

2-Tert-butoxy-2-(4-(4-chlorophenyl)-1-(4-fluorobenzyl)-2,3,6-trimethyl-1H-pyrrolo[2,3-b]pyridin-5-yl)acetic acid (8)

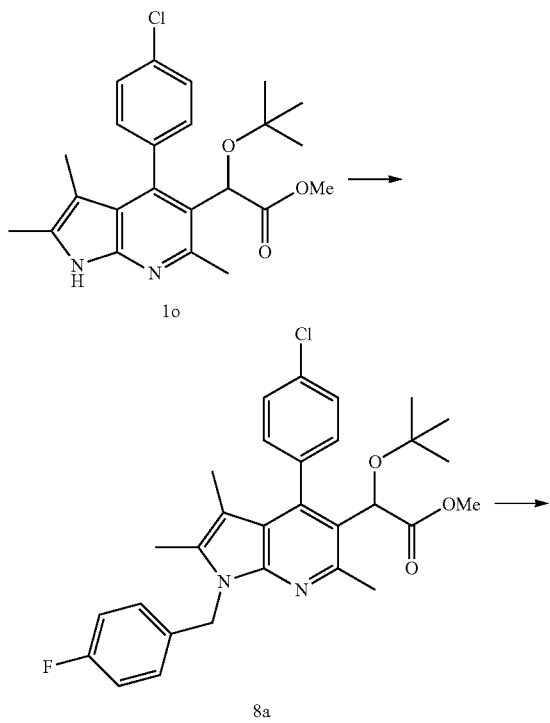

Step 1: Preparation of methyl 2-tert-butoxy-2-(4-(4-chlorophenyl)-1-(4-fluorobenzyl)-2,3,6-trimethyl-1H-pyrrolo[2,3-b]pyridin-5-yl)acetate (8a)

A target compound 8a (470 mg, 75%) was obtained by reacting the compound 1o (500 mg, 1.2 mmol) in the same manner as in Step 1 of Example 1, except that 4-fluorobenzyl bromide (3 equivalents) was used instead of iodomethyl.

$^1$H-NMR (300 MHz, CDCl$_3$) δ 0.99 (s, 9H), 1.50 (s, 3H), 2.16 (s, 3H), 2.72 (s, 3H), 3.70 (s, 3H), 5.12 (s, 1H), 5.46 (AB-q, J=21.4 Hz, 2H), 6.95-7.48 (m, 8H); MS (EI, m/e)=522 (M$^+$).

Step 2: Preparation of 2-tert-butoxy-2-(4-(4-chlorophenyl)-1-(4-fluorobenzyl)-2,3,6-trimethyl-1H-pyrrolo[2,3-b]pyridin-5-yl)acetic acid (8)

A pure target compound 8 (320 mg, 70%) was obtained in white solids by reacting the compound 8a (470 mg, 0.9 mmol) in the same manner as in Step 2 of Example 1 using the same solvents and reagents in the same ratio.

$^1$H-NMR (300 MHz, CD$_3$OD) δ 1.00 (s, 9H), 1.54 (s, 3H), 2.18 (s, 3H), 2.68 (s, 3H), 5.15 (s, 1H), 5.52 (s, 2H), 7.01-7.08 (m, 4H), 7.36 (m, 1H), 7.51 (m 2H), 7.61 (m, 1H); MS (EI, m/e)=407, 508 (M$^+$).

Example 9

2-Tert-butoxy-2-(4-(4-chlorophenyl)-1-(4-methoxybenzyl)-2,3,6-trimethyl-1H-pyrrolo[2,3-b]pyridin-5-yl)acetic acid (9)

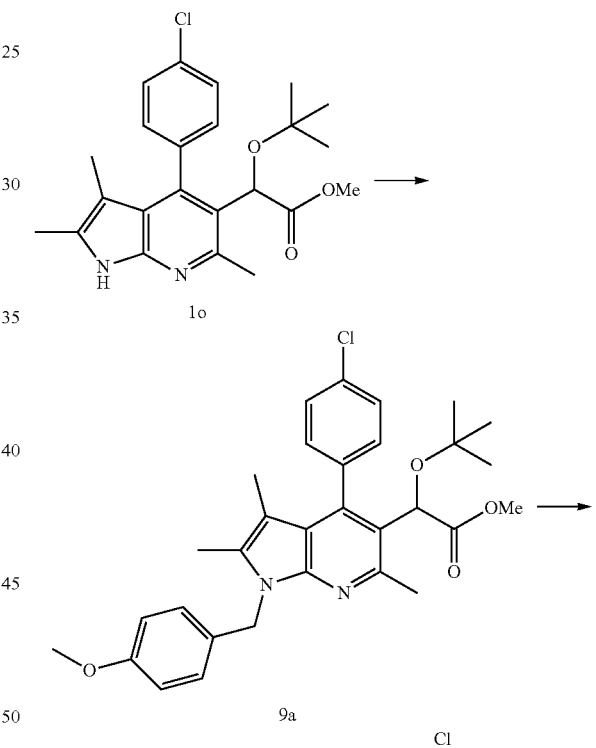

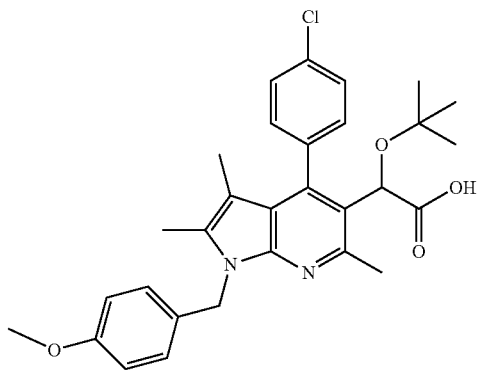

Step 1: Preparation of methyl 2-tert-butoxy-2-(4-(4-chlorophenyl)-1-(4-methoxybenzyl)-2,3,6-trimethyl-1H-pyrrolo[2,3-b]pyridin-5-yl)acetate (9a)

A target compound 9a (477 mg, 74%) was obtained by reacting the compound 1o (500 mg, 1.2 mmol) in the same manner as in Step 1 of Example 1, except that 4-methoxybenzyl bromide (3 equivalents) was used instead of iodomethyl.

$^1$H-NMR (300 MHz, CDCl$_3$) δ 0.99 (s, 9H), 1.47 (s, 3H), 2.16 (s, 3H), 2.70 (s, 3H), 3.76 (s, 3H), 5.09 (s, 1H), 5.42 (AB-q, J=21.4 Hz, 2H), 6.81 (d, J=8.6 Hz, 2H), 7.10 (d, J=8.6 Hz, 2H), 7.26 (m, 1H), 7.39-7.46 (m, 3H): LC/MS=534 (M$^+$).

Step 2: Preparation of 2-tert-butoxy-2-(4-(4-chlorophenyl)-1-(4-methoxybenzyl)-2,3,6-trimethyl-1H-pyrrolo[2,3-b]pyridin-5-yl)acetic acid (9)

A pure target compound 9 (180 mg, 66%) was obtained in white solids by reacting the compound 9a (280 mg, 0.523 mmol) in the same manner as in Step 2 of Example 1 using the same solvents and reagents in the same ratio.

$^1$H-NMR (300 MHz, CDCl$_3$) δ 1.00 (s, 9H), 1.53 (s, 3H), 2.18 (s, 3H), 2.69 (s, 3H), 5.15 (s, 1H), 5.47 (s, 2H), 6.83 (d, J=8.6 Hz, 2H), 6.98 (d, J=8.6 Hz, 2H), 7.38 (m, 1H), 7.49-7.55 (m, 2H), 7.62 (m 1H); MS (EI, m/e)=521 (M$^+$).

Example 10

2-Tert-butoxy-2-(4-(4-chlorophenyl)-2,3,6-trimethyl-1-(pyridin-4-ylmethyl)-1H-pyrrolo[2,3-b]pyridin-5-yl)acetic acid (10)

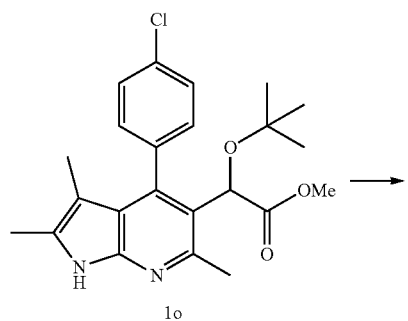

1o

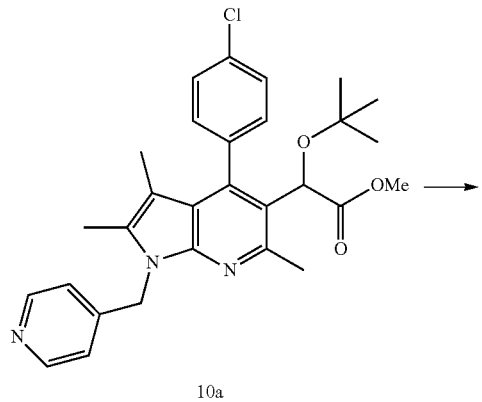

10a

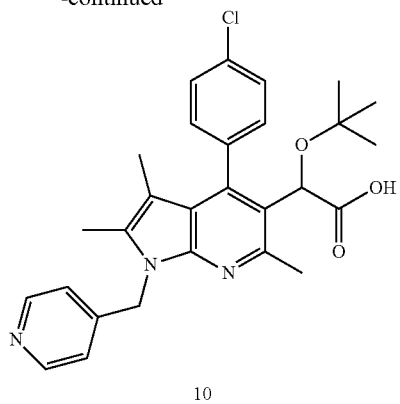

10

Step 1: Preparation of methyl 2-tert-butoxy-2-(4-(4-chlorophenyl)-2,3,6-trimethyl-1-(pyridin-4-ylmethyl)-1H-pyrrolo[2,3-b]pyridin-5-yl)acetate (10a)

A target compound 10a (385 mg, 63%) was obtained by reacting the compound 1o (498 mg, 1.2 mmol) in the same manner as in Step 1 of Example 1, except that 4-(bromomethyl)pyridine hydrobromide salt (2 equivalents) and potassium hydroxide (3 equivalents) were used instead of iodomethyl.

$^1$H-NMR (300 MHz, CDCl$_3$) δ 0.99 (s, 9H), 1.52 (s, 3H), 2.12 (s, 3H), 2.68 (s, 3H), 3.68 (s, 3H), 5.10 (s, 1H), 5.48 (AB-q, J=21.4 Hz, 2H), 7.01 (d, J=5.8 Hz, 2H), 7.28 (m, 1H), 7.42-7.48 (m, 3H), 8.51 (m, 2H); MS (EI, m/e)=505 (M$^+$).

Step 2: Preparation of 2-tert-butoxy-2-(4-(4-chlorophenyl)-2,3,6-trimethyl-1-(pyridin-4-ylmethyl)-1H-pyrrolo[2,3-b]pyridin-5-yl)acetic acid (10)

A pure target compound 10 (324 mg, 87%) was obtained in white solids by reacting the compound 10a (385 mg, 0.76 mmol) in the same manner as in Step 2 of Example 1 using the same solvents and reagents in the same ratio.

$^1$H-NMR (300 MHz, CDCl$_3$) δ 1.02 (s, 9H), 1.53 (s, 3H), 2.16 (s, 3H), 2.67 (s, 3H), 5.23 (s, 1H), 5.45 (AB-q, J=21.4 Hz, 2H), 7.01 (d, J=5.8 Hz, 2H), 7.28 (m, 1H), 7.46-7.50 (m, 2H), 7.69 (m, 1H), 8.54 (m, 2H); MS (EI, m/e)=491 (M$^+$).

Example 11

2-Tert-butoxy-2-(4-(4-chlorophenyl)-1-(2-cyanobenzyl)-2,3,6-trimethyl-1H-pyrrolo[2,3-b]pyridin-5-yl)acetic acid (11)

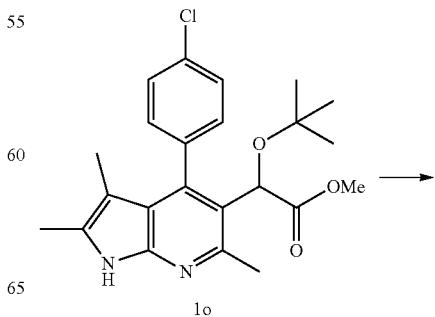

1o

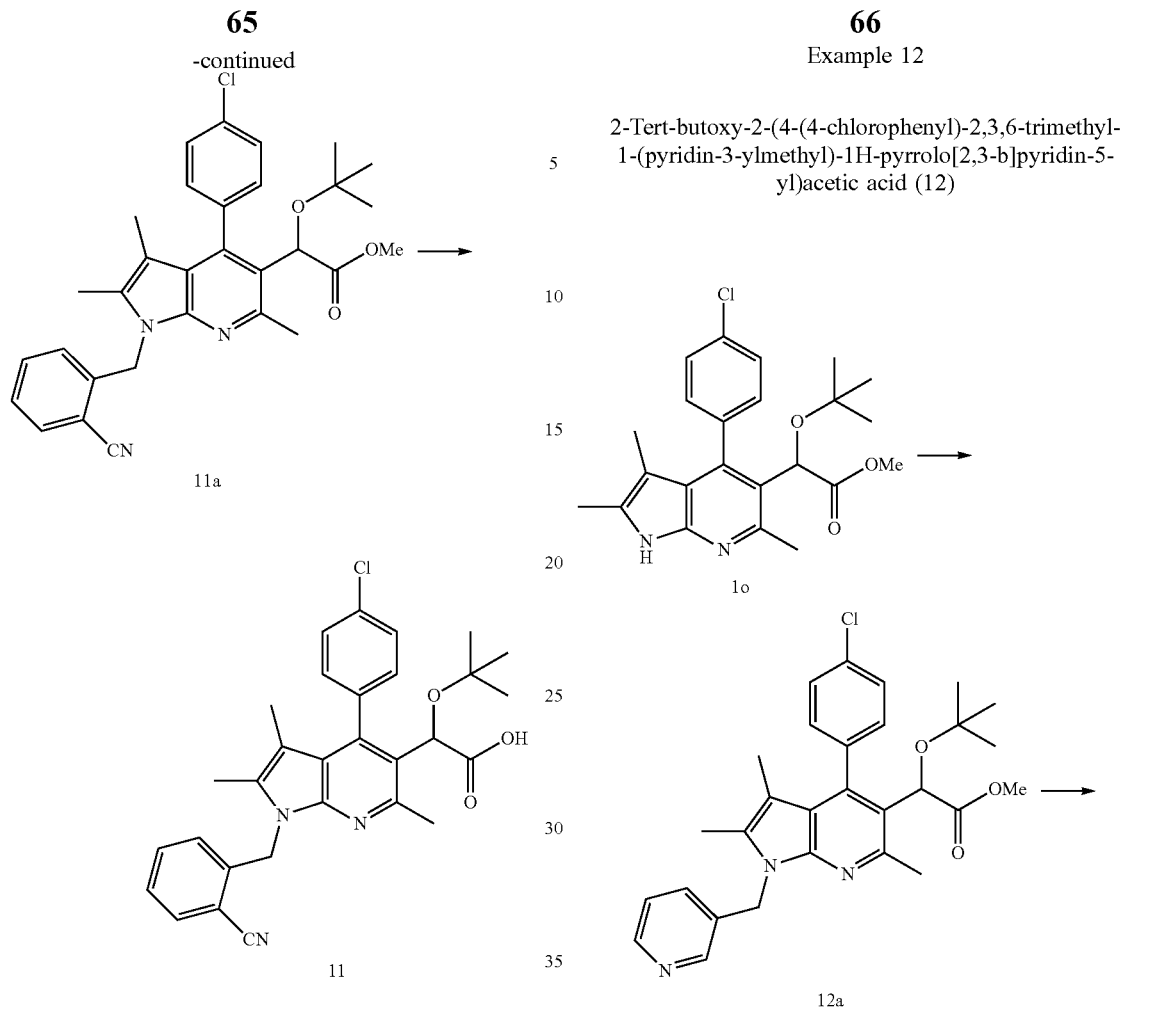

Step 1: Preparation of methyl 2-tert-butoxy-2-(4-(4-chlorophenyl)-1-(2-cyanobenzyl)-2,3,6-trimethyl-1H-pyrrolo[2,3-b]pyridin-5-yl)acetate (11a)

A target compound 11a (676 mg, 77%) was obtained by reacting the compound 1o (690 mg 1.66 mmol) in the same manner as in Step 1 of Example 1, except that 2-(bromomethyl)benzonitrile (2 equivalents) and potassium hydroxide (3.2 equivalents) were used instead of iodomethyl.

$^1$H-NMR (300 MHz, CDCl$_3$) δ 0.99 (s, 9H), 1.50 (s, 3H), 2.13 (s, 3H), 2.68 (s, 3H), 3.68 (s, 3H), 5.11 (s, 1H), 5.71 (s, 2H), 6.86 (d, J=8.6 Hz, 2H), 7.23 (m, 1H), 7.42-7.48 (m, 4H), 7.68 (m, 1H); MS (EI, m/e)=529 (M$^+$).

Step 2: Preparation of 2-tert-butoxy-2-(4-(4-chlorophenyl)-1-(2-cyanobenzyl)-2,3,6-trimethyl-1H-pyrrolo[2,3-b]pyridin-5-yl)acetic acid (11)

A pure target compound 11 (488 mg, 74%) was obtained in white solids by reacting the compound 11a (676 mg, 1.28 mmol) in the same manner as in Step 2 of Example 1 using the same solvents and reagents in the same ratio.

$^1$H-NMR (300 MHz, CDCl$_3$) δ 1.00 (s, 9H), 1.55 (s, 3H), 2.16 (s, 3H), 2.64 (s, 3H), 5.24 (s, 1H), 5.56 (d, 1H), 5.86 (d, 1H), 6.79 (d, J=8.6 Hz, 1H), 7.28-7.50 (m, 5H), 7.67-7.72 (m, 2H); MS (EI, m/e)=515 (M$^+$).

Example 12

2-Tert-butoxy-2-(4-(4-chlorophenyl)-2,3,6-trimethyl-1-(pyridin-3-ylmethyl)-1H-pyrrolo[2,3-b]pyridin-5-yl)acetic acid (12)

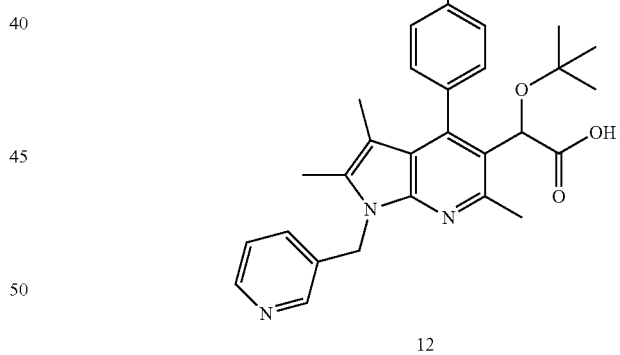

Step 1: Preparation of methyl 2-tert-butoxy-2-(4-(4-chlorophenyl)-2,3,6-trimethyl-1-(pyridin-3-ylmethyl)-1H-pyrrolo[2,3-b]pyridin-5-yl)acetate (12a)

A target compound 12a (490 mg, 67%) was obtained by reacting the compound 1o (600 mg, 1.446 mmol) in the same manner as in Step 1 of Example 1, except that a 3-(bromomethyl)pyridine hydrobromide salt (83 mg, 2.26 equivalents) and potassium hydroxide (40 mg, 5 equivalents) were used instead of iodomethyl and the stirring was carried out for 4 hours at 20° C.

¹H-NMR (300 MHz, CDCl₃) δ 1.01 (s, 9H), 1.49 (s, 3H), 2.19 (s, 3H), 2.72 (s, 3H), 3.70 (s, 3H), 5.11 (s, 1H), 5.51 (s, 2H), 7.22-7.29 (m, 2H), 7.33-7.52 (m, 4H), 8.50 (s, 2H); MS (EI, m/e)=505 (M⁺).

Step 2: Preparation of 2-tert-butoxy-2-(4-(4-chlorophenyl)-2,3,6-trimethyl-1-(pyridin-3-ylmethyl)-1H-pyrrolo[2,3-b]pyridin-5-yl)acetic acid (12)

A pure target compound 12 (272 mg, 60%) was obtained in white solids by reacting the compound 12a (465 mg, 0.92 mmol) in the same manner as in Step 2 of Example 1 using the same solvents and reagents in the same ratio.

¹H-NMR (300 MHz, CDCl₃) δ 1.02 (s, 9H), 1.51 (s, 3H), 2.18 (s, 3H), 2.69 (s, 3H), 5.21 (s, 1H), 5.46 (d, 1H), 5.56 (d, 1H), 7.20-7.24 (m, 2H), 7.42-7.50 (m, 3H), 7.63-7.66 (m, 1H), 8.50-8.51 (m, 2H); MS (EI, m/e)=491 (M⁺).

Example 13

2-Tert-butoxy-2-(4-(4-chlorophenyl)-2,3,6-trimethyl-1-(pyridin-2-ylmethyl)-1H-pyrrolo[2,3-b]pyridin-5-yl)acetic acid (13)

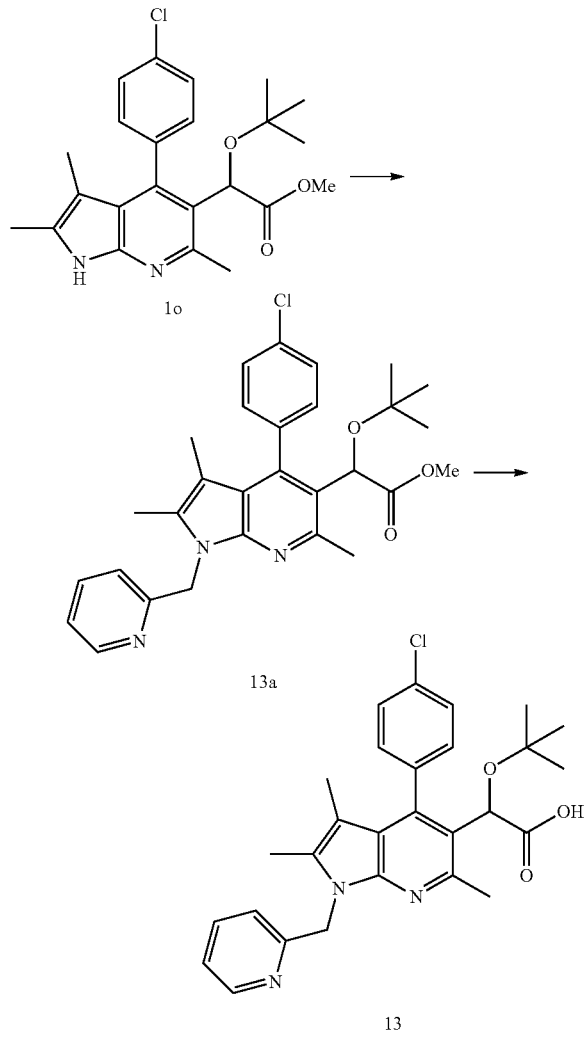

Step 1: Preparation of methyl 2-tert-butoxy-2-(4-(4-chlorophenyl)-2,3,6-trimethyl-1-(pyridin-2-ylmethyl)-1H-pyrrolo[2,3-b]pyridin-5-yl)acetate (13a)

A target compound 13a (650 mg, 89%) was obtained by reacting the compound 1o (600 mg 1.446 mmol) in the same manner as in Step 1 of Example 1, except that a 2-(bromomethyl)pyridine hydrobromide salt (83 mg, 2.26 equivalents) and potassium hydroxide (40 mg, 5 equivalents) were used instead of iodomethyl and the stirring was carried out for 4 hours at 20° C.

¹H-NMR (300 MHz, CDCl₃) δ 0.99 (s, 9H), 1.49 (s, 3H), 2.17 (s, 3H), 2.69 (s, 3H), 3.67 (s, 3H), 5.10 (s, 1H), 5.61 (s, 2H), 6.91 (d, J=7.65 Hz, 1H), 7.15 (m, 1H), 7.24 (m, 1H), 7.40-7.56 (m, 4H), 8.55-8.57 (m, 1H); MS (EI, m/e)=505 (M⁺).

Step 2: Preparation of 2-tert-butoxy-2-(4-(4-chlorophenyl)-2,3,6-trimethyl-1-(pyridin-2-ylmethyl)-1H-pyrrolo[2,3-b]pyridin-5-yl)acetic acid (13)

A pure target compound 13 (350 mg, 56%) was obtained in white solids by reacting the compound 13a (650 mg, 1.28 mmol) in the same manner as in Step 2 of Example 1 using the same solvents and reagents in the same ratio.

¹H-NMR (300 MHz, DMSO-d₆) δ 0.86 (s, 9H), 1.49 (s, 3H), 2.17 (s, 3H), 2.60 (s, 3H), 4.71 (s, 1H), 5.43 (d, 1H), 5.58 (d, 1H), 6.89 (d, J=4.62 Hz, 1H), 7.26-7.30 (m, 2H), 7.49-7.51 (m, 2H), 7.71 (m, 1H), 8.00 (m, 1H), 8.48-8.51 (m, 1H); MS (EI, m/e)=491 (M⁺).

Example 14

2-Tert-butoxy-2-(4-(4-chlorophenyl)-2,3,6-trimethyl-1-((6-methylpyridin-2-yl)methyl)-1H-pyrrolo[2,3-b]pyridin-5-yl)acetic acid (14)

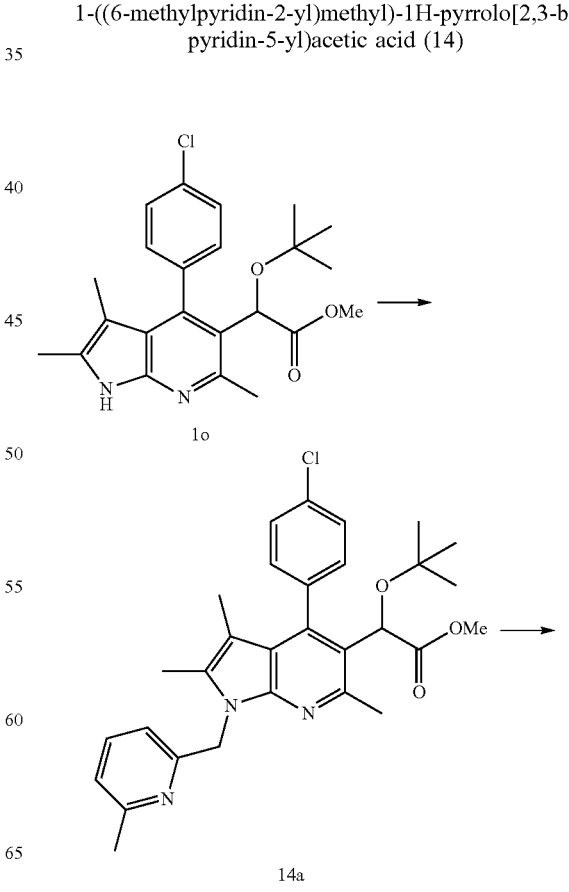

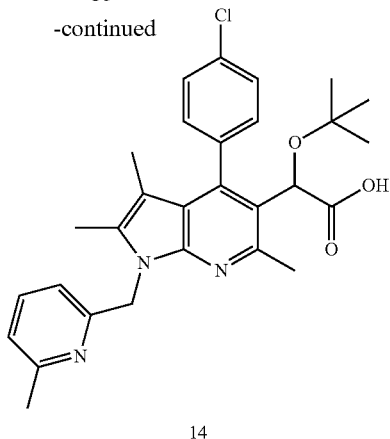

14

Step 1: Preparation of methyl 2-tert-butoxy-2-(4-(4-chlorophenyl)-2,3,6-trimethyl-1-((6-methylpyridin-2-yl)methyl)-1H-pyrrolo[2,3-b]pyridin-5-yl)acetate (14a)

A target compound 14a (750 mg, 100%) was obtained by reacting the compound 1o (600 mg, 1.446 mmol) in the same manner as in Step 1 of Example 1, except that 2-(bromomethyl)-6-methylpyridine (58 mg, 2.26 equivalents) and potassium hydroxide (40 mg, 5 equivalents) were used instead of iodomethyl and the stirring was carried out for 4 hours at 20° C.
$^1$H-NMR (300 MHz, CDCl$_3$) δ 0.99 (s, 9H), 1.53 (s, 3H), 2.17 (s, 3H), 2.57 (s, 3H), 2.68 (s, 3H), 3.67 (s, 3H), 5.10 (s, 1H), 5.57 (s, 2H), 6.56 (d, J=7.74 Hz, 1H), 7.08 (d, J=7.56 Hz, 1H), 7.28 (m, 1H), 7.40-7.47 (m, 3H); MS (EI, m/e)=520 (M$^+$).

Step 2: Preparation of 2-tert-butoxy-2-(4-(4-chlorophenyl)-2,3,6-trimethyl-1-((6-methylpyridin-2-yl)methyl)-1H-pyrrolo[2,3-b]pyridin-5-yl)acetic acid (14)

A pure target compound 14 (620 mg, 85%) was obtained in white solids by reacting the compound 14a (750 mg, 1.44 mmol) in the same manner as in Step 2 of Example 1 using the same solvents and reagents in the same ratio.
$^1$H-NMR (300 MHz, DMSO-d$_6$) δ 0.88 (s, 9H), 1.47 (s, 3H), 2.24 (s, 3H), 2.46 (s, 3H), 2.58 (s, 3H), 4.88 (s, 1H), 5.45 (AB-q, 2H), 6.54 (d, J=7.8 Hz, 1H), 7.12 (d, J=7.8 Hz, 1H), 7.32 (d, J=8.3 Hz, 1H),), 7.54-7.59 (m, 4H); MS (EI, m/e)=505 (M$^+$).

Example 15

2-Tert-butoxy-2-(4-(4-chlorophenyl)-2,3,6-trimethyl-1-propyl-1H-pyrrolo[2,3-b]pyridin-5-yl)acetic acid (15)

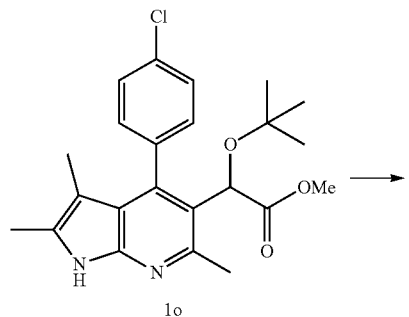

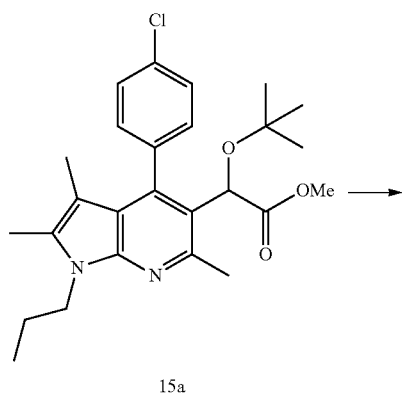

15a

15

Step 1: Preparation of methyl 2-tert-butoxy-2-(4-(4-chlorophenyl)-2,3,6-trimethyl-1-propyl-1H-pyrrolo[2,3-b]pyridin-5-yl)acetate (15a)

A target compound 15a (130 mg, 57%) was obtained by reacting the compound 1o (207 mg, 0.5 mmol) in the same manner as in Step 1 of Example 1, except that iodopropane (0.097 mL, 2.0 equivalents) and potassium hydroxide (164 mg, 5 equivalents) were used instead of iodomethyl and the stirring was carried out for 18 hours at 20° C.
$^1$H-NMR (300 MHz, CDCl$_3$) δ 0.97 (s, 9H), 0.94-0.99 (m, 3H), 1.48 (s, 3H), 1.77-1.79 (m, 2H), 2.28 (s, 3H), 2.69 (s, 3H), 3.65 (s, 3H), 4.16-4.17 (m, 2H), 5.07 (s, 1H), 7.25 (m, 1H), 7.39-7.44 (m, 3H); MS (EI, m/e)=457 (M$^+$).

Step 2: Preparation of 2-tert-butoxy-2-(4-(4-chlorophenyl)-2,3,6-trimethyl-1-propyl-1H-pyrrolo[2,3-b]pyridin-5-yl)acetic acid (15)

A pure target compound 15 (95.8 mg, 76%) was obtained in white solids by reacting the compound 15a (130 mg, 0.284 mmol) in the same manner as in Step 2 of Example 1 using the same solvents and reagents in the same ratio.
$^1$H-NMR (300 MHz, CD$_3$OD) δ 0.86 (s, 9H), 0.77-0.84 (m, 3H), 1.41 (s, 3H), 1.63-1.68 (m, 2H), 2.21 (s, 3H), 2.58 (s, 3H), 4.07-4.12 (m, 2H), 4.99 (s, 1H), 7.20 (m, 1H), 7.39 (m, 2H), 7.50 (m, 1H); MS (EI, m/e)=442 (M$^+$).

Example 16

2-Tert-butoxy-2-(1-butyl-4-(4-chlorophenyl)-2,3,6-trimethyl-1H-pyrrolo[2,3-b]pyridin-5-yl)acetic acid (16)

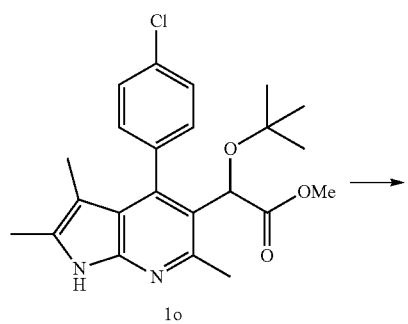

1o

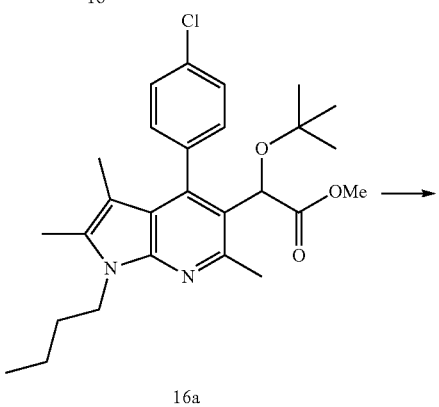

16a

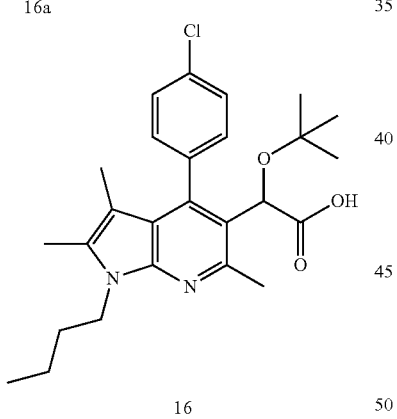

16

Step 1: Preparation of methyl 2-tert-butoxy-2-(1-butyl-4-(4-chlorophenyl)-2,3,6-trimethyl-1H-pyrrolo[2,3-b]pyridin-5-yl)acetate (16a)

A target compound 16a (388 mg, 57%) was obtained by reacting the compound 1o (600 mg, 5 mmol) in the same manner as in Step 1 of Example 1, except that 1-iodobutane (0.495 mL, 3.0 equivalents) and potassium hydroxide (400 mg, 5 equivalents) were used instead of iodomethyl and the stirring was carried out for 18 hours at 20° C.

$^1$H-NMR (300 MHz, CDCl$_3$) δ 0.97 (s, 9H), 0.94-0.97 (m, 3H), 1.35 (m, 2H), 1.48 (s, 3H), 1.72 (m, 2H), 2.27 (s, 3H), 2.69 (s, 3H), 3.65 (s, 3H), 4.19-4.21 (m, 2H), 5.07 (s, 1H), 7.25 (m, 1H), 7.41-7.44 (m, 3H); MS (EI, m/e)=471 (M$^+$).

Step 2: Preparation of 2-tert-butoxy-2-(1-butyl-4-(4-chlorophenyl)-2,3,6-trimethyl-1H-pyrrolo[2,3-b]pyridin-5-yl)acetic acid (16)

A pure target compound 16 (270 mg, 72%) was obtained in white solids by reacting the compound 16a (388 mg, 0.823 mmol) in the same manner as in Step 2 of Example 1 using the same solvents and reagents in the same ratio.

$^1$H-NMR (300 MHz, DMSO-d$_6$) δ 0.86-0.95 (m, 3H), 0.88 (s, 9H), 0.95-1.32 (m, 4H), 1.43 (s, 3H), 1.64 (m, 2H), 2.27 (s, 3H), 2.59 (s, 3H), 4.14 (m, 2H), 4.90 (s, 1H), 7.28 (m, 1H), 7.47-7.68 (m, 3H), 7.45; MS (EI, m/e)=457 (M$^+$).

Example 17

2-Tert-butoxy-2-(4-(4-chlorophenyl)-1-isobutyl-2,3,6-trimethyl-1H-pyrrolo[2,3-b]pyridin-5-yl)acetic acid (17)

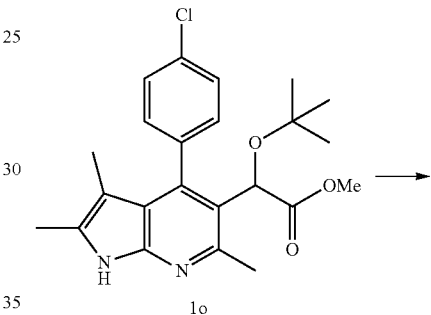

1o

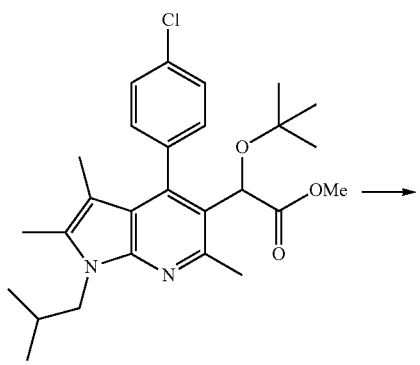

17a

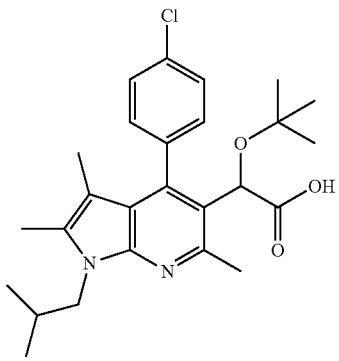

17

Step 1: Preparation of methyl 2-tert-butoxy-2-(4-(4-chlorophenyl)-1-isobutyl-2,3,6-trimethyl-1H-pyrrolo[2,3-b]pyridin-5-yl)acetate (17a)

A target compound 17a (56 mg, 24%) was obtained by reacting the compound 1o (207 mg, 0.5 mmol) in the same manner as in Step 1 of Example 1, except that 1-iodo-2-methylpropane (0.175 mL, 3.0 equivalents) and potassium hydroxide (164 mg, 5 equivalents) were used instead of iodomethyl and the stirring was carried out for 18 hours at 20° C.
$^1$H-NMR (300 MHz, CDCl$_3$) δ 0.95 (d, J=5.16 Hz, 6H), 1.00 (s, 9H), 1.51 (s, 3H), 2.28 (m, 1H), 2.29 (s, 3H), 2.71 (s, 3H), 3.68 (s, 3H), 4.00-4.15 (m, 2H), 5.10 (s, 1H), 7.26 (m, 1H), 7.42-7.47 (m, 3H); MS (EI, m/e)=471 (M$^+$).

Step 2: Preparation of 2-tert-butoxy-2-(4-(4-chlorophenyl)-1-isobutyl-2,3,6-trimethyl-1H-pyrrolo[2,3-b]pyridin-5-yl)acetic acid (17)

A pure target compound 17 (95.8 mg, 76%) was obtained in white solids by reacting the compound 17a (56 mg, 0.119 mmol) in the same manner as in Step 2 of Example 1 using the same solvents and reagents in the same ratio.
$^1$H-NMR (300 MHz, CD$_3$OD) δ 0.82 (d, J=5.16 Hz, 6H), 0.90 (s, 9H), 1.42 (s, 3H), 2.20 (m, 1H), 2.23 (s, 3H), 2.60 (s, 3H), 3.98 (m, 2H), 5.0 (s, 1H), 7.24 (m, 1H), 7.43-7.45 (m, 2H), 7.45-7.53 (m, 1H); MS (EI, m/e)=456 (M$^+$).

Example 18

2-Tert-butoxy-2-(4-(4-chlorophenyl)-1-isopentyl-2,3,6-trimethyl-1H-pyrrolo[2,3-b]pyridin-5-yl)acetic acid (18)

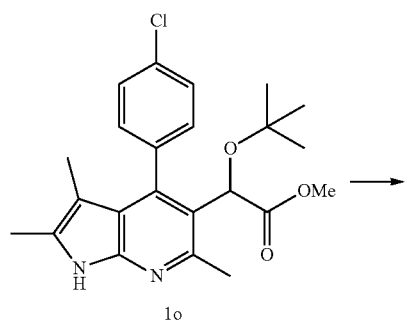

1o

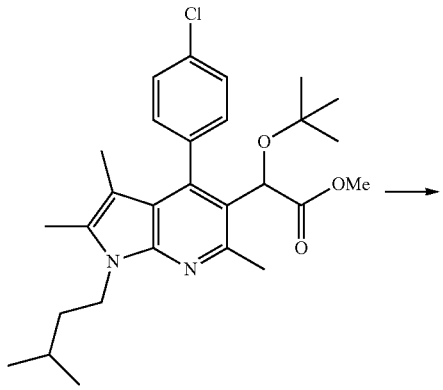

18a

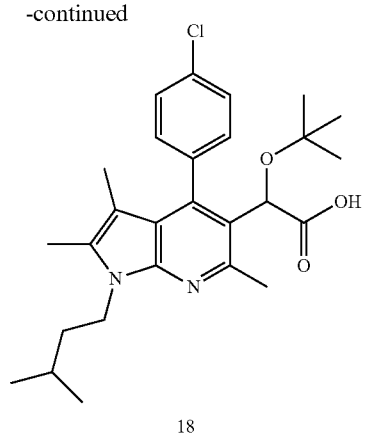

18

Step 1: Preparation of methyl 2-tert-butoxy-2-(4-(4-chlorophenyl)-1-isopentyl-2,3,6-trimethyl-1H-pyrrolo[2,3-b]pyridin-5-yl)acetate (18a)

A target compound 18a (290 mg, 42%) was obtained by reacting the compound 1o (600 mg, 1.446 mmol) in the same manner as in Step 1 of Example 1, except that 1-iodo-3-methylbutane (0.650 mL, 3.0 equivalents) and potassium hydroxide (400 mg, 5 equivalents) were used instead of iodomethyl and the stirring was carried out for 18 hours at 20° C.
$^1$H-NMR (300 MHz, CDCl$_3$) δ 0.95-1.01 (m, 6H), 0.99 (s, 9H), 1.48 (s, 3H), 1.58 (m, 2H), 1.64 (m, 1H), 2.27 (s, 3H), 2.69 (s, 3H), 3.66 (s, 3H), 4.19-4.24 (m, 2H), 5.07 (s, 1H), 7.25 (m, 1H), 7.39-7.44 (m, 3H); MS (EI, m/e)=485 (M$^+$).

Step 2: Preparation of 2-tert-butoxy-2-(4-(4-chlorophenyl)-1-isopentyl-2,3,6-trimethyl-1H-pyrrolo[2,3-b]pyridin-5-yl)acetic acid (18)

A pure target compound 18 (149 mg, 53%) was obtained in white solids by reacting the compound 18a (290 mg, 0.6 mmol) in the same manner as in Step 2 of Example 1 using the same solvents and reagents in the same ratio.
$^1$H-NMR (300 MHz, CD$_3$OD) δ 0.87-0.98 (m, 6H), 0.96 (s, 9H), 1.46-1.70 (m, 3H), 1.50 (s, 3H), 2.28 (s, 3H), 2.68 (s, 3H), 4.23-4.28 (m, 2H), 5.09 (s, 1H), 7.28 (m, 1H), 7.45-7.61 (m, 3H); MS (EI, m/e)=471 (M$^+$).

Example 19

2-Tert-butoxy-2-(4-(4-chlorophenyl)-1-((1,3-dioxoisoindolin-2-yl)methyl)-2,3,6-trimethyl-1H-pyrrolo[2,3-b]pyridin-5-yl)acetic acid (19)

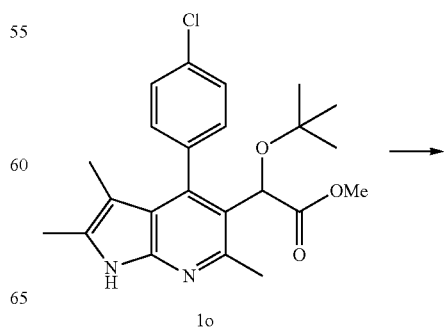

1o

Example 20

2-Tert-butoxy-2-(4-(4-chlorophenyl)-2,3,6-trimethyl-1-(prop-2-ynyl)-1H-pyrrolo[2,3-b]pyridin-5-yl)acetic acid (20)

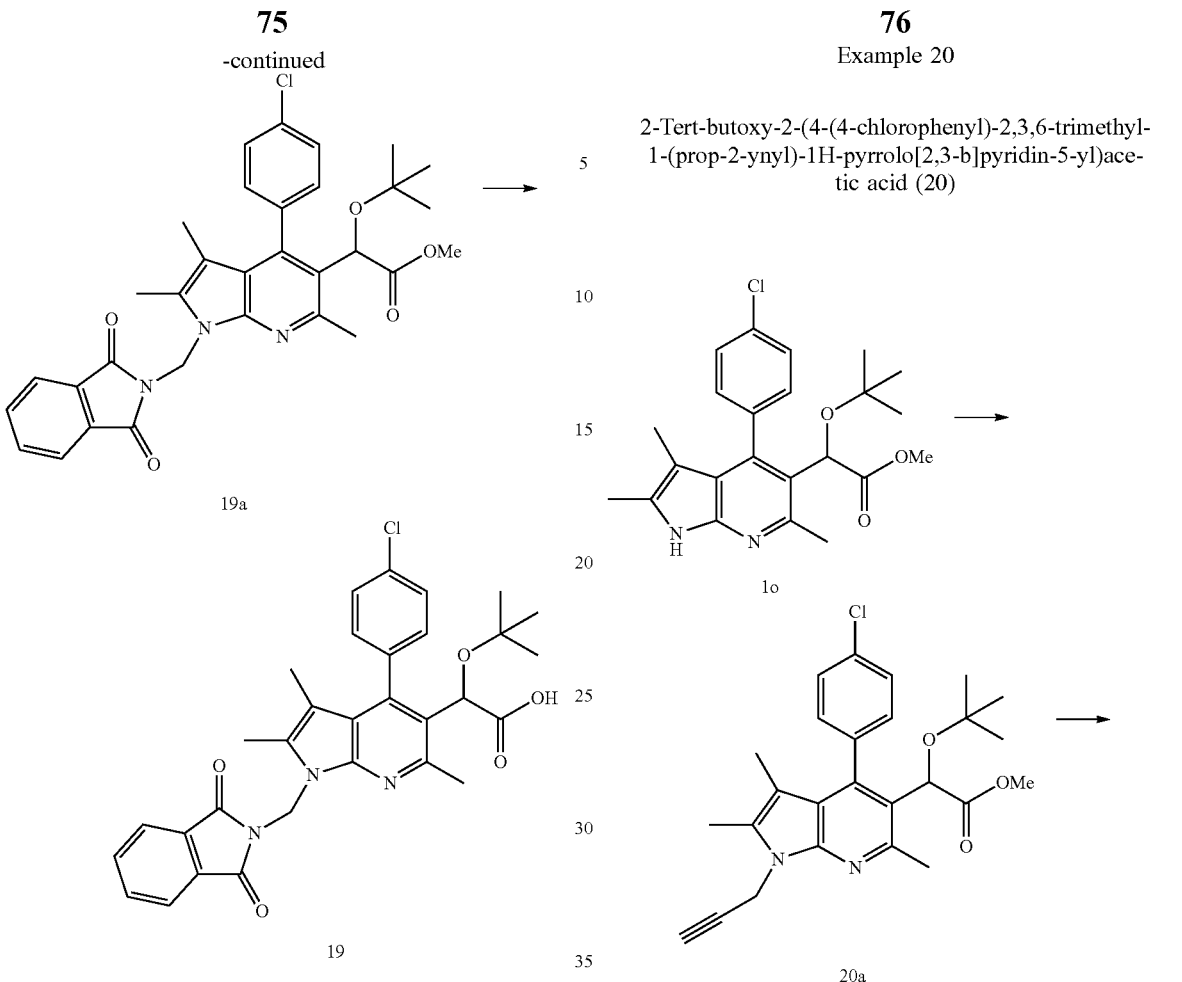

Step 1: Preparation of methyl 2-tert-butoxy-2-(4-(4-chlorophenyl)-1-((1,3-dioxoisoindolin-2-yl)methyl)-2,3,6-trimethyl-1H-pyrrolo[2,3-b]pyridin-5-yl)acetate (19a)

A target compound 19a (780 mg, 94%) was obtained by reacting the compound 1o (600 mg, 1.446 mmol) in the same manner as in Step 1 of Example 1, except that N-(bromomethyl)phthalimide (787 mg, 3.0 equivalents) and potassium hydroxide (400 mg, 5 equivalents) were used instead of iodomethyl and the stirring was carried out for 7 hours at 20° C.

$^1$H-NMR (300 MHz, CDCl$_3$) δ 0.98 (s, 9H), 1.46 (s, 3H), 2.45 (s, 3H), 2.65 (s, 3H), 3.63 (s, 3H), 5.04 (s, 1H), 6.08 (AB-q, 2H), 7.24 (m, 2H), 7.37 (m, 2H), 7.73 (m, 2H), 7.68 (m, 2H); MS (EI, m/e)=573 (M$^+$).

Step 2: Preparation of 2-tert-butoxy-2-(4-(4-chlorophenyl)-1-((1,3-dioxoisoindolin-2-yl)methyl)-2,3,6-trimethyl-1H-pyrrolo[2,3-b]pyridin-5-yl)acetic acid (19)

A pure target compound 19 (760 mg, 100%) was obtained in white solids by reacting the compound 19a (780 mg, 1.36 mmol) in the same manner as in Step 2 of Example 1 using the same solvents and reagents in the same ratio.

$^1$H-NMR (300 MHz, DMSO-d$_6$) δ 0.89 (s, 9H), 1.23 (s, 3H), 2.37 (s, 3H), 2.68 (s, 3H), 4.74 (s, 1H), 5.72 (s, 2H), 7.27 (m, 3H), 7.52 (m, 3H), 7.69 (m, 1H), 7.70 (m, 1H); MS (EI, m/e)=559 (M$^+$).

Step 1: Preparation of methyl 2-tert-butoxy-2-(4-(4-chlorophenyl)-2,3,6-trimethyl-1-(prop-2-ynyl)-1H-pyrrolo[2,3-b]pyridin-5-yl)acetate (20a)

A target compound 20a (63.3 mg, 58%) was obtained by reacting the compound 1o (100 mg, 0.241 mmol) in the same manner as in Step 1 of Example 1, except that 3-chloroprop-1-yne (0.053 mL, 3.0 equivalents) and potassium hydroxide (79.5 mg, 5 equivalents) were used instead of iodomethyl and the stirring was carried out for 4 hours at 20° C.

$^1$H-NMR (300 MHz, CDCl$_3$) δ 0.97 (s, 9H), 1.48 (s, 3H), 2.21 (s, 1H), 2.39 (s, 3H), 2.70 (s, 3H), 3.65 (s, 3H), 5.07 (s, 3H), 7.25 (m, 1H), 7.43 (m, 3H); MS (EI, m/e)=452 (M$^+$).

Step 2: Preparation of 2-tert-butoxy-2-(4-(4-chlorophenyl)-2,3,6-trimethyl-1-(prop-2-ynyl)-1H-pyrrolo[2,3-b]pyridin-5-yl)acetic acid (20)

A pure target compound 20 (52.8 mg, 94%) was obtained in white solids by reacting the compound 20a (58 mg, 0.128 mmol) in the same manner as in Step 2 of Example 1 using the same solvents and reagents in the same ratio.

$^1$H-NMR (300 MHz, CD$_3$OD) δ 0.99 (s, 9H), 1.53 (s, 3H), 2.39 (s, 3H), 2.64 (s, 1H), 2.66 (s, 3H), 5.10 (s, 2H), 5.12 (s, 1H), 7.32 (m, 1H), 7.52 (m, 3H); MS (EI, m/e)=438 (M$^+$).

Example 21

2-Tert-butoxy-2-(4-(4-chlorophenyl)-1-isopropyl-2,3,6-trimethyl-1H-pyrrolo[2,3-b]pyridin-5-yl)acetic acid (21)

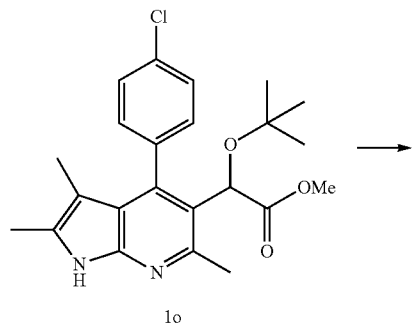

1o

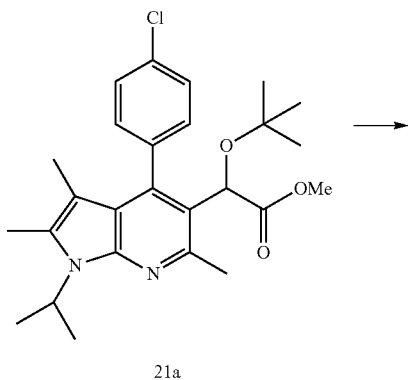

21a

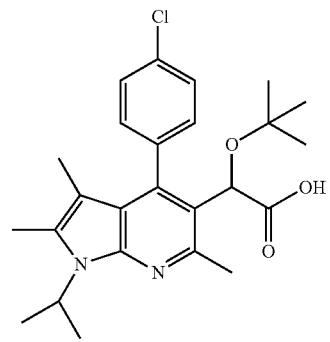

21

Step 1: Preparation of methyl 2-tert-butoxy-2-(4-(4-chlorophenyl)-1-isopropyl-2,3,6-trimethyl-1H-pyrrolo[2,3-b]pyridin-5-yl)acetate (21a)

A target compound 21a (118 mg, 14%) was obtained by reacting the compound 1o (800 mg, 1.93 mmol) in the same manner as in Step 1 of Example 1, except that 2-iodopropane (0.58 mL, 3.0 equivalents) and potassium hydroxide (640 mg, 5 equivalents) were used instead of iodomethyl and the stirring was carried out for 3 hours at 40° C.

$^1$H-NMR (300 MHz, CDCl$_3$) δ 0.98 (s, 9H), 1.49 (s, 3H), 1.64-1.67 (m, 6H), 2.35 (s, 3H), 2.72 (s, 3H), 3.68 (s, 3H), 5.09 (s, 3H), 5.11 (m, 1H), 7.25 (m, 1H), 7.41-7.49 (m, 3H); MS (EI, m/e)=457 (M$^+$).

Step 2: Preparation of 2-tert-butoxy-2-(4-(4-chlorophenyl)-1-isopropyl-2,3,6-trimethyl-1H-pyrrolo[2,3-b]pyridin-5-yl)acetic acid (21)

A pure target compound 21 (60 mg, 53%) was obtained in white solids by reacting the compound 21a (118 mg, 0.258 mmol) in the same manner as in Step 2 of Example 1 using the same solvents and reagents in the same ratio.

$^1$H-NMR (300 MHz, CD$_3$OD) δ 0.91 (s, 9H), 1.43 (s, 3H), 1.57 (d, J=6.69 Hz, 6H), 2.28 (s, 3H), 2.60 (s, 1H), 5.04 (s, 1H), 5.05 (m, 1H), 7.22 (m, 1H), 7.42 (m, 2H), 7.51 (m, 1H); MS (EI, m/e)=442 (M$^+$).

Example 22

2-Tert-butoxy-2-(4-(4-chlorophenyl)-1-cyanomethyl-2,3,6-trimethyl-1H-pyrrolo[2,3-b]pyridin-5-yl)acetic acid (22)

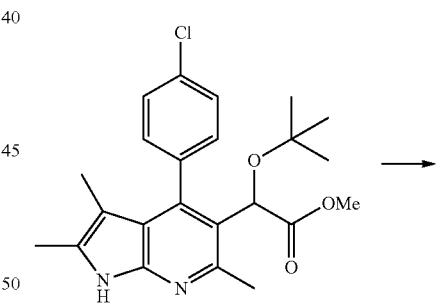

1o

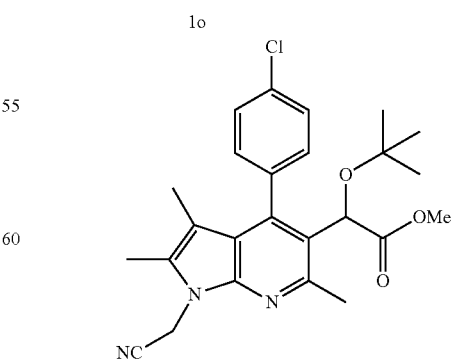

22a

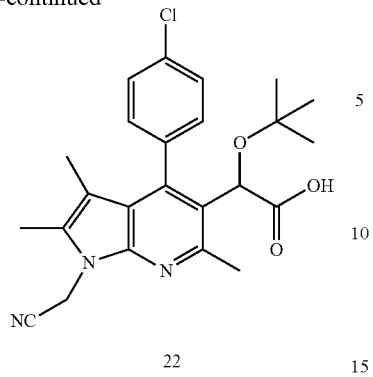

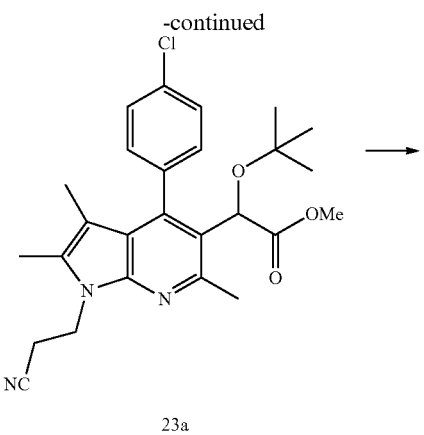

Step 1: Preparation of methyl 2-tert-butoxy-2-(4-(4-chlorophenyl)-1-cyanomethyl-2,3,6-trimethyl-1H-pyrrolo[2,3-b]pyridin-5-yl)acetate (22a)

A target compound 22a (91.5 mg, 84%) was obtained by reacting the compound 1o (100 mg, 0.241 mmol) in the same manner as in Step 1 of Example 1, except that chloroacetonitrile (0.046 mL, 3.0 equivalents) and potassium hydroxide (79.5 mg, 5 equivalents) were used instead of iodomethyl and the stirring was carried out for 4 hours at 20° C.

$^1$H-NMR (300 MHz, CDCl$_3$) δ 0.98 (s, 9H), 1.48 (s, 3H), 2.38 (s, 3H), 2.70 (s, 3H), 3.67 (s, 3H), 5.07 (s, 1H), 5.21 (s, 2H), 7.26 (m, 1H), 7.41 (m, 3H); MS (EI, m/e)=453 (M$^+$).

Step 2: Preparation of 2-tert-butoxy-2-(4-(4-chlorophenyl)-1-cyanomethyl-2,3,6-trimethyl-1H-pyrrolo[2,3-b]pyridin-5-yl)acetic acid (22)

A pure target compound 22 (76 mg, 100%) was obtained in white solids by reacting the compound 22a (81 mg, 0.178 mmol) in the same manner as in Step 2 of Example 1 using the same solvents and reagents in the same ratio.

$^1$H-NMR (300 MHz, CD$_3$OD) δ 0.95 (s, 9H), 1.55 (s, 3H), 2.26 (s, 3H), 2.70 (s, 3H), 4.96 (s, 2H), 5.05 (s, 1H), 7.34 (m, 1H), 7.46-7.51 (m, 2H), 7.74 (m, 1H); MS (EI, m/e)=439 (M$^+$).

Example 23

2-Tert-butoxy-2-(4-(4-chlorophenyl)-1-(2-cyanoethyl)-2,3,6-trimethyl-1H-pyrrolo[2,3-b]pyridin-5-yl)acetic acid (23)

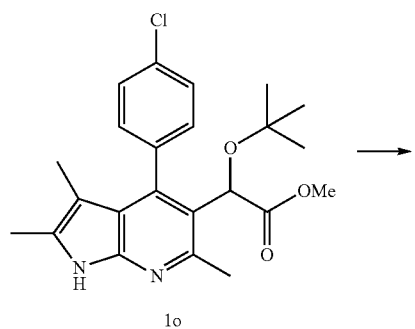

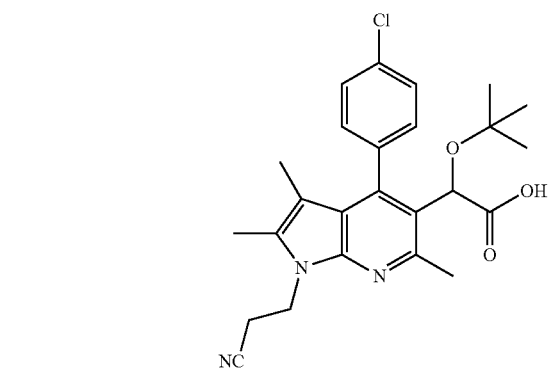

Step 1: Preparation of methyl 2-tert-butoxy-2-(4-(4-chlorophenyl)-1-(2-cyanoethyl)-2,3,6-trimethyl-1H-pyrrolo[2,3-b]pyridin-5-yl)acetate (23a)

A target compound 23a (75 mg, 67%) was obtained by reacting the compound 1o (100 mg, 0.241 mmol) in the same manner as in Step 1 of Example 1, except that iodopropionitrile (130 mg, 3.0 equivalents) and potassium hydroxide (79.5 mg, 5 equivalents) were used instead of iodomethyl and the stirring was carried out for 4 hours at 40° C.

$^1$H-NMR (300 MHz, CDCl$_3$) δ 1.01 (s, 9H), 1.50 (s, 3H), 2.37 (s, 3H), 2.70 (s, 3H), 2.99 (t, J=3.87 Hz, 2H), 3.70 (s, 3H), 4.51 (t, J=3.85 Hz, 2H), 5.10 (s, 1H), 7.26 (m, 1H), 7.41 (m, 3H); MS (EI, m/e)=467 (M$^+$).

Step 2: Preparation of 2-tert-butoxy-2-(4-(4-chlorophenyl)-1-(2-cyanoethyl)-2,3,6-triethyl-1H-pyrrolo[2,3-b]pyridin-5-yl)acetic acid (23)

A pure target compound 23 (53 mg, 77%) was obtained in white solids by reacting the compound 23a (70 mg, 0.15 mmol) in the same manner as in Step 2 of Example 1 using the same solvents and reagents in the same ratio.

$^1$H-NMR (300 MHz, CD$_3$OD) δ 0.87 (s, 9H), 1.42 (s, 3H), 2.27 (s, 3H), 2.59 (s, 3H), 2.87 (t, J=6.36 Hz, 2H), 4.44 (t, J=6.48 Hz, 2H), 5.02 (s, 1H), 7.23 (m, 1H), 7.39 (m, 2H), 7.44 (m, 1H); MS (EI, m/e)=453 (M$^+$).

Example 24

2-Tert-butoxy-2-(4-(4-chlorophenyl)-1-(2-hydroxyethyl)-2,3,6-trimethyl-1H-pyrrolo[2,3-b]pyridin-5-yl)acetic acid (24)

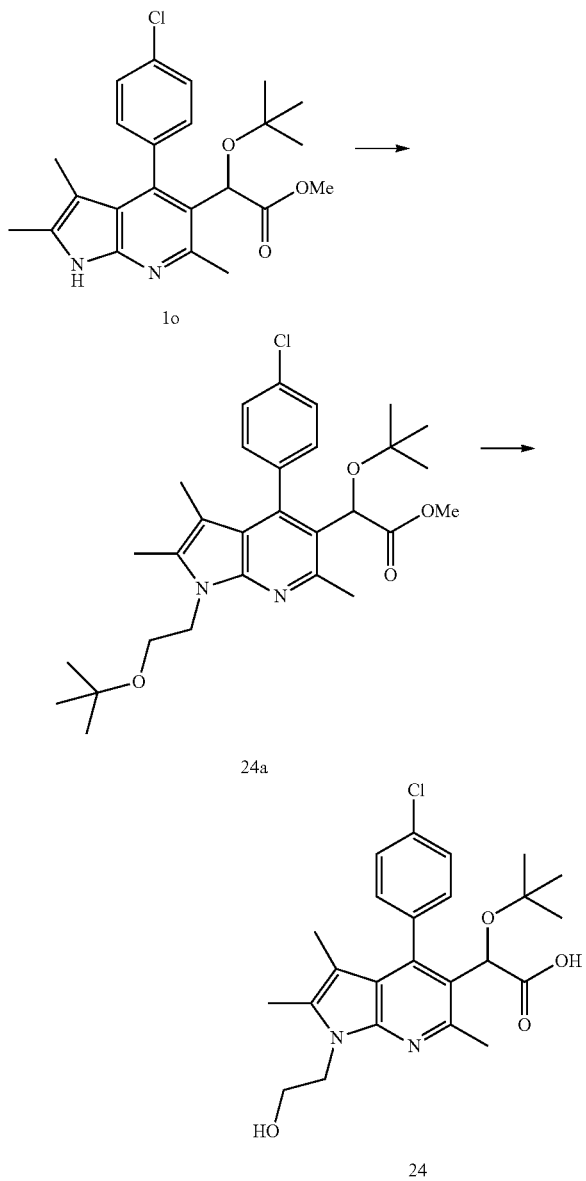

Preparation of tert-butyl(2-iodoethoxy)dimethylsilane

After 2-iodoethanol (1.72 g, 10 mmol) was dissolved in dimethylformamide (8 mL), imidazole (0.817 g, 12 mmol) and tert-butyldimethylsilyl chloride (1.66 g, 11 mmol) were added thereto, and the mixture was stirred for 4 hours at 30° C. to 40° C. Water (50 mL) was added to the reaction solution, and the result was extracted with an ethyl acetate/normal-hexane=1/1 solution (100 mL). The organic layer was washed again with salt water (30 mL×3), dried with anhydrous magnesium sulfate, and then concentrated under reduced pressure to give 2.85 g (90%) of a target compound. This compound was used as it was for the next reaction without purification.

Step 1: Preparation of methyl 2-tert-butoxy-2-(1-(2-((tert-butyldimethylsilyl)oxy)ethyl)-4-(4-chlorophenyl)-2,3,6-trimethyl-1H-pyrrolo[2,3-b]pyridin-5-yl)acetate (24a)

A target compound 24a (37 mg, 27%) was obtained by reacting the compound 1o (100 mg, 0.241 mmol) in the same manner as in Step 1 of Example 1, except that tert-butyl(2-iodoethoxy)dimethylsilane (206 mg, 3.0 equivalents) that was prepared using the method described above, and potassium hydroxide (79.5 mg, 5 equivalents) were used instead of iodomethyl and the stirring was carried out for 4 hours at 30° C.

$^1$H-NMR (300 MHz, CD$_3$OD) δ0.08 (s, 6H), 0.81 (s, 9H), 0.97 (s, 9H), 1.47 (s, 3H), 2.30 (s, 3H), 2.68 (s, 3H), 3.66 (s, 3H), 3.92 (m, 2H), 4.32 (m, 2H), 5.07 (s, 1H), 7.26 (m, 1H), 7.41 (m, 3H); MS (EI, m/e)=573 (M$^+$).

Step 2: Preparation of 2-tert-butoxy-2-(4-(4-chlorophenyl)-1-(2-hydroxyethyl)-2,3,6-trimethyl-1H-pyrrolo[2,3-b]pyridin-5-yl)acetic acid (24)

After the compound 24a (66 mg, 0.115 mmol) was dissolved in tetrahydrofuran (1 mL) and acetic acid (69.5 mg), a tetrabutylammonium fluoride 1M THF solution (0.46 mL) was added thereto, and the mixture was stirred for 3 hours at room temperature. The reaction material was concentrated under reduced pressure, dissolved by adding water (2 mL) and ethyl acetate (5 mL), and neutralized with a 2N aqueous sodium hydroxide solution. The organic layer was separated, dried with anhydrous magnesium sulfate, and concentrated under reduced pressure to give 1-hydroxyethyl compound (52 mg, 100%). This compound was used as it is for the nest reaction without purification.

After the above compound (52 mg) was dissolved in tetrahydrofuran (1.08 mL), a 4N sodium hydroxide/methanol solution (0.32 mL) was added thereto, and the mixture was stirred for 18 hours at 30° C. A target compound 24 (25 mg, 49%) was obtained by treating the result in the same manner as in Step 2 of Example 1.

$^1$H-NMR (300 MHz, CD$_3$OD) δ0.86 (s, 9H), 1.42 (s, 3H), 2.22 (s, 3H), 2.57 (s, 3H), 3.71 (m, 2H), 4.23 (m, 2H), 4.96 (s, 1H), 7.18 (m, 1H), 7.36 (m, 2H), 7.53 (m, 1H); MS (EI, m/e)=444 (M$^+$).

Example 25

2-Tert-butoxy-2-(4-(4-chlorophenyl)-2,3,6-trimethyl-1H-pyrrolo[2,3-b]pyridin-5-yl)acetic acid (25)

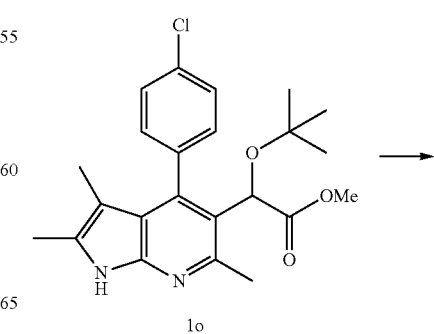

-continued

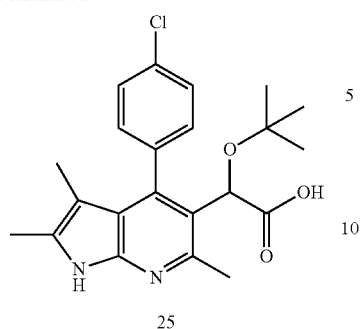

25

A pure target compound 25 (80 mg, 17%) was obtained in white solids by reacting the compound 1o (470 mg, 1.13 mmol) in the same manner as in Step 2 of Example 1 using the same solvents and reagents in the same ratio.

$^1$H-NMR (300 MHz, DMSO-D$_6$) δ 0.86 (s, 9H), 1.37 (s, 3H), 2.21 (s, 3H), 2.54 (s, 3H), 4.99 (s, 1H), 7.28 (m, 1H), 7.47 (m, 3H), 11.1 (s, 0.8H, —NH); MS (EI, m/e)=400 (M$^+$).

Example 26 and 27

(S)-2-Tert-butoxy-2-(4-(4-chlorophenyl)-1,2,3,6-tetramethyl-1H-pyrrolo[2,3-b]pyridin-5-yl)acetic acid (26) and (R)-2-tert-butoxy-2-(4-(4-chlorophenyl)-1,2,3,6-tetramethyl-1H-pyrrolo[2,3-b]pyridin-5-yl)acetic acid (27)

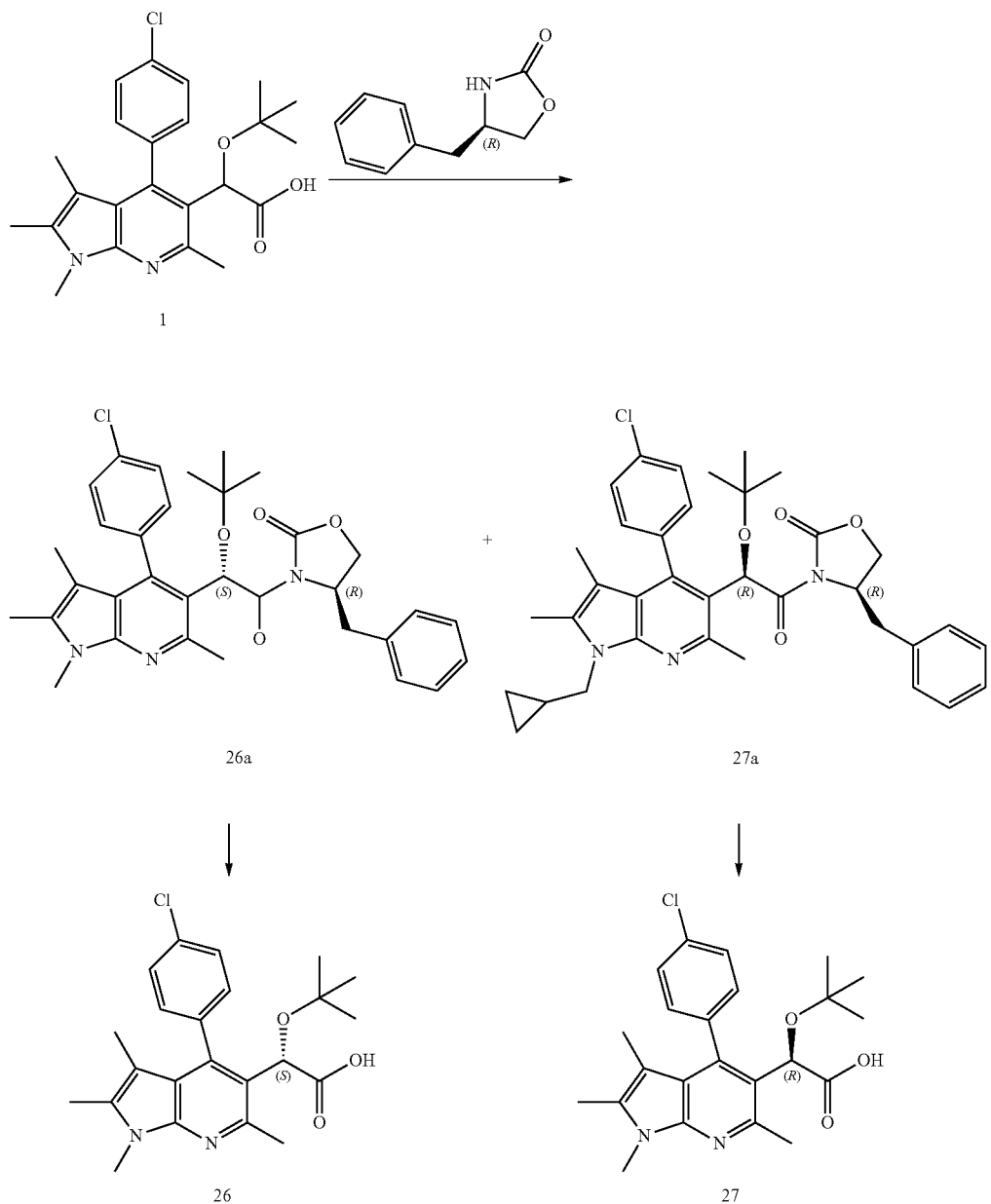

Step 1: Preparation of (R)-4-benzyl-3-((S)-2-tert-butoxy-2-(4-(4-chlorophenyl)-1,2,3,6-tetramethyl-1H-pyrrolo[2,3-b]pyridin-5-yl)acetyl)oxazolidin-2-one (26a) and (R)-4-benzyl-3-((R)-2-tert-butoxy-2-(4-(4-chlorophenyl)-1,2,3,6-tetramethyl-1H-pyrrolo[2,3-b]pyridin-5-yl)acetyl)oxazolidin-2-one (27a)

After a compound 1 (1.0 mmol) was dissolved in tetrahydrofuran (10 mL), diisopropylethylamine (1.04 mL, 6 mmol) and then O-(benzotriazol-1-yl)-N,N,N',N'-tetramethyluronium tetra fluoroborate (TBTU) (0.948 g, 2.5 mmol) were added thereto, and the mixture was stirred for 5 hours at 35° C. In another flask, (R)-(+)-4-benzyl-2-oxazolidinone (0.532 g, 3 mmol) was dissolved in anhydrous tetrahydrofuran (8 mL), 60% sodium hydride (0.2 g, 5 mmol) was added thereto, and the mixture was stirred for 30 minutes at room temperature. To this solution, the solution prepared above was added. After the result was stirred for 30 minutes, ice water (20 mL) was added thereto, and the result was extracted with ethyl acetate (40 mL×2), washed with salted water, dried with anhydrous magnesium sulfate, and concentrated under reduced pressure. The residue was separated using silica gel column chromatography (effluent, ethyl acetate/normal-hexane=1/4 or 1/6) to give a mixture of 26a and 27a. The mixture was separated once again using silica gel column chromatography (dichloromethane/acetone=1/50 or 1/100), and 26a (part with strong polarity, 22%) and 27a (part with weak polarity, 54%) were obtained from the mixture.

26a: $^1$H-NMR (300 MHz, CDCl$_3$) δ 1.17 (s, 9H), 1.46 (s, 3H), 2.29 (s, 3H), 2.75 (m, 1H), 2.96 (s, 3H), 3.24 (m, 1H), 3.79 (s, 3H), 4.08 (d, 2H), 4.40 (m, 1H), 6.14 (s, 1H), 7.16-7.43 (m, 9H); MS (EI, m/e)=574 (M$^+$).

27a: $^1$H-NMR (300 MHz, CDCl$_3$) δ 1.08 (s, 9H), 1.49 (s, 3H), 2.30 (s, 3H), 2.65 (m, 1H), 2.96 (s, 3H), 3.27 (m, 1H), 3.82 (s, 3H), 4.14 (d, 2H), 4.59 (m, 1H), 6.20 (s, 1H), 6.92-7.49 (m, 9H); MS (EI, m/e)=574 (M$^+$).

Step 2: Preparation of (S)-2-tert-butoxy-2-(4-(4-chlorophenyl)-1,2,3,6-tetramethyl-1H-pyrrolo[2,3-b]pyridin-5-yl)acetic acid (26) and (R)-2-tert-butoxy-2-(4-(4-chlorophenyl)-1,2,3,6-tetramethyl-1H-pyrrolo[2,3-b]pyridin-5-yl)acetic acid (27)

After the compounds 26a and 27a (0.5 mmol) were each dissolved in tetrahydrofuran (4 mL) and water (2 mL), 30% hydrogen peroxide (1.62 mmol) was added thereto, and a lithium hydroxide hydrate (0.5 mmol) was subsequently added thereto. This solution was stirred for 2 hours at 0° C. 10% Na$_2$SO$_3$ (0.63 mL) was added to the reaction material, and the result was stirred for 5 minutes. The reaction material was adjusted to pH 4 to 5 using a 1N aqueous hydrochloric acid solution, and extracted with dichloromethane (25 mL×3). After the organic layers were combined and extracted with a 0.5N aqueous sodium hydroxide solution (13 mL×3), the aqueous layers were combined and acidified with 10% hydrochloric acid, extracted 3 times with ethyl acetate, dried with anhydrous magnesium sulfate, and was concentrated under reduced pressure. The residue was separated using silica gel column chromatography (dichloromethane/methanol=50/1 or 20/1) to separately give target compounds 26 (62% yield) and 27 (72% yield).

26: $^1$H-NMR (300 MHz, CD$_3$OD) δ 0.97 (s, 9H), 1.53 (s, 3H), 2.32 (s, 3H), 2.70 (s, 3H), 3.75 (s, 3H), 5.10 (s, 1H), 7.31 (m, 1H), 7.48 (m, 2H), 7.61 (m, 1H); MS (EI, m/e)=414 (M$^+$).

27: $^1$H-NMR (300 MHz, CD$_3$OD) δ 0.97 (s, 9H), 1.53 (s, 3H), 2.32 (s, 3H), 2.70 (s, 3H), 3.75 (s, 3H), 5.10 (s, 1H), 7.31 (m, 1H), 7.48 (m, 2H), 7.61 (m, 1H); MS (EI, m/e)=414 (M$^+$).

Example 28 and 29

(S)-2-Tert-butoxy-2-(4-(4-chlorophenyl)-1-(cyclopropylmethyl)-2,3,6-trimethyl-1H-pyrrolo[2,3-b]pyridin-5-yl)acetic acid (28) and (R)-2-tert-butoxy-2-(4-(4-chlorophenyl)-1-(cyclopropylmethyl)-2,3,6-trimethyl-1H-pyrrolo[2,3-b]pyridin-5-yl)acetic acid (29)

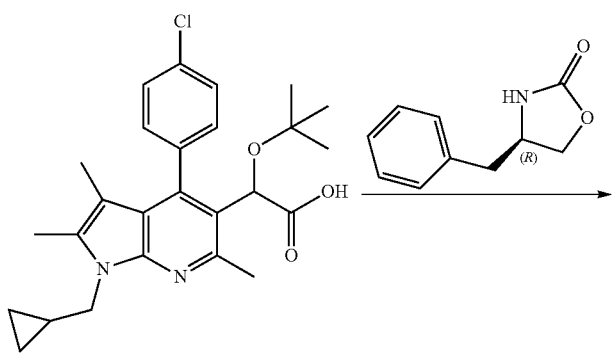

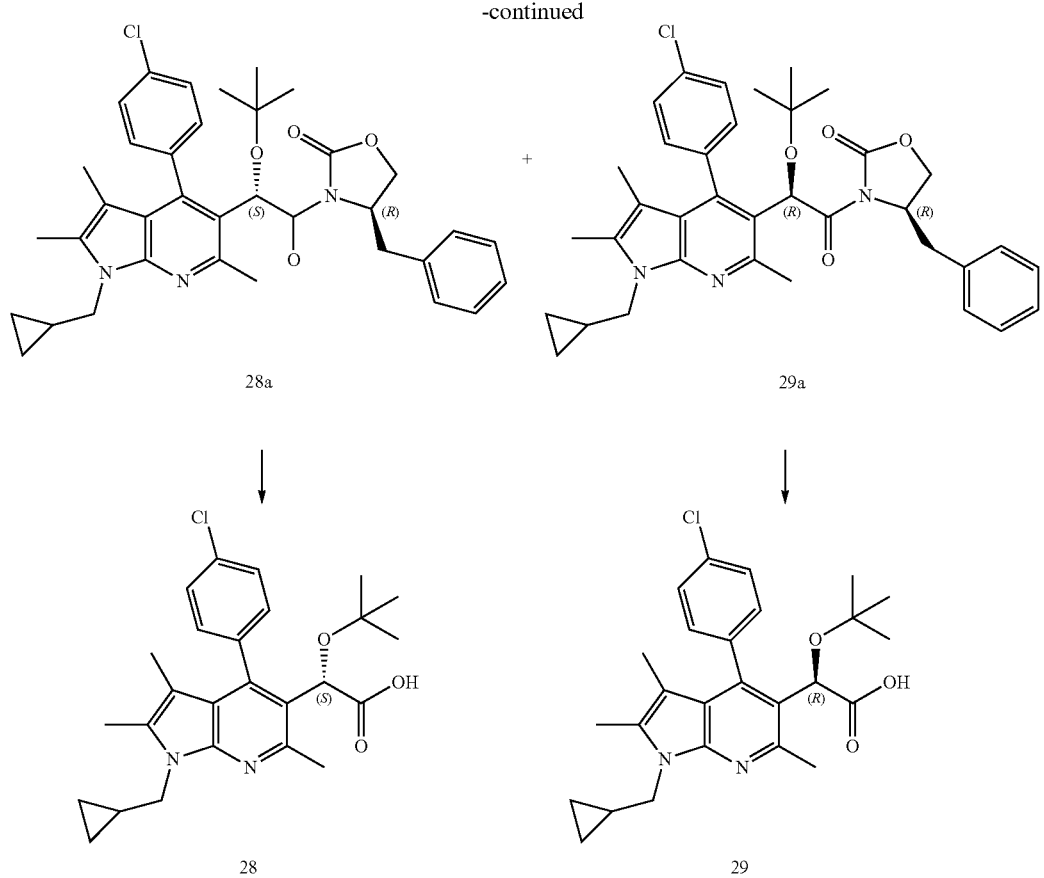

Step 1: Preparation of (R)-4-benzyl-3-((S)-2-tert-butoxy-2-(4-(4-chlorophenyl)-1-(cyclopropylmethyl)-2,3,6-trimethyl-1H-pyrrolo[2,3-b]pyridin-5-yl)acetyl)oxazolidin-2-one (28a) and (R)-4-benzyl-3-((R)-2-tert-butoxy-2-(4-(4-chlorophenyl)-1-(cyclopropylmethyl)-2,3,6-trimethyl-1H-pyrrolo[2,3-b]pyridin-5-yl)acetyl)oxazolidin-2-one (29a)

After a compound 4 (0.267 g, 0.589 mmol) was dissolved in dichloromethane (5 mL) and dimethylformamide (1 drop) was added thereto, the mixture was cooled to 0° C., and then oxalyl chloride (0.07 mL, 0.824 mmol) was slowly added thereto. The result was stirred for 30 minutes while slowly raising the temperature to room temperature, and then the result was concentrated under reduced pressure. In another flask, (R)-(+)-4-benzyl-2-oxazolidinone (0.313 g, 1.767 mmol) was dissolved in tetrahydrofuran (3 mL), and the mixture was cooled to −78° C. Normal-butyl lithium (2.5 M hexane solution) (0.8 mL, 2.06 mmol) was slowly added thereto under nitrogen atmosphere. After this solution was stirred for 30 minutes at −78° C., the above acid chloride, which was concentrated under reduced pressure, was dissolved in tetrahydrofuran (3 mL) and added to this solution. The result was stirred for 15 minutes at the same temperature, the temperature was raised to room temperature, and then the result was stirred for 30 minutes. A 20% aqueous ammonium chloride solution (3 mL) was added to the reaction material to terminate the reaction, water (10 mL) and ethyl acetate (20 mL) were added thereto, and the organic layer was separated. The aqueous layer was extracted with ethyl acetate (15 mL) once again, and the organic layers were combined, washed with salted water, dried with anhydrous magnesium sulfate, and concentrated under reduced pressure. The residue was separated using silica gel column chromatography (ethyl acetate/normal-hexane=1/4 or 1/6, 1% triethylamine) to give a mixture of 28a and 29a. The mixture was separated once again using silica gel column chromatography (dichloromethane/normal-hexane/acetone=50/50/1) to give 28a (part with strong polarity, 125 mg, 34%) and 29a (part with weak polarity, 122 mg, 34%).

28a: $^1$H-NMR (300 MHz, CDCl$_3$) δ 0.48 (m, 4H), 1.06 (s, 9H), 1.25 (m, 1H), 1.47 (s, 3H), 2.33 (s, 3H), 2.64 (m, 1H), 2.89 (s, 3H), 3.19 (m, 1H), 4.05-4.18 (m, 4H), 4.55 (m, 1H), 6.18 (s, 1H), 6.89 (d, 2H), 7.08 (m, 2H), 7.25 (m, 3H), 7.33 (m, 2H), 7.44 (m, 1H); MS (EI, m/e)=613 (M$^+$).

29a: $^1$H-NMR (300 MHz, CDCl$_3$) δ 0.50 (m, 4H), 1.16 (s, 9H), 1.25 (m, 1H), 1.44 (s, 3H), 2.31 (s, 3H), 2.76 (m, 1H), 2.91 (s, 3H), 3.26 (m, 1H), 4.05-4.13 (m, 4H), 4.39 (m, 1H), 6.12 (s, 1H), 7.16-7.40 (m, 9H); MS (EI, m/e)=613 (M$^+$).

Step 2: Preparation of (S)-2-tert-butoxy-2-(4-(4-chlorophenyl)-1-(cyclopropylmethyl)-2,3,6-trimethyl-1H-pyrrolo[2,3-b]pyridin-acid (28) and (R)-2-tert-butoxy-2-(4-(4-chlorophenyl)-1-(cyclopropylmethyl)-2,3,6-trimethyl-1H-pyrrolo[2,3-b]pyridin-5-yl)acetic acid (29)

After the compounds 28a and 29a (0.2 mmol) were each dissolved in tetrahydrofuran (2 mL) and water (1 mL), 30% hydrogen peroxide (0.085 mL) was added thereto, and then a lithium hydroxide hydrate (17 mg, 0.4 mmol) was subsequently added thereto. This solution was stirred for 2 hours at 0° C. A 10% aqueous sodium sulfite solution (0.4 mL) was added to the reaction material to terminate the reaction, and the result was stirred for 5 minutes. The reaction material was adjusted to pH 4 to 5 using a 1N aqueous hydrochloric acid solution, and extracted with dichloromethane (15 mL×3). The organic layer were combined, dried with anhydrous magnesium sulfate, and concentrated under reduced pressure. The residue was purified using silica gel column chromatography (dichloromethane/acetone=9/1 and dichloromethane/methanol=95/5) to separately give pure target compounds 28 (45% yield) and 29 (50% yield).

28: $^1$H-NMR (300 MHz, CD$_3$OD) δ 0.40 (m, 4H), 0.94 (s, 9H), 1.23 (m, 1H), 1.49 (s, 3H), 2.31 (s, 3H), 2.64 (s, 3H), 4.15 (m, 2H), 5.07 (s, 1H), 7.30 (m, 1H), 7.46 (m, 2H), 7.57 (m, 1H); MS (EI, m/e)=454 (M$^+$).

29: $^1$H-NMR (300 MHz, CD$_3$OD) δ 0.42 (m, 4H), 0.99 (s, 9H), 1.23 (m, 1H), 1.49 (s, 3H), 2.31 (s, 3H), 2.64 (s, 3H), 4.15 (m, 2H), 5.07 (s, 1H), 7.30 (m, 1H), 7.46 (m, 2H), 7.57 (m, 1H); MS (EI, m/e)=454 (M$^+$).

Example 30 and 31

(S)-2-Tert-butoxy-2-(4-(4-chlorophenyl)-1-(2-cyanoethyl)-2,3,6-trimethyl-1H-pyrrolo[2,3-b]pyridin-5-yl)acetic acid (30) and (R)-2-tert-butoxy-2-(4-(4-chlorophenyl)-1-(2-cyanoethyl)-2,3,6-trimethyl-1H-pyrrolo[2,3-b]pyridin-5-yl)acetic acid (31)

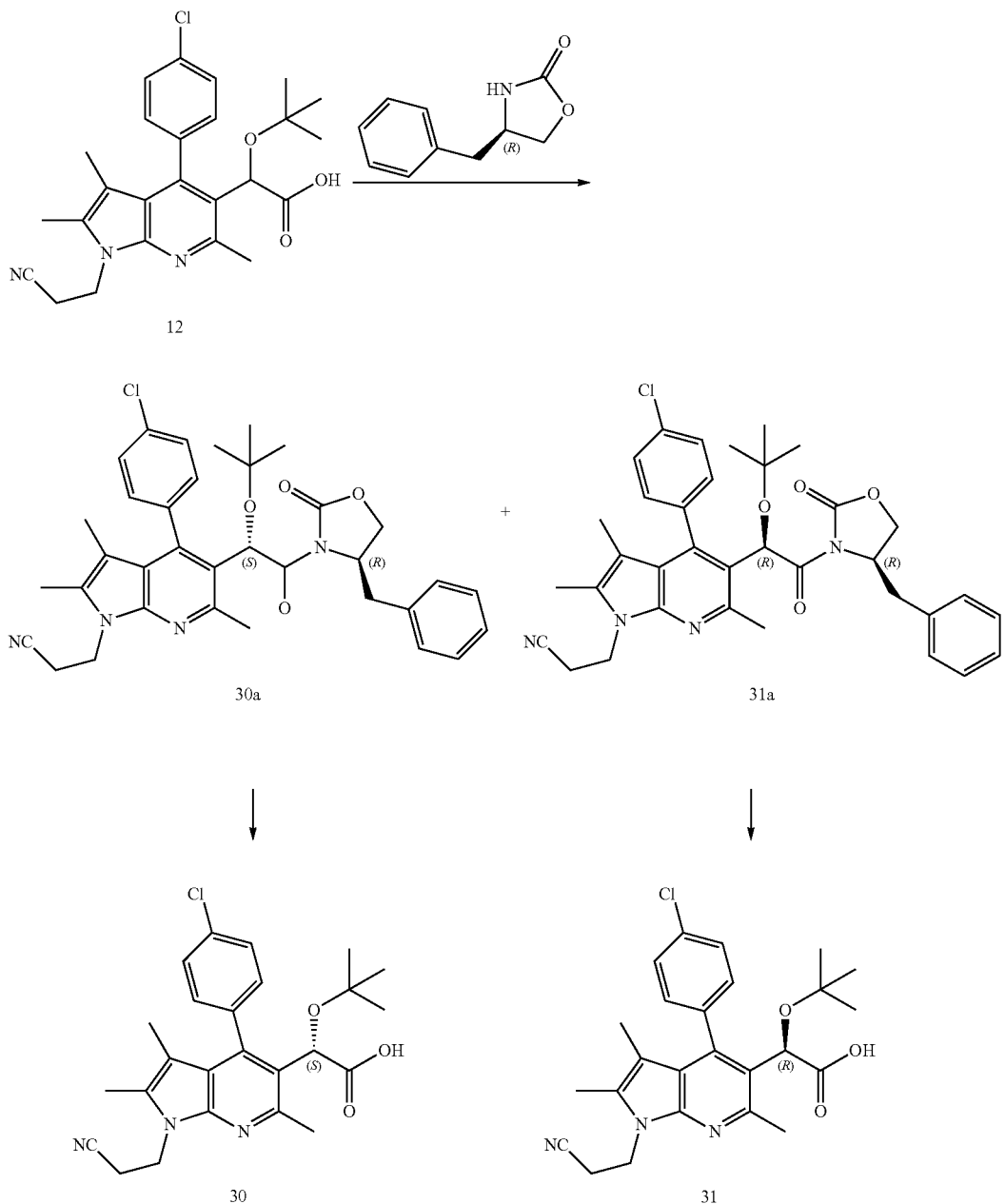

Step 1: Preparation of 3-(5-((S)-2-((R)-4-benzyl-2-oxazolidin-3-yl)-1-tert-butoxy-2-oxoethyl)-4-(4-chlorophenyl)-2,3,6-trimethyl-1H-pyrrolo[2,3-b]pyridin-1-yl)propanenitrile (30a) and 3-(5-((R)-2-((R)-4-benzyl-2-oxazolidin-3-yl)-1-tert-butoxy-2-oxoethyl)-4-(4-chlorophenyl)-2,3,6-trimethyl-1H-pyrrolo[2,3-b]pyridin-1-yl)propanenitrile (31a)

An (S)-isomer and (R)-isomer mixture obtained by reacting a compound 12 (720 mg, 1.588 mmol) in the same molar ratio as in Step 1 of Examples 28 and 29 was separated using silica gel column chromatography (ethyl acetate/normal-hexane=3/1) to give an (S)-isomer 30a (compound with weak polarity: 372 mg, 38%) and an (R)-isomer 31a (compound with strong polarity: 262 mg, 27%).

30a: $^1$H-NMR (300 MHz, CDCl$_3$) δ 1.06 (s, 9H), 1.46 (s, 3H), 2.35 (s, 3H), 2.64 (m, 1H), 2.89 (s, 3H), 2.97 (t, J=6 Hz, 2H), 3.27 (m, 1H), 4.06 (m, 2H), 4.27 (m, 3H), 6.18 (s, 1H), 6.89 (m, 1H), 7.12 (m, 2H), 7.25 (m, 3H), 7.33 (m, 2H), 7.47 (m, 1H); MS (EI, m/e)=612 (M$^+$).

31a: $^1$H-NMR (300 MHz, CDCl$_3$) δ 1.17 (s, 9H), 1.42 (s, 3H), 2.33 (s, 3H), 2.72-2.79 (m, 1H), 2.94 (s, 3H), 2.96 (t, J=7 Hz, 2H), 3.23 (m, 1H), 4.10 (m, 2H), 4.38-4.52 (m, 3H), 6.13 (s, 1H), 7.14-7.40 (m, 9H); MS (EI, m/e)=612 (M$^+$).

Step 2: Preparation of (S)-2-tert-butoxy-2-(4-(4-chlorophenyl)-1-(2-cyanoethyl)-2,3,6-trimethyl-1H-pyrrolo[2,3-b]pyridin-5-yl)acetic acid (30) and (R)-2-tert-butoxy-2-(4-(4-chlorophenyl)-1-(2-cyanoethyl)-2,3,6-trimethyl-1H-pyrrolo[2,3-b]pyridin-5-yl)acetic acid (31)

Target compounds (S)-isomer 30 (40 mg, 15%) and (R)-isomer 31 (169 mg, 88%) were separately obtained by separately reacting the (S)-isomer 30a (372 mg, 0.608 mmol) and the (R)-isomer 31a (230 mg, 0.372 mmol), respectively, in the same manner as in Step 2 of Examples 28 and 29.

30: $^1$H-NMR (500 MHz, CD$_3$OD) δ 0.88 (s, 9H), 1.45 (s, 3H), 2.30 (s, 3H), 2.62 (s, 3H), 2.89 (t, J=5 Hz, 2H), 4.46 (t, J=6 Hz, 2H), 5.01 (s, 1H), 7.23 (m, 1H), 7.42 (m, 2H), 7.54 (m, 1H); MS (EI, m/e)=453 (M$^+$).

31: $^1$H-NMR (500 MHz, CD$_3$OD) δ 0.97 (s, 9H), 1.52 (s, 3H), 2.37 (s, 3H), 2.69 (s, 3H), 2.97 (t, J=6 Hz, 2H), 4.54 (t, J=7 Hz, 2H), 5.11 (s, 1H), 7.30 (m, 1H), 7.51 (m, 2H), 7.58 (m, 1H); MS (EI, m/e)=453 (M$^+$).

Example 32 and 33

(S)-2-Tert-butoxy-2-(4-(4-chlorophenyl)-1-(ethyl)-2,3,6-trimethyl-1H-pyrrolo[2,3-b]pyridin-5-yl)acetic acid (32) and (R)-2-tert-butoxy-2-(4-(4-chlorophenyl)-1-(ethyl)-2,3,6-trimethyl-1H-pyrrolo[2,3-b]pyridin-5-yl)acetic acid (33)

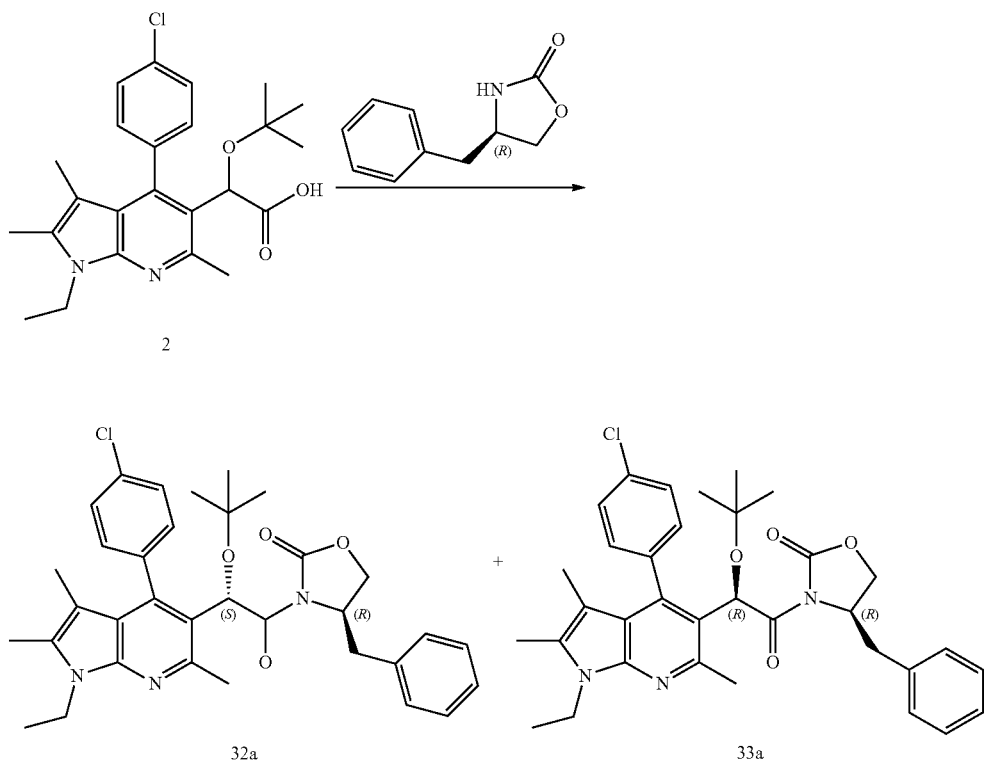

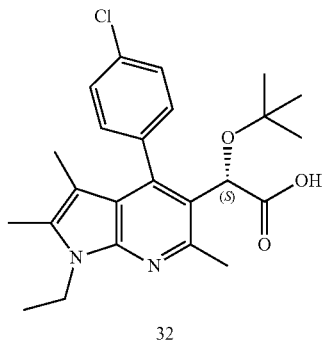

32

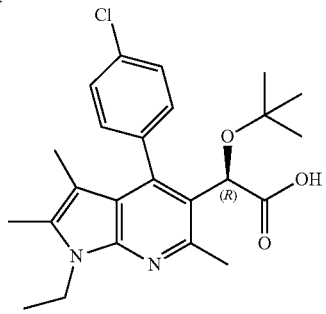

33

Step 1: Preparation of (R)-4-benzyl-3-((S)-2-tert-butoxy-2-(4-(4-chlorophenyl)-1-(ethyl)-2,3,6-trimethyl-1H-pyrrolo[2,3-b]pyridin-5-yl)acetyl)oxazolidin-2-one (32a) and (R-4-benzyl-3-((R)-2-tert-butoxy-2-(4-(4-chlorophenyl)-1-(ethyl)-2,3,6-trimethyl-1H-pyrrolo[2,3-b]pyridin-5-yl)acetyl) oxazolidin-2-one (33a)

An (S)-isomer and (R)-isomer mixture obtained by reacting the compound (250 mg, 0.708 mmol) of Example 2 in the same molar ratio as in Step 1 of Examples 28 and 29 was separated using silica gel column chromatography (ethyl acetate/normal-hexane=4/1) to give an (S)-isomer 32a (compound with weak polarity: 132 mg, 31.8%) and an (R)-isomer 33a (compound with strong polarity: 112 mg, 27%).

32a: $^1$H-NMR (300 MHz, CDCl$_3$) δ 1.06 (s, 9H), 1.35 (t, J=7.5 Hz, 3H), 1.46 (s, 3H), 2.29 (s, 3H), 2.62 (m, 1H), 2.91 (s, 3H), 3.23 (m, 1H), 4.05 (m, 1H), 4.14 (m, 1H), 4.27 (m, 2H), 4.56 (m, 1H), 6.18 (s, 1H), 6.91 (m, 1H), 7.11 (m, 2H), 7.25 (m, 3H), 7.33 (m, 2H), 7.45 (m, 1H); MS (EI, m/e)=587 (M$^+$).

33a: $^1$H-NMR (300 MHz, CDCl$_3$) δ 1.16 (s, 9H), 1.34 (t, J=7.5 Hz, 3H), 1.43 (s, 3H), 2.28 (s, 3H), 2.75 (m, 1H), 2.93 (s, 3H), 3.22 (m, 1H), 4.05 (m, 2H), 4.30 (m, 3H), 6.12 (s, 1H), 7.15-7.39 (m, 9H); MS (EI, m/e)=587 (M$^+$).

Step 2: Preparation of (S)-2-tert-butoxy-2-(4-(4-chlorophenyl)-1-(ethyl)-2,3,6-trimethyl-1H-pyrrolo[2,3-b]pyridin-5-yl)acetic acid (32) and (R)-2-tert-butoxy-2-(4-(4-chlorophenyl)-1-(ethyl)-2,3,6-trimethyl-1H-pyrrolo[2,3-b]pyridin-5-yl)acetic acid (33)

Target compound (S)-isomer 32 (31.5 mg, 30%) and (R)-isomer 33 (78 mg, 70%) were separately obtained by separately reacting the (S)-isomer 32a (132 mg, 0.224 mmol) and the (R)-isomer 33a (112 mg, 0.19 mmol), respectively, in the same manner as in Step 2 of Examples 28 and 29.

32: $^1$H-NMR (500 MHz, CD$_3$OD) δ 0.90 (s, 9H), 1.24 (t, J=7.25 Hz, 3H), 1.45 (s, 3H), 2.26 (s, 3H), 2.64 (s, 3H), 4.25 (q, J=7.25 Hz, 2H), 5.02 (s, 1H), 7.25 (d, J=9.5 Hz, 1H), 7.42 (m, 2H), 7.58 (d, J=9.5 Hz, 1H); MS (EI, m/e)=428 (M$^+$).

33: $^1$H-NMR (500 MHz, CD$_3$OD) δ 0.91 (s, 9H), 1.31 (t, J=7.25 Hz, 3H), 1.51 (s, 3H), 2.32 (s, 3H), 2.69 (s, 3H), 4.31 (q, J=7.25 Hz, 2H), 5.10 (s, 1H), 7.30 (d, J=9.5 Hz, 1H), 7.49 (m, 2H), 7.60 (d, J=9.5 Hz, 1H); MS (EI, m/e)=428 (M$^+$).

Example 34

(S)-2-Tert-butoxy-2-(4-(4-chlorophenyl)-1,6-dimethyl-1H-pyrrolo[2,3-b]pyridin-5-yl)acetic acid (34)

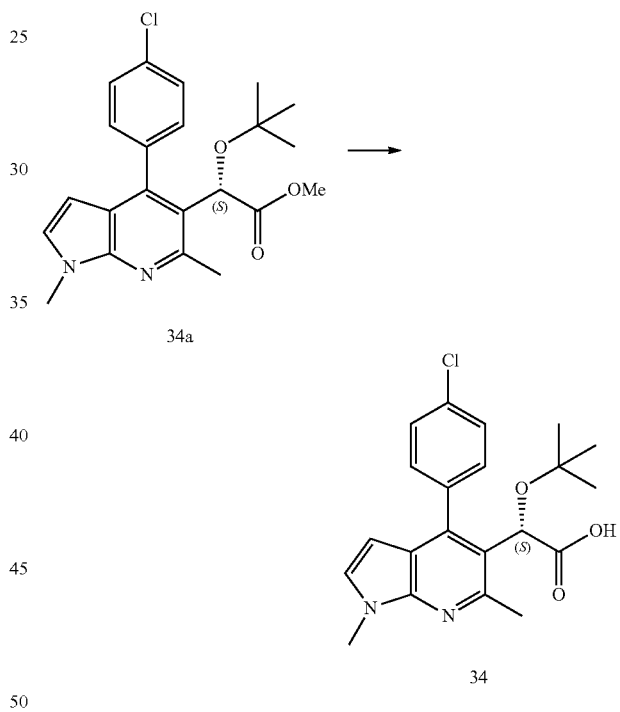

After (S)-methyl 2-tert-butoxy-2-(4-(4-chlorophenyl)-1,6-dimethyl-1H-pyrrolo[2,3-b]pyridin-5-yl)acetate 34a (350 mg, 0.87 mmol) was dissolved in tetrahydrofuran (7.4 mL), a 4N sodium hydroxide/methanol solution (1.48 mL) was added thereto, and the mixture was stirred at 18° C. until the starting material disappeared (18 hours). After the reaction was completed, the same amount of a 4N aqueous hydrochloric acid solution was added to neutralize the result, and the solvent was concentrated under reduced pressure and dried under a high vacuum. After a moderate amount of dichloromethane was added to the residue and the insoluble substances were removed by filtration, the result was concentrated under reduced pressure, and the residue was purified using silica gel column chromatography (dichloromethane/methanol=50/1) to give a pure target compound 34 (329 mg, 98%) in white solids.

¹H-NMR (300 MHz, CD₃OD) δ 0.87 (s, 9H), 2.73 (s, 3H), 3.85 (s, 3H), 5.23 (s, 1H), 6.05 (m, 1H), 7.17 (m, 1H), 7.47 (m, 3H), 7.83 (m, 1H); MS (EI, m/e)=386 (M⁺). [a]$_D^{20}$=+121 (c 0.01 MeOH)

Example 35

2-Tert-butoxy-2-(4-(4-chlorophenyl)-1-((2-chloro-6-methoxypyridin-4-yl)methyl)-2,3,6-trimethyl-1H-pyrrolo[2,3-b]pyridin-5-yl)acetic acid (35)

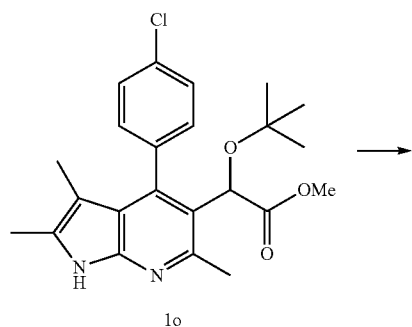

1o

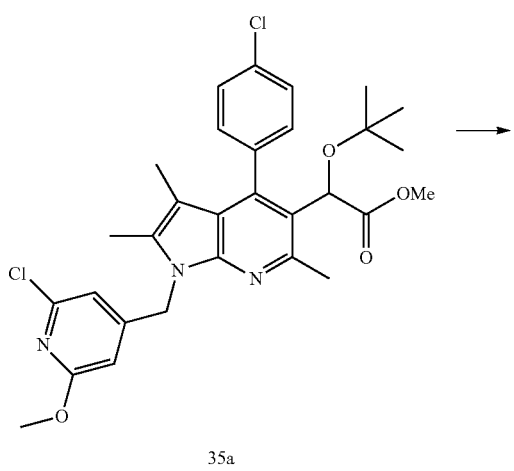

35a

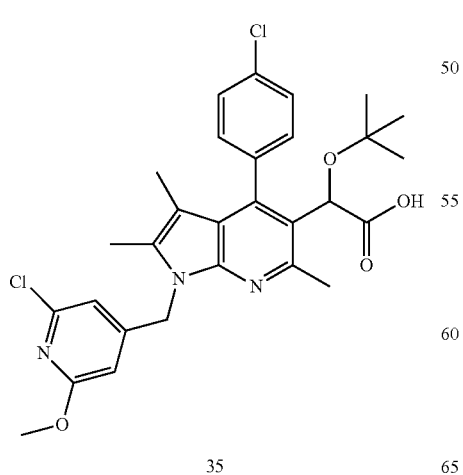

35

Step 1: Preparation of methyl 2-tert-butoxy-2-(4-(4-chlorophenyl)-1-((2-chloro-6-methoxypyridin-4-yl)methyl)-2,3,6-trimethyl-1H-pyrrolo[2,3-b]pyridin-5-yl)acetate (35a)

A target compound 35a (164 mg, 100%) was obtained by reacting the compound 1o (119 mg, 0.288 mmol) in the same manner as in Step 1 of Example 1, except that (2-chloro-6-methoxypyridin-4-yl)methyl-4-methylbenzenesulfonate (189 mg, 0.576 mmol) was used instead of iodomethyl and the stirring was carried out for 3 hours.

¹H-NMR (300 MHz, CDCl₃) δ 0.99 (s, 9H), 1.49 (s, 3H), 2.04 (s, 3H), 2.67 (s, 3H), 3.68 (s, 3H), 3.91 (s, 3H), 5.09 (s, 1H), 5.40 (s, 2H), 6.27 (s, 1H), 6.52 (s, 1H), 7.28 (m, 1H), 7.44 (m, 3H)); MS (EI, m/e)=570 (M⁺).

Step 2: Preparation of 2-tert-butoxy-2-(4-(4-chlorophenyl)-1-((2-chloro-6-methoxypyridin-4-yl)methyl)-2,3,6-trimethyl-1H-pyrrolo[2,3-b]pyridin-5-yl)acetic acid (35)

A pure target compound 35 (62 mg, 40%) was obtained in white solids by reacting the compound 35a (154 mg, 0.27 mmol) in the same manner as in Step 2 of Example 1 using the same solvents and reagents in the same ratio.

¹H-NMR (300 MHz, CD₃OD) δ 0.98 (s, 9H), 1.55 (s, 3H), 2.17 (s, 3H), 2.66 (s, 3H), 3.84 (s, 3H), 5.14 (s, 1H), 5.48 (s, 2H), 6.21 (s, 1H), 6.64 (s, 1H), 7.37 (d, J=9 Hz, 1H), 7.51 (m, 2H), 7.60 (d, J=9 Hz, 1H); MS (EI, m/e)=556 (M⁺).

Example 36

(S)-2-Tert-butoxy-2-(4-(4-chlorophenyl)-1-(pyridin-4-ylmethyl)-2,3,6-trimethyl-1H-pyrrolo[2,3-b]pyridin-5-yl)acetic acid (36)

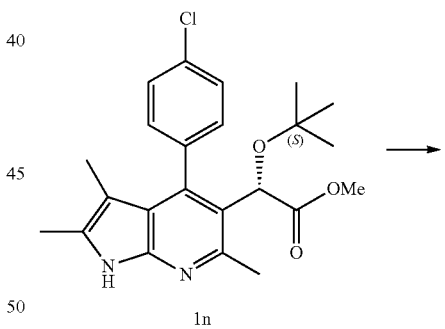

1n

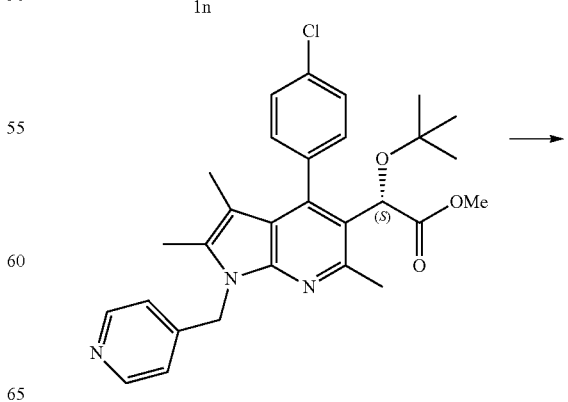

36a

97
-continued

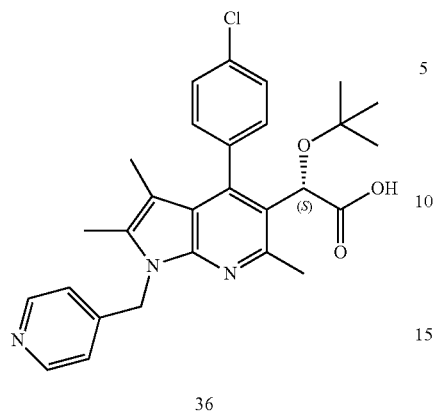

36

Step 1: Preparation of (S)-methyl 2-tert-butoxy-2-(4-(4-chlorophenyl)-1-(pyridin-4-ylmethyl)-2,3,6-trimethyl-1H-pyrrolo[2,3-b]pyridin-5-yl)acetate (36a)

A target compound 36a (164 mg, 100%) was obtained by reacting the compound 1n (200 mg, 0.482 mmol) in the same manner as in Step 1 of Example 1, except that (2-chloro-6-methoxypyridin-4-yl)methyl-4-methylbenzenesulfonate (189 mg, 0.576 mmol) was used instead of iodomethyl and the stirring was carried out for 3 hours.

$^1$H-NMR (300 MHz, CDCl$_3$) δ 1.02 (s, 9H), 1.52 (s, 3H), 2.15 (s, 3H), 2.70 (s, 3H), 3.71 (s, 3H), 5.13 (s, 1H), 5.50 (m, 2H), 7.04 (d, J=6 Hz, 2H), 7.30 (m, 1H), 7.44-7.52 (m, 3H), 8.54 (d, J=6 Hz, 2H); MS (EI, m/e)=505 (M$^+$).

Step 2: Preparation of (S)-2-tert-butoxy-2-(4-(4-chlorophenyl)-1-(pyridin-4-ylmethyl)-2,3,6-trimethyl-1H-pyrrolo[2,3-b]pyridin-5-yl)acetic acid (36)

After the compound 36a (160 mg, 0.316 mmol) was dissolved in tetrahydrofuran/methanol/water=2 mL/2 mL/1 mL, lithium chloride (20 mg, 0.835 mmol) was added thereto, and the mixture was stirred for 18 hours at 45° C. The reaction material was cooled to room temperature, and adjusted to pH 4.0 using a 2N aqueous hydrochloric acid solution. After the reaction material was concentrated under reduced pressure and water was completely dried under a high vacuum, the result was separated and purified using silica gel column chromatography (dichloromethane/methanol=95/5) to give a target compound 36 (117.7 mg, 75%) in a solid state.

$^1$H-NMR (300 MHz, CD$_3$OD) δ 0.96 (s, 9H), 1.54 (s, 3H), 2.16 (s, 3H), 2.64 (s, 3H), 5.11 (s, 1H), 5.58 (m, 2H), 7.03 (m, 2H), 7.34 (m, 1H), 7.51 (m, 2H), 7.64 (m, 1H), 8.41 (m, 2H); MS (EI, m/e)=491 (M$^+$). [a]$_D^{20}$=+123.4 (c 0.01 MeOH)

98
Example 37

2-Tert-butoxy-2-(1-ethyl-2,3,6-trimethyl-4-phenyl-1H-pyrrolo[2,3-b]pyridin-5-yl)acetic acid (37)

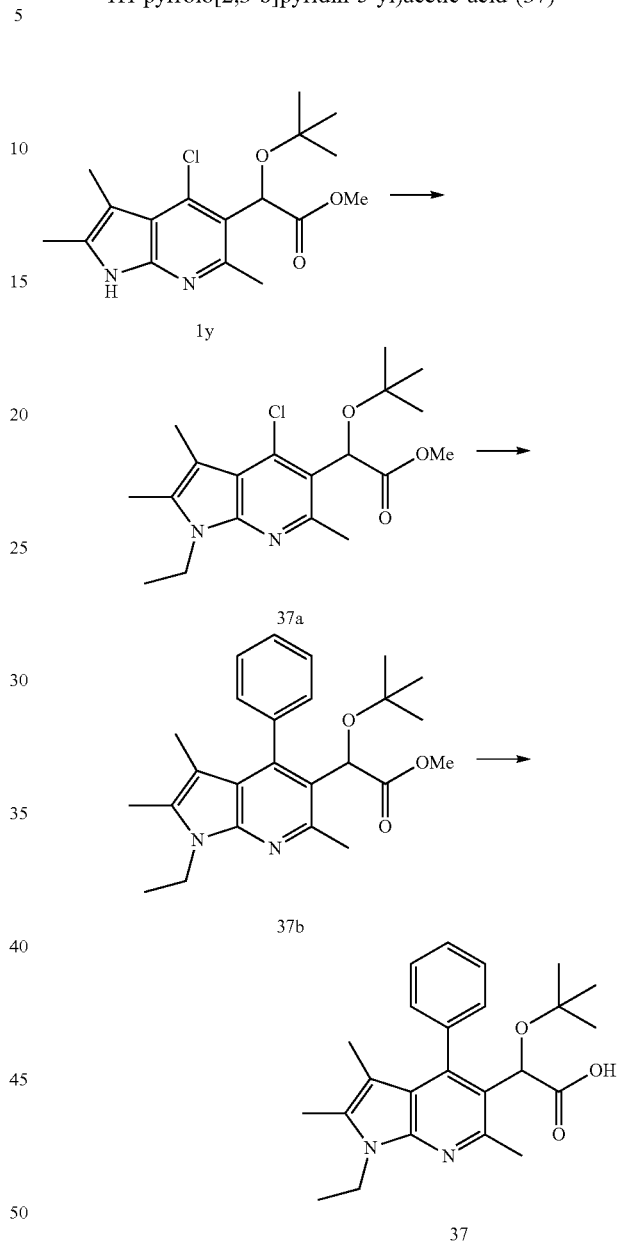

Step 1: Preparation of methyl 2-tert-butoxy-2-(1-ethyl-2,3,6-trimethyl-4-phenyl-1H-pyrrolo[2,3-b]pyridin-5-yl)acetate (37a)

A target compound 37a (1.52 g, 83%) was obtained by reacting the intermediate 1y (1.70 g, 5 mmol) synthesized in Preparation Example 3 in the same manner as in Step 1 of Example 1, except that iodoethyl (2.5 equivalents) was used instead of iodomethyl.

$^1$H-NMR (300 MHz, CDCl$_3$) δ 0.98 (s, 9H), 1.35 (t, J=7.11 Hz, 3H), 1.47 (s, 3H), 2.23 (s, 3H), 2.71 (s, 3H), 3.67 (s, 3H), 4.26 (q, J=7.11 Hz, 2H), 5.06 (s, 1H); MS (EI, m/e)=366 (M$^+$).

Step 2: Preparation of methyl 2-tert-butoxy-2-(1-ethyl-2,3,6-trimethyl-4-phenyl-1H-pyrrolo[2,3-b]pyridin-5-yl)acetate (37b)

After the compound 37a (400 mg, 1.09 mmol) was dissolved in dimethylacetamide (10.9 mL) and water (1.09 ml), phenylboronic acid (200 mg, 1.64 mmol), sodium bicarbonate (458 mg, 5.45 mmol) and bis(tri-tertbutylphosphine)palladium(0) (56 mg, 0.109 mmol) were added thereto, and the mixture was heated to 130° C. under nitrogen and then stirred for 16 hours. After the reaction material was cooled to room temperature and filtered through a celite pad, the filtrate was concentrated under reduced pressure and the residue was purified using silica gel column chromatography (normal-hexane/ethyl acetate=8/1 and 4/1) to give a target compound 37a (280 mg, 63%).
$^1$H-NMR (300 MHz, CDCl$_3$) δ 0.96 (s, 9H), 1.36 (t, J=6 Hz, 3H), 1.46 (s, 3H), 2.28 (s, 3H), 2.72 (s, 3H), 3.66 (s, 3H), 4.29 (q, J=6 Hz, 2H), 5.15 (s, 1H), 7.28 (m, 1H), 7.38-7.50 (m, 4H); MS (EI, m/e)=408 (M$^+$).

Step 3: Preparation of 2-tert-butoxy-2-(1-ethyl-2,3,6-trimethyl-4-phenyl-1H-pyrrolo[2,3-b]pyridin-5-yl)acetic acid (37)

A pure target compound 37 (173 mg, 66%) was obtained in white solids by reacting the compound 37b (270 mg, 0.66 mmol) in the same manner as in Step 2 of Example 1 using the same solvents and reagents in the same ratio.
$^1$H-NMR (300 MHz, CD$_3$OD) δ 0.94 (s, 9H), 1.30 (t, J=7.5 Hz, 3H), 1.47 (s, 3H), 2.31 (s, 3H), 2.67 (s, 3H), 4.30 (q, J=7.5 Hz, 2H), 5.17 (s, 1H), 7.31 (m, 1H), 7.47 (m, 3H), 7.58 (m, 1H); MS (EI, m/e)=394 (M$^+$).

Example 38

2-Tert-butoxy-2-(1-ethyl-2,3,6-trimethyl-4-(para-tolyl)-1H-pyrrolo[2,3-b]pyridin-5-yl)acetic acid (38)

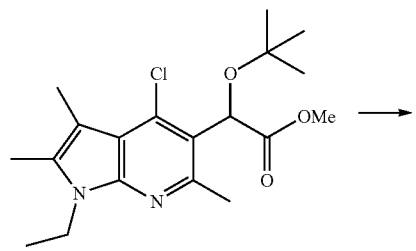

37a

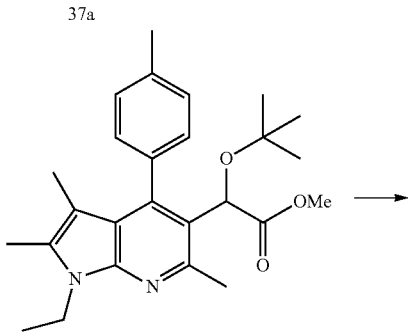

38a

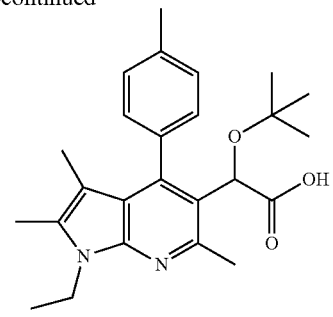

38

Step 1: Preparation of methyl 2-tert-butoxy-2-(1-ethyl-2,3,6-trimethyl-4-(para-tolyl)-1H-pyrrolo[2,3-b]pyridin-5-yl)acetate (38a)

After the compound 37a (380 mg, 1.03 mmol) was dissolved in dimethylacetamide (10.3 mL) and water (1.03 ml), para-tolylboronic acid (210 mg, 1.55 mmol), sodium bicarbonate (433 mg, 5.15 mmol) and bis(tri-tertbutylphosphine)palladium(0) (53 mg, 0.103 mmol) were added thereto, and the mixture was heated to 130° C. under nitrogen and then stirred for 16 hours. After the reaction solution was cooled to room temperature and filtered through a celite pad, the filtrate was concentrated under reduced pressure and the residue was purified using silica gel column chromatography (normal-hexane/ethyl acetate=10/1 and 5/1) to give a target compound 38a (382 mg, 88%).
$^1$H-NMR (300 MHz, CDCl$_3$) δ 0.96 (s, 9H), 1.36 (t, J=6 Hz, 3H), 1.46 (s, 3H), 2.28 (s, 3H), 2.72 (s, 3H), 3.66 (s, 3H), 4.29 (q, J=6 Hz, 2H), 5.15 (s, 1H), 7.28 (m, 1H), 7.38-7.50 (m, 4H); MS (EI, m/e)=408 (M$^+$).

Step 2: Preparation of 2-tert-butoxy-2-(1-ethyl-2,3,6-trimethyl-4-(para-tolyl)-1H-pyrrolo[2,3-b]pyridin-5-yl)acetic acid (38)

A pure target compound 38 (226 mg, 63.6%) was obtained in white solids by reacting the compound 38a (370 mg, 0.87 mmol) in the same manner as in Step 2 of Example 1 using the same solvents and reagents in the same ratio.
$^1$H-NMR (300 MHz, CD$_3$OD) δ 0.96 (s, 9H), 1.31 (t, J=7.5 Hz, 3H), 1.50 (s, 3H), 2.23 (s, 3H), 2.46 (s, 3H), 2.68 (s, 3H), 4.31 (q, J=7.5 Hz, 2H), 5.22 (s, 1H), 7.20 (d, J=9 Hz, 1H), 7.31 (m, 2H), 7.46 (d, J=9 Hz, 1H); MS (EI, m/e)-408 (M$^+$).

Example 39

2-Tert-butoxy-2-(1-ethyl-4-(4-fluorophenyl)-2,3,6-trimethyl-1H-pyrrolo[2,3-b]pyridin-5-yl)acetic acid (39)

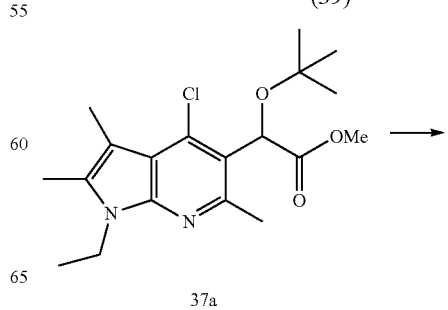

37a

101

-continued

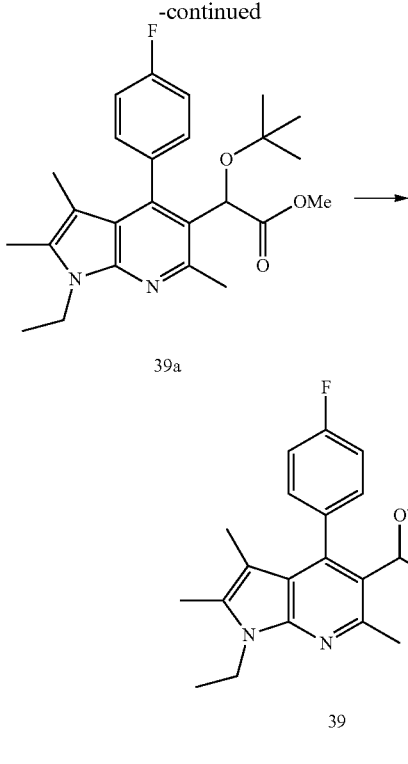

39a

39

Step 1: Preparation of methyl 2-tert-butoxy-2-(1-ethyl-4-(4-fluorophenyl)-2,3,6-trimethyl-1H-pyrrolo[2,3-b]pyridin-5-yl)acetate (39a)

After the compound 37a (450 mg, 1.03 mmol) was dissolved in dimethylacetamide (12.2 mL) and water (1.22 ml), 4-fluorophenylboronic acid (256 mg, 1.83 mmol), sodium bicarbonate (512 mg, 6.1 mmol) and bis(tri-tertbutylphosphine)palladium(0) (62.3 mg, 0.122 mmol) were added thereto, and the mixture was heated to 130° C. under nitrogen and then stirred for 6 hours. After the reaction material was cooled to room temperature and filtered through a celite pad, the filtrate was concentrated under reduced pressure and the residue was purified using silica gel column chromatography (normal-hexane/ethyl acetate=10/1 and 7/1) to give a target compound 39a (324 mg, 62%).

$^1$H-NMR (300 MHz, CDCl$_3$) δ 0.97 (s, 9H), 1.35 (t, J=6 Hz, 3H), 1.48 (s, 3H), 2.21 (s, 3H), 2.64 (s, 3H), 3.66 (s, 1H), 4.28 (q, J=7.5 Hz, 2H), 5.11 (s, 1H), 7.09-7.17 (m, 2H), 7.25 (m, 1H), 7.48 (m, 1H); MS (EI, m/e)=426 (M$^+$).

Step 2: Preparation of 2-tert-butoxy-2-(1-ethyl-4-(4-fluorophenyl)-2,3,6-trimethyl-1H-pyrrolo[2,3-b]pyridin-5-yl)acetic acid (39)

A pure target compound 39 (227 mg, 75%) was obtained in white solids by reacting the compound 39a (314 mg, 0.736 mmol) in the same manner as in Step 2 of Example 1 using the same solvents and reagents in the same ratio.

$^1$H-NMR (300 MHz, CD$_3$OD) δ 0.98 (s, 9H), 1.31 (t, J=7.5 Hz, 3H), 1.52 (s, 3H), 2.33 (s, H), 2.69 (s, 3H), 4.32 (q, J=7.5 Hz, 2H), 5.15 (s, 1H), 7.23 (m, 2H), 7.33 (m, 1H), 7.61 (m, 1H); MS (EI, m/e)=412 (M$^+$).

102

Example 40

2-Tert-butoxy-2-(4-(4-cyanophenyl)-1-ethyl-2,3,6-trimethyl-1H-pyrrolo[2,3-b]pyridin-5-yl)acetic acid (40)

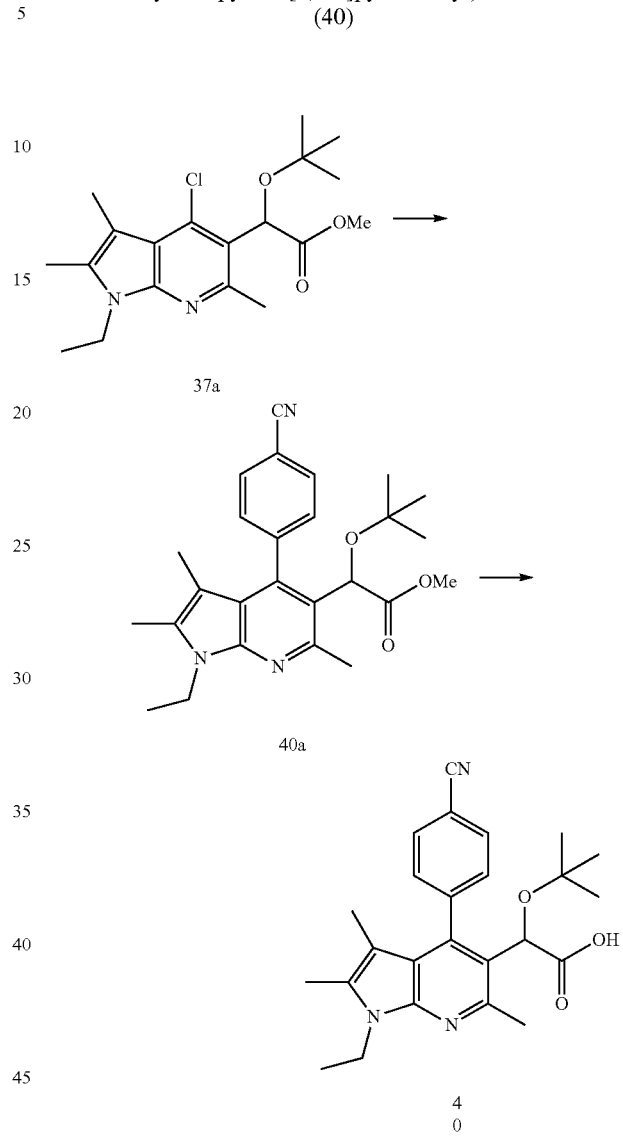

37a

40a

40

Step 1: Preparation of methyl 2-tert-butoxy-2-(4-(4-cyanophenyl)-1-ethyl-2,3,6-trimethyl-1H-pyrrolo[2,3-b]pyridin-5-yl)acetate (40a)

After the compound 37a (450 mg, 1.03 mmol) was dissolved in dimethylacetamide (12.2 mL) and water (1.22 ml), 4-cyanophenylboronic acid (420 mg, 1.83 mmol), sodium bicarbonate (512 mg, 6.1 mmol) and bis(tri-tertbutylphosphine)palladium(0) (62.3 mg, 0.122 mmol) were added thereto, and the mixture was heated to 130° C. under nitrogen and then stirred for 6 hours. After the reaction material was cooled to room temperature and filtered through a celite pad, the filtrate was concentrated under reduced pressure and the residue was purified using silica gel column chromatography (normal-hexane/ethyl acetate=10/1 and 7/1) to give a target compound 40a (227 mg, 43%).

¹H-NMR (300 MHz, CDCl₃) δ 0.99 (s, 9H), 1.34 (t, J=10.5 Hz, 3H), 1.45 (s, 3H), 2.31 (s, 3H), 2.74 (s, 3H), 3.68 (s, 3H), 4.32 (q, J=10.5 Hz, 2H), 4.99 (s, 1H), 7.43 (d, J=9 Hz 1H), 7.68 (d, J=6 Hz 1H), 7.61 (m, 2H); MS (EI, m/e)=433 (M⁺).

Step 2: Preparation of 2-tert-butoxy-2-(4-(4-cyano-phenyl)-1-ethyl-2,3,6-trimethyl-1H-pyrrolo[2,3-b]pyridin-5-yl)acetic acid (40)

A pure target compound 40 (164 mg, 76.6%) was obtained in white solids by reacting the compound 40a (222 mg, 0.512 mmol) in the same manner as in Step 2 of Example 1 using the same solvents and reagents in the same ratio.

¹H-NMR (300 MHz, CD₃OD) δ 0.96 (s, 9H), 1.29 (t, J=7.5 Hz, 3H), 1.45 (s, 3H), 2.31 (s, 3H), 2.69 (s, 3H), 4.30 (q, J=7.5 Hz, 2H), 5.01 (s, 1H), 7.50 (d, J=9 Hz, 1H), 7.76 (d, J=9 Hz, 1H), 7.85 (m, 2H); MS (EI, m/e)=419 (M⁺).

Example 41

2-(Tert-butoxy)-2-(1-ethyl-4-(4-methoxyphenyl)-2,3,6-trimethyl-1H-pyrrolo[2,3-b]pyridin-5-yl)acetic acid (41)

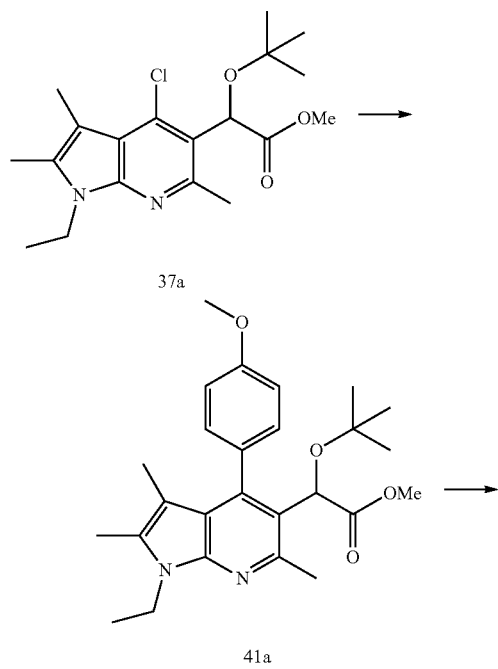

Step 1: Preparation of methyl 2-(tert-butoxy)-2-(1-ethyl-4-(4-methoxyphenyl)-2,3,6-trimethyl-1H-pyrrolo[2,3-b]pyridin-5-yl)acetate (41a)

After the compound 37a (440 mg, 1.03 mmol) was dissolved in dimethylacetamide (11.9 mL) and water (1.19 ml), 4-methoxyphenylboronic acid (270 mg, 1.79 mmol), sodium bicarbonate (500 mg, 5.95 mmol) and bis(tri-tert-butylphosphine)palladium(0) (61 mg, 0.119 mmol) were added thereto, and the mixture was heated to 130° C. under nitrogen and then stirred for 6 hours. After the reaction material was cooled to room temperature and filtered through a celite pad, the filtrate was concentrated under reduced pressure and the residue was purified using silica gel column chromatography (normal-hexane/ethyl acetate=10/1 and 5/1) to give a target compound 41a (316 mg, 61%).

¹H-NMR (300 MHz, CDCl₃) δ 0.99 (s, 9H), 1.37 (t, J=7.5 Hz, 3H), 1.61 (s, 3H), 2.31 (s, 3H), 2.72 (s, 3H), 3.69 (s, 3H), 3.92 (s, 3H), 4.31 (q, J=7.5 Hz, 2H), 5.23 (s, 1H), 6.96-7.01 (m, 2H), 7.21 (d, J=10 Hz, 1H), 7.49 (d, J=10 Hz, 1H); MS (EI, m/e)=438 (M⁺).

Step 2: Preparation of 2-(tert-butoxy)-2-(1-ethyl-4-(4-methoxyphenyl)-2,3,6-trimethyl-1H-pyrrolo[2,3-b]pyridin-5-yl)acetic acid (41)

A pure target compound 41 (257 mg, 85.6%) was obtained in white solids by reacting the compound 41a (310 mg, 0.707 mmol) in the same manner as in Step 2 of Example 1 using the same solvents and reagents in the same ratio.

¹H-NMR (300 MHz, CD₃OD) δ 0.95 (s, 9H), 1.29 (t, J=7.5 Hz, 3H), 1.52 (s, 3H), 2.31 (s, 3H), 2.66 (s, 3H), 3.87 (s, 3H), 4.29 (q, J=7.5 Hz, 2H), 5.24 (s, 1H), 7.00 (m, 2H), 7.21 (d, J=9 Hz, 1H), 7.49 (d, J=9 Hz, 1H); MS (EI, m/e)=424 (M⁺).

Example 42

(S)-2-(Tert-butoxy)-2-(4-(4-chlorophenyl)-2,3,6-trimethyl-1-(thiophen-2-ylmethyl)-1H-pyrrolo[2,3-b]pyridin-5-yl)acetic acid (42)

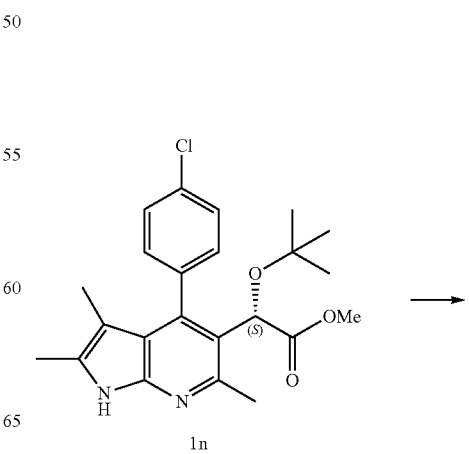

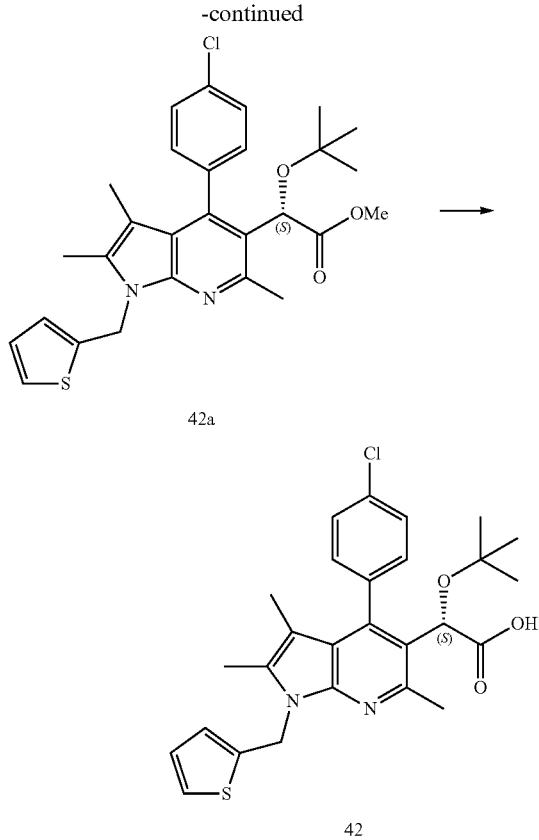

42a

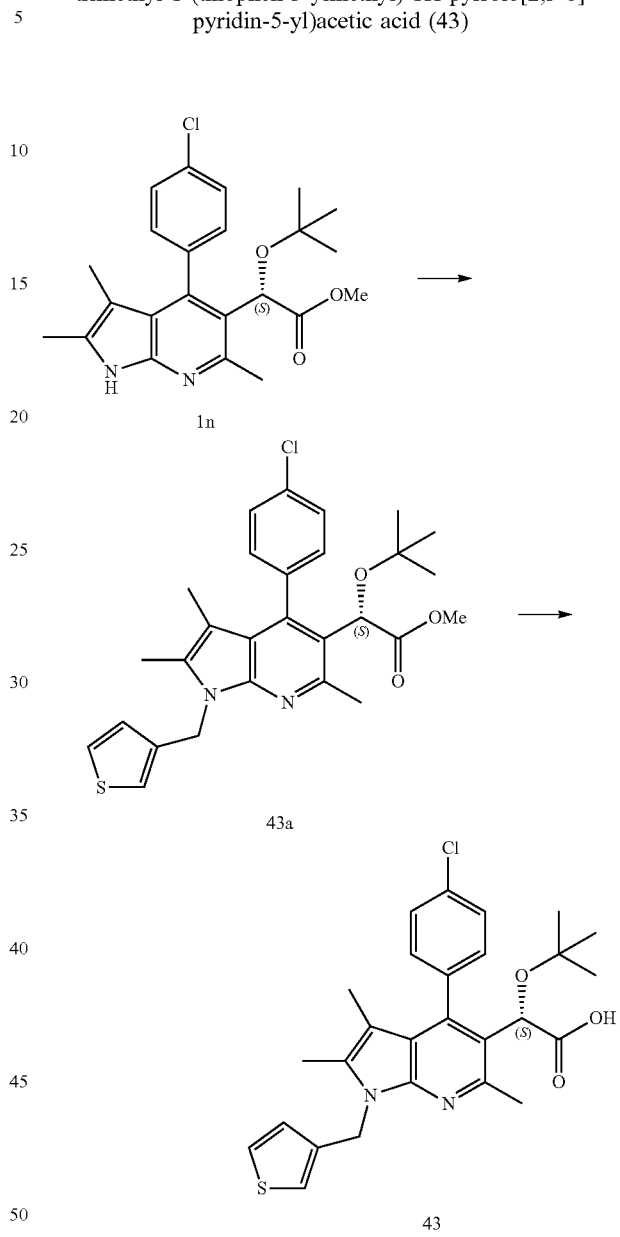

42

Step 1: Preparation of (S)-methyl 2-(tert-butoxy)-2-(4-(4-chlorophenyl)-2,3,6-trimethyl-1-(thiophen-2-ylmethyl)-1H-pyrrolo[2,3-b]pyridin-5-yl)acetate (42a)

A target compound 42a (125 mg, 51%) was obtained by reacting the compound 1n (200 mg, 0.482 mmol) in the same manner as in Step 1 of Example 1, except that 2-(bromomethyl)thiophene (170 mg, 0.964 mmol) was used instead of iodomethyl and the stirring was carried out for 3 hours.

$^1$H-NMR (300 MHz, CDCl$_3$) δ 0.98 (s, 9H), 1.47 (s, 3H), 2.28 (s, 3H), 2.72 (s, 3H), 3.66 (s, 3H), 5.08 (s, 1H), 5.59 (m, 2H), 6.90-6.96 (m, 2H), 7.15 (m, 1H), 7.24 (m, 1H), 7.38-7.44 (m, 3H)); MS (EI, m/e)=510 (M$^+$).

Step 2: Preparation of (S)-2-(tert-butoxy)-2-(4-(4-chlorophenyl)-2,3,6-trimethyl-1-(thiophen-2-ylmethyl)-1H-pyrrolo[2,3-b]pyridin-5-yl)acetic acid (42)

A pure target compound 42 (89.8 mg, 78%) was obtained in white solids by reacting the compound 42a (119 mg, 0.232 mmol) in the same manner as in Step 2 of Example 1 using the same solvents and reagents in the same ratio.

$^1$H-NMR (300 MHz, CD$_3$OD) δ 0.96 (s, 9H), 1.50 (s, 3H), 2.27 (s, 3H), 2.70 (s, 3H), 5.09 (s, 1H), 5.65 (s, 2H), 6.89 (m, 2H), 7.15 (m, 1H), 7.21 (m, 1H), 7.30 (m, 1H), 7.50 (m, 2H)), 7.63 (m, 1H): MS (EI, m/e)=496 (M$^+$): [a]$_D^{20}$=+183 (c 0.01 MeOH)

Example 43

(S)-2-(Tert-butoxy)-2-(4-(4-chlorophenyl)-2,3,6-trimethyl-1-(thiophen-3-ylmethyl)-1H-pyrrolo[2,3-b]pyridin-5-yl)acetic acid (43)

Step 1: Preparation of (S)-methyl 2-(tert-butoxy)-2-(4-(4-chlorophenyl)-2,3,6-trimethyl-1-(thiophen-3-ylmethyl)-1H-pyrrolo[2,3-b]pyridin-5-yl)acetate (43a)

A target compound 43a (166 mg, 67%) was obtained by reacting the compound 1n (200 mg, 0.482 mmol) in the same manner as in Step 1 of Example 1, except that 3-(bromomethyl)thiophene (170 mg, 0.964 mmol) was used instead of iodomethyl and the stirring was carried out for 3 hours.

$^1$H-NMR (300 MHz, CDCl$_3$) δ 0.99 (s, 9H), 1.47 (s, 3H), 2.21 (s, 3H), 2.71 (s, 3H), 3.67 (s, 3H), 5.09 (s, 1H), 5.51 (m, 2H), 7.00 (m, 2H), 7.23 (m, 2H), 7.39-7.48 (m, 3H)); MS (EI, m/e)=511 (M$^+$).

Step 2: Preparation of (S)-2-(tert-butoxy)-2-(4-(4-chlorophenyl)-2,3,6-trimethyl-1-(thiophen-3-ylmethyl)-1H-pyrrolo[2,3-b]pyridin-5-yl)acetic acid (43)

A pure target compound 43 (129.3 mg, 83%) was obtained in white solids by reacting the compound 43a (160 mg, 0.313 mmol) in the same manner as in Step 2 of Example 1 using the same solvents and reagents in the same ratio.

$^1$H-NMR (300 MHz, CD$_3$OD) δ 0.98 (s, 9H), 1.51 (s, 3H), 2.22 (s, 3H), 2.68 (s, 3H), 5.13 (s, 1H), 5.50 (m, 2H), 6.87-6.94 (m, 2H), 7.30-7.34 (m, 2H), 7.48-7.52 (m, 2H)), 7.59 (m, 1H); MS (EI, m/e)=497 (M$^+$). [a]$_D^{20}$=+255.7 (c 0.01 MeOH)

Example 44

(S)-2-(Tert-butoxy)-2-(4-(4-chlorophenyl)-1-(furan-2-ylmethyl)-2,3,6-trimethyl-1H-pyrrolo[2,3-b]pyridin-5-yl)acetic acid (44)

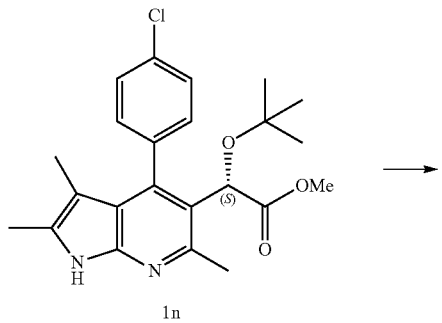

1n

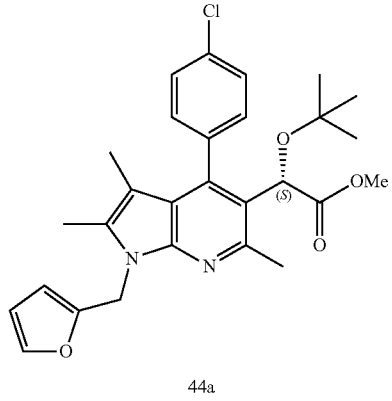

44a

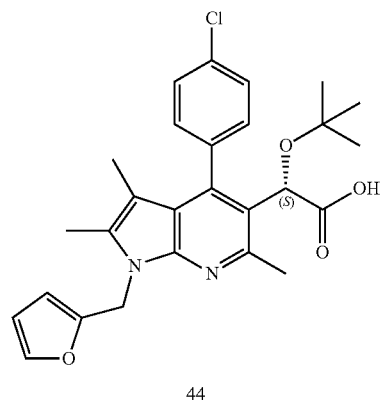

44

Step 1: Preparation of (S)-methyl 2-(tert-butoxy)-2-(4-(4-chlorophenyl)-1-(furan-2-ylmethyl)-2,3,6-trimethyl-1H-pyrrolo[2,3-b]pyridin-5-yl)acetate (44a)

A target compound 44a (73 mg, 31%) was obtained by reacting the compound 1n (200 mg, 0.482 mmol) in the same manner as in Step 1 of Example 1, except that 2-(bromomethyl)furan (155 mg, 0.962 mmol) was used instead of iodomethyl and the stirring was carried out for 3 hours.

$^1$H-NMR (300 MHz, CDCl$_3$) δ0.97 (s, 9H), 1.47 (s, 3H), 2.30 (s, 3H), 2.71 (s, 3H), 3.66 (s, 3H), 5.07 (s, 1H), 5.40 (m, 2H), 7.22 (m, 1H), 7.31 (m, 1H), 7.40 (m, 3H); MS (EI, m/e)=494 (M$^+$)

Step 2: Preparation of (S)-2-(tert-butoxy)-2-(4-(4-chlorophenyl)-1-(furan-2-ylmethyl)-2,3,6-trimethyl-1H-pyrrolo[2,3-b]pyridin-5-yl)acetic acid (44)

A pure target compound 44 (49.2 mg, 72.7%) was obtained in white solids by reacting the compound 44a (68 mg, 0.141 mmol) in the same manner as in Step 2 of Example 36 using the same solvents and reagents in the same ratio.

$^1$H-NMR (300 MHz, CD$_3$OD) δ 0.99 (s, 9H), 1.53 (s, 3H), 2.33 (s, 3H), 2.71 (s, 3H), 5.49 (s, 2H), 6.14 (s, 1H), 7.34 (m, 2H), 7.52 (m, 2H), 7.60 (m, 1H); MS (EI, m/e)=480 (M$^+$). [a]$_D^{20}$=+243.7 (c 0.01 MeOH)

Example 45

(S)-2-(1-((1H-pyrazol-3-yl)methyl)-4-(4-chlorophenyl)-2,3,6-trimethyl-1H-pyrrolo[2,3-b]pyridin-5-yl)-2-(tert-butoxy)acetic acid (45)

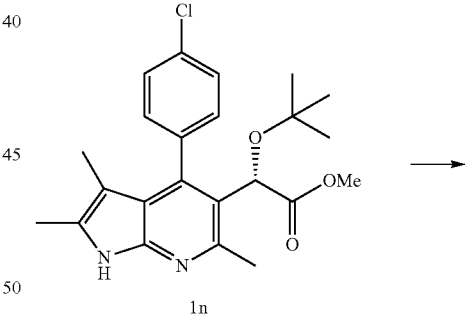

1n

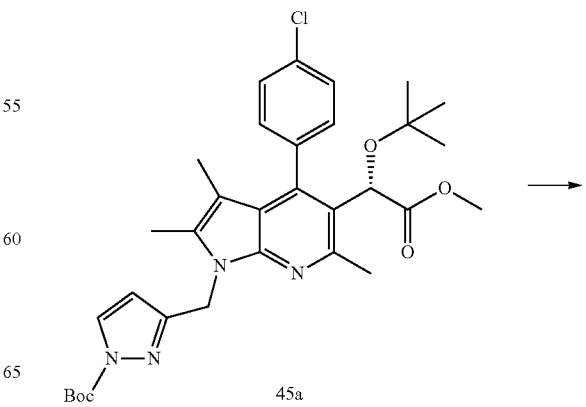

45a

-continued

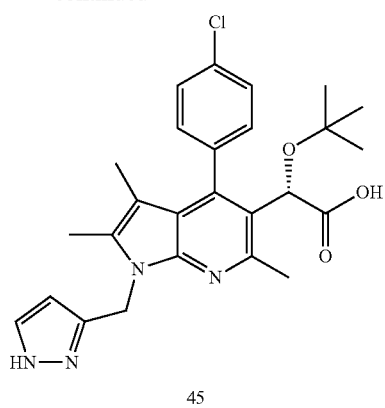

45

Preparation of tert-butyl 3-(bromomethyl)-1H-pyrazole-1-carboxylate

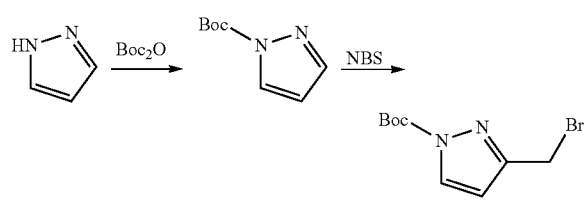

After 3-methyl-1-pyrazole (2.0 g, 24.3 mmol) was dissolved in acetonitrile (25 mL), tert-butyl dicarbonate (6.5 g, 29.8 mmol) and 4-dimethylaminopyridine (0.31 g, 2.49 mmol) were added thereto at 0° C., and the mixture was slowly warmed to room temperature and then stirred for 2 hours. Ethyl acetate (50 mL) was added to the reaction material, and the result was washed with a 1N aqueous hydrochloric acid solution (50 mL), a saturated aqueous sodium hydrogen carbonate solution (50 mL) and salted water (50 mL), dried with anhydrous magnesium sulfate, and then concentrated under reduced pressure. The residue was purified using silica gel column chromatography (ethyl acetate/normal-hexane=1/4) to give tert-butyl 3-methyl-1H-pyrazole-1-carboxylate (4.13 g, 93%).

$^1$H-NMR (300 MHz, CDCl$_3$) δ 1.64 (s, 9H), 2.34 (s, 3H), 6.17 (s, 1H), 7.96 (s, 1H).

After the tert-butyl 3-methyl-1H-pyrazole-1-carboxylate (4.0 g, 21.95 mmol) was dissolved in carbon tetrachloride (73 mL), N-bromosuccinimide (5.47 g, 50.37 mmol) and benzoyl peroxide (0.744 g, 3.07 mmol) were added thereto, and the mixture was refluxed for 5.5 hours. The reaction material was cooled to room temperature, and stirred for 10 minutes after normal-hexane (150 mL) was added thereto. After the produced solids were removed by filtration, the filtrate was concentrated under reduced pressure, and the residue was purified using silica gel column chromatography (ethyl acetate/normal-hexane=5/95 and 10/90) to give tert-butyl 3-(bromomethyl)-1H-pyrazole-1-carboxylate (2.96 g, 52%).

$^1$H-NMR (300 MHz, CDCl$_3$) δ 1.64 (s, 9H), 4.48 (s, 2H), 6.46 (s, 1H), 8.02 (s, 1H).

Step 1: Preparation of tert-butyl (S)-3-((5-(1-(tert-butoxy)-2-methoxy-2-oxoethyl)-4-(4-chlorophenyl)-2,3,6-trimethyl-1H-pyrrolo[2,3-b]pyridin-1-yl)methyl)-1H-pyrazole-1-carboxylate(45a)

A target compound 45a (192 mg, 67%) was obtained by reacting the compound 1n (200 mg, 0.482 mmol) in the same manner as in Step 1 of Example 1, except that the tert-butyl 3-(bromomethyl)-1H-pyrazole-1-carboxylate (251 mg, 0.964 mmol) prepared above was used instead of iodomethyl and the stirring was carried out for 18 hours.

$^1$H-NMR (300 MHz, CDCl$_3$) δ 0.98 (s, 9H), 1.46 (s, 3H), 1.64 (s, 9H), 2.25 (s, 3H), 2.71 (s, 3H), 3.67 (s, 3H), 5.09 (s, 1H), 5.52 (s, 2H), 6.12 (s, 1H), 7.24 (m, 1H), 7.42 (m, 3H), 7.89 (s, 1H); MS (EI, m/e)=581 (M$^+$).

Step 2: Preparation of (S)-2-(1-((1H-pyrazol-3-yl)methyl)-4-(4-chlorophenyl)-2,3,6-trimethyl-1H-pyrrolo[2,3-b]pyridin-5-yl)-2-(tert-butoxy)acetic acid (45)

A pure target compound 45 (78 mg, 52%) was obtained in white solids by reacting the compound 45a (185 mg, 0.311 mmol) in the same manner as in Step 2 of Example 1 using the same solvents and reagents in the same ratio.

$^1$H-NMR (300 MHz, CD$_3$OD) δ 0.91 (s, 9H), 1.44 (s, 3H), 2.16 (s, 3H), 2.63 (s, 3H), 5.06 (s, 1H), 5.42 (s, 2H), 5.45 (s, 1H), 5.87 (s, 1H), 7.25 (m, 1H), 7.42 (m, 3H), 7.55 (m, 1H); MS (EI, m/e)=480 (M$^+$). [a]$_D^{20}$=+126.4 (c 1, MeOH); mp 140° C.

Example 46

(S)-2-(1-((1H-Pyrazol-4-yl)methyl)-4-(4-chlorophenyl)-2,3,6-trimethyl-1H-pyrrolo[2,3-b]pyridin-5-yl)-2-(tert-butoxy)acetic acid (46)

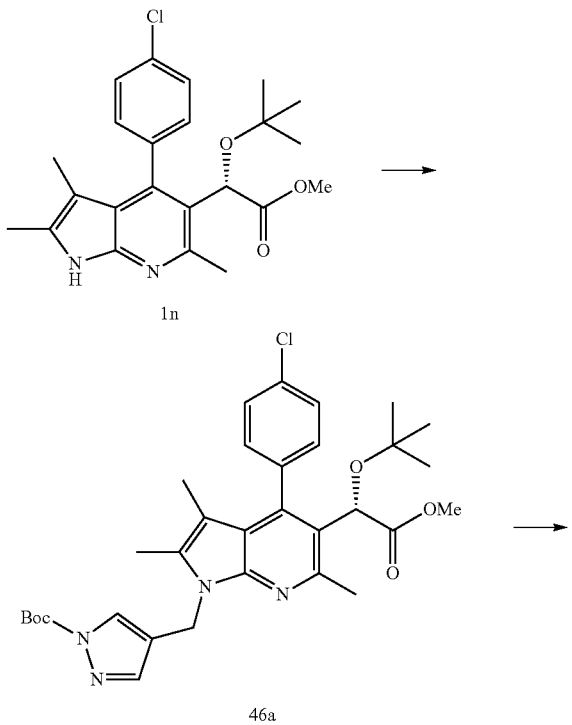

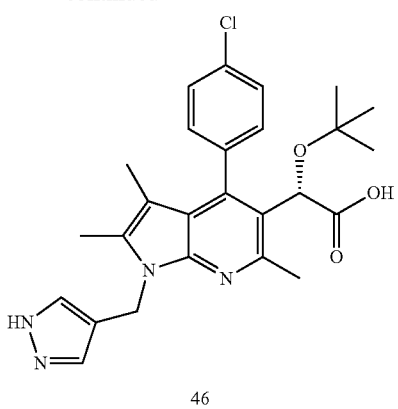

46

Preparation of tert-butyl
4-(bromomethyl)-1H-pyrazole-1-carboxylate

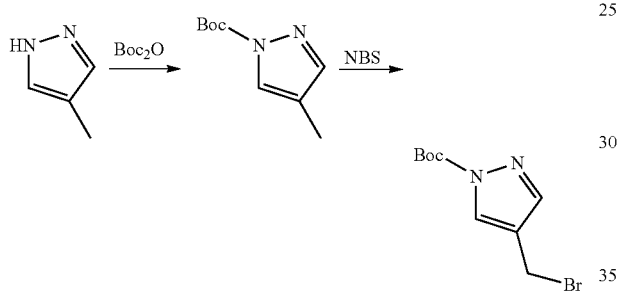

Tert-butyl 4-(bromomethyl)-1H-pyrazole-1-carboxylate (1.54 g, 38%) was prepared in the same manner as in the preparation example of Example 45, except that 4-methyl-1H-pyrazole (2.8 g, 15.3 mmol) was used instead of 3-methyl-1H-pyrazole.

4-methyl-1H-pyrazole-1-carboxylate: $^1$H-NMR (300 MHz, CDCl$_3$) δ 1.66 (s, 9H), 2.11 (s, 3H), 7.55 (s, 1H), 7.85 (s, 1H).

4-bromomethyl-1H-pyrazole-1-carboxylate: $^1$H-NMR (300 MHz, CDCl$_3$) δ 1.65 (s, 9H), 4.39 (s, 2H), 7.74 (s, 1H), 8.10 (s, 1H).

Step 1: Preparation of tert-butyl (S)-4-((5-(1-(tert-butoxy)-2-methoxy-2-oxoethyl)-4-(4-chlorophenyl)-2,3,6-trimethyl-1H-pyrrolo-[2,3-b]pyridin-1-yl)methyl)-1H-pyrazole-1-carboxylate(46a)

A target compound 46a (217 mg, 76%) was obtained by reacting the compound 1n (200 mg, 0.482 mmol) in the same manner as in Step 1 of Example 1, except that the tert-butyl 4-(bromomethyl)-1H-pyrazole-1-carboxylate (251 mg, 0.964 mmol) prepared above was used instead of iodomethyl and the stirring was carried out for 18 hours.

$^1$H-NMR (300 MHz, CDCl$_3$) δ 0.98 (s, 9H), 1.46 (s, 3H), 1.62 (s, 9H), 2.25 (s, 3H), 2.42 (s, 3H), 3.67 (s, 3H), 5.08 (s, 1H), 5.31 (s, 2H), 7.26 (s, 1H), 7.42 (m, 1H), 7.66 (m, 3H), 7.93 (s, 1H); MS (EI, m/e)=594 (M$^+$).

Step 2: Preparation of (S)-2-(1-((1H-pyrazol-4-yl)methyl)-4-(4-chlorophenyl)-2,3,6-trimethyl-1H-pyrrolo[2,3-b]pyridin-5-yl)-2-(tert-butoxy)acetic acid (46)

A pure target compound 46 (148 mg, 92%) was obtained in white solids by reacting the compound 46a (200 mg, 0.336 mmol) in the same manner as in Step 2 of Example 1 using the same solvents and reagents in the same ratio.

$^1$H-NMR (300 MHz, CD$_3$OD) δ 0.96 (s, 9H), 1.51 (s, 3H), 2.26 (s, 3H), 2.73 (s, 3H), 5.07 (s, 1H), 5.43 (m, 2H), 7.33 (m, 1H), 7.46 (m, 4H), 7.72 (m, 1H); MS (EI, m/e)=480 (M$^+$); $[α]_D^{20}$=+117 (c 1, MeOH); mp >230° C.

Example 47

Preparation of (S)-2-(tert-butoxy)-2-(4-(4-chlorophenyl)-1-((1-cyanocyclopropyl)methyl)-2,3,6-trimethyl-1H-pyrrolo[2,3-b]pyridin-5-yl)acetic acid (47)

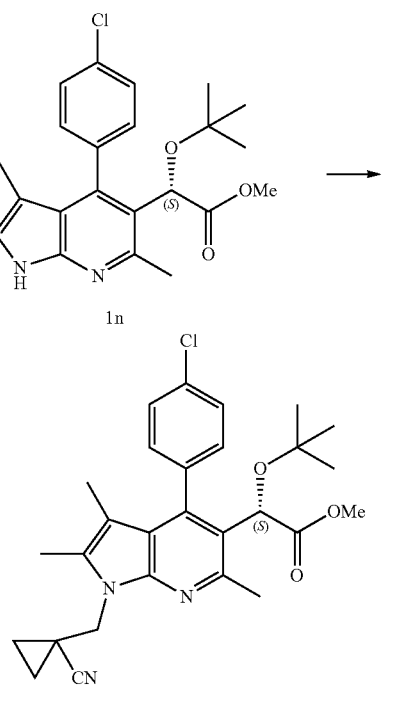

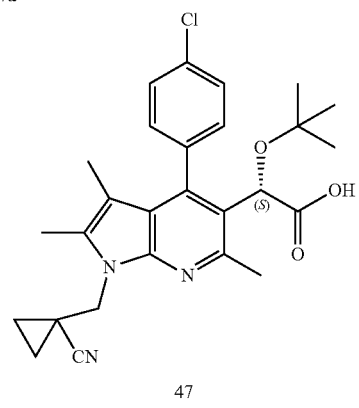

47

Preparation of
1-(iodomethyl)cyclopropanecarbonitrile

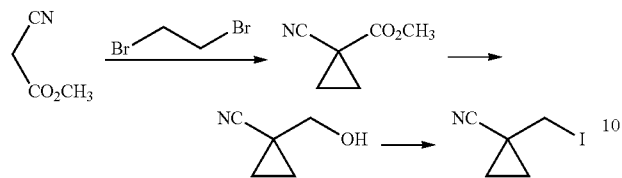

1-(iodomethyl)cyclopropanecarbonitrile was prepared as follows according to a method published in a literature (*J. A. Chem. Soc.*, 1988, 110, 8050-8052).

1) Preparation of methyl 1-cyanocyclopropanecarboxylate 1,2-dibromoethane (10.2 g), cyanoacetate (3.8 g) and potassium carbonate (11.7 g) were added to dimethylformamide (220 mL), and the mixture was stirred for 20 hours at room temperature. The formed crystals were removed by filtration, and the filtrate was concentrated under a high vacuum. After diethyl ether (100 mL) was added to the residue, the produced crystals were removed by filtration, and the filtrate was concentrated under reduced pressure. The residue was distilled (bp 65 to 70° C./0.5 mmHg) under a high vacuum to give a target compound (1.08 g, 22.5%) in a colorless liquid state.

$^1$H-NMR (300 MHz, CDCl$_3$) δ 1.63 (m, 2H), 1.69 (m, 2H), 3.83 (s, 3H)

2) Preparation of 1-(hydromethyl)cyclopropanecarbonitrile

After methyl 1-cyanocyclopropanecarboxylate (1.08 g, 8.5 mmol) was dissolved in tetrahydrofuran (26 mL), lithium borohydrate (0.2 g, 9.35 mmol) was added thereto, and the mixture was refluxed for 1 hour. After water (3.5 mL) was added to the reaction material, the result was neutralized using a 1N aqueous hydrochloric acid solution and extracted 10 times with ether (20 mL), and the organic layer was dried with anhydrous magnesium sulfate and concentrated under reduced pressure. The residue was purified using silica gel column chromatography (ethyl acetate/normal-hexane=2/1) to give a target compound (625 mg, 75.7%) in a colorless liquid state.

$^1$H-NMR (300 MHz, CDCl$_3$) δ 0.98 (m, 2H), 1.28 (m, 2H), 2.05 (s, 1H), 3.64 (s, 2H)

3) Preparation of 1-(iodomethyl)cyclopropanecarbonitrile

After 1-(hydromethyl)cyclopropanecarbonitrile (600 mg, 6.17 mmol) was dissolved in dimethylformamide (11 mL), triphenylphosphine (1.94 g, 7.4 mmol) and imidazole (504 mg, 7.4 mmol) were added thereto, and the mixture was stirred. Iodine (1.72 g, 6.78 mmol) was added in portions thereto over 5 minutes at −20° C., and the result was stirred for 2 hours. Water (30 mL) was added to the reaction material, and the result was extracted with diethyl ether (30 mL×2). The organic layer was dried with anhydrous magnesium sulfate and then concentrated under reduced pressure. The residue was purified using silica gel column chromatography (diethyl ether/normal-hexane=1/4) to give a target compound (908 mg, 72%) in a colorless liquid state.

$^1$H-NMR (300 MHz, CDCl$_3$) δ 1.04 (m, 2H), 1.60 (m, 2H), 3.20 (s, 2H)

Step 1: Preparation of (S)-methyl 2-(tert-butoxy)-2-(4-(4-chlorophenyl)-1-((1-cyanocyclopropyl)methyl)-2,3,6-trimethyl-1H-pyrrolo[2,3-b]pyridin-5-yl)acetate (47a)

A target compound 47a (160 mg, 67%) was obtained by reacting the compound 1n (200 mg, 0.482 mmol) in the same manner as in Step 1 of Example 1, except that the 1-(iodomethyl)cyclopropanecarbonitrile (199 mg, 0.964 mmol) prepared above was used instead of iodomethyl and the stirring was carried out for 18 hours.

$^1$H-NMR (300 MHz, CDCl$_3$) δ 1.00 (s, 9H), 1.28 (m, 2H), 1.51 (s, 3H), 1.57 (m, 2H), 2.46 (s, 3H), 2.67 (s, 3H), 4.36 (s, 2H), 5.09 (s, 1H), 7.25 (m, 1H), 7.45 (m, 3H); MS (EI, m/e)=494 (M$^+$).

Step 2: Preparation of (S)-2-(tert-butoxy)-2-(4-(4-chlorophenyl)-1-((1-cyanocyclopropyl)methyl)-2,3,6-trimethyl-1H-pyrrolo[2,3-b]pyridin-5-yl)acetic acid (47)

A pure target compound 47 (126.7 mg, 86.5%) was obtained in white solids by reacting the compound 47a (150 mg, 0.303 mmol) in the same manner as in Step 2 of Example 1 using the same solvents and reagents in the same ratio.

$^1$H-NMR (300 MHz, CD$_3$OD) δ 0.97 (s, 9H), 1.28 (m, 2H), 1.53 (s, 3H), 2.24 (s, 3H), 2.66 (s, 3H), 4.43 (s, 2H), 5.10 (s, 1H), 7.33 (m, 1H), 7.48-7.52 (m, 2H)), 7.59 (m, 1H); MS (EI, m/e)=480 (M$^+$). [a]$_D^{20}$=+103 (c 1, MeOH)

Example 48

(S)-2-(Tert-butoxy)-2-(4-(4-chlorophenyl)-1-(cyclobutylmethyl)-2,3,6-trimethyl-1H-pyrrolo[2,3-b]pyridin-5-yl)acetic acid (48)

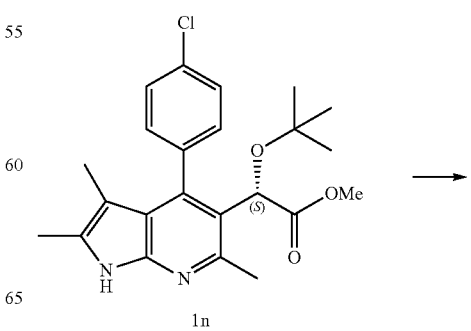

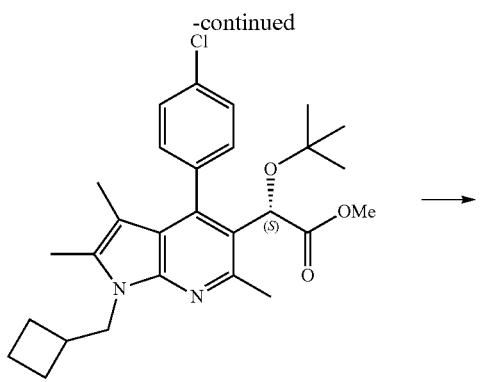

48a

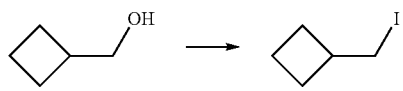 [SMILES: OCC1CCC1 ; ICC1CCC1]

48

Preparation of (iodomethyl)cyclobutane

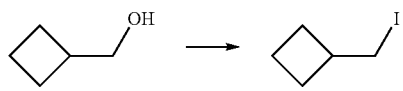 [SMILES: OCC1CCC1 ; ICC1CCC1]

After cyclobutylmethanol (1.59 g, 18.5 mmol) was dissolved in dimethylformamide (33 mL), triphenylphosphine (5.82 g, 22.19 mmol) and imidazole (1.51 g, 22.2 mmol) were added thereto, and the mixture was stirred. Iodine (5.16 g, 20.33 mmol) was added in portions thereto over 5 minutes at −20° C., and the result was stirred for 2 hours. Water (30 mL) was added to the reaction material, and the result was extracted with diethyl ether (30 mL×2). The organic layer was dried with anhydrous magnesium sulfate and then concentrated under reduced pressure. The residue was purified using silica gel column chromatography (normal-hexane) to give a target compound (868 mg, 24%) in a colorless liquid state.

$^1$H-NMR (500 MHz, CDCl$_3$) δ 1.65 (m, 2H), 1.83 (m, 2H), 2.11 (m, 2H), 2.67 (m, 1H), 3.26 (d, 2H)

Step 1: Preparation of (S)-methyl 2-(tert-butoxy)-2-(4-(4-chlorophenyl)-1-(cyclobutylmethyl)-2,3,6-trimethyl-1H-pyrrolo[2,3-b]pyridin-5-yl)acetate (48a)

A target compound 48a (20 mg, 9.6%) was obtained by reacting the compound 1n (200 mg, 0.482 mmol) in the same manner as in Step 1 of Example 1, except that the (iodomethyl)cyclobutane (186 mg, 0.964 mmol) prepared above was used instead of iodomethyl and the stirring was carried out for 18 hours at 30° C.

$^1$H-NMR (300 MHz, CDCl$_3$) δ 0.97 (s, 9H), 1.47 (s, 3H), 1.88-2.00 (m, 6H), 2.27 (s, 3H), 2.70 (m, 3H), 2.79 (m, 1H), 3.65 (s, 3H), 4.22-4.25 (m, 2H), 5.07 (s, 1H), 7.24 (m, 1H), 7.41 (m, 3H); MS (EI, m/e)=482 (M$^+$).

Step 2: Preparation of (S)-2-(tert-butoxy)-2-(4-(4-chlorophenyl)-1-(cyclobutylmethyl)-2,3,6-trimethyl-1H-pyrrolo[2,3-b]pyridin-5-yl)acetic acid (48)

A pure target compound 48 (16.5 mg, 85%) was obtained in white solids by reacting the compound 48a (20 mg, 0.0414 mmol) in the same manner as in Step 2 of Example 1 using the same solvents and reagents in the same ratio.

$^1$H-NMR (300 MHz, CD$_3$OD) δ 0.88 (s, 9H), 1.41 (s, 3H), 1.78-1.88 (m, 6H), 2.21 (s, 3H), 2.58 (m, 3H), 2.71 (m, 1H), 4.17-4.19 (m, 2H), 5.02 (s, 1H), 7.21 (d, J=9 Hz, 1H), 7.40 (m, 2H), 7.49 (d, J=9 Hz, 1H); MS (EI, m/e)=468 (M$^+$).

Example 49

(S)-2-(Tert-butoxy)-2-(4-(4-chlorophenyl)-1-(cyclopentylmethyl)-2,3,6-trimethyl-1H-pyrrolo[2,3-b]pyridin-5-yl)acetic acid (49)

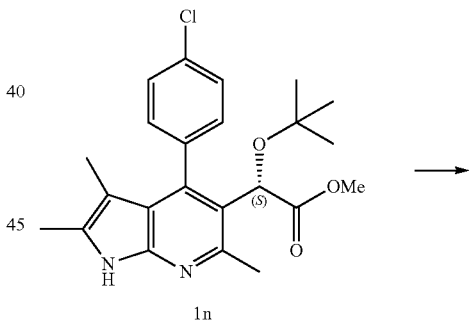

1n

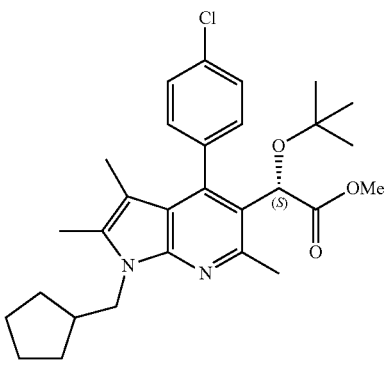

49a

-continued

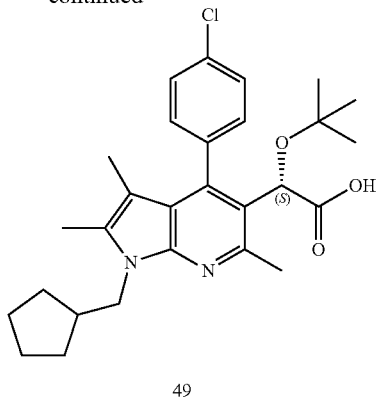

49

Step 1: Preparation of (S)-methyl 2-(tert-butoxy)-2-(4-(4-chlorophenyl)-1-(cyclopentylmethyl)-2,3,6-trimethyl-1H-pyrrolo[2,3-b]pyridin-5-yl)acetate (49a)

A target compound 49a (20 mg, 16.8%) was obtained by reacting the compound 1n (100 mg, 0.241 mmol) in the same manner as in Step 1 of Example 1, except that (iodomethyl)cyclopentane (200 mg, 0.964 mmol) was used instead of iodomethyl and the stirring was carried out for 18 hours at 30° C.

$^1$H-NMR (300 MHz, CDCl$_3$) δ 0.98 (s, 9H), 1.27-1.44 (m, 4H), 1.48 (s, 3H), 1.58-1.77 (m, 4H), 2.29 (s, 3H), 2.40-2.49 (m, 1H), 2.69 (s, 3H), 3.66 (s, 3H), 4.05-4.20 (m, 2H), 5.07 (s, 1H), 7.24 (m, 1H), 7.43 (m, 3H); MS (EI, m/e)=496 (M$^+$).

Step 2: Preparation of (S)-2-(tert-butoxy)-2-(4-(4-chlorophenyl)-1-(cyclopentylmethyl)-2,3,6-trimethyl-1H-pyrrolo[2,3-b]pyridin-5-yl)acetic acid (49)

A pure target compound 49 (13 mg, 68%) was obtained in white solids by reacting the compound 49a (20 mg, 0.041 mmol) in the same manner as in Step 2 of Example 1 using the same solvents and reagents in the same ratio.

$^1$H-NMR (300 MHz, CD$_3$OD) δ 0.97 (s, 9H), 1.30-1.40 (m, 2H), 1.50 (s, 3H), 1.50-1.77 (m, 6H), 2.33 (s, 3H), 2.44-2.53 (m, 1H), 2.69 (s, 3H), 4.18 (m, 2H), 5.08 (s, 1H), 7.32 (d, J=9 Hz, 1H), 7.48 (m, 2H), 7.66 (d, J=9 Hz, 1H); MS (EI, m/e)=482 (M$^+$).

Example 50

(S)-2-(Tert-butoxy)-2-(4-(4-chlorophenyl)-1-(cyclohexylmethyl)-2,3,6-trimethyl-1H-pyrrolo[2,3-b]pyridin-5-yl)acetic acid (50)

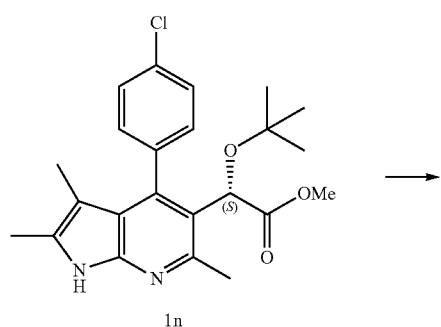

1n

-continued

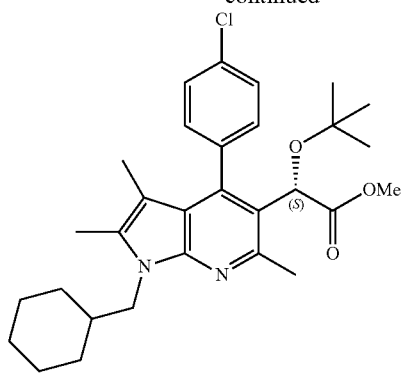

50a

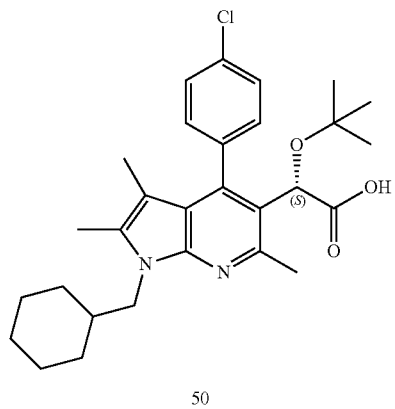

50

Step 1: Preparation of (S)-methyl 2-(tert-butoxy)-2-(4-(4-chlorophenyl)-1-(cyclohexylmethyl)-2,3,6-trimethyl-1H-pyrrolo[2,3-b]pyridin-5-yl)acetate (50a)

A target compound 50a (42 mg, 17%) was obtained by reacting the compound 1n (200 mg, 0.482 mmol) in the same manner as in Step 1 of Example 1, except that (iodomethyl)cyclohexane (279 mg, 1.446 mmol) was used instead of iodomethyl and the stirring was carried out for 18 hours at 30° C.

$^1$H-NMR (300 MHz, CDCl$_3$) δ 0.98 (s, 9H), 1.02-1.25 (m, 5H), 1.48 (s, 3H), 1.54-1.81 (m, 6H), 2.26 (s, 3H), 2.69 (m, 3H), 3.66 (s, 3H), 3.99-4.11 (m, 2H), 5.07 (s, 1H), 7.24 (m, 1H), 7.43 (m, 3H); MS (EI, m/e)=510 (M$^+$).

Step 2: Preparation of (S)-2-(tert-butoxy)-2-(4-(4-chlorophenyl)-1-(cyclohexylmethyl)-2,3,6-trimethyl-1H-pyrrolo[2,3-b]pyridin-5-yl)acetic acid (50)

A pure target compound 50 (40.3 mg, 98%) was obtained in white solids by reacting the compound 50a (42 mg, 0.082 mmol) in the same manner as in Step 2 of Example 1 using the same solvents and reagents in the same ratio.

$^1$H-NMR (300 MHz, CD$_3$OD) δ 0.98 (s, 9H), 1.06-1.25 (m, 5H), 1.52 (s, 3H), 1.52-1.91 (m, 6H), 2.31 (s, 3H), 2.69 (m, 3H), 4.08-4.10 (m, 2H), 5.12 (s, 1H), 7.32 (d, J=9 Hz, 1H), 7.50 (m, 2H), 7.61 (d, J=9 Hz, 1H); MS (EI, m/e)=496 (M$^+$).

Example 51

(S)-2-(Tert-butoxy)-2-(4-(4-chlorophenyl)-1-(2-(dimethylamino)-2-oxoethyl)-2,3,6-trimethyl-1H-pyrrolo[2,3-b]pyridin-5-yl)acetic acid (51)

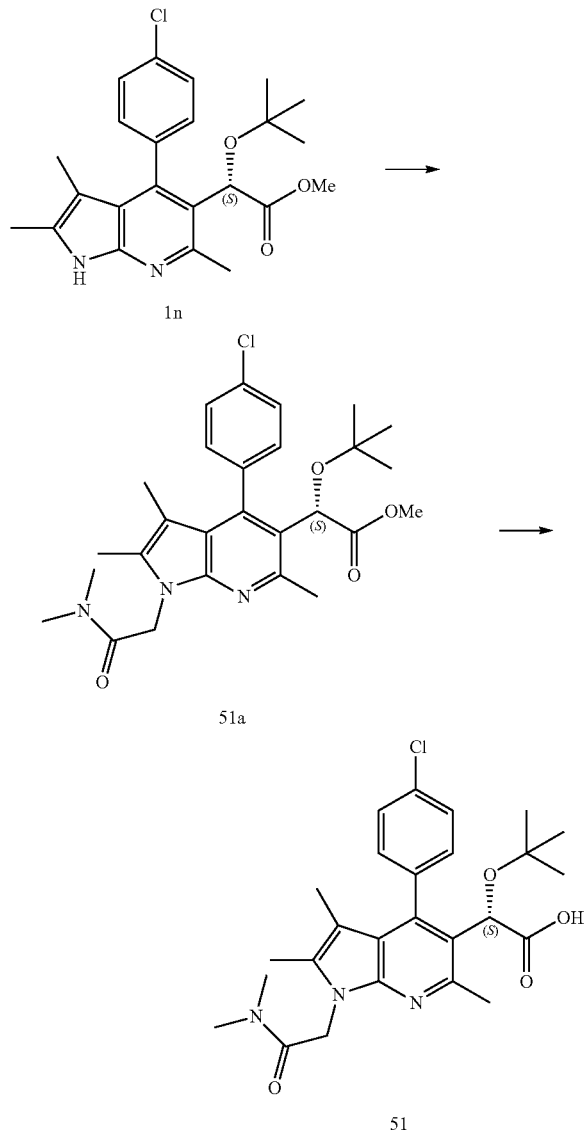

Preparation of 2-iodo-N,N-dimethylacetamide

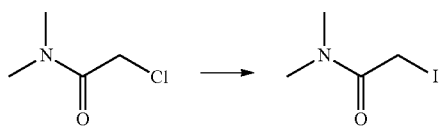

After 2-chloro-N,N-dimethylacetamide (1.3 g, 10.69 mmol) was dissolved in acetonitrile (33 mL), sodium iodide (7.23 g, 48 mmol) was added thereto, and the mixture was stirred for 2 hours at 60° C. Water (30 mL) was added to the reaction material and the result was extracted with ethyl acetate (30 mL×2). The organic layer was dried with anhydrous magnesium sulfate, and concentrated under reduced pressure to give a target compound (1.2 g, 53%).

$^1$H-NMR (300 MHz, CDCl$_3$) δ 2.96 (s, 3H), 3.05 (s, 3H), 3.74 (m, 2H)

Step 1: Preparation of (S)-methyl 2-(tert-butoxy)-2-(4-(4-chlorophenyl)-1-(2-(dimethylamino)-2-oxoethyl)-2,3,6-trimethyl-1H-pyrrolo[2,3-b]pyridin-5-yl)acetate (51a)

A target compound 51a (114 mg, 95%) was obtained by reacting the compound 1n (100 mg, 0.241 mmol) in the same manner as in Step 1 of Example 1, except that the 2-iodo-N,N-dimethylacetamide (200 mg, 0.964 mmol) prepared above was used instead of iodomethyl and the stirring was carried out for 18 hours at 30° C.

$^1$H-NMR (300 MHz, CDCl$_3$) δ 0.96 (s, 9H), 1.49 (s, 3H), 2.23 (s, 3H), 2.66 (s, 3H), 2.99 (s, 3H), 3.22 (s, 3H), 3.64 (s, 3H), 5.05-5.07 (m, 2H), 5.07 (s, 1H), 7.25 (m, 1H), 7.41 (m, 3H); MS (EI, m/e)=499 (M$^+$).

Step 2: Preparation of (S)-2-(tert-butoxy)-2-(4-(4-chlorophenyl)-1-(2-(dimethylamino)-2-oxoethyl)-2,3,6-trimethyl-1H-pyrrolo[2,3-b]pyridin-5-yl)acetic acid (51)

A pure target compound 51 (69 mg, 63%) was obtained in white solids by reacting the compound 51a (114 mg, 0.228 mmol) in the same manner as in Step 2 of Example 1 using the same solvents and reagents in the same ratio.

$^1$H-NMR (300 MHz, CD$_3$OD) δ 0.96 (s, 9H), 1.54 (s, 3H), 2.21 (s, 3H), 2.69 (s, 3H), 2.99 (s, 3H), 3.26 (s, 3H), 5.07 (s, 1H), 5.20 (m, 2H), 7.33 (d, J=9 Hz, 1H), 7.49 (m, 2H), 7.70 (d, J=9 Hz, 1H); MS (EI, m/e)=485 (M$^+$).

Example 52

(S)-2-(Tert-butoxy)-2-(4-(4-chlorophenyl)-1-(1-hydroxy cyclopropyl)-2,3,6-trimethyl-1H-pyrrolo[2,3-b]pyridin-5-yl)acetic acid (52)

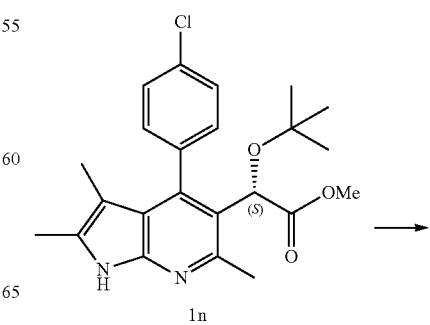

-continued

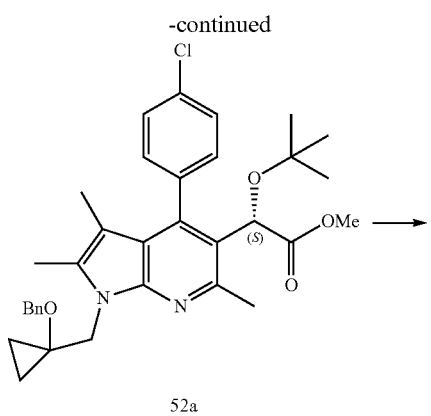

52a

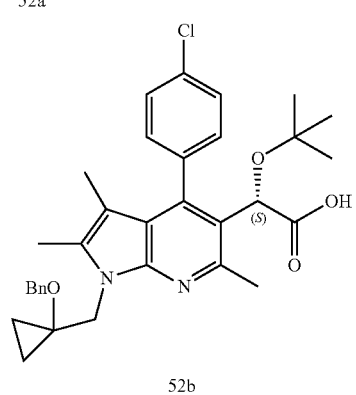

52b

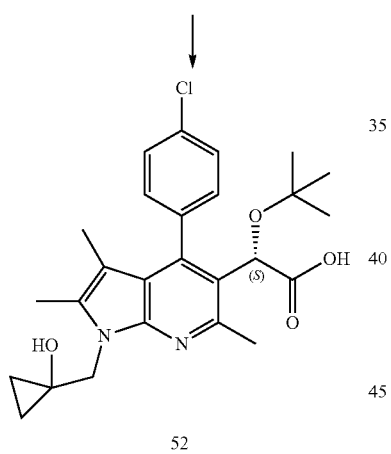

52

Step 1: Preparation of (S)-methyl 2-(tert-butoxy)-2-(4-(4-chlorophenyl)-1-((1-(benzyloxy)cyclopropyl)methyl)-2,3,6-trimethyl-1H-pyrrolo[2,3-b]pyridin-5-yl)acetate (52a)

A target compound 52a (76.5 mg, 27.7%) was obtained by reacting the compound 1n (200 mg, 0.482 mmol) in the same manner as in Step 1 of Example 1, except that ((1-(iodomethyl)cyclopropyl)methoxy)benzene (278 mg, 0.964 mmol) was used instead of iodomethyl and the stirring was carried out for 18 hours at 30° C.

$^1$H-NMR (300 MHz, CDCl$_3$) δ 0.95-0.97 (m, 4H), 0.97 (s, 9H), 1.47 (s, 3H), 2.33 (s, 3H), 2.66 (s, 3H), 3.65 (s, 3H), 4.50 (m, 2H), 4.57-4.62 (m, 2H), 5.07 (s, 1H), 7.12 (m, 2H), 7.23 (m, 4H), 7.42 (m, 3H); MS (EI, m/e)=574 (M$^+$).

Step 2: Preparation of (S)-2-(tert-butoxy)-2-(4-(4-chlorophenyl)-1-((1-(benzyloxy)cyclopropyl)methyl)-2,3,6-trimethyl-1H-pyrrolo[2,3-b]pyridin-5-yl)acetic acid (52b)

A pure target compound 52b (38 mg, 67.8%) was obtained in white solids by reacting the compound 52a (59 mg, 0.1 mmol) in the same manner as in Step 2 of Example 1 using the same solvents and reagents in the same ratio.

$^1$H-NMR (300 MHz, CD$_3$OD) δ 0.90-0.98 (m, 4H), 0.98 (s, 9H), 1.52 (s, 3H), 2.35 (s, 3H), 2.66 (s, 3H), 4.52-4.57 (m, 2H), 4.57-4.60 (m, 2H), 5.13 (s, 1H), 7.04 (m, 2H), 7.26 (m, 3H), 7.31 (d, J=6 Hz, 1H), 7.50 (t, J=6 Hz, 2H), 7.60 (d, J=9 Hz, 1H); MS (EI, m/e)=560 (M$^+$).

Step 3: Preparation of (S)-2-(tert-butoxy)-2-(4-(4-chlorophenyl)-1-(1-hydroxycyclopropyl)-2,3,6-trimethyl-1H-pyrrolo[2,3-b]pyridin-5-yl)acetic acid (52)

After the compound 52b (40 mg, 0.0713 mmol) was dissolved in methanol (1 mL), 10%-palladium carbon (4 mg) was added thereto, and the mixture was stirred under hydrogen atmosphere for 2 hours at room temperature. The reaction material was filtered through a celite pad and sufficiently washed with methanol. The filtrate was concentrated under reduced pressure to give a target compound 52 (30 mg, 90%) in white solids.

$^1$H-NMR (300 MHz, CD$_3$OD) δ 0.77-0.84 (m, 4H), 0.98 (s, 9H), 1.54 (s, 3H), 2.38 (s, 3H), 2.77 (s, 3H), 4.46 (s, 2H), 5.12 (s, 1H), 7.35 (m, 1H), 7.57 (m, 3H); MS (EI, m/e)=470 (M$^+$).

Example 53

(S)-2-(Tert-butoxy)-2-(4-(4-chlorophenyl)-2,3,6-trimethyl-1-(pyridin-3-ylmethyl)-1H-pyrrolo[2,3-b]pyridin-5-yl)acetic acid (53)

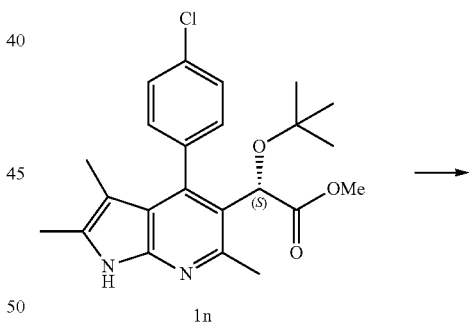

1n

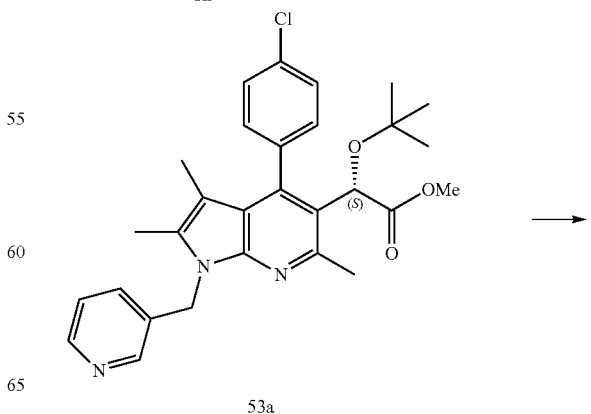

53a

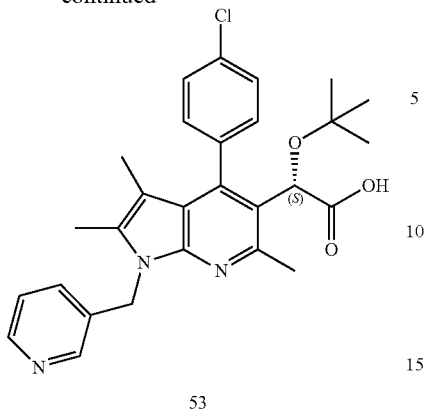

53

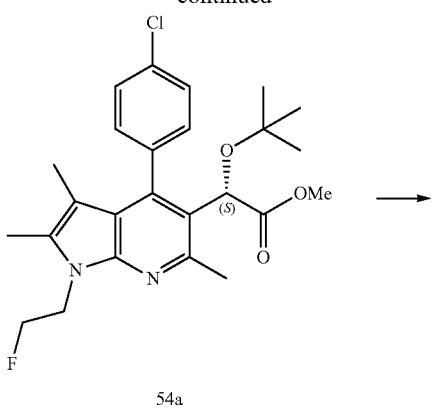

54a

Step 1: Preparation of (S)-methyl 2-(tert-butoxy)-2-(4-(4-chlorophenyl)-2,3,6-trimethyl-1-(pyridin-3-ylmethyl)-1H-pyrrolo[2,3-b]pyridin-5-yl)acetate (53a)

A target compound 53a (129 mg, 53%) was obtained by reacting the compound 1n (200 mg, 0.482 mmol) in the same manner as in Step 1 of Example 1, except that 3-bromomethylpyridine (243 mg, 0.96 mmol) was used instead of iodomethyl and the stirring was carried out for 4 hours at 30° C.

$^1$H-NMR (300 MHz, CDCl$_3$) δ 1.01 (s, 9H), 1.50 (s, 3H), 2.19 (s, 3H), 2.72 (s, 3H), 3.70 (s, 3H), 5.11 (s, 1H), 5.51 (s, 2H), 7.23 (m, 2H), 7.43-7.52 (m, 4H), 8.50 (m, 2H); MS (EI, m/e)=505 (M$^+$).

Step 2: Preparation of (S)-2-(tert-butoxy)-2-(4-(4-chlorophenyl)-2,3,6-trimethyl-1-(pyridin-3-ylmethyl)-1H-pyrrolo[2,3-b]pyridin-5-yl)acetic acid (53)

A pure target compound 53 (107 mg, 85.6%) was obtained in white solids by reacting the compound 53a (129 mg, 0.255 mmol) in the same manner as in Step 2 of Example 1 using the same solvents and reagents in the same ratio.

$^1$H-NMR (300 MHz, CD$_3$OD) δ 0.97 (s, 9H), 1.55 (s, 3H), 2.23 (s, 3H), 2.70 (s, 3H), 5.10 (s, 1H), 5.58 (m, 2H), 7.35 (m, 2H), 7.52 (m, 3H), 7.72 (m, 1H), 8.30 (m, 1H), 8.42 (m, 1H); MS (EI, m/e)=491 (M$^+$).

Example 54

(S)-2-(Tert-butoxy)-2-(4-(4-chlorophenyl)-1-(2-fluoroethyl)-2,3,6-trimethyl-1H-pyrrolo[2,3-b]pyridin-5-yl)acetic acid (54)

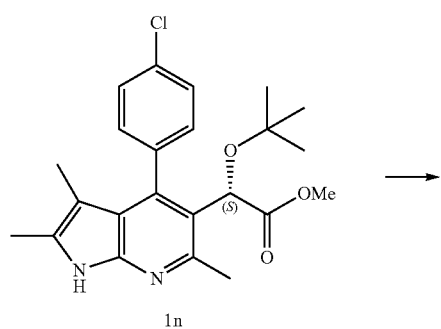

54

Step 1: Preparation of (S)-methyl 2-(tert-butoxy)-2-(4-(4-chlorophenyl)-1-(2-fluoroethyl)-2,3,6-trimethyl-1H-pyrrolo[2,3-b]pyridin-5-yl)acetate (54a)

A target compound 54a (140 mg, 63.6%) was obtained by reacting the compound 1n (200 mg, 0.482 mmol) in the same manner as in Step 1 of Example 1, except that 2-fluoroethyl 4-methylbenzenesulfonate (315 mg, 1.446 mmol) was used instead of iodomethyl and the stirring was carried out for 18 hours at 35° C.

$^1$H-NMR (300 MHz, CDCl$_3$) δ 0.98 (s, 9H), 1.49 (s, 3H), 2.30 (s, 3H), 2.68 (s, 3H), 3.66 (s, 3H), 4.48 (m, 1H), 4.54 (m, 1H), 4.67 (m, 1H), 4.85 (m, 1H), 5.08 (s, 1H), 7.24 (m, 1H), 7.39 (m, 3H); MS (EI, m/e)=460 (M$^+$).

Step 2: Preparation of (S)-2-(tert-butoxy)-2-(4-(4-chlorophenyl)-1-(2-fluoroethyl)-2,3,6-trimethyl-1H-pyrrolo[2,3-b]pyridin-5-yl)acetic acid (54)

A pure target compound 54 (95 mg, 84%) was obtained in white solids by reacting the compound 54a (120 mg, 0.260 mmol) in the same manner as in Step 2 of Example 1 using the same solvents and reagents in the same ratio.

$^1$H-NMR (300 MHz, CD$_3$OD) δ 0.98 (s, 9H), 1.53 (s, 3H), 2.33 (s, 3H), 2.69 (s, 3H), 4.53 (m, 1H), 4.61 (m, 2H), 4.77 (m, 1H), 5.12 (s, 1H), 7.32 (d, J=9 Hz, 1H), 7.51 (m, 2H), 7.61 (d, J=9 Hz, 1H); MS (EI, m/e)=446 (M$^+$); [a]$_D^{20}$=+116 (c 1, MeOH)

Example 55

(S)-2-(Tert-butoxy)-2-(4-(4-chlorophenyl)-2,3,6-trimethyl-1-(pyrimidin-5-ylmethyl)-1H-pyrrolo[2,3-b]pyridin-5-yl)acetic acid (55)

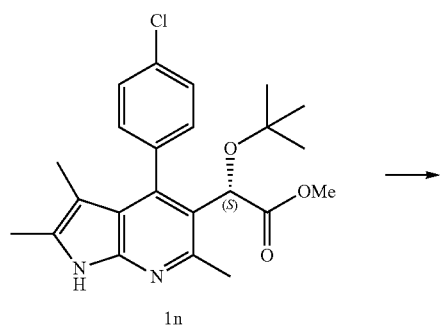

1n

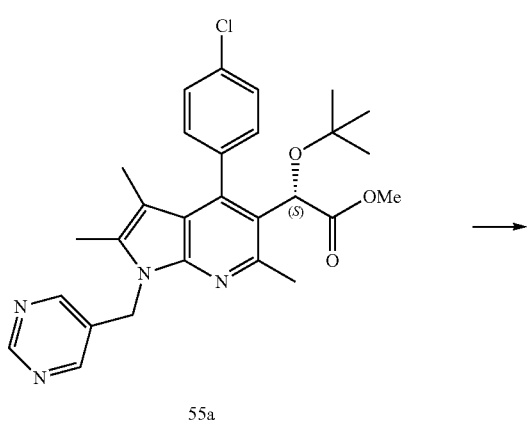

55a

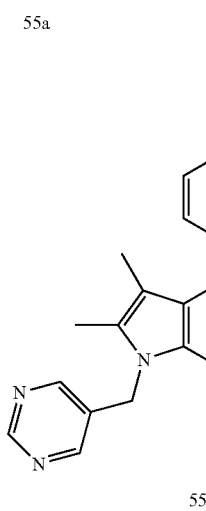

55

Step 1: Preparation of (S)-methyl 2-(tert-butoxy)-2-(4-(4-chlorophenyl)-2,3,6-trimethyl-1-(pyrimidin-5-ylmethyl)-1H-pyrrolo[2,3-b]pyridin-5-yl)acetate (55a)

A target compound 55a (365 mg, 75%) was obtained by reacting the compound 1n (200 mg, 0.482 mmol) in the same manner as in Step 1 of Example 1, except that 5-(chloromethyl)pyrimidine (372 mg, 2.98 mmol) was used instead of iodomethyl and the stirring was carried out for 18 hours at 40° C.

$^1$H-NMR (300 MHz, CDCl$_3$) δ 0.99 (s, 9H), 1.48 (s, 3H), 2.04 (s, 3H), 2.22 (s, 3H), 2.69 (s, 3H), 5.08 (s, 1H), 5.47 (s, 2H), 7.23 (m, 1H), 7.43 (m, 3H), 8.62 (s, 1H), 9.11 (s, 1H); MS (EI, m/e)=507 (M$^+$).

Step 2: Preparation of (S)-2-(tert-butoxy)-2-(4-(4-chlorophenyl)-2,3,6-trimethyl-1-(pyrimidin-5-ylmethyl)-1H-pyrrolo[2,3-b]pyridin-5-yl)acetic acid (55)

A pure target compound 55 (315 mg, 93%) was obtained in white solids by reacting the compound 55a (349 mg, 0.688 mmol) in the same manner as in Step 2 of Example 1 using the same solvents and reagents in the same ratio.

$^1$H-NMR (300 MHz, CD$_3$OD) δ 0.97 (s, 9H), 1.56 (s, 3H), 2.28 (s, 3H), 2.69 (s, 3H), 5.10 (s, 1H), 5.60 (m, 2H), 7.35 (d, J=9 Hz, 1H), 7.50 (m, 2H), 7.66 (d, J=9 Hz, 1H), 8.56 (s, 2H), 9.04 (s, 1H); MS (EI, m/e)=493 (M$^+$).

Example 56

(S)-2-(Tert-butoxy)-2-(4-(4-chlorophenyl)-2,3,6-trimethyl-1-(oxazol-4-ylmethyl)-1H-pyrrolo[2,3-b]pyridin-5-yl)acetic acid (56)

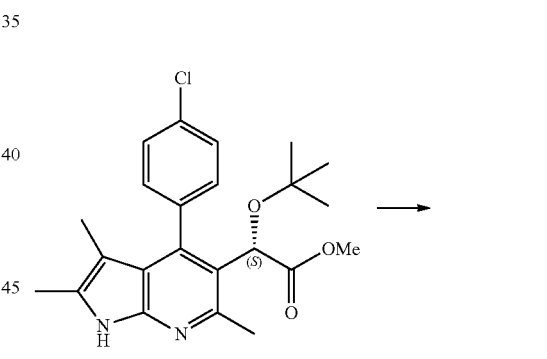

1n

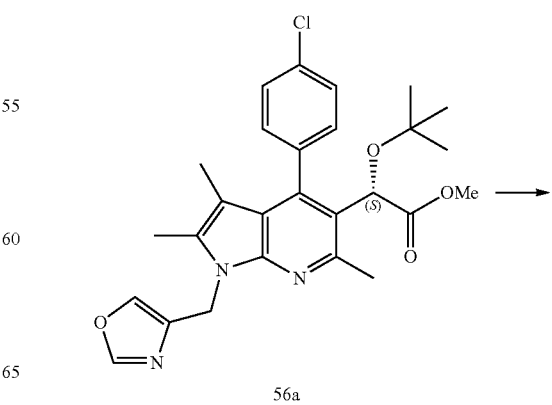

56a

-continued

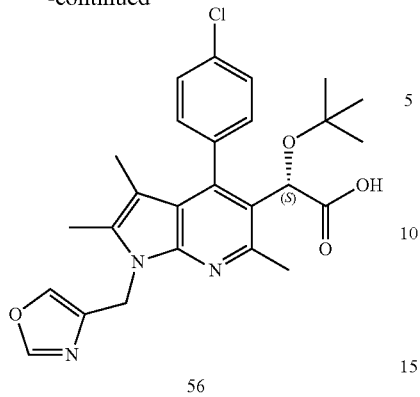

56

Step 1: Preparation of (S)-methyl 2-(tert-butoxy)-2-(4-(4-chlorophenyl)-2,3,6-trimethyl-1-(oxazol-4-ylmethyl)-1H-pyrrolo[2,3-b]pyridin-5-yl)acetate (56a)

A target compound 56a (148 mg, 34%) was obtained by reacting the compound 1n (360 mg, 0.869 mmol) in the same manner as in Step 1 of Example 1, except that 4-(iodomethyl)oxazole (544 mg, 2.603 mmol) was used instead of iodomethyl and the stirring was carried out for 18 hours at 35° C.
$^1$H-NMR (300 MHz, CDCl$_3$) δ 0.98 (s, 9H), 1.48 (s, 3H), 2.35 (s, 3H), 2.70 (s, 3H), 3.66 (s, 3H), 5.07 (s, 1H), 5.38 (s, 2H), 7.26 (m, 1H), 7.39-7.50 (m, 4H), 7.81 (s, 1H); MS (EI, m/e)=495 (M$^+$).

Step 2: Preparation of (S)-2-(tert-butoxy)-2-(4-(4-chlorophenyl)-2,3,6-trimethyl-1-(oxazol-4-ylmethyl)-1H-pyrrolo[2,3-b]pyridin-5-yl)acetic acid (56)

A pure target compound 56 (117 mg, 81.8%) was obtained in white solids by reacting the compound 56a (148 mg, 0.298 mmol) in the same manner as in Step 2 of Example 1 using the same solvents and reagents in the same ratio.
$^1$H-NMR (300 MHz, CD$_3$OD) δ 0.92 (s, 9H), 1.47 (s, 3H), 2.28 (s, 3H), 2.63 (s, 3H), 5.07 (s, 1H), 5.37 (s, 2H), 7.43 (m, 1H), 7.45-7.54 (m, 4H), 8.03 (s, 1H); MS (EI, m/e)=481 (M$^+$).

Example 57

(S)-2-(Tert-butoxy)-2-(1-carboxymethyl)-(4-(4-chlorophenyl)-2,3,6-trimethyl-1H-pyrrolo[2,3-b]pyridin-5-yl)acetic acid (57)

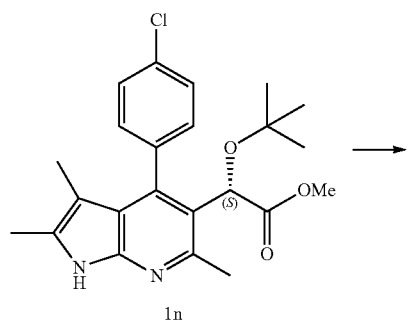

1n

-continued

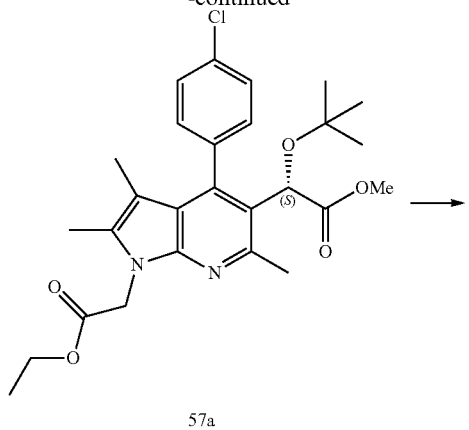

Step 1: Preparation of (S)-methyl 2-(tert-butoxy)-2-(1-carboxymethyl)-(4-(4-chlorophenyl)-2,3,6-trimethyl-1H-pyrrolo[2,3-b]pyridin-5-yl)acetate A target compound 57a (153.8 mg, 87%) was obtained by reacting the compound 1n (145 mg, 0.35 mmol) in the same manner as in Step 1 of Example 1, except that ethyl bromoacetate (117 mg, 0.07 mmol) was used instead of iodomethyl and the stirring was carried out for 18 hours at 35° C.
$^1$H-NMR (300 MHz, CDCl$_3$) δ 0.97 (s, 9H), 1.31 (t, J=7.2 Hz, 3H), 1.49 (s, 3H), 2.21 (s, 3H), 2.67 (s, 3H), 3.65 (s, 3H), 4.24 (q, J=7.5 Hz, 2H), 5.04 (m, 3H), 7.23 (m, 1H), 7.41 (m, 3H); MS (EI, m/e)=501 (M$^+$).

Step 2: Preparation of (S)-2-(tert-butoxy)-2-(1-carboxymethyl)-(4-(4-chlorophenyl)-2,3,6-trimethyl-1H-pyrrolo[2,3-b]pyridin-5-yl)acetic acid (57)

A pure target compound 57 (57.3 mg, 90%) was obtained in white solids by reacting the compound 57a (70 mg, 0.14 mmol) in the same manner as in Step 2 of Example 1 using the same solvents and reagents in the same ratio.
$^1$H-NMR (300 MHz, CD$_3$OD) δ 0.90 (s, 9H), 1.49 (s, 3H), 2.22 (s, 3H), 2.63 (s, 3H), 3.55 (t, OH), 4.77 (m, 2H), 4.99 (s, H), 7.32 (m, 1H), 7.51 (m, 3H); MS (LC-ES, m/e)=459 (M+1$^+$).

Example 58

(S)-2-(Tert-butoxy)-2-(1-(cyclopropyl)methyl)-(4-(4-hydroxy-3,5-dimethylphenyl)-2,3,6-trimethyl-1H-pyrrolo[2,3-b]pyridin-5-yl)acetic acid (58)

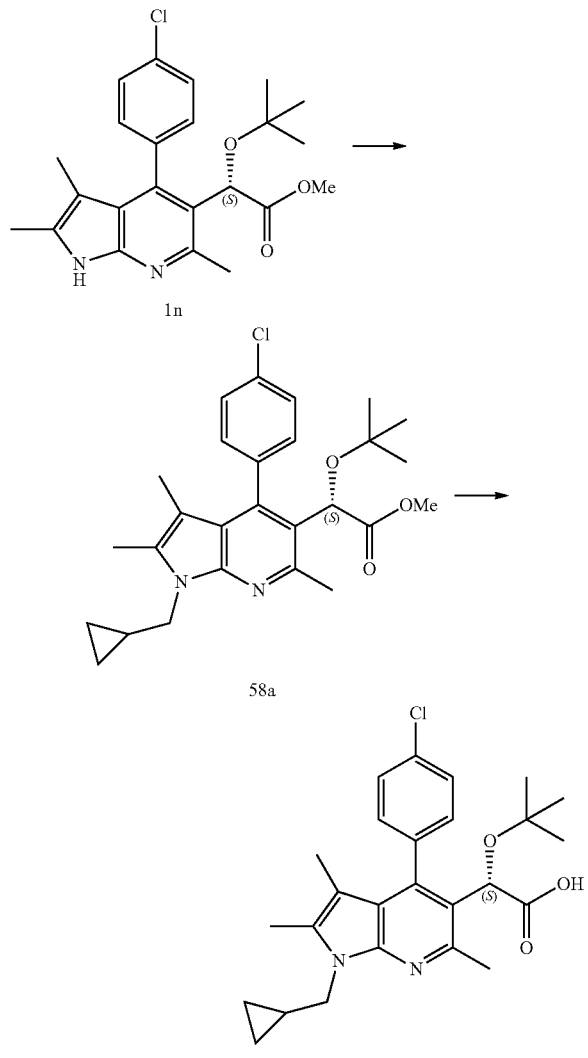

Step 1: Preparation of (S)-methyl 2-(tert-butoxy)-2-(1-(cyclopropyl)methyl)-(4-(4-hydroxy-3,5-dimethylphenyl)-2,3,6-trimethyl-1H-pyrrolo[2,3-b]pyridin-5-yl)acetate (58a)

After the compound 1n (260 mg, 0.66 mmol) was dissolved in dimethylformamide (3 mL) under nitrogen, 2,6-dimethyl-4-(4,4,5,5-tetramethyl-1,3,2-dioxaboran-2-yl)phenol (188 mg, 1.76 mmol), potassium carbonate (463 mg, 3.35 mmol) and tetrakis(triphenylphosphine)palladium (153 mg, 1.13 mmol) were added thereto, and the mixture was stirred for 6 hours at 130° C. After the reaction material was filtered through a celite pad and washed with ethyl acetate, the filtrate was concentrated under reduced pressure, and then the residue was purified using silica gel column chromatography (ethyl acetate/normal-hexane=1/7) to give a target compound 58a (31 mg, 10%).

$^1$H-NMR (300 MHz, CDCl$_3$) δ 0.41-0.49 (m, 4H), 0.98 (s, 9H), 1.24 (m, 1H), 1.59 (s, 3H), 2.20 (s, 3H), 2.31 (s, 3H), 2.35 (s, 3H), 2.67 (s, 3H), 3.65 (s, 3H), 4.10 (m, 2H), 4.84 (br.s, OH), 5.23 (s, 1H), 6.91 (s, 1H), 7.08 (s, 1H); MS (EI, m/e)=478 (M$^+$).

Step 2: Preparation of (S)-2-(tert-butoxy)-2-(1-(cyclopropyl)methyl)-(4-(4-hydroxy-3,5-dimethylphenyl)-2,3,6-trimethyl-1H-pyrrolo[2,3-b]pyridin-5-yl) acetic acid (58)

A pure target compound 58 (23.5 mg, 81%) was obtained in white solids by reacting the compound 58a (30 mg, 0.0626 mmol) in the same manner as in Step 2 of Example 1 using the same solvents and reagents in the same ratio.

$^1$H-NMR (300 MHz, CD$_3$OD) δ 0.36-0.44 (m, 4H), 0.91 (s, 9H), 1.24 (m, 1H), 1.50 (s, 3H), 2.20 (s, 3H), 2.23 (s, 3H), 2.29 (s, 3H), 2.59 (s, 3H), 4.11 (m, 2H), 5.25 (s, 1H), 6.79 (s, 1H), 7.09 (s, 1H); MS (EI, m/e)=464 (M$^+$).

Example 59

(S)-2-(Tert-butoxy)-2-(4-(4-chlorophenyl)-2,3,6-trimethyl-1-(2,2,2-trifluoromethyl)-1H-pyrrolo[2,3-b]pyridin-5-yl)acetic acid (59)

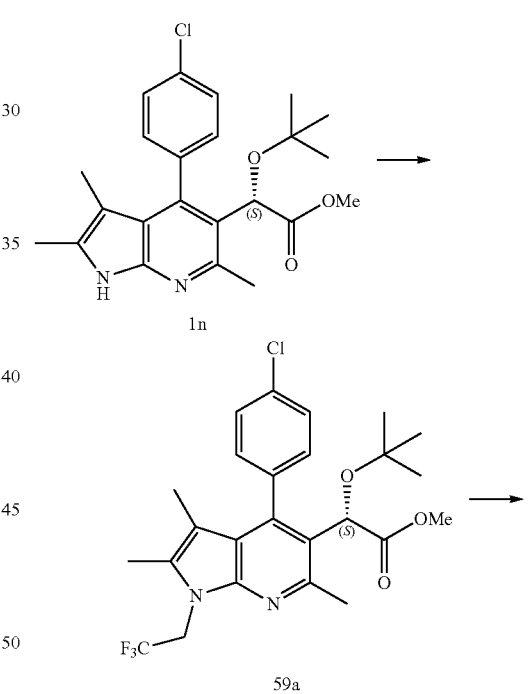

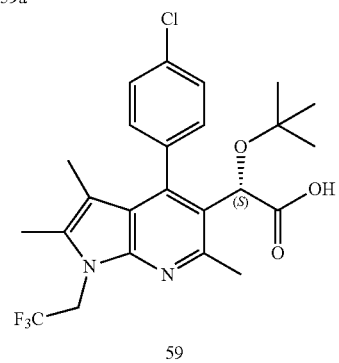

Preparation of 2,2,2-trifluoroethyl trifluoromethanesulfonate

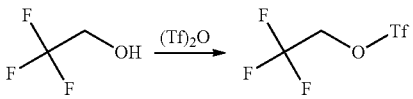

Trifluoromethanesulfonate (12.5 mL, 44.3 mmol) and 2,2,2-trifluoroethanol (6.25 mL, 62.4 mmol) were stirred under nitrogen for 30 minutes at room temperature, and then refluxed at 90 to 95° C. After 3 hours, the result was cooled to room temperature and atmospheric distilled (90 to 91° C.) to give a target compound (12.3 g, 85%) in a colorless liquid state.
$^1$H-NMR (300 MHz, CDCl$_3$) δ 4.70 (q, 2H)

Step 1: Preparation of (S)-methyl 2-(tert-butoxy)-2-(4-(4-chlorophenyl)-2,3,6-trimethyl-1-(2,2,2-trifluoromethyl)-1H-pyrrolo[2,3-b]pyridin-5-yl)acetate (59a)

After the compound 1n (100 mg, 0.241 mmol) was dissolved in dimethylaminopyridine, 2,2,2-trifluoroethyl trifluoromethanesulfonate (223 mg, 0.964 mmol) and potassium carbonate (167 mg, 1.205 mmol) were added thereto, and the mixture was stirred for 18 hours at 50° C. Water (30 mL) was added to the reaction material, and the result was extracted with ethyl acetate (30 mL×2). After the organic layer was dried with anhydrous magnesium sulfate and concentrated under reduced pressure, the residue was purified using silica gel column chromatography (ethyl acetate/normal-hexane=1/4) to give a target compound 59a (15 mg, 12.6%).
$^1$H-NMR (300 MHz, CDCl$_3$) δ 0.98 (s, 9H), 1.48 (s, 3H), 2.29 (s, 3H), 2.69 (s, 3H), 3.66 (s, 3H), 4.76-4.89 (m, 2H), 5.07 (s, 1H), 7.22 (m, 1H), 7.40-7.44 (m, 3H); MS (EI, m/e)=496 (M$^+$).

Step 2: Preparation of (S)-2-(tert-butoxy)-2-(4-(4-chlorophenyl)-2,3,6-trimethyl-1-(2,2,2-trifluoromethyl)-1H-pyrrolo[2,3-b]pyridin-5-yl)acetic acid (59)

A pure target compound 59 (14.4 mg, 97%) was obtained in white solids by reacting the compound 59a (15 mg, 0.03 mmol) in the same manner as in Step 2 of Example 1 using the same solvents and reagents in the same ratio.
$^1$H-NMR (300 MHz, CD$_3$OD) δ 0.99 (s, 9H), 1.54 (s, 3H), 2.34 (s, 3H), 2.69 (s, 3H), 4.99-5.02 (m, 2H), 5.13 (s, 1H), 7.34 (m, 1H), 7.50-7.61 (m, 3H); MS (EI, m/e)=482 (M$^+$).

Example 60

(S)-2-(Tert-butoxy)-2-(4-(4-chlorophenyl)-1-(3-cyanopropyl)-2,3,6-trimethyl-1H-pyrrolo[2,3-b]pyridin-5-yl)acetic acid (60)

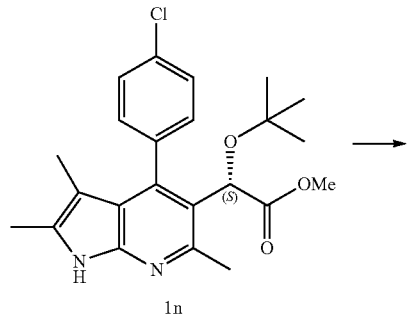

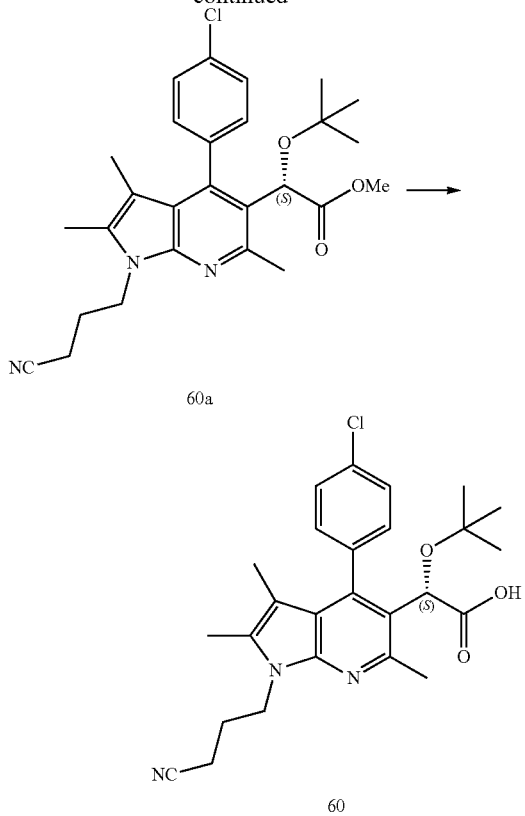

Preparation of 4-iodobutanenitrile

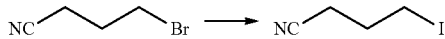

After 4-bromobutanenitrile (1.48 g, 10 mmol) was dissolved in acetonitrile (30 mL), sodium iodide (6 g, 40 mmol) was added thereto, and the mixture was stirred for 70 minutes at 60° C. After the temperature was lowered to room temperature, water (30 mL) was added to the reaction material, and the result was extracted with ethyl acetate (30 mL×2). Excess iodine was removed by washing the organic layer with a 1% aqueous sodium thiosulfate solution, and the organic layer was washed with salted water, dried with anhydrous magnesium sulfate, and concentrated under reduced pressure to give a target compound (1.86 g, 95%).
$^1$H-NMR (300 MHz, CDCl$_3$) δ 2.13 (m, 2H), 2.53 (t, J=13.8 Hz, 2H), 3.30 (t, J=13 Hz, 2H)

Step 1: Preparation of (S)-methyl 2-(tert-butoxy)-2-(4-(4-chlorophenyl)-1-(3-cyanopropyl)-2,3,6-trimethyl-1H-pyrrolo[2,3-b]pyridin-5-yl)acetate (60a)

A target compound 60a (93 mg, 83%) was obtained by reacting the compound 1n (100 mg, 0.241 mmol) in the same manner as in Step 1 of Example 1, except that the 4-iodobutanenitrile (140 mg, 0.723 mmol) prepared above was used instead of iodomethyl and the stirring was carried out for 18 hours at 35° C.
$^1$H-NMR (300 MHz, CDCl$_3$) δ 0.98 (s, 9H), 1.48 (s, 3H), 2.16-2.30 (m, 2H), 2.36 (s, 3H), 2.37-2.41 (t, J=6 Hz, 2H), 2.68 (s, 3H), 3.67 (s, 3H), 4.31-4.35 (m, 2H), 5.07 (s, 1H), 7.21 (m, 1H), 7.40-7.44 (m, 3H); MS (EI, m/e)=481 (M+).

Step 2: Preparation of (S)-2-(tert-butoxy)-2-(4-(4-chlorophenyl)-1-(3-cyanopropyl)-2,3,6-trimethyl-1H-pyrrolo[2,3-b]pyridin-5-yl)acetic acid ((S)-I) (60)

A pure target compound 60 (78.5 mg, 92%) was obtained in white solids by reacting the compound 60a (85 mg, 0.181 mmol) in the same manner as in Step 2 of Example 1 using the same solvents and reagents in the same ratio.

$^1$H-NMR (300 MHz, CD$_3$OD) δ 0.96 (s, 9H), 1.51 (s, 3H), 2.06-2.09 (m, 2H), 2.33 (s, 3H), 2.44-2.49 (t, J=7.5 Hz, 2H), 2.67 (s, 3H), 4.33-4.37 (m, 2H), 5.48 (s, 1H), 7.29 (m, 1H), 7.47-7.55 (m, 3H); MS (EI, m/e)=467 (M+).

Example 61

(S)-2-(Tert-butoxy)-2-(4-(4-chlorophenyl)-1-(3-cyanobenzyl)-2,3,6-trimethyl-1H-pyrrolo[2,3-b]pyridin-5-yl)acetic acid (61)

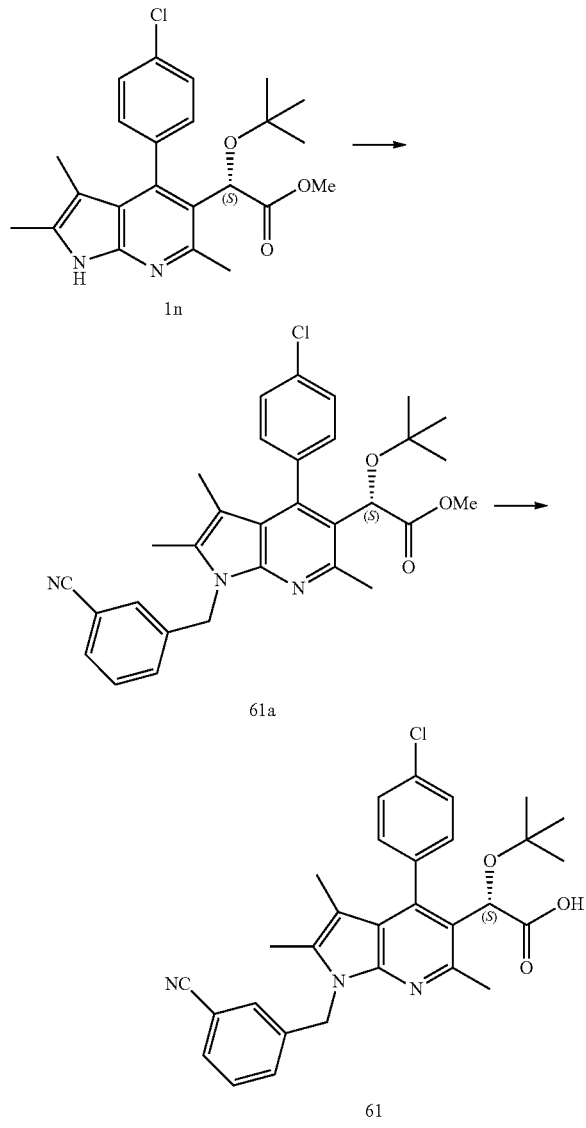

Preparation of 3-(iodomethyl)benzonitrile

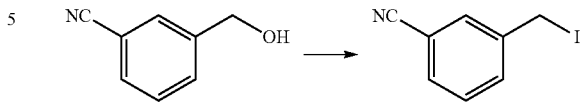

After 3-(hydroxymethyl)benzonitrile (1.33 g, 10 mmol) was dissolved in dimethylformamide (18 mL), triphenylphosphine (3.14 g, 12 mmol) and imidazole (0.82 g, 12 mmol) were added thereto, and the mixture was cooled to −20° C. Iodine (2.79 g, 11 mmol) was added dividing in 5 portions thereto, and the result was stirred for 2 hours at −10° C. A 5% aqueous ammonium chloride solution (60 mL) was added to the reaction solution, and the result was extracted with a diethyl ether/ethyl acetate=1/1 solution (60 mL×2). The organic layers were combined, washed with a 1% aqueous sodium thiosulfate solution to remove excess iodine, washed with salted water, dried with anhydrous magnesium sulfate, and then concentrated under reduced pressure. The residue was separated and purified using silica gel column chromatography (ethyl acetate/normal-hexane=1/9) to give a target compound (1.9 g, 78%) in a white powder state.

$^1$H-NMR (300 MHz, CDCl$_3$) δ 4.41 (s, 2H), 7.2-7.66 (m, 4H); MS (EI, m/e)=243 (M+).

Step 1: Preparation of (S)-methyl 2-(tert-butoxy)-2-(4-(4-chlorophenyl)-1-(3-cyanobenzyl)-2,3,6-trimethyl-1H-pyrrolo[2,3-b]pyridin-5-yl)acetate (61a)

A target compound 61a (94 mg, 73%) was obtained by reacting the compound 1n (100 mg, 0.241 mmol) in the same manner as in Step 1 of Example 1, except that 3-(iodomethyl)benzonitrile (117 mg, 0.482 mmol) was used instead of iodomethyl and the stirring was carried out for 18 hours at 35° C.

$^1$H-NMR (300 MHz, CDCl$_3$) δ 1.02 (s, 9H), 1.52 (s, 3H), 2.15 (s, 3H), 2.71 (s, 3H), 3.70 (s, 3H), 5.12 (s, 1H), 5.45-5.59 (m, 2H), 7.26-7.56 (m, 8H); MS (EI, m/e)=529 (M+).

Step 2: Preparation of (S)-2-(tert-butoxy)-2-(4-(4-chlorophenyl)-1-(3-cyanobenzyl)-2,3,6-trimethyl-1H-pyrrolo[2,3-b]pyridin-5-yl)acetic acid (61)

After the compound 61a (89 mg, 0.167 mmol) was dissolved in tetrahydrofuran/methanol/water=1.2 mL/1.2 mL/0.6 mL, lithium chloride (20 mg, 0.835 mmol) was added thereto, and the mixture was stirred for 18 hours while heating to 45° C. The reaction material was cooled to room temperature, and was adjusted to pH 4.0 using a 2N aqueous hydrochloric acid solution. After the reaction material was concentrated under reduced pressure and dried under a high vacuum, the residue was separated and purified using silica gel column chromatography (dichloromethane/methanol=95/5) to give a target compound 61 (58.7 mg, 68%) in solids.

$^1$H-NMR (300 MHz, CD$_3$OD) δ 1.00 (s, 9H), 1.56 (s, 3H), 2.19 (s, 3H), 2.68 (s, 3H), 5.15 (s, 1H), 5.60 (s, 2H), 7.34-7.62 (m, 8H); MS (EI, m/e)=515 (M+).

Example 62

(S)-2-(Tert-butoxy)-2-(4-(4-chlorophenyl)-1-(furan-3-ylmethyl)-2,3,6-trimethyl-1H-pyrrolo[2,3-b]pyridin-5-yl)acetic acid (62)

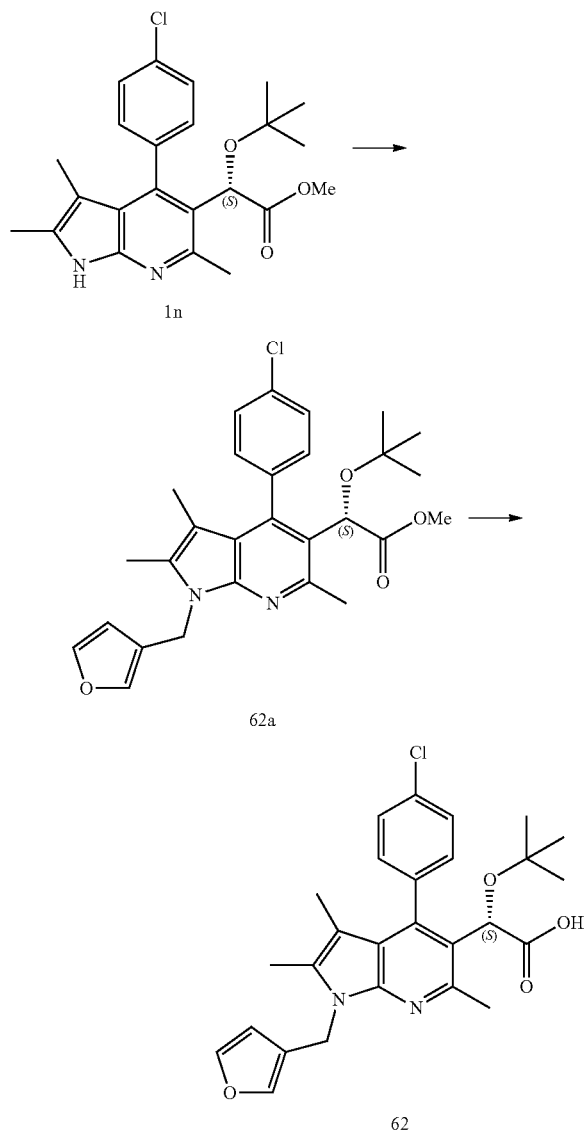

Preparation of 2-(iodomethyl)furan

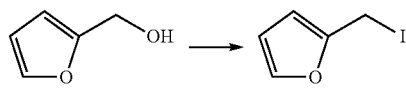 [SMILES: OCc1ccco1 ; ICc1ccco1]

After furan-2-ylmethanol (981 mg, 10 mmol) was dissolved in dimethylformamide (18 mL), triphenylphosphine (3.14 g, 12 mmol) and imidazole (0.82 g, 12 mmol) were added thereto, and the mixture was cooled to −20° C. Iodine (2.79 g, 11 mmol) was added dividing in 5 portions thereto, and the result was stirred for 2 hours at −10° C. A 5% aqueous ammonium chloride solution (60 mL) was added to the reaction solution, and the result was extracted with a diethyl ether/ethyl acetate=1/1 solution (60 mL×2). The organic layers were combined, washed with a 1% aqueous sodium thiosulfate solution to remove excess iodine, washed with salted water, dried with anhydrous magnesium sulfate, and distilled under reduced pressure to give a target compound (960 mg, 46%) in a colorless liquid state.

Step 1: Preparation of (S)-methyl 2-(tert-butoxy)-2-(4-(4-chlorophenyl)-1-(furan-3-ylmethyl)-2,3,6-trimethyl-1H-pyrrolo[2,3-b]pyridin-5-yl)acetate (62a)

A compound 62a (122 mg, 51.2%) was obtained by reacting the compound 1n (200 mg, 0.481 mmol) in the same manner as in Step 1 of Example 1, except that the 2-(iodomethyl)furan (200 mg, 0.964 mmol) prepared above was used instead of iodomethyl and the stirring was carried out for 18 hours at 35° C.

$^1$H-NMR (300 MHz, CDCl$_3$) δ 0.98 (s, 9H), 1.47 (s, 3H), 2.25 (s, 3H), 2.71 (s, 3H), 3.66 (s, 3H), 5.08 (s, 1H), 5.28 (s, 2H), 6.35 (s, 1H), 7.25 (m, 1H), 7.30 (m, 2H), 7.41 (m, 3H); MS (EI, m/e)=494 (M$^+$).

Step 2: Preparation of (S)-2-(tert-butoxy)-2-(4-(4-chlorophenyl)-1-(furan-3-ylmethyl)-2,3,6-trimethyl-1H-pyrrolo[2,3-b]pyridin-5-yl)acetic acid (62)

A pure target compound 62 (107 mg, 96.1%) was obtained in white solids by reacting the compound 62a (115 mg, 0.236 mmol) in the same manner as in Step 2 of Example 36 using the same solvents and reagents in the same ratio.

$^1$H-NMR (300 MHz, CD$_3$OD) δ 0.98 (s, 9H), 1.50 (s, 3H), 2.26 (s, 3H), 2.68 (s, 3H), 5.12 (s, 1H), 5.48 (s, 2H), 6.25 (s, 1H), 7.28-7.38 (m, 3H), 7.47-7.59 (m, 3H); MS (EI, m/e)=480 (M$^+$).

Example 63

(S)-2-(Tert-butoxy)-2-(4-(4-chlorophenyl)-2,3,6-trimethyl-1-(thiazol-5-ylmethyl)-1H-pyrrolo[2,3-b]pyridin-5-yl)acetic acid (63)

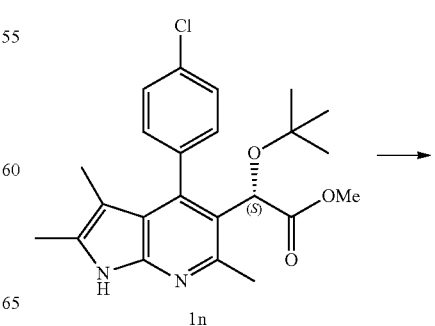

-continued

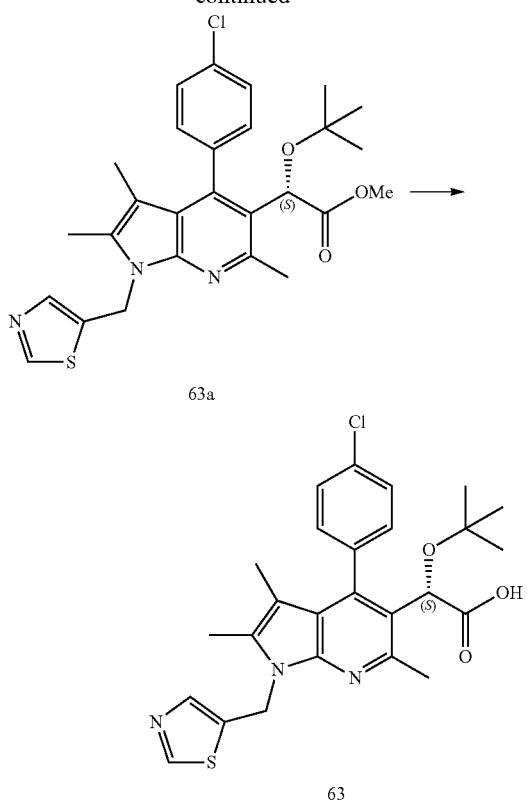

63a

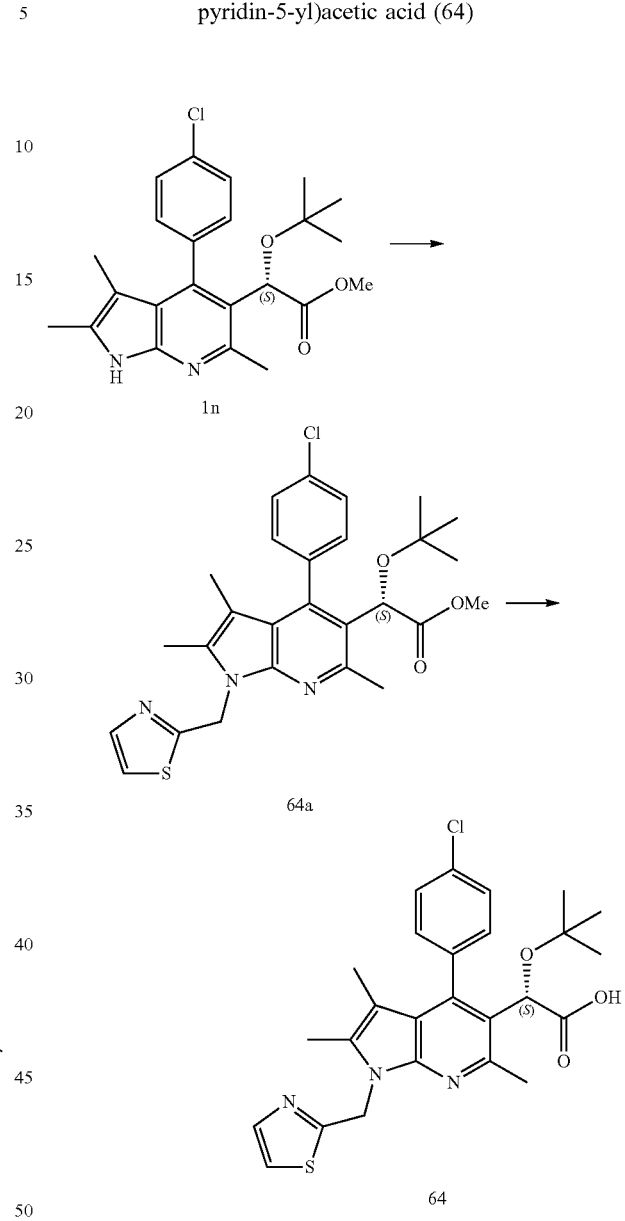

63

Step 1: Preparation of (S)-methyl 2-(tert-butoxy)-2-(4-(4-chlorophenyl)-2,3,6-trimethyl-1-(thiazol-5-ylmethyl)-1H-pyrrolo[2,3-b]pyridin-5-yl)acetate (63a)

A target compound 63a (190 mg, 77%) was obtained by reacting the compound 1n (200 mg, 0.482 mmol) in the same manner as in Step 1 of Example 1, except that 5-(chloromethyl)thiazole (129 mg, 0.964 mmol) was used instead of iodomethyl and the stirring was carried out for 2 hours at 35° C.

$^1$H-NMR (300 MHz, CDCl$_3$) δ 0.98 (s, 9H), 1.47 (s, 3H), 2.29 (s, 3H), 2.72 (s, 3H), 3.67 (s, 3H), 5.08 (s, 1H), 5.63 (s, 2H), 7.22 (m, 1H), 7.39-7.44 (m, 3H), 7.77 (s, 1H), 8.67 (s, 1H); MS (EI, m/e)=512 (M$^+$).

Step 2: Preparation of (S)-2-(tert-butoxy)-2-(4-(4-chlorophenyl)-2,3,6-trimethyl-1-(thiazol-5-ylmethyl)-1H-pyrrolo[2,3-b]pyridin-5-yl)acetic acid (63)

A pure target compound 63 (168 mg, 97%) was obtained in white solids by reacting the compound 63a (178 mg, 0.347 mmol) in the same manner as in Step 2 of Example 36 using the same solvents and reagents in the same ratio.

$^1$H-NMR (300 MHz, CD$_3$OD) δ 0.98 (s, 9H), 1.52 (s, 3H), 2.32 (s, 3H), 2.73 (s, 3H), 5.11 (s, 1H), 5.74 (s, 2H), 7.33 (d, J=9 Hz, 1H), 7.49 (d, J=9 Hz, 2H), 7.65 (d, J=6 Hz, 1H), 7.76 (s, 1H), 8.87 (s, 1H); MS (EI, m/e)=498 (M$^+$).

Example 64

(S)-2-(Tert-butoxy)-2-(4-(4-chlorophenyl)-2,3,6-trimethyl-1-(thiazol-2-ylmethyl)-1H-pyrrolo[2,3-b]pyridin-5-yl)acetic acid (64)

Step 1: Preparation of (S)-methyl 2-(tert-butoxy)-2-(4-(4-chlorophenyl)-2,3,6-trimethyl-1-(thiazol-2-ylmethyl)-1H-pyrrolo[2,3-b]pyridin-5-yl)acetate (64a)

A target compound 64a (178 mg, 72%) was obtained by reacting the compound 1n (200 mg, 0.482 mmol) in the same manner as in Step 1 of Example 1, except that 2-(chloromethyl)thiazole (129 mg, 0.964 mmol) was used instead of iodomethyl and the stirring was carried out for 2 hours at 35° C.

$^1$H-NMR (300 MHz, CDCl$_3$) δ 0.98 (s, 9H), 1.48 (s, 3H), 2.28 (s, 3H), 2.71 (s, 3H), 3.67 (s, 3H), 5.09 (s, 1H), 5.76 (s, 2H), 7.23 (m, 2H), 7.40-7.45 (m, 3H), 7.71 (s, 1H); MS (EI, m/e)=512 (M$^+$).

Step 2: Preparation of (S)-2-(tert-butoxy)-2-(4-(4-chlorophenyl)-2,3,6-trimethyl-1-(thiazol-2-ylmethyl)-1H-pyrrolo[2,3-b]pyridin-5-yl)acetic acid (64)

A pure target compound 64 (164 mg, 95%) was obtained in white solids by reacting the compound 64a (178 mg, 0.347 mmol) in the same manner as in Step 2 of Example 36 using the same solvents and reagents in the same ratio.
$^1$H-NMR (300 MHz, CD$_3$OD) δ 0.96 (s, 9H), 1.51 (s, 3H), 2.26 (s, 3H), 2.68 (s, 3H), 5.10 (s, 1H), 5.79 (s, 2H), 7.32 (m, 1H), 7.44-7.51 (m, 4H), 7.65 (m, 1H), 7.71 (m, 1H); MS (EI, m/e)=498 (M$^+$).

Example 65

(S)-2-(Tert-butoxy)-2-(4-(4-chlorophenyl)-1-(2-dimethylaminoethyl)-2,3,6-trimethyl-1H-pyrrolo[2,3-b]pyridin-5-yl)acetic acid (65)

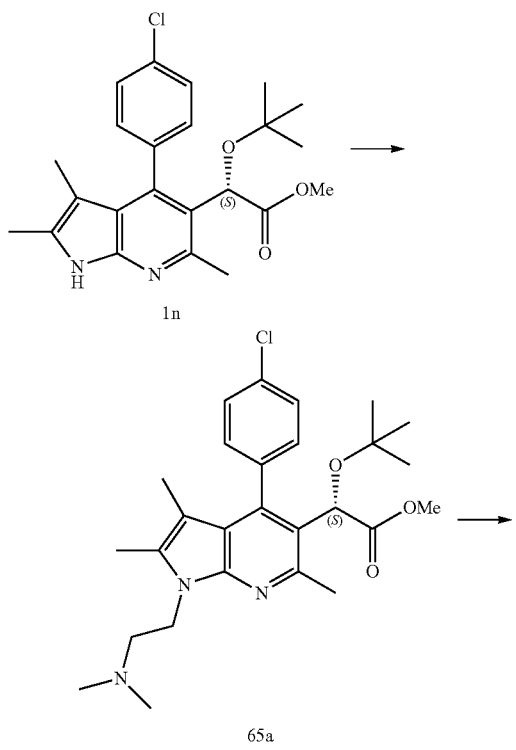

2-Iodo-N,N-dimethylethanamine hydrochloric acid salt

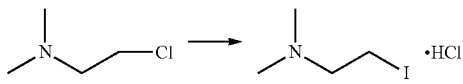

After a 2-chloro-N,N-dimethylethanamine hydrochloric acid salt (1.44 g, 10 mmol) was dissolved in ethanol (60 mL), sodium iodide (3.74 g, 25 mmol) was added thereto, and the mixture was heated under reflux for 3 hours. The reaction material was cooled to room temperature, and the insoluble substances were removed by filtration. The filtrate was concentrated under reduced pressure, and the obtained residue was used as it is for the next reaction without purification.

Step 1: Preparation of (S)-methyl 2-(tert-butoxy)-2-(4-(4-chlorophenyl)-1-(2-dimethylaminoethyl)-2,3,6-trimethyl-1H-pyrrolo[2,3-b]pyridin-5-yl)acetate (65a)

A target compound 65a (52 mg, 45%) was obtained by reacting the compound 1n (100 mg, 0.241 mmol) in the same manner as in Step 1 of Example 1, except that the 2-iodo-N,N-dimethylethanamine hydrochloric acid salt (236 mg, 0.723 mmol) prepared above was used instead of iodomethyl and the stirring was carried out for 18 hours at 35° C.
$^1$H-NMR (300 MHz, CDCl$_3$) δ 1.01 (s, 9H), 1.50 (s, 3H), 2.35 (s, 3H), 2.62 (s, 6H), 2.66 (s, 3H), 2.93 (t, J=6 Hz, 2H), 3.67 (s, 3H), 4.47 (t, J=6 Hz, 2H), 5.15 (s, 1H), 7.28 (m, 1H), 7.46-7.52 (m, 3H); MS (EI, m/e)=485 (M$^+$).

Step 2: Preparation of (S)-2-(tert-butoxy)-2-(4-(4-chlorophenyl)-1-(2-dimethylaminoethyl)-2,3,6-trimethyl-1H-pyrrolo[2,3-b]pyridin-5-yl)acetic acid (65)

A pure target compound 65 (24.3 mg, 49%) was obtained in white solids by reacting the compound 65a (52 mg, 0.107 mmol) in the same manner as in Step 2 of Example 36 using the same solvents and reagents in the same ratio.
$^1$H-NMR (300 MHz, CD$_3$OD) δ 0.91 (s, 9H), 1.50 (s, 3H), 2.22 (s, 3H), 2.73 (t, 2H), 2.87 (s, 6H), 3.22 (t, J=6 Hz, 2H), 4.39-4.24 (m, 2H), 4.99 (s, 1H), 7.24 (d, 1H), 7.47 (m, 3H), 7.85 (d, J=9 Hz, 1H); MS (EI, m/e)=471 (M$^+$).

Example 66

(S)-2-(Tert-butoxy)-2-(4-(4-chlorophenyl)-1-((2-fluoropyridin-4-yl)methyl)-2,3,6-trimethyl-1H-pyrrolo[2,3-b]pyridin-5-yl)acetic acid (66)

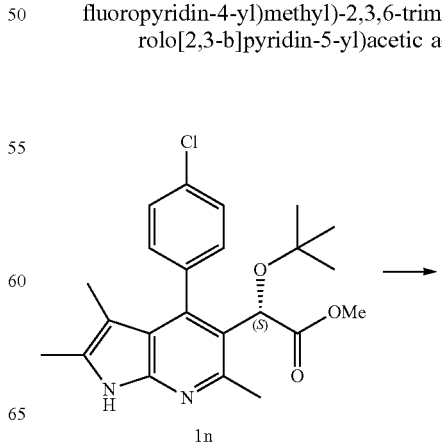

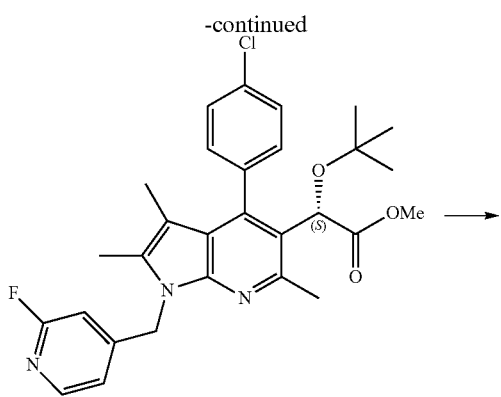

66a

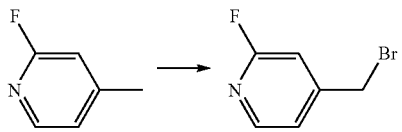

66

Preparation of 4-(bromomethyl)-2-fluoropyridine

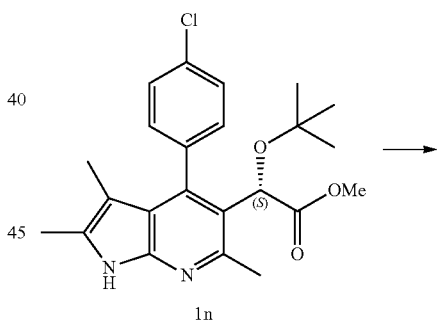

After 4-methyl-2-fluoropyridine (1.0 g, 9 mmol) was dissolved in carbon tetrachloride (20 mL), N-bromosuccinimide (1.76 g, 9.9 mmol) and benzoyl peroxide (12.6 mg) were added thereto, and the mixture was refluxed for 18 hours. The reaction material was cooled to room temperature, and stirred for 10 minutes after normal-hexane (150 mL) was added thereto. After the produced solids were removed by filtration, the filtrate was concentrated under reduced pressure, and then the residue was purified using silica gel column chromatography (ethyl acetate/normal-hexane=1/20) to give a target compound (525 mg, 44.9%).
$^1$H-NMR (300 MHz, CDCl$_3$) δ 4.39 (s, 2H), 6.96 (s, 1H), 7.20 (d, 1H), 8.10 (d, 1H); MS (EI, m/e)=190 (M$^+$)

Step 1: Preparation of (S)-methyl 2-(tert-butoxy)-2-(4-(4-chlorophenyl)-1-((2-fluoropyridin-4-yl)methyl)-2,3,6-trimethyl-1H-pyrrolo[2,3-b]pyridin-5-yl)acetate (66a)

A target compound 66a (233 mg, 92.3%) was obtained by reacting the compound 1n (200 mg, 0.482 mmol) in the same manner as in Step 1 of Example 1, except that the 4-(bromomethyl)-2-fluoropyridine (183 mg, 0.962 mmol) prepared above was used instead of iodomethyl and the stirring was carried out for 18 hours at 35° C.
$^1$H-NMR (300 MHz, CDCl$_3$) δ 0.99 (s, 9H), 1.48 (s, 3H), 2.14 (s, 3H), 2.67 (s, 3H), 3.67 (s, 3H), 5.10 (s, 1H), 5.50 (m, 2H), 6.58 (s, 1H), 6.95 (m, 1H), 7.26 (m, 1H), 7.42-7.51 (m, 3H), 8.13 (d, J=3 Hz, 1H); MS (EI, m/e)=523 (M$^+$).

Step 2: Preparation of (S)-2-(tert-butoxy)-2-(4-(4-chlorophenyl)-1-((2-fluoropyridin-4-yl)methyl)-2,3,6-trimethyl-1H-pyrrolo[2,3-h]pyridin-5-yl)acetic acid (66)

A pure target compound 66 (103 mg, 46%) was obtained in white solids by reacting the carboxylic acid ester compound 66a (230 mg, 0.439 mmol) obtained in Step 1 in the same manner as in Step 2 of Example 36 using the same solvents and reagents in the same ratio.
$^1$H-NMR (300 MHz, CD$_3$OD) δ 1.01 (s, 9H), 1.54 (s, 3H), 2.15 (s, 3H), 2.64 (s, 3H), 5.21 (s, 1H), 5.47 (m, 2H), 6.59 (s, 1H), 6.92 (m, 1H), 7.29 (m, 1H), 7.44-7.48 (m, 2H), 7.65 (m, 1H), 8.13 (d, J=3 Hz, 1H); MS (EI, m/e)=509 (M$^+$).

Example 67

(S)-2-(Tert-butoxy)-2-(4-(4-chlorophenyl)-1-((6-fluoropyridin-3-yl)methyl)-2,3,6-trimethyl-1H-pyrrolo[2,3-b]pyridin-5-yl)acetic acid (67)

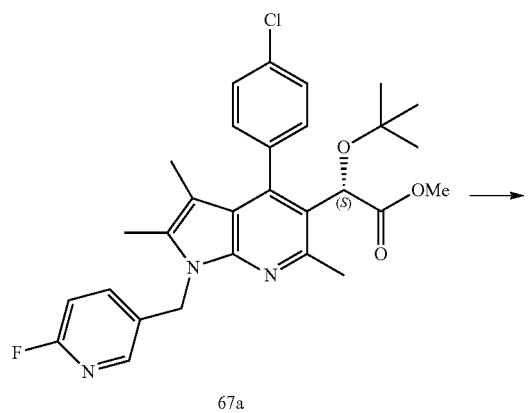

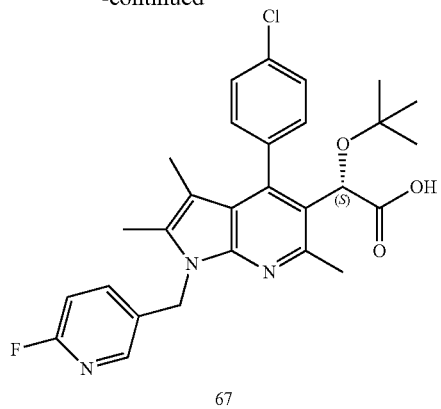

67

Preparation of 5-(bromomethyl)-2-fluoropyridine

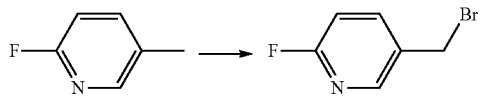

After 5-methyl-2-fluoropyridine (1.0 g, 9 mmol) was dissolved in carbon tetrachloride (20 mL), N-bromosuccinimide (1.76 g, 9.9 mmol) and benzoyl peroxide (12.6 mg) were added thereto, and the mixture was refluxed for 18 hours. The reaction material was cooled to room temperature, and stirred for 10 minutes after normal-hexane (150 mL) was added thereto. After the produced solids were removed by filtration, the filtrate was concentrated under reduced pressure, and then the residue was purified using silica gel column chromatography (effluent, ethyl acetate/normal-hexane=1/20) to give a target compound (1.28 mg, 74.8%).

$^1$H-NMR (300 MHz, CDCl$_3$) δ 4.47 (s, 2H), 6.94 (d, 1H), 7.84 (t, 1H), 8.23 (s, 1H); MS (EI, m/e)=190 (M$^+$).

Step 1: Preparation of (S)-methyl 2-(tert-butoxy)-2-(4-(4-chlorophenyl)-1-((6-fluoropyridin-3-yl)methyl)-2,3,6-trimethyl-1H-pyrrolo[2,3-b]pyridin-5-yl)acetate (67a)

A target compound 67a (225 mg, 89%) was obtained by reacting the compound 1n (200 mg, 0.482 mmol) in the same manner as in Step 1 of Example 1, except that the 5-(bromomethyl)-2-fluoropyridine (183 mg, 0.962 mmol) prepared above was used instead of iodomethyl and the stirring was carried out for 18 hours at 35° C.

$^1$H-NMR (300 MHz, CDCl$_3$) δ 0.99 (s, 9H), 1.47 (s, 3H), 2.19 (s, 3H), 2.52 (s, 3H), 3.68 (s, 3H), 5.09 (s, 1H), 5.46 (m, 2H), 6.84 (d, J=9 Hz, 1H), 7.24 (m, 1H), 7.40-7.45 (m, 3H), 7.66 (t, J=7.5 Hz, 1H), 8.10 (s, 1H); MS (EI, m/e)=523 (M$^+$).

Step 2: Preparation of (S)-2-(tert-butoxy)-2-(4-(4-chlorophenyl)-1-((6-fluoropyridin-3-yl)methyl)-2,3,6-trimethyl-1H-pyrrolo[2,3-b]pyridin-5-yl)acetic acid (67)

A pure target compound 67 (196 mg, 92%) was obtained in white solids by reacting the compound 67a (220 mg, 0.42 mmol) in the same manner as in Step 2 of Example 36 using the same solvents and reagents in the same ratio.

$^1$H-NMR (300 MHz, CD$_3$OD) δ 0.99 (s, 9H), 1.54 (s, 3H), 2.24 (s, 3H), 2.69 (s, 3H), 5.14 (s, 1H), 5.53 (m, 2H), 6.99 (d, J=9 Hz, 1H), 7.35 (m, 1H), 7.50-7.54 (m, 2H), 7.62-7.67 (m, 2H), 7.99 (s, 1H); MS (EI, m/e)=509 (M$^+$).

Example 68

(S)-2-(Tert-butoxy)-2-(4-(4-chlorophenyl)-1-((2-fluoropyridin-3-yl)methyl)-2,3,6-trimethyl-1H-pyrrolo[2,3-b]pyridin-5-yl)acetic acid (68)

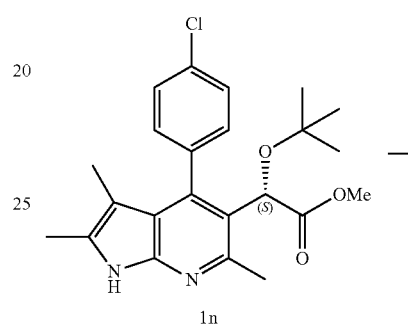

1n

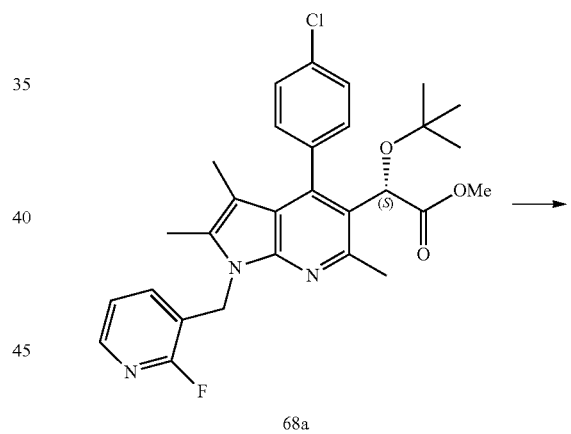

68a

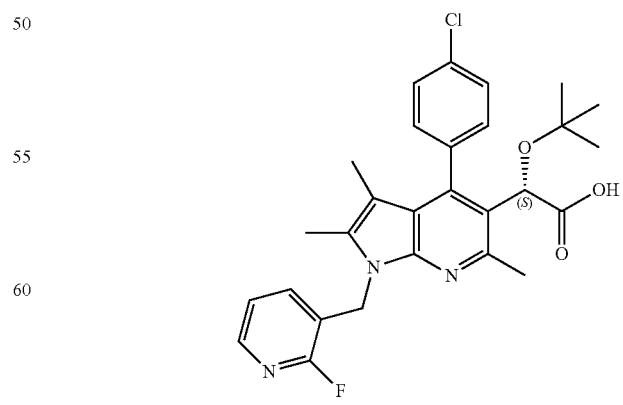

68

Preparation of 3-(bromomethyl)-2-fluoropyridine

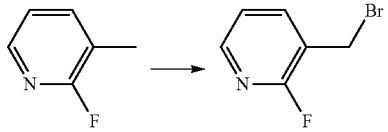

After 2-fluoro-3-methylpyridine (1.0 g, 9 mmol) was dissolved in carbon tetrachloride (20 mL), N-bromosuccinimide (1.76 g, 9.9 mmol) and benzoyl peroxide (12.6 mg) were added thereto, and the mixture was refluxed for 18 hours. The reaction material was cooled to room temperature, and stirred for 10 minutes after normal-hexane (150 mL) was added thereto. After the produced solids were removed by filtration, the filtrate was concentrated under reduced pressure, and the residue was purified using silica gel column chromatography (ethyl acetate/normal-hexane=1/20) to give a target compound (1.02 mg, 61%).

$^1$H-NMR (300 MHz, CDCl$_3$) δ 4.50 (s, 2H), 7.22 (t, 1H), 7.84 (t, 1H), 8.21 (d, 1H); MS (EI, m/e)=190 (M$^+$).

Step 1: Preparation of (S)-methyl 2-(tert-butoxy)-2-(4-(4-chlorophenyl)-1-((2-fluoropyridin-3-yl)methyl)-2,3,6-trimethyl-1H-pyrrolo[2,3-b]pyridin-5-yl)acetate (68a)

A target compound 68a (180 mg, 71.4%) was obtained by reacting the compound 1n (200 mg, 0.482 mmol) in the same manner as in Step 1 of Example 1, except that the 3-(bromomethyl)-2-fluoropyridine (183 mg, 0.962 mmol) prepared above was used instead of iodomethyl and the stirring was carried out for 18 hours at 35° C.

$^1$H-NMR (300 MHz, CDCl$_3$) δ 0.99 (s, 9H), 1.49 (s, 3H), 2.18 (s, 3H), 2.68 (s, 3H), 3.68 (s, 3H), 5.10 (s, 1H), 5.49 (s, 2H), 7.06 (t, J=6 Hz, 1H), 7.26 (m, 1H), 7.32 (t, J=4.5 Hz, 1H), 7.41-7.46 (m, 3H), 8.09 (m, 1H); MS (EI, m/e)=523 (M$^+$).

Step 2: Preparation of (S)-2-(tert-butoxy)-2-(4-(4-chlorophenyl)-1-((2-fluoropyridin-3-yl)methyl)-2,3,6-trimethyl-1H-pyrrolo[2,3-b]pyridin-5-yl)acetic acid (68)

A pure target compound 68 (122.7 mg, 73%) was obtained in white solids by reacting the compound 68a (174 mg, 0.33 mmol) in the same manner as in Step 2 of Example 36 using the same solvents and reagents in the same ratio.

$^1$H-NMR (300 MHz, CD$_3$OD) δ 0.92 (s, 9H), 1.50 (s, 3H), 2.16 (s, 3H), 2.59 (s, 3H), 5.08 (s, 1H), 5.52 (m, 2H), 6.54-7.11 (m, 2H), 7.29 (m, 1H), 7.45-7.57 (m, 3H), 7.93-8.02 (m, 1H); MS (EI, m/e)=509 (M$^+$).

Example 69

(S)-2-(Tert-butoxy)-2-(4-(4-chlorophenyl)-1-((2,2-difluorocyclopropyl)methyl)-2,3,6-trimethyl-1H-pyrrolo[2,3-b]pyridin-5-yl)acetic acid (69)

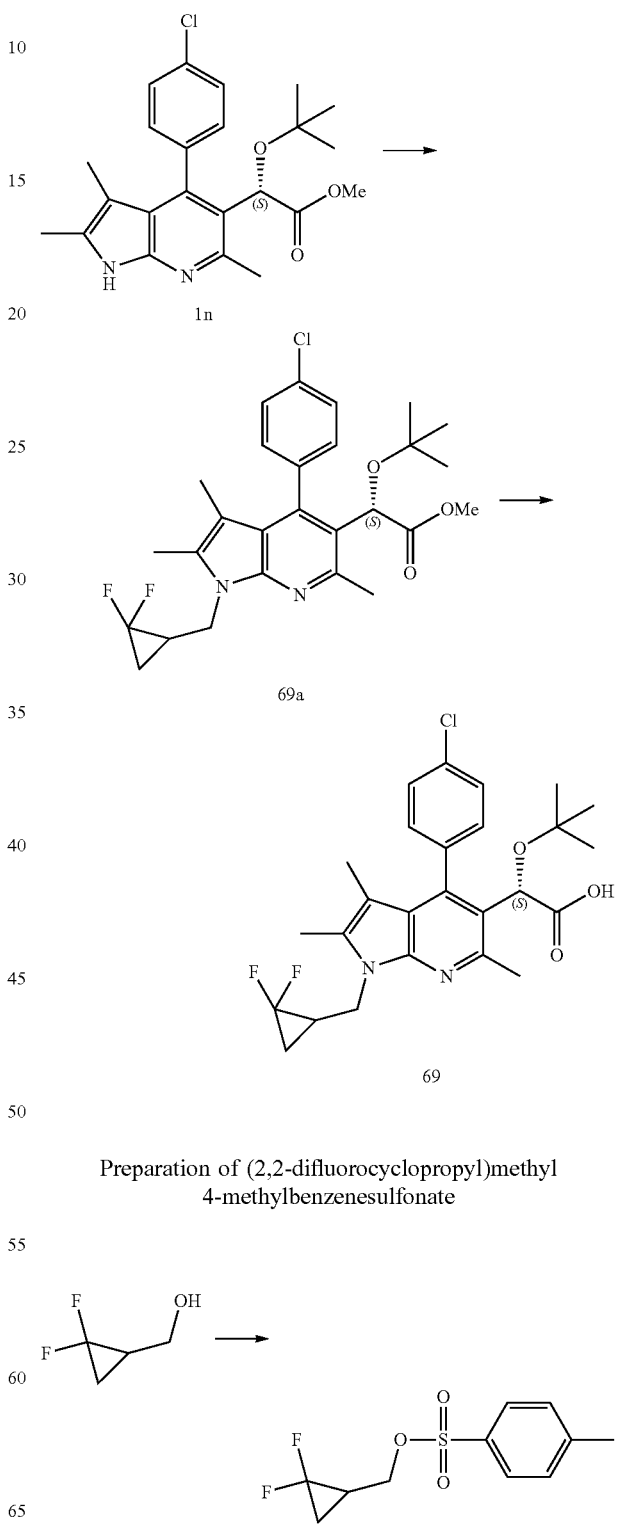

Preparation of (2,2-difluorocyclopropyl)methyl 4-methylbenzenesulfonate

After (2,2-difluorocyclopropyl)methanol (550 mg, 5 mmol) synthesized according to a known method (reference: *J. of Fluorine Chemistry*, 2003, 119, 39-51) was dissolved in dichloromethane (50 mL) and cooled with ice water, triethylamine (0.83 mL, 6 mmol) and p-toluenesulfonyl chloride (0.97 g, 5 mmol) were added thereto in order, and the mixture was stirred for 18 hours while slowly raising the temperature to room temperature. The reaction material was washed with a 5% aqueous sodium bicarbonate solution and water, dried with anhydrous magnesium sulfate, and then concentrated under reduced pressure. The residue was separated and purified using silica gel column chromatography (ethyl acetate/normal-hexane=1/6) to give a target compound (470 mg, 61%) in an oil state.

$^1$H-NMR (300 MHz, CDCl$_3$) δ 1.16-1.21 (m, 1H), 1.19-1.56 (m, 1H), 1.88-1.96 (m, 1H), 2.45 (s, 3H), 4.09 (d, J=7.92 Hz, 2H), 7.35 (d, J=7.92 Hz, 2H), 7.80 (d, J=8.04 Hz, 2H).

Step 1: Preparation of (S)-methyl 2-(tert-butoxy)-2-(4-(4-chlorophenyl)-1-((2,2-difluorocyclopropyl)methyl)-2,3,6-trimethyl-1H-pyrrolo[2,3-b]pyridin-5-yl)acetate (69a)

A target compound 69a (143 mg, 62%) was obtained by reacting the compound 1n (200 mg, 0.482 mmol) in the same manner as in Step 1 of Example 1, except that the (2,2-difluorocyclopropyl)methyl 4-methylbenzenesulfonate (253 mg, 0.964 mmol) prepared above was used instead of iodomethyl and the stirring was carried out for 18 hours at 35° C.

$^1$H-NMR (300 MHz, CDCl$_3$) δ 0.97 (s, 9H), 1.29-1.37 (m, 2H), 1.42 (s, 3H), 2.07-2.09 (m, 1H), 2.22 (s, 3H), 2.62 (s, 3H), 3.58 (s, 3H), 4.01-4.03 (m, 1H), 4.40-4.47 (m, 1H), 5.01 (s, 1H), 7.17 (m, 1H), 7.26-7.36 (m, 3H); MS (EI, m/e)=504 (M$^+$).

Step 2: Preparation of (S)-2-(tert-butoxy)-2-(4-(4-chlorophenyl)-1-((2,2-difluorocyclopropyl)methyl)-2,3,6-trimethyl-1H-pyrrolo[2,3-b]pyridin-5-yl)acetic acid (69)

A pure target compound 69 (40 mg, 46%) was obtained in white solids by reacting the compound 69a (90 mg, 0.178 mmol) in the same manner as in Step 2 of Example 36 using the same solvents and reagents in the same ratio.

$^1$H-NMR (300 MHz, CDCl$_3$) δ 0.99 (s, 9H), 1.38-1.45 (m, 2H), 1.52 (s, 3H), 2.02-2.19 (m, 1H), 2.33 (s, 3H), 2.69 (s, 3H), 4.25-4.33 (m, 1H), 4.46-4.86 (m, 1H), 5.13 (s, 1H), 7.32 (m, 1H), 7.48-7.60 (m, 3H); MS (EI, m/e)=490 (M$^+$).

Example 70

(S)-2-(Tert-butoxy)-2-(4-(4-chlorophenyl)-2,3,6-trimethyl-1-(2-(2-oxopyrrolidin-1-yl)ethyl)-1H-pyrrolo[2,3-b]pyridin-5-yl)acetic acid (70)

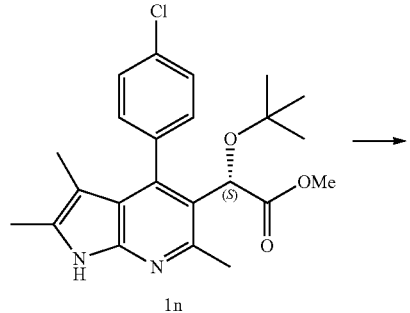

1n

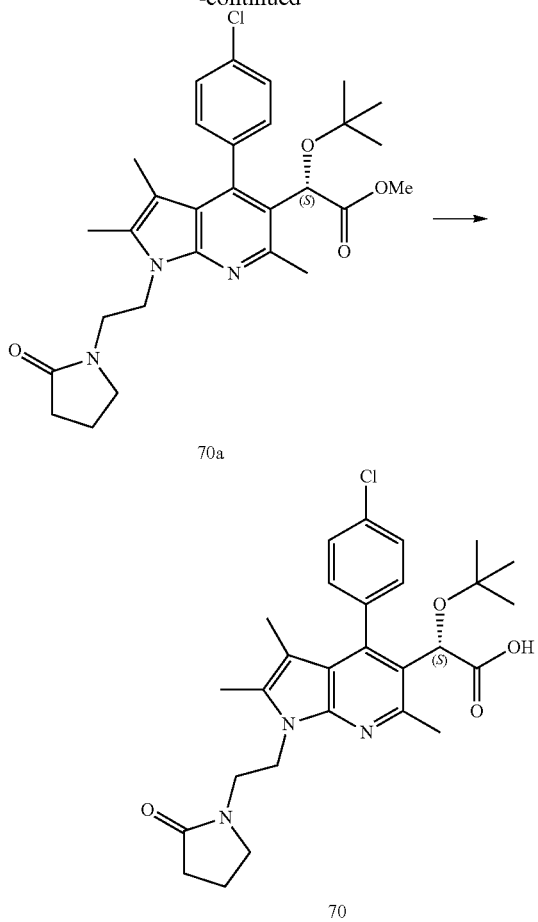

Preparation of 1-(2-iodoethyl)pyrrolidin-2-one

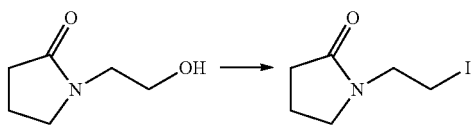 [SMILES: O=C1CCCN1CCO ; O=C1CCCN1CCI]

After 1-(2-hydroxyethyl)pyrrolidin-2-one (2.28 g, 17.7 mmol) was dissolved in dimethylformamide (32 mL), triphenylphosphine (5.5 g, 21.24 mmol) and imidazole (1.43 g, 21.24 mmol) were added thereto, and the mixture was stirred. Iodine (5 g, 19.47 mmol) was added in portions thereto over 5 minutes at −20° C., and the result was stirred for 2 hours. Water (30 mL) was added to the reaction material, and the result was extracted with diethyl ether (100 mL×2). The organic layer was dried with anhydrous magnesium sulfate and then concentrated under reduced pressure. The residue was purified using silica gel column chromatography (effluent, diethyl ether/normal-hexane=1/1) to give a target compound (2.14 mg, 51%) in a colorless liquid state.

¹H-NMR (300 MHz, CDCl₃) δ 2.04-2.09 (m, 2H), 2.37-2.40 (m, 2H), 3.23-3.28 (m, 2H), 3.45-3.50 (m, 2H), 3.64-3.69 (m, 2H); MS (EI, m/e)=239 (M⁺).

Step 1: Preparation of (S)-methyl 2-(tert-butoxy)-2-(4-(4-chlorophenyl)-2,3,6-trimethyl-1-(2-(2-oxopyrrolidin-1-yl)ethyl)-1H-pyrrolo[2,3-b]pyridin-5-yl)acetate (70a)

A target compound 70a (60 mg, 24%) was obtained by reacting the compound 1n (200 mg, 0.482 mmol) in the same manner as in Step 1 of Example 1, except that the 1-(2-iodoethyl)pyrrolidin-2-one (230 mg, 0.964 mmol) prepared above was used instead of iodomethyl and the stirring was carried out for 18 hours at 35° C.

¹H-NMR (300 MHz, CDCl₃) δ 0.97 (s, 9H), 1.48 (s, 3H), 1.85 (m, 2H), 2.22 (t, J=6 Hz, 2H), 2.31 (s, 3H), 2.68 (s, 3H), 3.33 (t, J=6.0 Hz, 2H), 3.61 (t, J=6.0 Hz, 2H), 3.66 (s, 3H), 4.39 (t, J=6.0 Hz, 2H), 5.08 (s, 1H), 7.25 (t, J=4.5 Hz, 1H), 7.43-7.39 (m, 3H); MS (EI, m/e)=525 (M⁺).

Step 2: Preparation of (S)-2-(tert-butoxy)-2-(4-(4-chlorophenyl)-2,3,6-trimethyl-1-(2-(2-oxopyrrolidin-1-yl)ethyl)-1H-pyrrolo[2,3-b]pyridin-5-yl)acetic acid (70)

A pure target compound 70 (64 mg, 92%) was obtained in white solids by reacting the compound 70a (60 mg, 0.114 mmol) in the same manner as in Step 2 of Example 36 using the same solvents and reagents in the same ratio.

¹H-NMR (300 MHz, CD₃OD) δ 0.98 (s, 9H), 1.53 (s, 3H), 1.72-1.77 (m, 2H), 2.08 (t, J=6 Hz, 2H), 2.35 (s, 3H), 2.69 (s, 3H), 3.26-3.35 (m, 2H), 4.44-4.50 (m, 2H), 3.58 (t, J=4.5 Hz, 2H), 4.44-4.50 (m, 2H), 5.13 (s, 1H), 7.25 (t, J=4.5 Hz, 1H), 7.43-7.39 (m, 3H); MS (EI, m/e)=511 (M⁺).

Example 71

(S)-2-(Tert-butoxy)-2-(4-(4-chlorophenyl)-2,3,6-trimethyl-1-(2-(2-(pyrrolidin-1-yl)ethyl)-1H-pyrrolo[2,3-b]pyridin-5-yl)acetic acid (71)

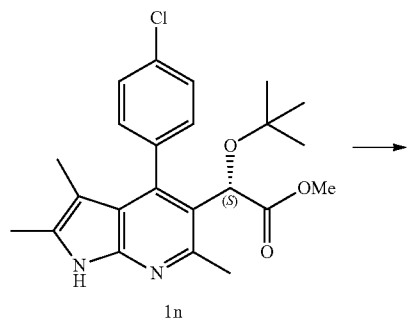

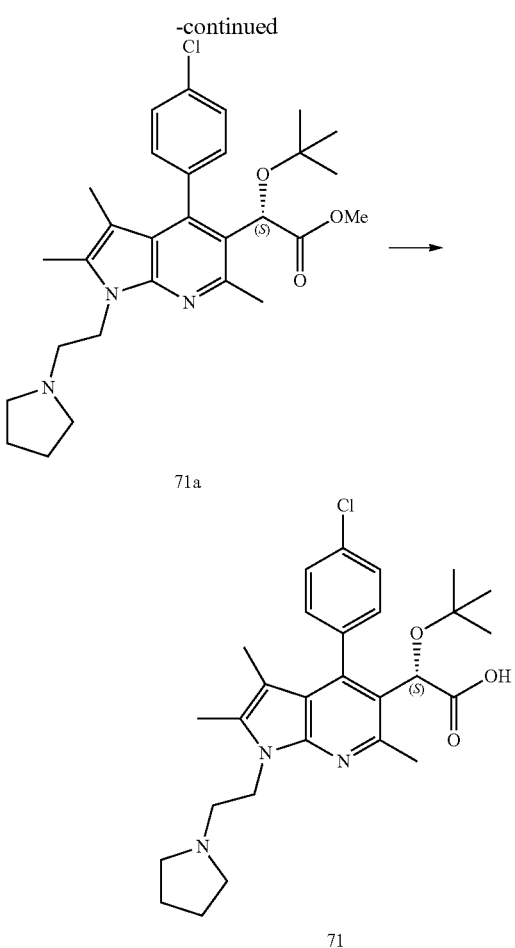

Preparation of 1-(iodoethyl)pyrrolidine HI salt

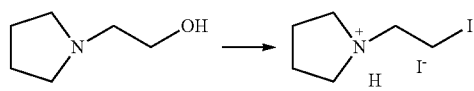

Triphenylphosphine (4.46 g, 17.7 mmol), imidazole (1.2 g, 17.7 mmol) and iodine (4.5 g, 17.7 mmol) were dissolved in tetrahydrofuran (90 mL), and the mixture was stirred for 5 minutes.

1-(pyrrolidin-1-yl)ethanol (2.0 mL, 17.7 mmol) was slowly added thereto, and the result was stirred for 4 hours at room temperature. The produced white solids were filtered, combined, sufficiently washed with ethyl acetate, and dried to give a target compound (3.8 g, 61%).

Step 1: Preparation of (S)-methyl 2-(tert-butoxy)-2-(4-(4-chlorophenyl)-2,3,6-trimethyl-1-(2-(2-(pyrrolidin-1-yl)ethyl)-1H-pyrrolo[2,3-b]pyridin-5-yl)acetate (71a)

A target compound 71a (97 mg, 39%) was obtained by reacting the compound 1n (200 mg, 0.482 mmol) in the same manner as in Step 1 of Example 1, except that the 1-(2-iodoethyl)pyrrolidine iodic acid salt (510 mg, 1.446 mmol) prepared above was used instead of iodomethyl and the stirring was carried out for 18 hours at 35° C.

$^1$H-NMR (300 MHz, CDCl$_3$) δ 0.98 (s, 9H), 1.51 (s, 3H), 2.02 (m, 4H), 2.34 (s, 3H), 2.75 (s, 3H), 3.10 (m, 4H), 3.29-3.25 (m, 2H), 3.67 (s, 3H), 4.56-4.51 (t, J=7.5 Hz, 2H), 5.07 (s, 1H), 7.23-7.21 (m, 1H), 7.43-7.39 (m, 3H); MS (EI, m/e)=511 (M$^+$)

Step 2: Preparation of (S)-2-(tert-butoxy)-2-(4-(4-chlorophenyl)-2,3,6-trimethyl-1-(2-(2-(pyrrolidin-1-yl)ethyl)-1H-pyrrolo[2,3-b]pyridin-5-yl)acetic acid (71)

A pure target compound 71 (52 mg, 67%) was obtained in white solids by reacting the compound 71a (97 mg, 0.189 mmol) in the same manner as in Step 2 of Example 36 using the same solvents and reagents in the same ratio.

$^1$H-NMR (300 MHz, CD$_3$OD) δ 0.93 (s, 9H), 1.53 (s, 3H), 1.93 (m, 4H), 2.30 (s, 3H), 2.75 (s, 3H), 2.94-3.02 (m, 6H), 4.37 (t, J=7.5 Hz, 2H), 4.97 (s, 1H), 7.28 (d, J=8.16 Hz, 1H), 7.45 (d, J=8.01 Hz, 2H), 7.89 (d, J=8.13 Hz, 1H); MS (EI, m/e)=497 (M$^+$).

Example 72 and 73

(S)-2-((R)-4-(5-chlorochroman-6-yl)-1,2,3,6-tetramethyl-1H-pyrrolo[2,3-b]pyridin-5-yl)acetic acid (72) and (S)-2-(tert-butoxy)-2-((S)-4-(5-chlorochroman-6-yl)-1,2,3,6-tetramethyl-1H-pyrrolo[2,3-b]pyridin-5-yl)acetic acid (73)

Step 1: Preparation of (2S)-methyl 2-(tert-butoxy)-2-(4-(5-chlorochroman-6-yl)-2,3,6-trimethyl-1H-pyrrolo[2,3-b]pyridin-5-yl)acetate (72b)

After the compound 1x (425 mg, 1.25 mmol) was dissolved in dimethylformamide (6 mL), 2-(5-chlorochroman-6-yl)-4,4,5,5-tetramethyl-1,3,2-dioxaborolane (424 mg, 1.44 mmol), potassium carbonate (520 mg, 3.76 mmol) and tetrakis(triphenylphosphine)palladium(0) (290 mg, 0.25 mmol) were added thereto, and the mixture was heated to 130° C. under nitrogen atmosphere and stirred for 18 hours. The reaction material was cooled to room temperature, concentrated under reduced pressure, and then the residue was separated and purified using silica gel column chromatography (effluent, normal-hexane/ethyl acetate=3/1) to give a target compound 72b (318 mg, 54%) as a mixture of 2 isomers.

$^1$H-NMR (300 MHz, CDCl$_3$) δ 0.96 (s, 4.5H), 1.11 (s, 4.5H), 1.44 (s, 1.5H), 1.46 (s, 1.5H), 2.07 (t, 3H), 2.16 (s, 2H), 2.28 (m, 3H), 2.31 (s, 1H), 2.69 (s, 3H), 2.80 (s, 1H), 2.83 (m, 2H), 3.57 (s, 1.5H), 3.64 (s, 1.5H), 3.66 (s, 3H), 4.21 (m, 2H), 5.11 (s, 0.5H), 5.12 (s, 0.5H), 6.7-6.8 (m, 1.26H), 7.22-7.25 (m, 0.67H), 7.26 (m, 0.5H), 8.24 (s, 1H), 8.24 (s, 1H), 8.40 (bs, 1H); MS (EI, m/e)=470 (M$^+$).

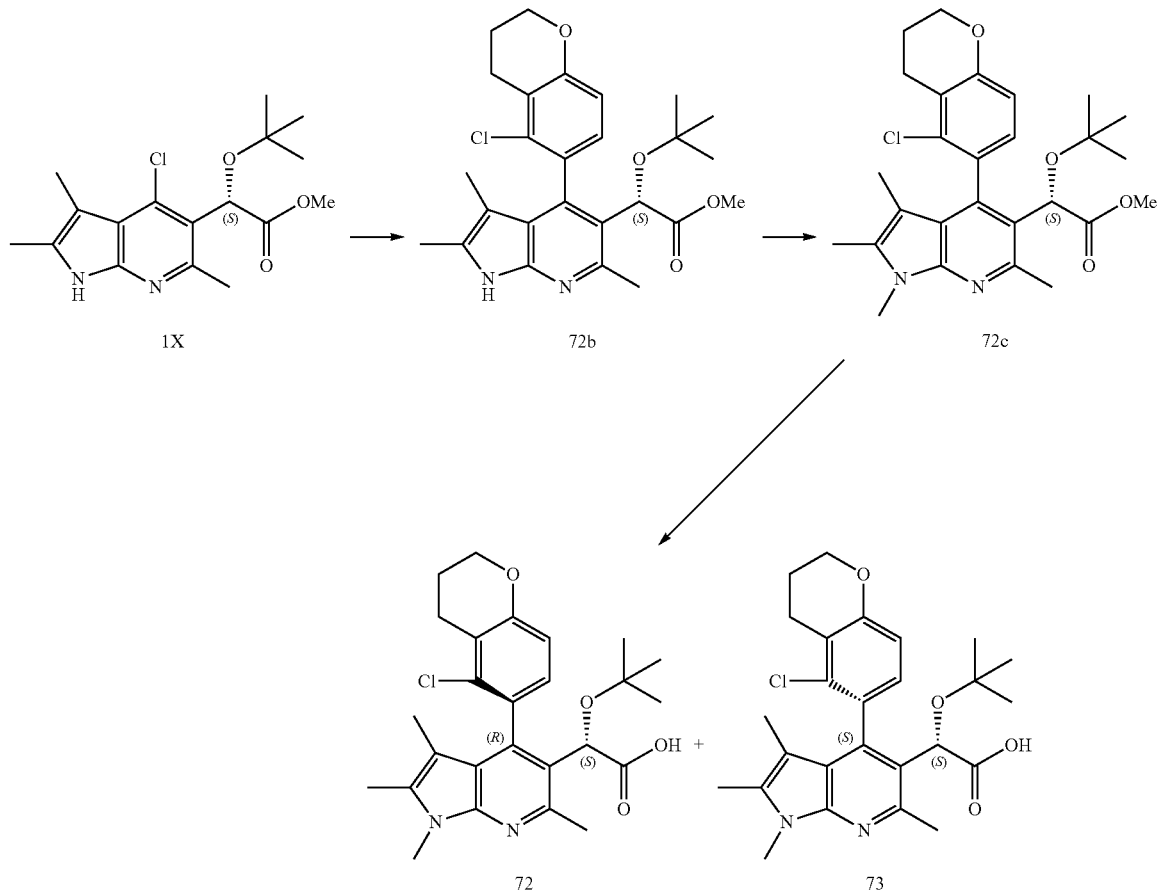

Step 2: Preparation of (2S)-methyl 2-(tert-butoxy)-2-(4-(5-chlorochroman-6-yl)-1,2,3,6-tetramethyl-1H-pyrrolo[2,3-b]pyridin-5-yl)acetate (72c)

After the compound 72b (317 mg, 0.673 mmol) prepared in Step 1 was dissolved in dichloromethane (10 mL), potassium hydroxide (111 mg, 1.68 mmol) and tetrabutylammonium bromide (34 mg) were added thereto, and iodomethyl (0.21 mL, 3.36 mmol) was slowly added thereto at room temperature. The reaction material was stirred for 18 hours at 30° C., cooling water was added thereto, and the result was adjusted to pH 5 to 6 using a 2N aqueous hydrochloric acid solution. The organic layer was separated, and the aqueous layer was extracted once with dichloromethane. The organic layers were combined, dried with anhydrous magnesium sulfate, concentrated under reduced pressure, and then the residue was purified using silica gel column chromatography (effluent, normal-hexane/ethyl acetate=6/1) to give 72c (216 mg, 66%) as a mixture of 2 isomers, and the compound was used as it is for the next reaction.

MS (EI, m/e)=484 (M+).

Step 3: Preparation of (S)-2-(tert-butoxy)-2-((R)-4-(5-chlorochroman-6-yl)-1,2,3,6-tetramethyl-1H-pyrrolo[2,3-b]pyridin-5-yl)acetic acid (72) and (S)-2-(tert-butoxy)-2-((S)-4-(5-chlorochroman-6-yl)-1,2,3,6-tetramethyl-1H-pyrrolo[2,3-b]pyridin-5-yl)acetic acid (73)

The compound, which was obtained by reacting the compound 72c (216 mg, 0.445 mmol) obtained in Step 2 in the same manner as in Step 2 of Example 36 using the same solvents and reagents in the same ratio, was separated into 2 isomers and purified using silica gel column chromatography (effluent, methylene chloride/methanol=95/5) to separately give compounds 72 (58 mg, 29%) with weak polarity and 73 (68 mg, 34%) with strong polarity.

72: $^1$H-NMR (300 MHz, CD$_3$OD) δ 1.12 (s, 9H), 1.50 (s, 3H), 2.11-2.06 (m, 2H), 2.31 (s, 3H), 2.80 (s, 3H), 2.87-2.82 (m, 2H), 3.75 (s, 3H), 4.85-4.19 (m, 2H), 5.18 (s, 1H), 6.79 (d, J=9 Hz, 1H), 6.96 (d, J=9 Hz, 1H); MS (EI, m/e)=470 (M+).

73: $^1$H-NMR (300 MHz, CD$_3$OD) δ 1.03 (s, 9H), 1.56 (s, 3H), 2.19-2.09 (m, 2H), 2.32 (s, 3H), 2.71 (s, 3H), 2.87-2.77 (m, 2H), 3.75 (s, 3H), 4.23-4.20 (m, 2H), 5.16 (s, 1H), 6.88 (d, J=9 Hz, 1H), 7.36 (d, J=9 Hz, 1H); MS (EI, m/e)=470 (M+).

Example 74 and 75

(S)-2-(Tert-butoxy)-2-((R)-4-(8-fluoro-5-methyl-chroman-6-yl)-1,2,3,6-tetramethyl-1H-pyrrolo[2,3-b]pyridin-5-yl)acetic acid (74) and (S)-2-(tert-butoxy)-2-((S)-4-(8-fluoro-5-methylchroman-6-yl)-1,2,3,6-tetramethyl-1H-pyrrolo[2,3-b]pyridin-5-yl)acetic acid (75)

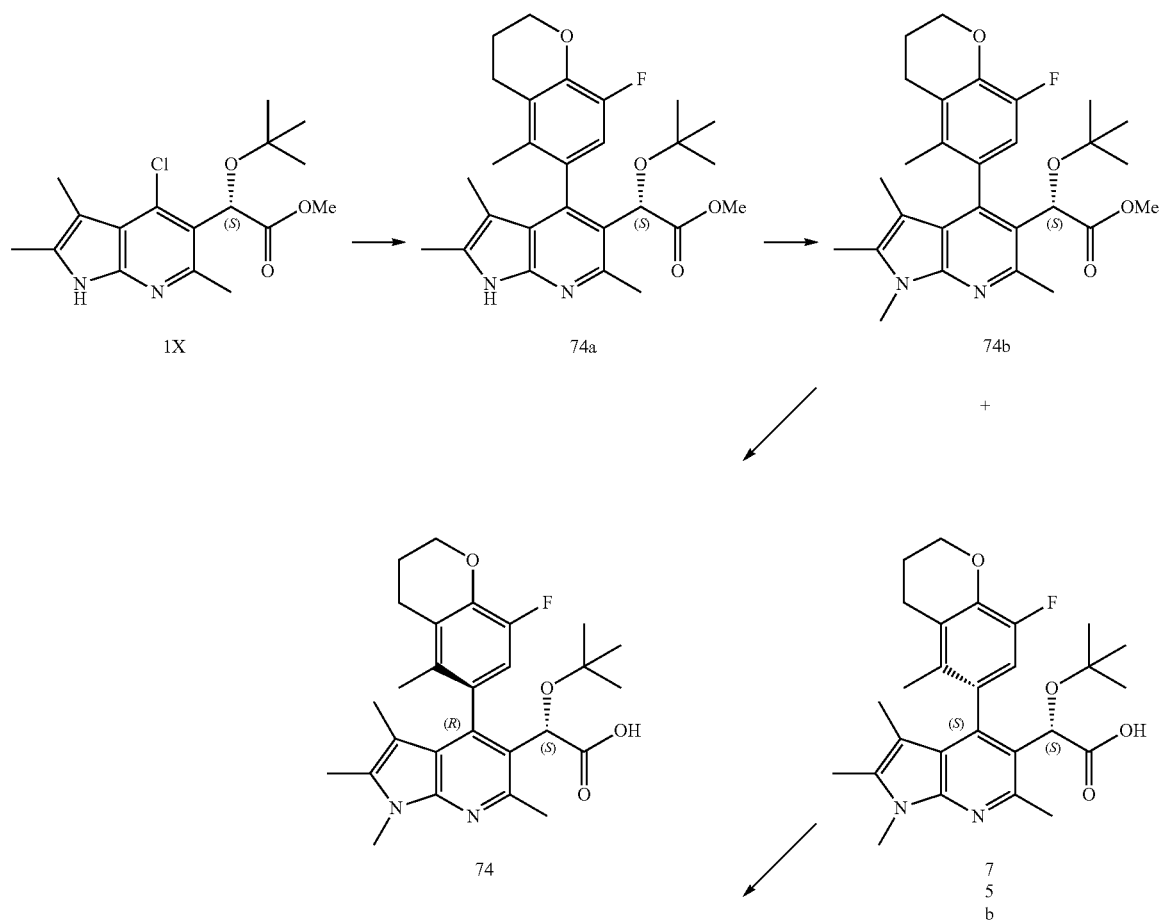

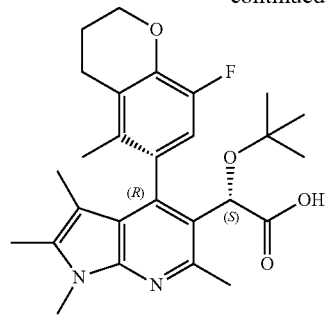

75

Step 1: Preparation of (S)-methyl 2-(tert-butoxy)-2-(8-fluoro-5-methylchroman-6-yl)-2,3,6-trimethyl-1H-pyrrolo[2,3-b]pyridin-5-yl)acetate (74a)

After the compound 1x (425 mg, 1.25 mmol) was dissolved in dimethylformamide (6 mL), 2-(8-fluoro-5-methylchroman-6-yl)-4,4,5,5-tetramethyl-1,3,2-dioxaborolane (420 mg, 1.44 mmol), potassium carbonate (520 mg, 3.76 mmol) and tetrakis(triphenylphosphine)palladium(0) (290 mg, 0.25 mmol) were added thereto, and the mixture was heated to 130° C. under nitrogen atmosphere and stirred for 18 hours at. The reaction material was cooled to room temperature, concentrated under reduced pressure, and then the residue was separated and purified using silica gel column chromatography (normal-hexane/ethyl acetate=6/1) to give a target compound 74a (263 mg, 45%) as a mixture of 2 isomers.

$^1$H-NMR (300 MHz, CDCl$_3$) δ 1.00 (s, 5.2H), 1.09 (s, 3.8H), 1.23 (s, 2H), 1.39 (s, 1.5H), 1.42 (s, 1.5H), 1.74 (s, 1.5H), 1.77 (s, 1.5H), 2.04 (t, 2H), 2.28 (s, 3H), 2.62 (m, 2H), 2.64 (s, 1.5H), 2.69 (s, 1.5H), 3.58 (s, 1.5H), 3.64 (s, 1.5H), 4.30 (m, 2H), 5.15 (s, 1H), 6.75 (d, j=11.4 Hz, 0.5H), 7.06 (d, J=10.7 Hz, 0.5H), 8.30 (bs, 1H); MS (EI, m/e)=468 (M$^+$).

Step 2: Preparation of (2S)-methyl 2-(tert-butoxy)-((S)-4-(8-fluoro-5-methylchroman-6-yl)-1,2,3,6-tetramethyl-1H-pyrrolo[2,3-b]pyridin-5-yl)acetate (74b) and (2S)-methyl 2-(tert-butoxy)-2-((R)-4-(8-fluoro-5-methylchroman-6-yl)-1,2,3,6-tetramethyl-1H-pyrrolo[2,3-b]pyridin-5-yl)acetate (75b)

After the compound 74a (260 mg, 0.555 mmol) prepared in Step 1 was dissolved in dichloromethane (9 mL), potassium hydroxide (91 mg, 1.38 mmol) and tetrabutylammonium bromide (28 mg) were added thereto, and iodomethyl (0.17 mL, 2.77 mmol) was slowly added thereto at room temperature. The reaction material was stirred for 18 hours at 30° C., cooling water was added thereto, and the result was adjusted to pH 5 to 6 using a 2N aqueous hydrochloric acid solution. After the organic layer was separated and the aqueous layer was extracted once with dichloromethane, the organic layers were combined, dried with anhydrous magnesium sulfate, and concentrated under reduced pressure. The residue of the 2 isomers was separated and purified using silica gel column chromatography (normal-hexane/ethyl acetate=6/1) to separately give an isomer 74b (112 mg, 43%) with strong polarity and an isomer 75b (80 mg, 30%) with weak polarity.

74b: $^1$H-NMR (300 MHz, CDCl$_3$) δ 1.00 (s, 9H), 1.47 (s, 3H), 1.73 (s, 3H), 2.11-2.15 (m, 2H), 2.27 (s, 3H), 2.65-2.67 (m, 2H), 2.73 (s, 3H), 3.63 (s, 3H), 3.74 (s, 3H), 4.27-4.30 (m, 2H), 5.12 (s, 1H), 7.03 (d, J=12 Hz, 1H); MS (EI, m/e)=482 (M$^+$)

75b: $^1$H-NMR (300 MHz, CDCl$_3$) δ, 1.11 (s, 9H), 1.42 (s, 3H), 2.16-2.13 (m, 2H), 2.26 (s, 3H), 2.73-2.69 (m, 2H), 2.77 (s, 3H), 3.57 (s, 3H), 3.74 (s, 3H), 4.31-4.29 (m, 2H), 5.11 (s, 1H), 6.76 (d, J=12 Hz, 1H); MS (EI, m/e)=482 (M$^+$)

Step 3: Preparation of (S)-2-(tert-butoxy)-2-((R)-4-(8-fluoro-5-methylchroman-6-yl)-1,2,3,6-tetramethyl-1H-pyrrolo[2,3-b]pyridin-5-yl)acetic acid (74) and (S)-2-(tert-butoxy)-2-((S)-4-(8-fluoro-5-methylchroman-6-yl)-1,2,3,6-tetramethyl-1H-pyrrolo[2,3-b]pyridin-5-yl)acetic acid (75)

The (S)-isomer 74b (80 mg, 0.166 mmol) and the (R)-isomer 75b (112 mg, 0.232 mmol) were hydrolyzed in the same manner as in Step 3 of Examples 70 and 71 to separately give target compounds (S)-isomer 74 (59 mg, 76%) and (R)-isomer 75 (91 mg, 84%).

74: $^1$H-NMR (300 MHz, CD$_3$OD) δ 0.90 (s, 9H), 1.37 (s, 3H), 1.61 (s, 3H), 2.02-1.98 (m, 2H), 2.19 (s, 3H), 2.60 (s, 3H), 2.60-2.58 (m, 2H), 3.62 (s, 3H), 4.14-4.11 (m, 2H), 5.08 (s, 1H), 6.98 (d, J=12 Hz, 1H); MS (EI, m/e)=468 (M$^+$).

75: $^1$H-NMR (300 MHz, CD$_3$OD) δ 1.12 (s, 9H), 1.45 (s, 3H), 1.82 (s, 3H), 2.15-2.12 (m, 2H), 2.30 (s, 3H), 2.76 (s, 3H), 2.76 (m, 2H), 3.75 (s, 3H), 4.27-4.24 (m, 2H), 5.12 (s, 1H), 6.72 (d, J=12 Hz, 1H); MS (EI, m/e)=468 (M$^+$)

Example 76

(S)-2-(Tert-butoxy)-2-((R)-1-(cyclopropylmethyl)-4-((R)-8-fluoro-5-methylchroman-6-yl)-2,3,6-trimethyl-1H-pyrrolo[2,3-b]pyridin-5-yl)acetic acid (76)

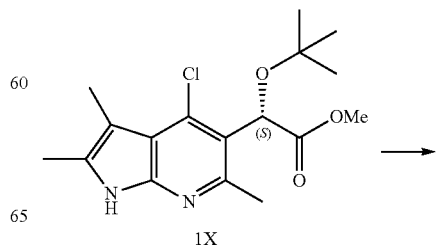

1X

-continued

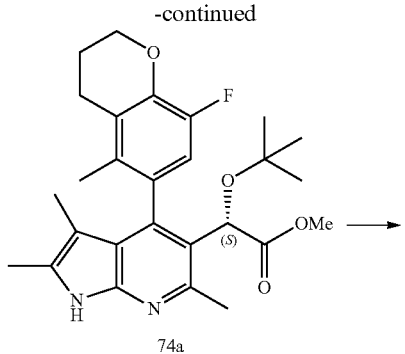

74a

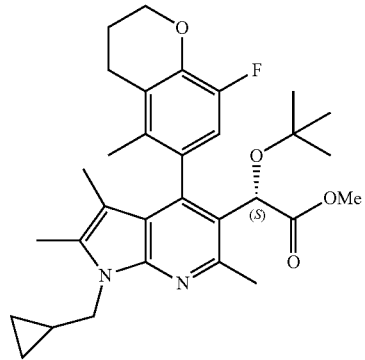

76a

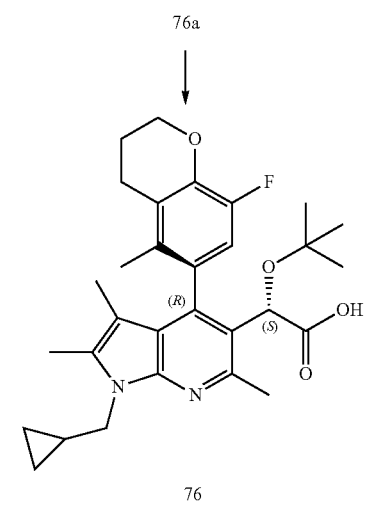

76

Step 1: Preparation of methyl (S)-2-(tert-butoxy)-2-((R)-1-(cyclopropylmethyl)-4-((R)-8-fluoro-5-methylchroman-6-yl)-2,3,6-trimethyl-1H-pyrrolo[2,3-b]pyridin-5-yl)acetate (76a)

A target compound 76a was obtained in a 65% yield using the same methods of Step 1 and Step 2 of Examples 74 and 75, except that, in Step 2, cyclopropyl iodide was used instead of iodomethyl. The obtained substance was an (R)-isomer, and an (S)-isomer was ignored since it was produced in a very small amount.

$^1$H-NMR (300 MHz, CDCl$_3$) δ 0.46-0.51 (m, 4H), 1.15 (s, 9H), 1.22 (m, 1H), 1.42 (s, 3H), 1.79 (s, 3H), 2.15 (m, 2H), 2.30 (s, 3H), 2.71 (m, 2H), 2.74 (s, 3H), 3.57 (s, 3H), 4.10 (m, 2H), 4.29 (m, 2H), 5.10 (s, 1H), 6.77 (d, J=12 Hz, 1H); MS (EI, m/e)=522 (M$^+$).

Step 2: Preparation of (S)-2-(tert-butoxy)-2-((R)-1-(cyclopropylmethyl)-4-((R)-8-fluoro-5-methylchroman-6-yl)-2,3,6-trimethyl-1H-pyrrolo[2,3-b]pyridin-5-yl)acetic acid (76)

The methyl ester compound of the (R)-isomer 76a (68 mg, 0.13 mmol) was hydrolyzed in the same manner as in Step 3 of Examples 72 and 73 to give a target compound 76 (54 mg, 82%).

$^1$H-NMR (300 MHz, CD$_3$OD) δ 0.44-0.51 (m, 4H), 1.13 (s, 9H), 1.22 (m, 1H), 1.46 (s, 3H), 1.83 (s, 3H), 2.14 (m, 2H), 2.34 (s, 3H), 2.73 (s, 3H), 2.74 (m, 2H), 4.17 (m, 2H), 4.26 (m, 2H), 5.13 (s, 1H), 6.72 (d, J=12 Hz, 1H); MS (EI, m/e)=508 (M$^+$).

Example 77

(S)-2-(Tert-butoxy)-2-(4-(4-chlorophenyl)-2,3,6-trimethyl-1-(pyrazin-2-ylmethyl)-1H-pyrrolo[2,3-b]pyridin-5-yl)acetic acid (77)

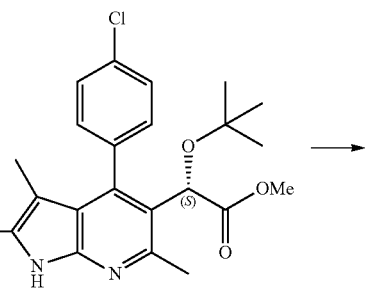

1n

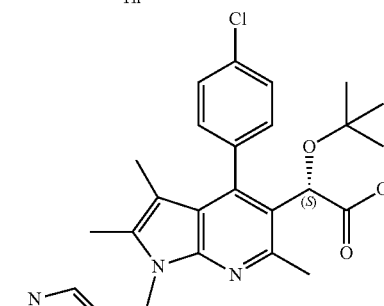

77a

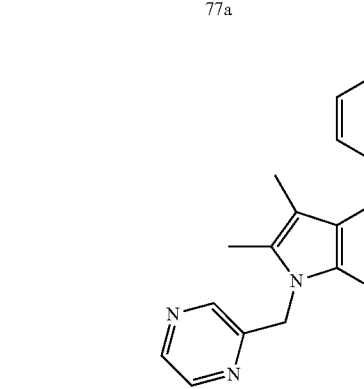

77

Step 1: Preparation of (S)-methyl 2-(tert-butoxy)-2-(4-(4-chlorophenyl)-2,3,6-trimethyl-1-(pyrazin-2-ylmethyl)-1H-pyrrolo[2,3-b]pyridin-5-yl)acetate (77a)

A target compound 77a (186 mg, 76%) was obtained by reacting the compound 1n (200 mg, 0.482 mmol) in the same manner as in Step 1 of Example 1, except that 2-(iodomethyl)pyrazine (212 mg, 0.864 mmol) was used instead of iodomethyl and the stirring was carried out for 18 hours at 35° C.

$^1$H-NMR (300 MHz, CDCl$_3$) δ 0.98 (s, 9H), 1.49 (s, 3H), 2.23 (s, 3H), 2.69 (s, 3H), 3.67 (s, 3H), 5.08 (s, 1H), 5.62 (s, 2H), 7.26 (m, 1H), 7.40-7.45 (m, 3H), 8.36 (s, 1H), 8.45 (s, 1H), 8.51 (s, 1H): MS (EI, m/e)=507 (M$^+$).

Step 2: Preparation of (S)-2-(tert-butoxy)-2-(4-(4-chlorophenyl)-2,3,6-trimethyl-1-(pyrazin-2-ylmethyl)-1H-pyrrolo[2,3-b]pyridin-5-yl)acetic acid (77)

A pure target compound 77 (135 mg, 92%) was obtained in white solids by reacting the compound 77a (156 mg, 0.307 mmol) in the same manner as in Step 2 of Example 36 using the same solvents and reagents in the same ratio.

$^1$H-NMR (300 MHz, CD$_3$OD) δ 0.96 (s, 9H), 1.55 (s, 3H), 2.27 (s, 3H), 2.68 (s, 3H), 5.10 (s, 1H), 5.67 (q, J=8.13 Hz, 2H), 7.35 (d, J=7.98 Hz, 1H), 7.49 (t, J=6.18 Hz, 2H), 7.71 (d, J=7.68 Hz, 1H), 8.23 (s, 1H), 8.46 (s, 1H), 8.55 (s, 1H): MS (EI, m/e)=493 (M$^+$).

Example 78

(S)-2-(tert-butoxy)-2-(4-(4-chlorophenyl)-1-(2-methoxyethyl)-2,3,6-trimethyl-1H-pyrrolo[2,3-b]pyridin-5-yl)acetic acid (78)

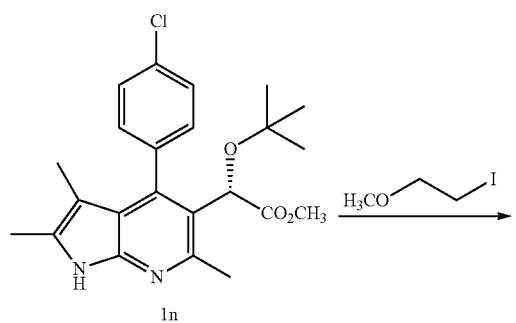

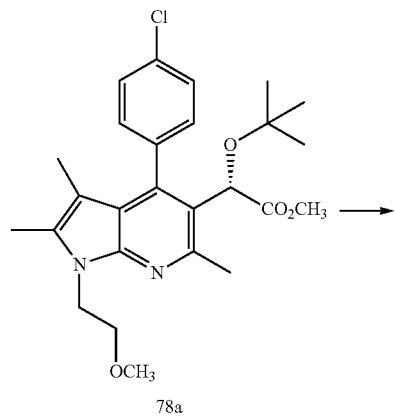

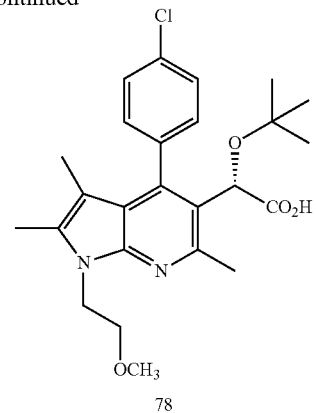

Step 1: Preparation of (S)-methyl 2-tert-butoxy-2-(4-(4-chlorophenyl)-1-(2-methoxyethyl)-2,3,6-trimethyl-1H-pyrrolo[2,3-b]pyridin-5-yl)acetate (78a)

A target compound 78a (178 mg, 78%) was obtained by reacting the compound 1n (200 mg, 0.482 mmol) in the same manner as in Step 1 of Example 1, except that iodo-2-methoxyethane (269 mg, 0.964 mmol) and potassium hydroxide (159 mg, 2.41 mmol) was used instead of iodomethyl and the stirring was carried out for 5 hours at 30° C.

$^1$H-NMR (300 MHz, CDCl$_3$) δ 0.97 (s, 9H), 1.48 (s, 3H), 2.30 (s, 3H), 2.69 (s, 3H), 3.34 (s, 3H), 3.66 (s, 3H), 3.73 (t, J=5.74 Hz, 2H), 4.40 (t, J=5.75 Hz, 2H), 5.07 (s, 1H), 7.22 (s, 1H), 7.43 (m, 3H): MS (EI, m/e)=472 (M$^+$).

Step 2: Preparation of (S)-2-(tert-butoxy)-2-(4-(4-chlorophenyl)-1-(2-methoxyethyl)-2,3,6-trimethyl-1H-pyrrolo[2,3-b]pyridin-5-yl)acetic acid (78)

A pure target compound 78 (141 mg, 87%) was obtained by reacting the compound 78a (167 mg, 0.353 mmol) dissolved in tetrahydrofuran (3.8 mL) and 4N sodium hydroxide/methanol solution (0.274 mL) for 18 hours at 30° C., and then treating in the same manner as in Step 2 of Example 1.

$^1$H-NMR (300 MHz, CD$_3$OD) δ 0.87 (s, 9H), 1.40 (s, 3H), 2.21 (s, 3H), 2.57 (s, 3H), 3.18 (s, 3H), 3.56 (t, J=5.38 Hz, 3H), 4.30 (t, J=5.22 Hz, 2H), 5.01 (s, 1H), 7.21 (d, J=7.44 Hz, 1H), 7.39 (t, J=6.63 Hz, 2H), 7.45 (d, J=7.4 Hz, 1H): MS (EI, m/e)=458 (M$^+$).

Example 79

(S)-2-(tert-butoxy)-2-(4-(4-chlorophenyl)-2,3,6-trimethyl-1-((1-methyl-1H-pyrazol-3-yl)methyl)-1H-pyrrolo[2,3-b]pyridin-5-yl)acetic acid (79)

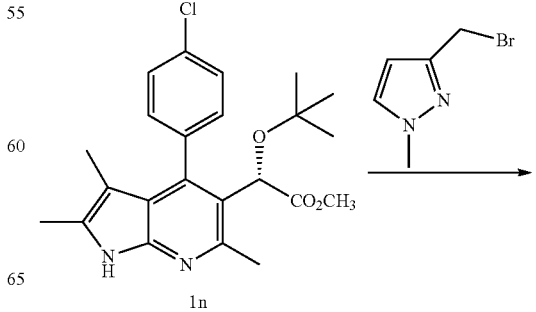

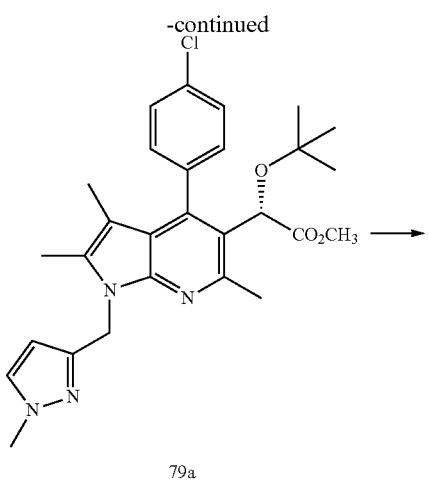

79a

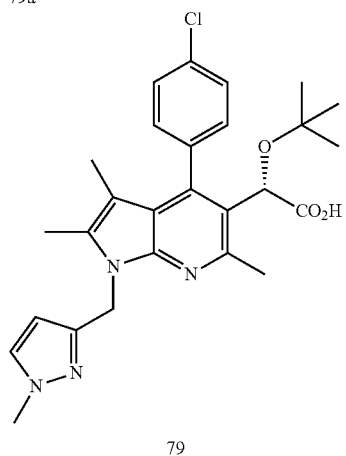

79

Step 1: Preparation of (S)-methyl 2-tert-butoxy-2-(4-(4-chlorophenyl)-2,3,6-trimethyl-1-((1-methyl-1H-pyrazol-3-yl)methyl)-1H-pyrrolo[2,3-b]pyridin-5-yl)acetate (79a)

A target compound 79a (211 mg, 86%) was obtained by reacting the compound 1n (200 mg, 0.482 mmol) in the same manner as in Step 1 of Example 1, except that 3-(bromomethyl)-1-methyl-1H-pyrazole (157 mg, 0.964 mmol) and potassium hydroxide (159 mg, 2.41 mmol) was used instead of iodomethyl and the stirring was carried out for 7 hours at 30° C.

$^1$H-NMR (300 MHz, CDCl$_3$) δ 0.98 (s, 9H), 1.47 (s, 3H), 2.25 (s, 3H), 2.69 (s, 3H), 3.67 (s, 3H), 3.96 (s, 3H), 5.08 (s, 3H), 5.49 (d, d, J=11.07 Hz, 2H), 6.03 (s, 1H), 7.35 (d, J=1.53 Hz, 1H), 7.40 (s, 1H), 7.44 (m, 3H): MS (EI, m/e)=509 (M$^+$).

Step 2: Preparation of (S)-2-(tert-butoxy)-2-(4-(4-chlorophenyl)-2,3,6-trimethyl-1-((1-methyl-1H-pyrazol-3-yl)methyl)-1H-pyrrolo[2,3-b]pyridin-5-yl)acetic acid (79)

A pure target compound 79 (183 mg, 89%) was obtained in white solids by reacting the compound 79a (211 mg, 0.414 mmol) in the same manner as in Step 2 of Example 1.

$^1$H-NMR (300 MHz, CD$_3$OD) δ 0.99 (s, 9H), 1.55 (s, 3H), 2.27 (s, 3H), 2.69 (s, 3H), 3.94 (s, 3H), 5.15 (s, 1H), 5.57 (s, 2H), 5.74 (s, 1H), 7.31 (s, 1H), 7.35 (d, J=8.15, 1H), 7.53 (d, J=8.92 Hz, 2H), 7.61 (d, J=8.25 Hz, 1H): MS (EI, m/e)=495 (M$^+$).

Experimental Example 1

Investigation of Inhibitory Effects Against HIV-1 and Toxicity Test of Compounds of Present Invention In order to look into the HIV-1 inhibition effects of the compound of the present invention, an in vitro test for HIV-1 inhibition effects was carried out as follows according to a known method (H. Tanaka et al., *J. Med. Chem.*, 1991, 34, 349). MT-4 cells were used as host cells, and the degree of the compound of the present invention inhibiting the cytotoxicity of the virus-infected MT-4 cells was investigated.

First, MT-4 cells were diffused at a concentration of 1×10$^4$ cell/well to a culture medium, and HIV-1 was inoculated so that the concentration was 500 TCI$_{50}$ (concentration at which 50% of the cell is infected)/well. Immediately after the inoculation, the cell dispersion was transferred in 100 µL each to a flat microtiter plate in which the sample of the compound of the present invention was placed. The sample was incubated for approximately for 4 to 5 days at 17° C., and the virus suppression effect was determined using an MTT method. In addition, the cytotoxicity was also determined by measuring the survivability of the experimentally virus-infected cells using an MTT method. As a comparative compound, azidothymidine (AZT) and raltegravir were used. The results are shown in the following Table 1.

TABLE 1

| Compound No. of Examples | Wild Type HIV-1 (IIIB) in MT-4 Cells | | Compound No. of Examples | Wild Type HIV-1 (IIIB) in MT-4 Cells | |
|---|---|---|---|---|---|
| | EC$_{60}$ (nM) * | CC$_{60}$ (µM) ** | | EC$_{60}$ (nM)* | CC$_{60}$ (µM) ** |
| 1 | 29 | 25 | 41 | 32.98 | 31.49 |
| 2 | 400 | >233 | 42 | 26.15 | 20.54 |
| 3 | 31.7 | 26.19 | 43 | 28.17 | 17.74 |
| 4 | 33 | 18 | 44 | 29.1 | 18.06 |
| 5 | 692 | 17 | 45 | 22.87 | 19.33 |
| 6 | 154 | 9.74 | 46 | 24.9 | 20.89 |
| 7 | — | — | 47 | 1.67 | 16.64 |
| 8 | 147 | 12.8 | 48 | 27.7 | 14.22 |
| 9 | 134 | 18.04 | 49 | 144.9 | 15.3 |
| 10 | 671 | >203 | 50 | 144.8 | 10.32 |
| 11 | 103 | 15.19 | 51 | 39.1 | 96.68 |
| 12 | 26.4 | 56.14 | 52 | 20.6 | 34.33 |

TABLE 1-continued

| Compound No. of Examples | Wild Type HIV-1 (IIIB) in MT-4 Cells | | Compound No. of Examples | Wild Type HIV-1 (IIIB) in MT-4 Cells | |
|---|---|---|---|---|---|
| | $EC_{60}$ (nM) * | $CC_{60}$ (μM) ** | | $EC_{60}$ (nM)* | $CC_{60}$ (μM) ** |
| 13 | 144 | 85.91 | 53 | 15.0 | 53.33 |
| 14 | 125 | 36.6 | 54 | 5.82 | 18.82 |
| 15 | 29.3 | 20.7 | 55 | 5.48 | 64.73 |
| 16 | 16 | >219 | 56 | 9.75 | 24.56 |
| 17 | 107 | 17.57 | 57 | 2040 | >217.9 |
| 18 | 153 | 17.32 | 58 | 4600 | 18.59 |
| 19 | 5510 | >179 | 59 | 5.8 | 5.3 |
| 20 | 29.6 | 18.77 | 60 | 6.2 | 18.23 |
| 21 | 79 | 24.51 | 61 | 26.94 | 9.43 |
| 22 | 341 | 114.47 | 62 | 26.16 | 15.34 |
| 23 | 6.39 | 25.49 | 63 | 9.0 | 38.3 |
| 24 | 19.1 | 75.04 | 64 | <683 | 48.57 |
| 25 | 399 | 108 | 65 | 90.46 | 70.86 |
| 26 | 6.27 | 55.84 | 66 | 14.5 | 14.55 |
| 27 | >99000 | 29 | 67 | 7.65 | 13.65 |
| 28 | 31.0 | 20.4 | 68 | 5.49 | 17.14 |
| 29 | >100000 | 100 | 69 | 26.5 | 17.55 |
| 30 | 5.29 | 30.86 | 70 | 25.3 | 49.2 |
| 31 | 286 | 86.73 | 71 | 124 | 73.54 |
| 32 | 6.53 | 23.48 | 82 | 3.4 | 16.18 |
| 33 | 1120 | 25.5 | 73 | 6.16 | 25.1 |
| 34 | 222 | 78 | 74 | 5.33 | 23.92 |
| 35 | 111 | 14.86 | 75 | 116 | 37.22 |
| 36 | 7.72 | 24.49 | 76 | 6.68 | 13.94 |
| 37 | 692 | 17 | 77 | 4.66 | 38.86 |
| 38 | 26.9 | 40.34 | 78 | 6.31 | 18.36 |
| 39 | 116.4 | 78.47 | 79 | 8.0 | 25.09 |
| 40 | 667 | 91.58 | | | |
| Raltegravir | 4.05 | 95 | AZT | 1.50 | 6.36 |

* $EC_{60}$: concentration at which HIV-1 infection is 50% suppressed
** $CC_{60}$: concentration at 50% cell damage with respect to MT-4 cells

The invention claimed is:

1. A compound represented by the following Chemical Formula I, a racemate or a stereoisomer thereof, or a pharmaceutically acceptable salt thereof:

[Chemical Formula I]

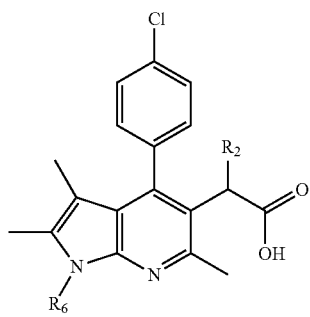

wherein, in the formula, $R_2$ is tert-butoxy;

$R_6$ is hydrogen, or $-(CH_2)_n-R_7$;

$R_7$ is hydrogen; halogen; hydroxy; amino; cyano; trifluoromethyl; $C_{2-6}$ alkenyl; $C_{2-6}$ alkynyl; $C_{1-6}$ alkoxy; carbamoyl; $CONH(C_{1-3}$ alkyl); $CON(C_{1-3}$ alkyl)$_2$; COOH; $C_{3-6}$ cycloalkyl unsubstituted or substituted with 1 or 2 substituents each selected from the group consisting of halogen, cyano, hydroxy, hydroxymethyl, carboxy and carbamoyl; phenyl unsubstituted or substituted with 1 to 3 substituents each selected from the group consisting of cyano, $C_{1-6}$ alkyl, $C_{1-6}$ alkoxy and amino; pyridinyl unsubstituted or substituted with 1 or 2 substituents each selected from the group consisting of halogen, cyano, $C_{1-6}$ alkyl, $C_{1-6}$ alkoxy and amino; pyrimidinyl unsubstituted or substituted with amino or halogen; dioxoisoindolinyl; oxazolyl; furanyl unsubstituted or substituted with $C_{1-6}$ alkyl or halogen; thiophenyl unsubstituted or substituted with $C_{1-6}$ alkyl or halogen; pyrrolidinyl unsubstituted or substituted with $C_{1-6}$ alkyl or halogen; 2-oxopyrrolidinyl; pyrazolyl unsubstituted or substituted with $C_{1-3}$ alkyl; or thiazolyl; and n is an integer of 1 to 5.

2. The compound, the racemate or the stereoisomer thereof, or the pharmaceutically acceptable salt thereof according to claim 1, wherein, $R_7$ is hydrogen; halogen; hydroxy; amino; cyano; trifluoromethyl; $C_{2-6}$ alkenyl; $C_{2-6}$ alkynyl; $C_{1-6}$ alkoxy; carbamoyl; $CONH(C_{1-3}$ alkyl); $CON(C_{1-3}$ alkyl)$_2$; COOH; $C_{3-6}$ cycloalkyl unsubstituted or substituted with 1 or 2 substituents each selected from the group consisting of halogen, cyano, hydroxy, hydroxymethyl, carboxy and carbamoyl; phenyl unsubstituted or substituted with 1 to 3 substituents each selected from the group consisting of cyano, $C_{1-6}$ alkyl, $C_{1-6}$ alkoxy and amino; pyridinyl unsubstituted or substituted with 1 or 2 substituents each selected from the group consisting of halogen, cyano, $C_{1-6}$ alkyl, $C_{1-6}$ alkoxy and amino; pyrimidinyl unsubstituted or substituted with amino or halogen; dioxoisoindolinyl; oxazolyl; furanyl unsubstituted or substituted with $C_{1-6}$ alkyl or halogen; thiophenyl unsubstituted or substituted with $C_{1-6}$ alkyl or halogen; pyrrolidinyl unsubstituted or substituted with $C_{1-6}$ alkyl or halogen; 2-oxopyrrolidinyl; pyrazolyl unsubstituted or substituted with $C_{1-3}$ alkyl; or thiazolyl; and n is an integer of 1 to 5.

3. The compound, the racemate or the stereoisomer thereof according to claim 1, or the pharmaceutically acceptable salt thereof, wherein, $R_7$ is hydrogen; halogen; hydroxy; amino; cyano; trifluoromethyl; $C_{2-6}$ alkenyl; $C_{2-6}$ alkynyl; $C_{1-6}$ alkoxy; carbamoyl; CONH($C_{1-3}$ alkyl); CON($C_{1-3}$ alkyl)$_2$; COOH; $C_{3-6}$ cycloalkyl unsubstituted or substituted with 1 or 2 substituents each selected from the group consisting of halogen, cyano, hydroxy, hydroxymethyl, carboxy and carbamoyl; phenyl unsubstituted or substituted with 1 to 3 substituents each selected from the group consisting of cyano, $C_{1-6}$ alkyl, $C_{1-6}$ alkoxy and amino; pyridinyl unsubstituted or substituted with 1 or 2 substituents each selected from the group consisting of halogen, cyano, $C_{1-6}$ alkyl, $C_{1-6}$ alkoxy and amino; pyrimidinyl unsubstituted or substituted with amino or halogen; dioxoisoindolinyl; oxazolyl; furanyl unsubstituted or substituted with $C_{1-6}$ alkyl or halogen; thiophenyl unsubstituted or substituted with $C_{1-6}$ alkyl or halogen; pyrrolidinyl unsubstituted or substituted with $C_{1-6}$ alkyl or halogen; 2-oxopyrrolidinyl; pyrazolyl unsubstituted or substituted with $C_{1-3}$ alkyl; or thiazolyl; and n is an integer of 1 to 5.

4. The compound, the racemate or the stereoisomer thereof, or the pharmaceutically acceptable salt thereof according to claim 1, wherein, $R_7$ is F; hydroxy; cyano; trifluoromethyl; $C_{1-6}$ alkoxy; dimethylaminocarbonyl; dimethylamino; COOH; $C_{3-6}$ cycloalkyl unsubstituted or substituted with 1 or 2 substituents each selected from the group consisting of F, cyano and hydroxy; phenyl unsubstituted or substituted with substituents each selected from the group consisting of cyano and methoxy; pyridinyl unsubstituted or substituted with 1 or 2 substituents each selected from the group consisting of F, Cl, methyl and methoxy; pyrimidinyl; dioxoisoindolinyl; oxazolyl; furanyl; thiophenyl; pyrrolidinyl; 2-oxopyrrolidinyl; pyrazolyl unsubstituted or substituted with $C_{1-3}$ alkyl; or thiazolyl; and n is an integer of 1 to 3.

5. A compound comprising a racemate or a stereoisomer thereof, or a pharmaceutically acceptable salt thereof such that the compound is any one selected from the group consisting of:

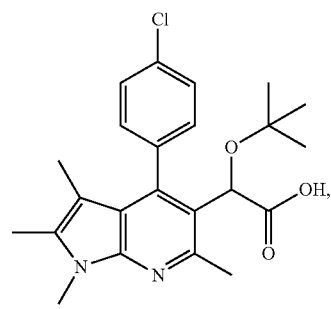

-continued

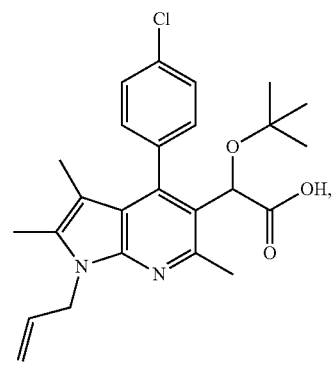

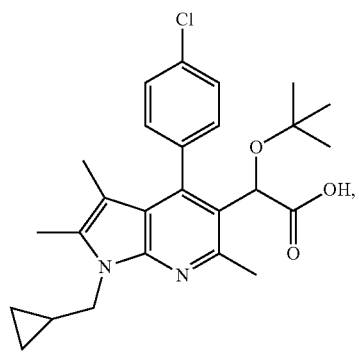

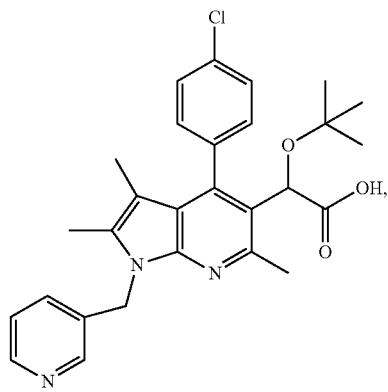

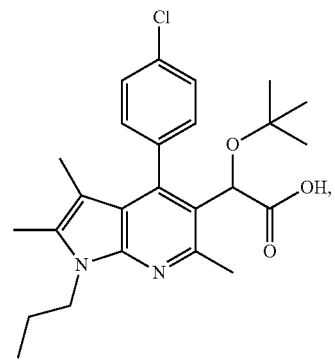

167
-continued
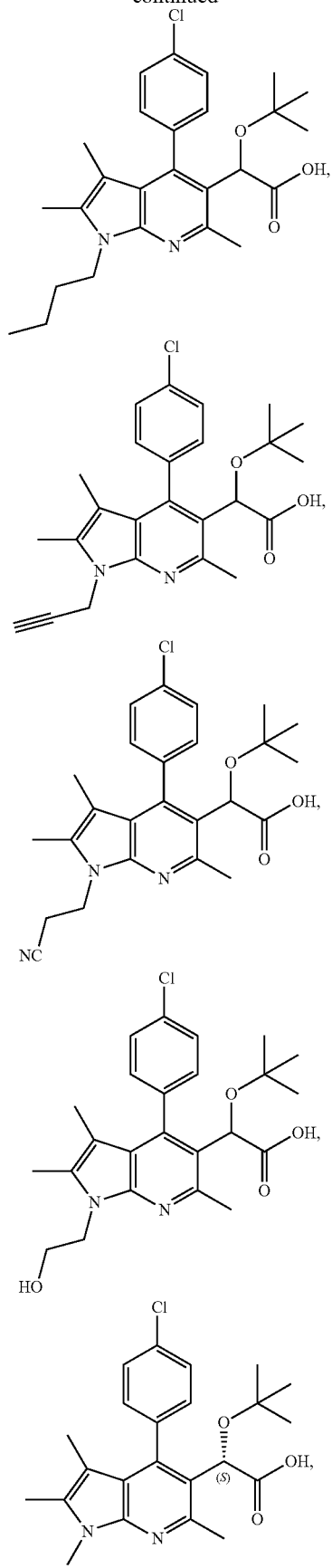
168
-continued
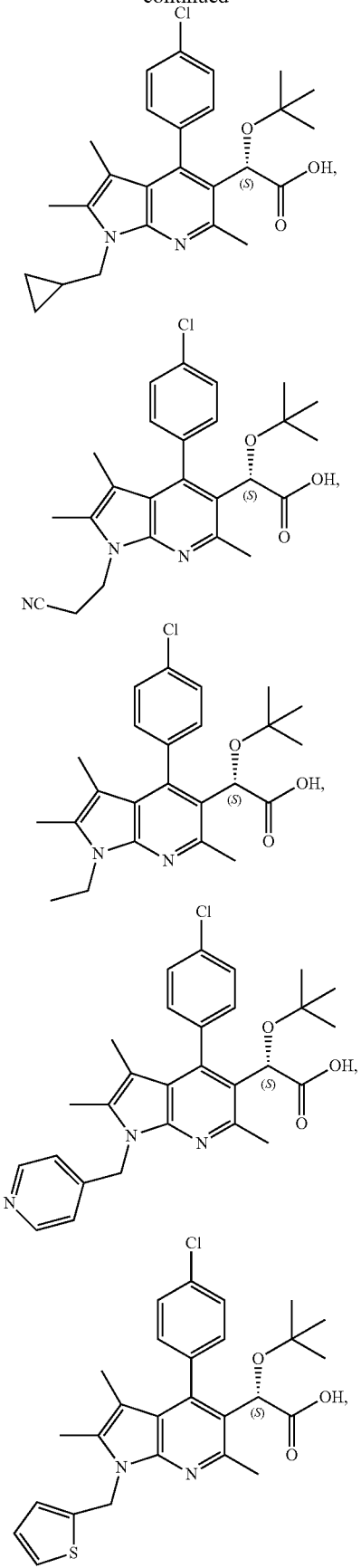

169
-continued
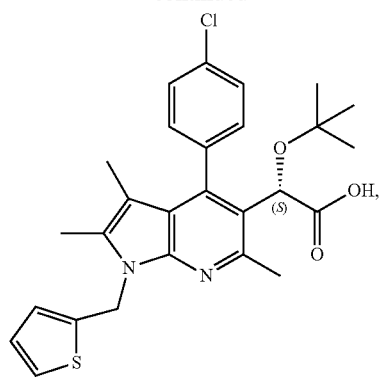
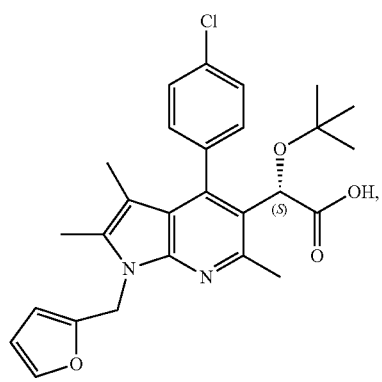
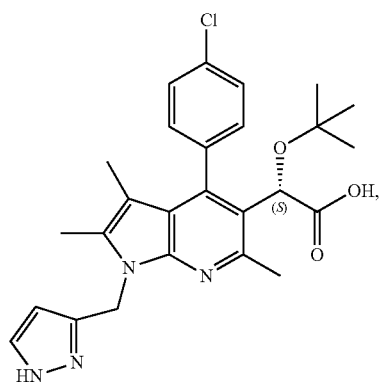
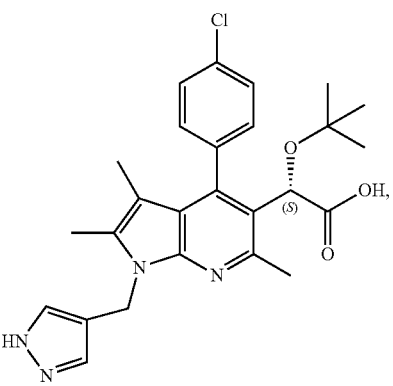
170
-continued
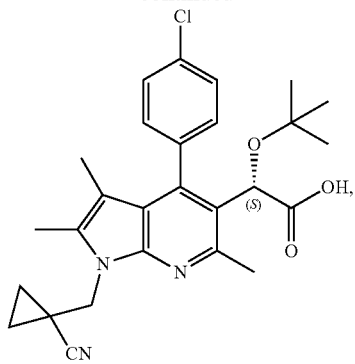
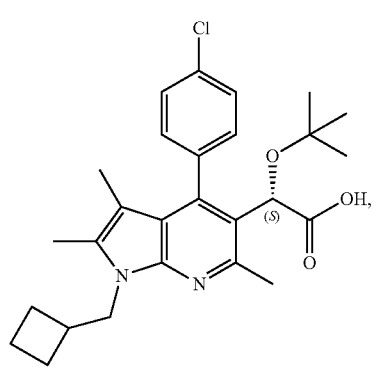
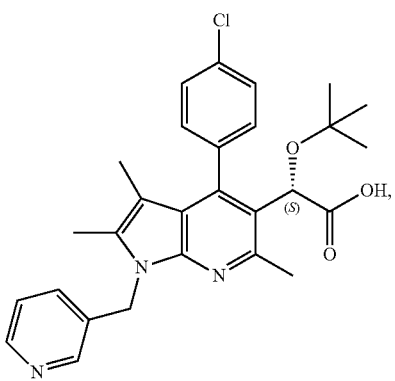
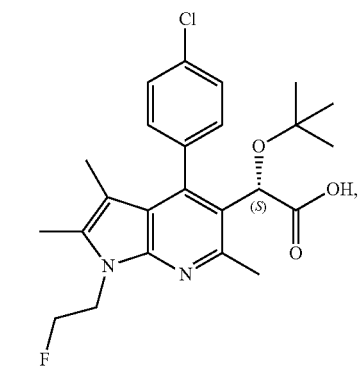

-continued
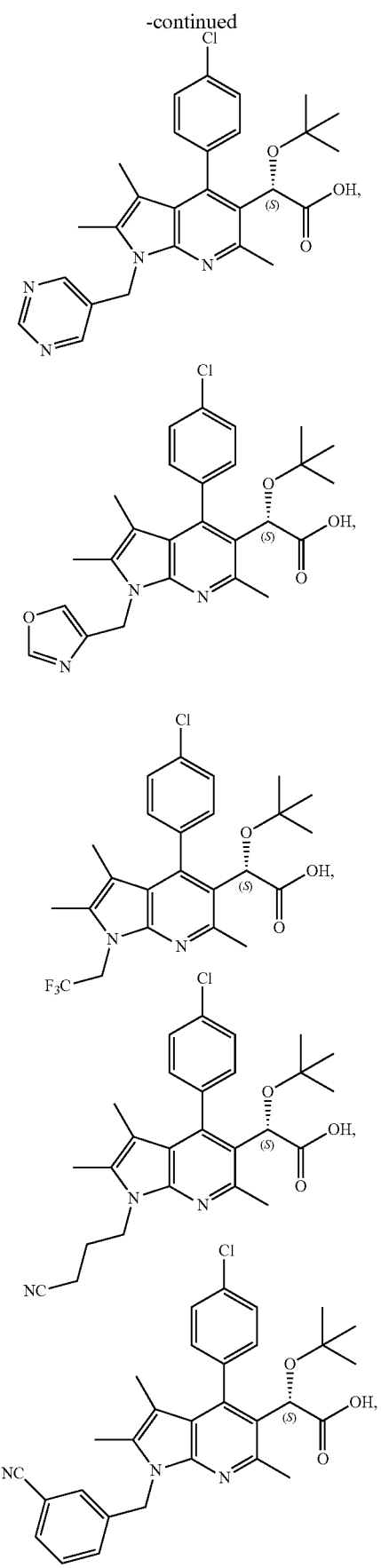
-continued
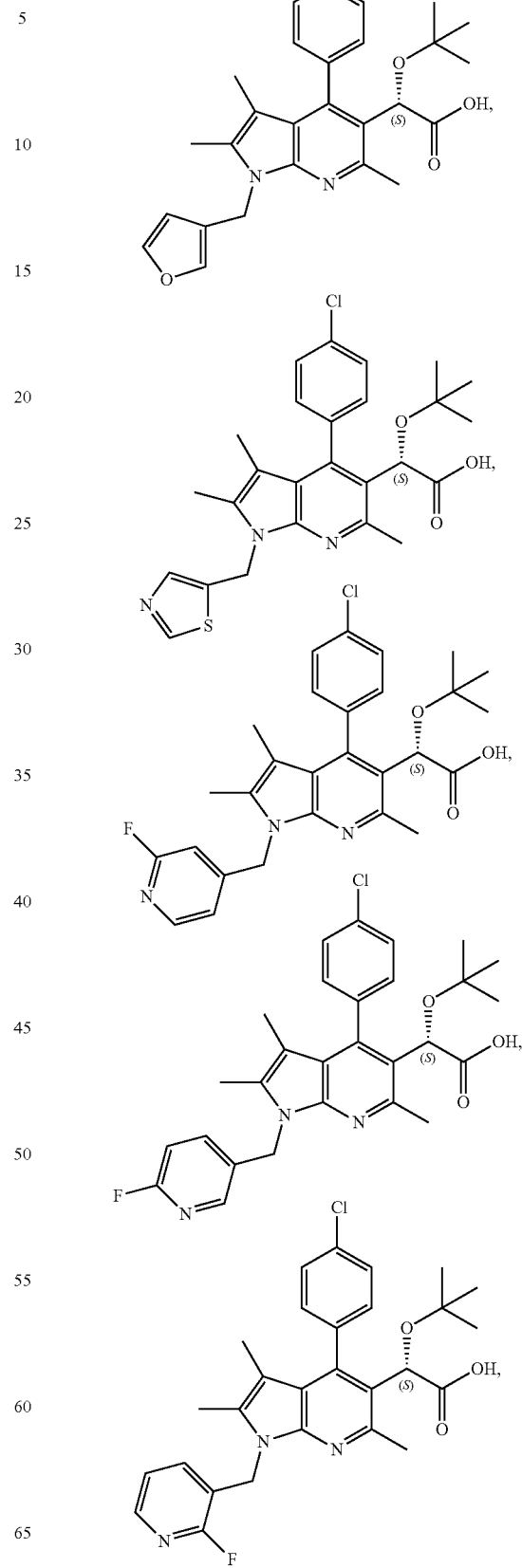

-continued

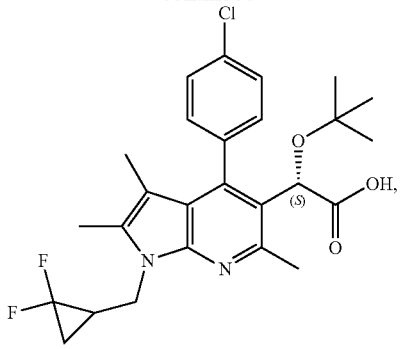

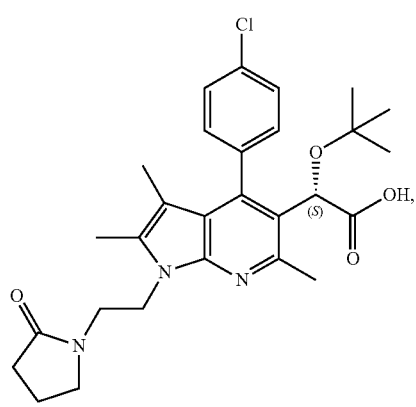

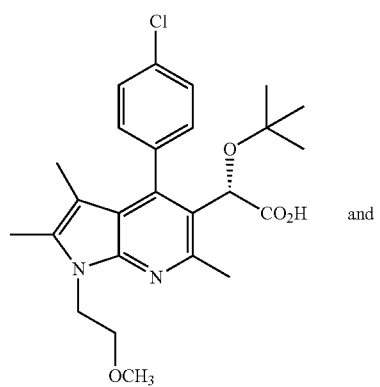 and

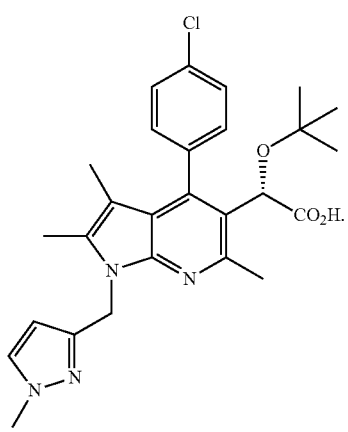 [SMILES: Cc1nc2c(c(C)c(C)n2Cc2ccn(C)n2)c(-c2ccc(Cl)cc2)c1[C@H](OC(C)(C)C)C(=O)O]

6. A compound represented by the following Chemical Formula II or IV:

[Chemical Formula II]

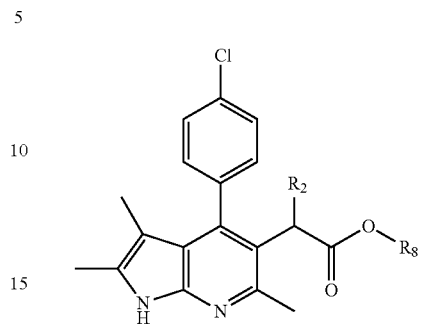

[Chemical Formula IV]

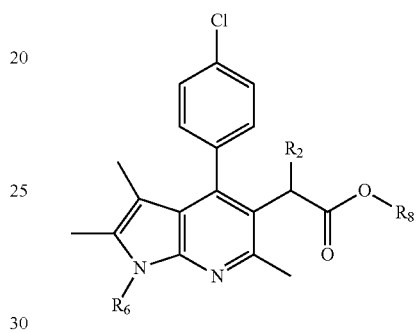

wherein, in the formula, $R_2$ is tert-butoxy;

$R_6$ is hydrogen, or —$(CH_2)_n$—$R_7$;

$R_7$ is hydrogen; halogen; hydroxy; amino; cyano; trifluoromethyl; $C_{2-6}$ alkenyl; $C_{2-6}$ alkynyl; $C_{1-6}$ alkoxy; carbamoyl; CONH($C_{1-3}$ alkyl); CON($C_{1-3}$ alkyl)$_2$; COOH; $C_{3-6}$ cycloalkyl unsubstituted or substituted with 1 or 2 substituents each selected from the group consisting of halogen, cyano, hydroxy, hydroxymethyl, carboxy and carbamoyl; phenyl unsubstituted or substituted with 1 to 3 substituents each selected from the group consisting of cyano, $C_{1-6}$ alkyl, $C_{1-6}$ alkoxy and amino; pyridinyl unsubstituted or substituted with 1 or 2 substituents each selected from the group consisting of halogen, cyano, $C_{1-6}$ alkyl, $C_{1-6}$ alkoxy and amino; pyrimidinyl unsubstituted or substituted with amino or halogen; dioxoisoindolinyl; oxazolyl; furanyl unsubstituted or substituted with $C_{1-6}$ alkyl or halogen; thiophenyl unsubstituted or substituted with $C_{1-6}$ alkyl or halogen; pyrrolidinyl unsubstituted or substituted with $C_{1-6}$ alkyl or halogen; 2-oxopyrrolidinyl; pyrazolyl unsubstituted or substituted with $C_{1-3}$ alkyl; or thiazolyl;

n is an integer of 1 to 5; and $R_8$ is $C_{1-6}$ alkyl.

7. A method for preparing a compound represented by the following Chemical Formula I, comprising the steps of:

preparing a compound represented by the following Chemical Formula IV by reacting a compound represented by the following Chemical Formula II with a compound represented by the following Chemical Formula III (Step 1); and hydrolyzing the compound represented by Chemical Formula IV (Step 2),

[Chemical Formula I]

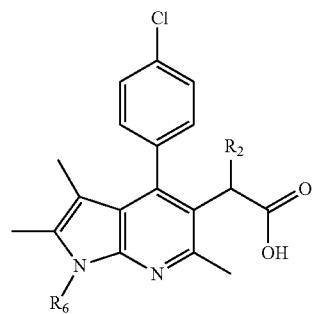

[Chemical Formula II]

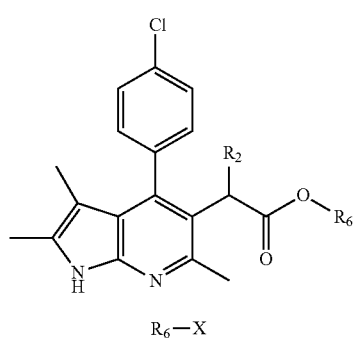

$R_6$—X

[Chemical Formula III]

[Chemical Formula IV]

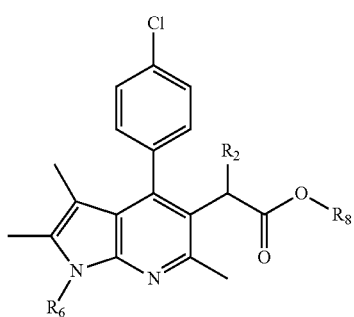

wherein, in the formula,
$R_2$ is tert-butoxy;
$R_6$ is hydrogen, or —$(CH_2)_n$—$R_7$;
$R_7$ is hydrogen; halogen; hydroxy; amino; cyano; trifluoromethyl; $C_{2-6}$ alkenyl; $C_{2-6}$ alkynyl; $C_{1-6}$ alkoxy; carbamoyl; $CONH(C_{1-3}$ alkyl); $CON(C_{1-3}$ alkyl$)_2$; COOH; $C_{3-6}$ cycloalkyl unsubstituted or substituted with 1 or 2 substituents each selected from the group consisting of halogen, cyano, hydroxy, hydroxymethyl, carboxy and carbamoyl; phenyl unsubstituted or substituted with 1 to 3 substituents each selected from the group consisting of cyano, $C_{1-6}$ alkyl, $C_{1-6}$ alkoxy and amino; pyridinyl unsubstituted or substituted with 1 or 2 substituents each selected from the group consisting of halogen, cyano, $C_{1-6}$ alkyl, $C_{1-6}$ alkoxy and amino; pyrimidinyl unsubstituted or substituted with amino or halogen; dioxoisoindolinyl; oxazolyl; furanyl unsubstituted or substituted with $C_{1-6}$ alkyl or halogen; thiophenyl unsubstituted or substituted with $C_{1-6}$ alkyl or halogen; pyrrolidinyl unsubstituted or substituted with $C_{1-6}$ alkyl or halogen; 2-oxopyrrolidinyl; pyrazolyl unsubstituted or substituted with $C_{1-3}$ alkyl; or thiazolyl;
n is an integer of 1 to 5;
$R_8$ is $C_{1-6}$ alkyl; and
X is halogen, methanesulfonyl, p-toluenesulfonyl or trifluoromethanesulfonyl.

8. A composition comprising the compound represented by Chemical Formula I, the racemate or the stereoisomer thereof, or the pharmaceutically acceptable salt thereof according to claim 1, and
a pharmaceutically acceptable carrier.

9. The composition according to claim 8, wherein the composition is an antiviral composition.

10. A composition comprising the compound represented by Chemical Formula I, the racemate or the stereoisomer thereof, or the pharmaceutically acceptable salt thereof according to claim 2, and
a pharmaceutically acceptable carrier.

11. A composition comprising the compound represented by Chemical Formula I, the racemate or the stereoisomer thereof, or the pharmaceutically acceptable salt thereof according to claim 3, and
a pharmaceutically acceptable carrier.

12. A composition comprising the compound represented by Chemical Formula I, the racemate or the stereoisomer thereof, or the pharmaceutically acceptable salt thereof according to claim 4, and
a pharmaceutically acceptable carrier.

13. A composition comprising the compound, the racemate or the stereoisomer thereof, or the pharmaceutically acceptable salt thereof according to claim 5, and
a pharmaceutically acceptable carrier.

14. A method for treating virus infection using a composition according to claim 8.

15. The method according to claim 14, wherein the virus infection is a human immunodeficiency virus (HIV) infection.

16. A method for treating virus infection using a composition according to claim 10.

17. A method for treating virus infection using a composition according to claim 11.

18. A method for treating virus infection using a composition according to claim 12.

19. A method for treating virus infection using a composition according to claim 13.

* * * * *